US011440969B2

(12) United States Patent
Lackner et al.

(10) Patent No.: US 11,440,969 B2
(45) Date of Patent: Sep. 13, 2022

(54) USE OF HUMAN EPIDIDYMIS PROTEIN 4 (HE4) FOR ASSESSING RESPONSIVENESS OF MUC 16-POSITIVE CANCER TREATMENT

(71) Applicant: Genentech, Inc., South San Francisco, CA (US)

(72) Inventors: Mark Lackner, South San Francisco, CA (US); Daniel Maslyar, San Carlos, CA (US); Yulei Wang, South San Francisco, CA (US); Walter Darbonne, San Mateo, CA (US); Eric Humke, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 428 days.

(21) Appl. No.: 16/239,663

(22) Filed: Jan. 4, 2019

(65) Prior Publication Data

US 2019/0233538 A1   Aug. 1, 2019

Related U.S. Application Data

(63) Continuation of application No. PCT/US2017/041119, filed on Jul. 7, 2017.

(60) Provisional application No. 62/360,027, filed on Jul. 8, 2016.

(51) Int. Cl.
| | |
|---|---|
| *C07K 16/30* | (2006.01) |
| *A61K 47/68* | (2017.01) |
| *G01N 33/574* | (2006.01) |
| *A61K 47/65* | (2017.01) |
| *A61P 35/00* | (2006.01) |
| *A61K 31/22* | (2006.01) |
| *A61K 31/7048* | (2006.01) |
| *C07K 16/28* | (2006.01) |
| *A61K 39/00* | (2006.01) |

(52) U.S. Cl.
CPC ......... *C07K 16/3092* (2013.01); *A61K 31/22* (2013.01); *A61K 31/7048* (2013.01); *A61K 47/65* (2017.08); *A61K 47/6803* (2017.08); *A61K 47/6817* (2017.08); *A61K 47/6859* (2017.08); *A61K 47/6869* (2017.08); *A61P 35/00* (2018.01); *C07K 16/2896* (2013.01); *G01N 33/57407* (2013.01); *G01N 33/57449* (2013.01); *G01N 33/57484* (2013.01); *A61K 2039/505* (2013.01); *C07K 2317/94* (2013.01)

(58) Field of Classification Search
CPC ......... C07K 16/3092; G01N 33/57407; G01N 33/57484; G01N 33/57449
See application file for complete search history.

(56) References Cited

U.S. PATENT DOCUMENTS

| | | |
|---|---|---|
| 4,970,198 A | 11/1990 | Lee |
| 4,975,278 A | 12/1990 | Senter |
| 5,079,233 A | 1/1992 | Lee |
| 5,428,130 A | 6/1995 | Capon |
| 5,585,089 A | 12/1996 | Queen |
| 5,606,040 A | 2/1997 | Mcgahren |
| 5,693,762 A | 12/1997 | Queen |
| 5,739,116 A | 4/1998 | Hamann |
| 5,767,285 A | 6/1998 | Hamann |
| 5,773,001 A | 6/1998 | Hamann |
| 6,054,297 A | 4/2000 | Carter |
| 6,582,959 B2 | 6/2003 | Kim |
| 6,703,020 B1 | 3/2004 | Thorpe |
| 6,884,879 B1 | 4/2005 | Baca |
| 7,060,269 B1 | 6/2006 | Baca |
| 7,202,346 B2 | 4/2007 | Payne |
| 7,521,441 B2 | 4/2009 | Gentles |
| 7,723,485 B2 | 5/2010 | Junutula |
| 7,989,595 B2 | 8/2011 | Dennis |
| 8,623,828 B2 | 1/2014 | Ho |
| 2003/0124140 A1 | 7/2003 | Bangur |
| 2003/0190317 A1 | 10/2003 | Baca |
| 2003/0203409 A1 | 10/2003 | Kim |
| 2003/0206899 A1 | 11/2003 | Ferrara |
| 2005/0112126 A1 | 5/2005 | Baca |
| 2005/0186208 A1 | 8/2005 | Fyfe |
| 2005/0276812 A1 | 12/2005 | Ebens, Jr. |
| 2006/0009360 A1 | 1/2006 | Pifer |

(Continued)

FOREIGN PATENT DOCUMENTS

| | | |
|---|---|---|
| CN | 103954761 A | 7/2014 |
| CN | 104039343 A | 9/2014 |

(Continued)

OTHER PUBLICATIONS

Akobeng, AK (Acta Paediatrica 2007 96: 644-647) (Year: 2007).*
Angioli et al. (Tumor Biology. 2014 35:7009-7015), (Year: 2014).*
Bafna, S. et al. (2010, e-pub. Mar. 29, 2010). "Membrane-Bound Mucins: The Mechanistic Basis for Alterations in the Growth and Survival of Cancer Cells," Oncogene 29:2893-2904.

(Continued)

*Primary Examiner* — Peter J Reddig
(74) *Attorney, Agent, or Firm* — Morrison & Foerster LLP

(57) ABSTRACT

The present invention relates to methods and kits or articles of manufacture related thereto that may find use, inter alia, in assessing responsiveness of cancers to MUC16 antagonists by monitoring HE4 expression. In some embodiments, the methods include measuring the level of expression of HE4 in a sample from a subject; comparing the level of expression of HE4 in the sample with the level of expression of HE4 in a sample previously obtained from the subject; and, optionally, administering to the subject a therapeutically effective amount of a MUC16 antagonist.

28 Claims, 23 Drawing Sheets
(20 of 23 Drawing Sheet(s) Filed in Color)
Specification includes a Sequence Listing.

(56) References Cited

U.S. PATENT DOCUMENTS

| | | | | |
|---|---|---|---|---|
| 2007/0286865 | A1* | 12/2007 | Moore | A61P 35/00 424/158.1 |
| 2013/0302270 | A1 | 11/2013 | Spitzer | |
| 2016/0145313 | A1 | 5/2016 | Kufe et al. | |

FOREIGN PATENT DOCUMENTS

| | | |
|---|---|---|
| CN | 104080928 A | 10/2014 |
| EP | 1391213 A1 | 2/2004 |
| EP | 0666868 B2 | 6/2006 |
| WO | WO9321232 A1 | 10/1993 |
| WO | WO9410202 A1 | 5/1994 |
| WO | WO9411026 A2 | 5/1994 |
| WO | WO9411026 A3 | 8/1994 |
| WO | WO9630046 A1 | 10/1996 |
| WO | WO9845332 A2 | 10/1998 |
| WO | WO9845332 A3 | 12/1998 |
| WO | WO02083866 A2 | 10/2002 |
| WO | WO02092836 A2 | 11/2002 |
| WO | WO02083866 A3 | 2/2004 |
| WO | WO2004045553 A2 | 6/2004 |
| WO | WO2005012359 A2 | 2/2005 |
| WO | WO2005044853 A2 | 5/2005 |
| WO | WO02092836 A3 | 8/2005 |
| WO | WO2005012359 A3 | 12/2005 |
| WO | WO2005044853 A3 | 1/2006 |
| WO | WO2004045553 A3 | 2/2006 |
| WO | WO2006034488 A2 | 3/2006 |
| WO | WO2006089125 A2 | 8/2006 |
| WO | WO2006034488 A3 | 9/2006 |
| WO | WO2006089125 A3 | 12/2006 |
| WO | WO2007001851 A2 | 1/2007 |
| WO | WO2007001851 A3 | 3/2007 |
| WO | WO2007081767 A2 | 7/2007 |
| WO | WO2007081768 A2 | 7/2007 |
| WO | WO2007090076 A2 | 8/2007 |
| WO | WO2007090076 A3 | 11/2007 |
| WO | WO2007081767 A3 | 4/2008 |
| WO | WO2007081768 A3 | 4/2008 |
| WO | WO2008141044 A2 | 11/2008 |
| WO | WO2008141044 A3 | 12/2008 |
| WO | WO201 1156328 A1 | 12/2011 |
| WO | WO2012170513 A2 | 12/2012 |
| WO | WO2012170513 A3 | 1/2013 |
| WO | 2013074044 A1 | 5/2013 |
| WO | WO2013181452 A1 | 12/2013 |
| WO | WO2014160368 A2 | 10/2014 |
| WO | WO2014160368 A9 | 12/2014 |

OTHER PUBLICATIONS

Bai, R. et al. (Oct. 5, 1990). "Binding of Dolastatin 10 to Tubulin at a Distinct Site for Peptide Antimitotic Agents Near the Exchangeable Nucleotide and Vinca Alkaloid Sites," J. Biol. Chem. 265(28):17141-17149.
Baldwin, R.W. et al. (Mar. 15, 1986). "Monoclonal Antibodies in Cancer Treatment," Lancet 1(8481)603-605.
Bast, C.R. et al. (Oct. 13, 1983). "A Radioimmunoassay Using a Monoclonal Antibody to Monitor the Course of Epithelial Ovarian Cancer," New England Journal of Medicine 309(15):883-887.
Bast, R.C. et al. (Jan. 1, 2002). "Early Detection of Ovarian Cancer: Promise and Reality," Chapter 3 in Cancer Treatment and Resea 107:61-97.
Bast, R.C. et al. (Nov. 1981). "Reactivity of a Monoclonal Antibody With Human Ovarian Carcinoma," J. Clin. Invest. 68:1331-1337.
Bast, R.C. et al. (Oct.-Dec. 1998). "CA 125: the Past and the Future," Int. J. Biol. Markers 13(4):179-187.
Bloss, J.D. et al. (1993). "Extraovarian Peritoneal Serous Papillary Carcinoma: A Case-Control Retrospective Comparison to Papillary Adenocarcinoma of the Ovary," Gynecol. Oncol. 50:347-351.
Burris, H.A et al. (Jun. 1997). "Improvements in Survival and Clinical Benefit With Gemcitabine as First-Line Therapy for Patients With Advanced Pancreas Cancer: A Randomized Trial," J. Clin. Oncol. 15(6):2403-2313.

Chen, Y. et al. (May 15, 2007). "Armed Antibodies Targeting The Mucin Repeats of The Ovarian Cancer Antigen, MUC16, Are Highly Efficacious In Animal Tumor Models," Cancer Res. 67(10):4924-4932.
Clackson, T. et al. (Aug. 15, 1991). "Making antibody fragments using phage display libraries," Nature 352:624-628.
Clauss, A. et al. (Nov. 15, 2002). "A Locus on Human Chromosome 20 Contains Several Genes Expressing Protease Inhibitor Domains With Homology To Whey Acidic Protein," Biochem. J. 368(Part 1):233-242.
De Kok, J.B. et al. (Jan. 2005, e-pub. Nov. 15, 2004). "Normalization of Gene Expression Measurements in Tumor Tissues: Comparison of 13 Endogenous Control Genes," Lab. Invest. 85(1):154-159.
DeGeorge, J.J. et al. (1998). "Regulatory Considerations for Preclinical Development of Anticancer Drugs," Cancer Chemother. Pharmacol. 41(3)173-185.
Doronina, S.O. et al. (Aug. 2003). "Erraturm: Development of Potent Monoclonal Antibody Auristatin Conjugates for Cancer Therapy," Nat. Biotechnol. 21(8):941.
Doronina, S.O. et al. (Jul. 2003). "Development of Potent Monoclonal Antibody Auristatin Conjugates for Cancer Therapy," Nat. Biotechnol. 21(7):778-784.
Drapkin, R. et al. (Mar. 15, 2005). "Human Epididymis Protein 4 (HE4) is a Secreted Glycoprotein That is Overexpressed by Serous and Endometrioid Ovarian Carcinomas," Cancer Res. 65(6):2162-2169.
Eagle, K. et al. (1997) "Tumor Markers in Ovarian Malignancies," Oncologist 2(5):324-329.
Ehlen, T.G. et al. (Nov.-Dec. 2005). "A Pilot Phase 2 Study of Oregovomab Murine Monoclonal Antibody to CA125 as an Immunotherapeutic Agent for Recurrent Ovarian Cancer," International Journal of Gynecological cancer 15 (6):1023-1034.
Eisenhauser, E.A. et al. (Jan. 2009). "New Response Evaluation Criteria in Solid Tumours: Revised RECIST Guideline (version 1.1)," Eur. J. Cancer 45(2):228-247.
Fanale, M. et al. (2009). "The Antibody-Drug Conjugate Brentuximab Vedotin (SGN-35) Induced Multiple Objective Responses in Patients With Relapsed or Refactory CD30-Positive Lymphomas in a Phase 1 Weekly Dosing Study," Blood 114:2731, 5 pages.
Felder, M. et al. (May 29, 2014). "MUC16 (CA125): Tumor Biomarker to Cancer Therapy, A Work in Progress," Molecular Cancer 129(13):1-15.
Fendrick, J.L. et al. (1997). "CA125 Phosphorylation is Associated With its Secretion From the WISH Human Amnion Cell Line," Tumor Biol. 18(5):278-289.
Flatman, S. et al. (2007, e-pub. Dec. 11, 2006). "Process analytics for Purification of Monoclonal Antibodies," J. Chromatogr. B. 848:79-87.
Francisco, J.A. et al. (2003, e-pub. May 8, 2003). "cAC10-vcMMAE, An Anti-CD30-Monomethyl Auristatin E Conjugate With Potent and Selective Antitumor Activity," Blood 102:1458-1465.
Gadducci, A. et al. (2004). "Serum Tumor Markers In The Management of Ovarian, Endometrial And Cervical Cancer," Biomed. Pharmacother. 58:24-38.
Garg, G. et al. (Jan. 21, 2014). "Novel Treatment Option for MUC16-Positive Malignancies With the Targeted TRAIL-Based Fusion Protein Meso-TR3," BMC Cancer 14(35):1-12.
Gilks, C.B. et al. (Mar. 2005, e-pub. Dec. 30, 2004). "Distinction Between Serous Tumors of Low Malignant Potential and Serous Carcinomas Based on Global mRNA Expression Profiling," Gynecol. Oncol. 96(3):684-694.
Haglund, C. (1986). Tumor Marker Antigen CA125 in Pancreatic Cancer: a Comparison With CA19-9 and CEA, Br. J. Cancer 54:897-901.
Haisma, H.J. et al. (1987). "Antibody-Antigen Complex Formation Following Injection of OC125 Monoclonal Antibody in Patients With Ovarian Cancer," Int. J. Cancer 40:758-762.
Hamid, O. et al. (2010). "Frequent Dosing and GPNMB Expression With DCX-011 (CRO11-vcMMAE), an Antibody-Drug Conjugate (ADC), in Patients With Advanced Melanoma," J. Clin. Oncol. 28:Abstract No. 8525, 3 pages.

(56) References Cited

OTHER PUBLICATIONS

Hellstrom, I. et al. (May 1, 2011). "Two Novel Biomarkers, Mesothelin and HE4, for Diagnosis of Ovarian Carcinoma," Expert Opinion on Medical Diagnostics 5(3):227-240.
Hinman, L.M. et al. (Jul. 15, 1993). "Preparation and Characterization of Monoclonal Antibody Conjugates of the Calicheamicins: A Novel and Potent Family of Antitumor Antibiotics," Cancer Res. 53:3336-3342.
Hough, C.D. et al. (Nov. 15, 2000). "Large-Scale Serial Analysis of Gene Expression Reveals Genes Differentially Expressed in Ovarian Cancer," Cancer Res. 60(22):6281-6287.
International Preliminary Report on Patentability, dated Jan. 8, 2019, for PCT Application No. PCT/US2017/041119, filed on Jul. 7, 2017, 11 pages.
International Search Report dated Sep. 22, 2017, for PCT Application No. PCT/US2017/041119, filed on Jul. 7, 2017, 8 pages.
Jemal, A, et al. (Sep./Oct. 2010). "Cancer Statistics, 2010," CA Cancer J. Clin. 60(5):277-300.
Karlan, B.Y. et al. (Jul. 2014). "Use of CA125 and HE4 Serum Markers to Predict Ovarian Cancer in Elevated-Risk Women," Cancer Epidemiology 23(7):1383-1393.
Kindt, T.J. et al. (2007). "Antigens And Antibodies," Chapter 4 In Kuby Immunology 6th Ed., W.H. Freeman and Co., p. 91.
Kirchhoff, C. et al. (Aug. 1991). "A Major Human Epididymis-Specific cDNA Encodes a Protein With Sequence Homology to Extracellular Proteinase Inhibitors," Biol. Reprod. 45(2):350-357.
Liu, C. et al. (Aug. 1996). "Eradication of Large Colon Tumor Xenografts by Targeted Delivery of Maytansinoids," Proc. Natl. Acad. Sci. USA 93:8618-8623.
Lode, H.N. et al. (Jul. 15, 1998). "Targeted Therapy with a Novel Enediyene Antibiotic Calicheamicin θ11 Effectively Suppresses Growth and Dissemination of Liver Metastases in a Syngeneic Model of Murine Neuroblastoma," Cancer Res. 58:2925-2928.
Lu, K.H. et al. (May 15, 2004). "Selection of Potential Markers for Epithelial Ovarian Cancer With Gene Expression Arrays and Recursive Descent Partition Analysis," Clinical Cancer Research 10:3291-3300.
MacDonald, F. et al. (1988). "Expression of CA125 in Pancreatic Carcinoma and Chronic Pancreatitis," Br. J. Cancer 58:505-506.
Mandler, R. et al. (2000). "Immunoconjugates of Geldananlycin and Anti-HER2 Monoclonal Antibodies: Antiproliferative Activity on Human Breast Carcinoma Cell Lines," J. Nat. Cancer Inst. 92(19):1573-1581.
Mandler, R. et al. (2000). "Synthesis and Evaluation of Antiproliferative Activity of a Geldanamycin-Herceptin TM Immunoconjugate," Bioorganic & Med. Chem. Letters 10:1025-1028.
Mandler, R. et al. (2002). "Modifications in Synthesis Strategy Improve the Yield and Efficacy of Geldanamycin-Herceptin Immunoconjugates," Bioconjugate Chem. 13:786-791.
Martin, L.P. et al. (Apr. 2009). "Management of Recurrent Ovarian Carcinoma: Current Status and Future Directions," Semin. Oncol. 36(2):112-125.
Mclemore, M.R. et al. (2005). "Introducing the MUC16 Gene: Implications For Prevention and Early Detection in Epithelial Ovarian Cancer," Biol. Res. Nurs. 6:262-267.
McQuarrie, S.A. et al. (1998). "The Effects of Circulating Antigen on the Pharmacokinetics and Radioimmunoscintigraphic Properties of 99mTc Labelled Monoclonal Antibodies in Cancer Patients," J. Pharm. Pharmaceut. Sci. 1(3):115-125.
Meden, H. et al. (Oct.-Dec. 1998). "CA 125 in Benign Gynecological Conditions," Int. J. Biol. Markers 13(4):231-237.
Menon, U. et al. (Feb. 2000). "Recent Developments in Ovarian Cancer Screening," Curr. Opin. Obstet. Gynecol. 12(1):39-42.
Meyer, T. et al. (May 2000). "Role of Tumour Markers in Monitoring Epithelial Ovarian Cancer," Br. J. Cancer 82(9):1535-1538.
Monk, B.J. et al. (Jul. 1, 2010). "Trabectedin Plus Pegylated Liposomal Doxorubicin in Recurrent Ovarian Cancer," J. Clin. Oncol. 28(19):3107-3114.
Moore, M.J. et al. (May 20, 2007). "Erlotinib Plus Gemcitabine Compared With Gemcitabine Alone in Patients With Advanced Pancreatic Cancer: A Phase III Trial of the National Cancer Institute of Canada Clinical Trials Group," J. Clin. Oncol. 25(15):1960-1966.
Moore, R.G. et al. (Aug. 2008). "Utility of A Novel Serum Tumor Biomarker HE4 in Patients With Endometrioid Adenocarcinoma of the Uterus," Gynecologic Oncology 110(2):196-201.
Moore, R.G. et al. (Jan. 2009). "A Novel Multiple Marker Bioassay Utilizing HE4 and CA125 for the Prediction of Ovarian Cancer in Patients With a Pelvic Mass," Gynecologic Oncology 112(1):40-46.
Murakami, M.S. et al. (1995). "Cell Cycle Regulation, Oncogenes, and Antineoplastic Drugs," Chapter 1 in The Molecular Basis of Cancer, W.B. Saunders Company, Philadelphia, pp. 3-17.
Möbus, V.J. et al. (Jul. 1, 2003). "Immune Responses to Murine Monoclonal Antibody-B43.13 Correlate With Prolonged Survival of Women with Recurrent Ovarian Cancer," American Journal of Obstetrics & Gynecology 189(1):28-36.
NCBI. (Apr. 15, 2019). "WFDC2 Wap Four-Disulfide Core Domain 2 [Homo sapiens (human)], Gene No. 10406," NCBI 5 pages.
NCBI. (Jul. 15, 2006), "WAP Four-Disulfide Core Domain 2 [Homo sapiens] GenBank Accession No. AAH46106.1," located at http://www.ncbi.nlm.nih.gov/protein/28374248, last visited on Jun. 201, 2019, 2 pages.
Neoptolemos, J.P. et al. (2004). "A Randomized Trial of Chemoradiotherapy and Chemotherapy After Resection of Pancreatic Cancer," N Engl. J Med. 350:1200-1210.
Niculesu-Duvaz, I. et al. (1997). "Antibody-Directed Enzyme Prodrug Therapy (ADEPT): A Review," Adv. Drug Del. Rev. 26:151-172.
O'Brien, T.J. et al. (2001). "The CA 125 Gene: An Extracellular Superstructure Dominated by Repeat Sequences," Tumour Biol. 22:348-366.
O'Brien, T.J. et al. (May-Jun. 2002). "The CA 125 Gene: A Newly Discovered Extension of the Glycosylated N-Terminal Domain Doubles the Size of this Extracellular Superstructure," Tumour Biol. 23(3):154-169.
Pastuskovas, C. et al. (Sep. 7, 2010). "Effect of Immune Complex Formation on the Distribution of a Novel Antibody to the Ovarian Tumor Antigen CA125," Drug Metab. Dispos. 38:2309-2319.
Popkov, M. et al. (May 2004). "Human/Mouse Cross-Reactive Anti-VEGF Receptor 2 Recombinant Antibodies Selected From an Immune b9 Allotype Rabbit Antibody Library," Journal of Immunological Methods 288(1-2):149-164.
Portolano, S. et al. (Feb. 1, 1993). "Lack of Promiscuity in Autoantigen-Specific H and L Chain Combinations as Revealed by Human H and L Chain "Roulete"," J. Immunol. 150(3):880-887.
Pujade-Lauraine, D. et al. (2002). "Predicting the Effectiveness of Chemotherapy (Cx) in Patients With Recurrent Ovarian Cancer (ROC): A GINECO study," Proc. Am. Soc. Clin. Oncol. 21:Abstract 829.
Rabasseda, A. et al. (2000). "Gemtzumab Ozogamicin-Treatment of Acute Myeloid Leukemia," Drugs of the Future 25(7):686-692.
Rosen, D.G. et al. (2005, e-pub. Aug. 2, 2005). "Potential Markers That Complement Expression of CA125 in Epithelial Ovarian Cancer," Gynecol. Oncol. 99:267-277.
Rowland, G.F. et al. (1986). "Drug Localisation and Growth Inhibition Studies of Vindesine-Monoclonal Anti-CEA Conjugates in a Human Tumour Xenograft," Cancer Immunol. Immunother. 21:183-187.
Sarojini, S. et al. (Jan. 1, 2012). "Early Detection Biomarkers for Ovarian Cancer," Journal of Oncology pp. 1-15.
Schneider, C. et al. (2000). "Primary Carcinoma of the Fallopian Tube: A Report of 19 Cases with Literature Review," Eur. J. Gynecol. Oncol. 21:578-582.
Seelenmeyer, C. et al. (2003). "The Cancer Antigen CA125 Represents a Novel Counter Receptor For Galectin-1," Journal of Cell Science 116(7):1305-1318.
Shaib, Y. et al. (2007). "The Impact of Curative Intent Surgery on the Survival of Pancreatic Cancer Patients: A U.S. Population-Based Study," Am. J. Gastroenterol. 102:1377-1382.
Syrigos, K.N. et al. (1999). "Antibody Directed Enzyme Prodrug Therapy (ADEPT): A Review of the Experimental and Clinical Considerations," Anticancer Research 19:605-614.
Therasse, P. et al. (Feb. 2, 2000). "New Guidelines to Evaluate the Response to Treatment in Solid Tumors," J. Natl. Cancer Inst. 92(3):205-216.

(56) References Cited

OTHER PUBLICATIONS

Thorpe, P.E. (1985). "Antibody Carriers of Cytotoxic Agents in Cancer Therapy: A Review," in Monoclonal Antibodies 84: Biological and Clinical Applications, A. Pinchera et al. eds., Editrice Kurtis s.r.l., pp. 475-506.

Thériault, C. et al. (2011, e-pub. Mar. 21, 2011). "MUC16 (CA125) Regulates Epithelial Ovarian Cancer Cell Growth, Tumorigenesis and Metastasis," Gynecol. Oncol. 121(3):434-443.

Tolcher, A.W. et al. (2003). "Catuzumab Mertasine, A Maytansinoid Immunoconjugate Directed to the CanAg Antigen: A Phase I, Pharmacokinetic, and Biologic Correlative Study," J. Clin. Oncol. 21:211-222.

Topalian, S.L. et al. (Jun. 28, 2012). "Safety, activity, and immune correlates of anti-PD-1 antibody in cancer," New England Journal of Medicine 366:2443-2454.

Tse, B.W.C. et al. (Nov. 26, 2013). "Antibody-Based Immunotherapy for Ovarian Cancer: Where are we at?," Annals of Oncology 25(2):322-331.

Vergote, I. et al. (Sep. 20, 2000). "Re: New Guidelines to Evaluate the Response to Treatment in Solid Tumors [Ovarian Cancer]," Journal of the National Cancer Institute 92(18):1534-1535.

Verheijen, R.H. et al. (Apr. 1999). "CA 125: Fundamental and Clinical Aspects," Sem. Cancer Biol. 9(2):117-124.

Vitetta, E.S. et al. (Nov. 20, 1987). "Redesigning Nature's Poisons to Create Anti-Tumor Reagents," Science 238:1098-1104.

Wang, K. et al. (Mar. 18, 1999). "Monitoring Gene Expression Profile Changes in Ovarian Carcinomas Using cDNA Microarray," Gene 229(1-2):101-108.

Wiseman, G.A. et al. (2002). "Ibritumomab Tiuxetan Radioimmunotherapy for Patients With Relapsed or Refactory Non-Hodgkin Lymphoma and Mild Thrombocytopenia: A Phase II Multicenter Trial," Blood 99(12);4336-4342.

Wiseman, G.A. et al. (Jul. 2000). "Phase I/II 90Y-Zevalin (Yttrium-90 Ibritumomab Tiuxetan, IDEC-Y2B8) Radioimmunotherapy Dosimetry Results in Relapsed or Refractory Non-Hodgkin's Lymphoma," Eur. Jour. Nucl. Med. 27(7):766-777.

Witzig, T.E. et al. (2002). "Treatment With Ibritumomab Tiuxetan Radioimmunotherapy in Patients With Rituximab-Reftactory Follicular Non-Hodgkin's Lymphoma," J. Clinc. Oncol. 20(15):3262-3269.

Witzig, T.E. et al. (May 2002). "Randomized Conlrolled Trial of Yttrium-90-Labeled Ibritumomab Tiuxetan Radioimmunotherapy Versus Rituximab Immunotherapy for Patients With Relapsed or Refactory Low-Grade, Follicular, or Transformed B-Cell Non-Hodgkin's Lymphoma," J. Clin. Oncol. 20(10):2453-2463.

Wolchok, J.D. et al. (Dec. 1, 2009, e-pub. Nov. 24, 2009). "Guidelines for The Evaluation of Immune Therapy Activity in Solid Tumors: Immune-Related Response Criteria," Clin. Can. Res. 15(23):7412-7420.

Wong, N.K. et al. (Aug. 1, 2003, e-pub. May 6, 2003). "Characterization of the Oligosaccharides Associated With the Human Ovarian Tumor Marker CA125," J. Biol. Chem. 278:28619-28634.

Written Opinion dated Sep. 22, 2017, for PCT Application No. PCT/US2017/041119, filed on Jul. 7, 2017, 10 pages.

Xiang, X. et al. (Jan. 1, 2011). "HN125: A Novel Immunoadhesin Targeting MUC16 With Potential for Cancer Therapy," Journal of Cancer 2:281-290.

Yin, B.W.T. et al. (2002). "Ovarian Cancer Antigen CA125 is Encoded by the MUC16 Mucin Gene," Int. J. Cancer 98:737-740.

Yin, B.W.T. et al. (Jul. 20, 2001, e-pub. May 21, 2001). "Molecular Cloning of the CA125 Ovarian Cancer Antigen: Identification as a New Mucin, MUC16," J. Biol. Chem. 276:27371-27375.

Chudecka-Glax, A. et al. (Mar. 27, 2018). "Could HE4 Lvel Measurements During First-Line Chemotherapy Predict Response to Treatment Among Ovarian Cancer Patients?," Plos One 13(3):30194270, pp. 1-16.

Vallius, T et al. (2014, e-pub, Sep. 5, 2014), "Serum HE4 and CA125 as Predictors of Response and Outcome During Neoadjuvant Chemotherapy of Advanced High-Grade Serous Ovarian Cancer," Tumr. Biol. 35:12389-12395.

* cited by examiner

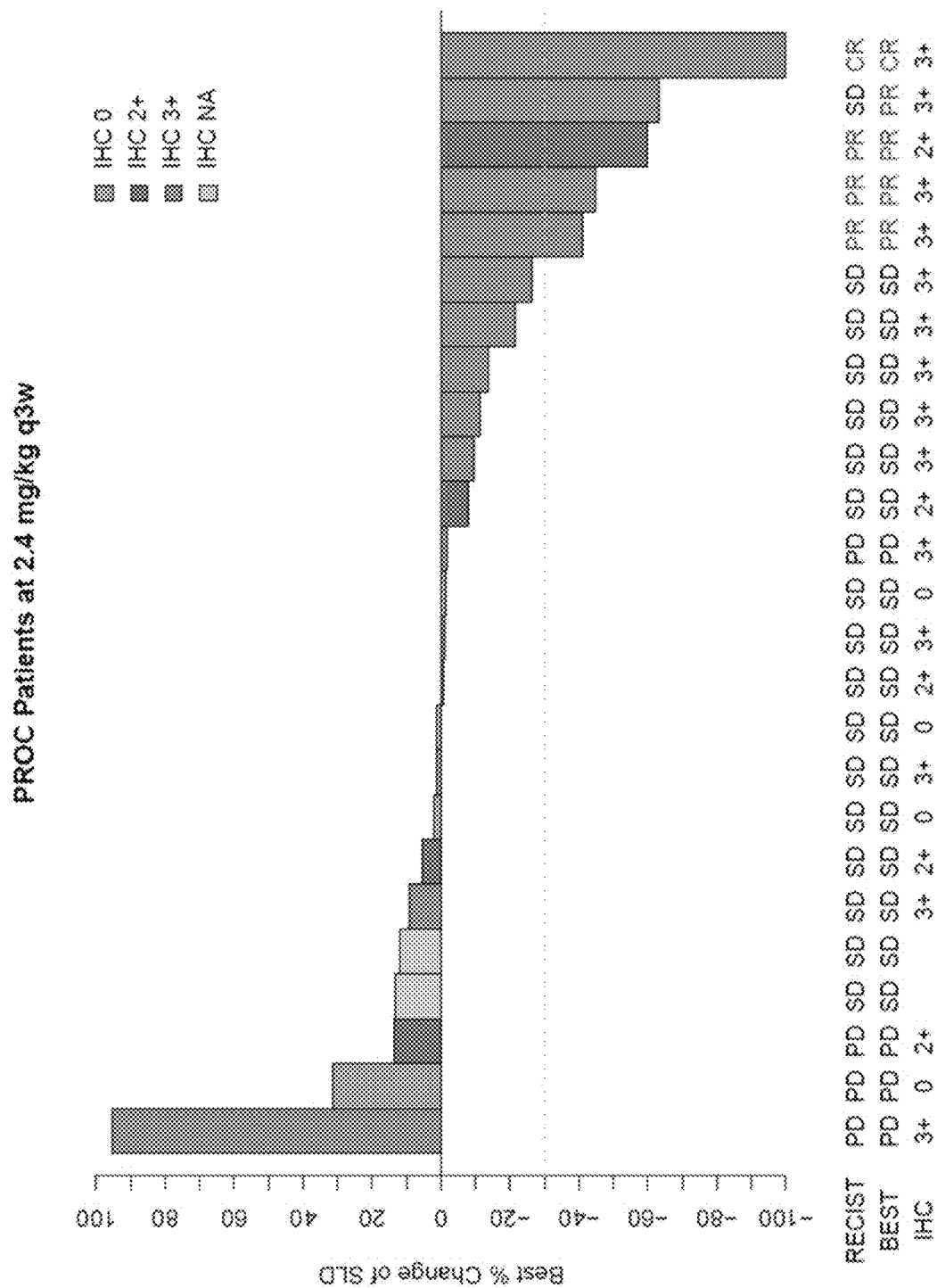

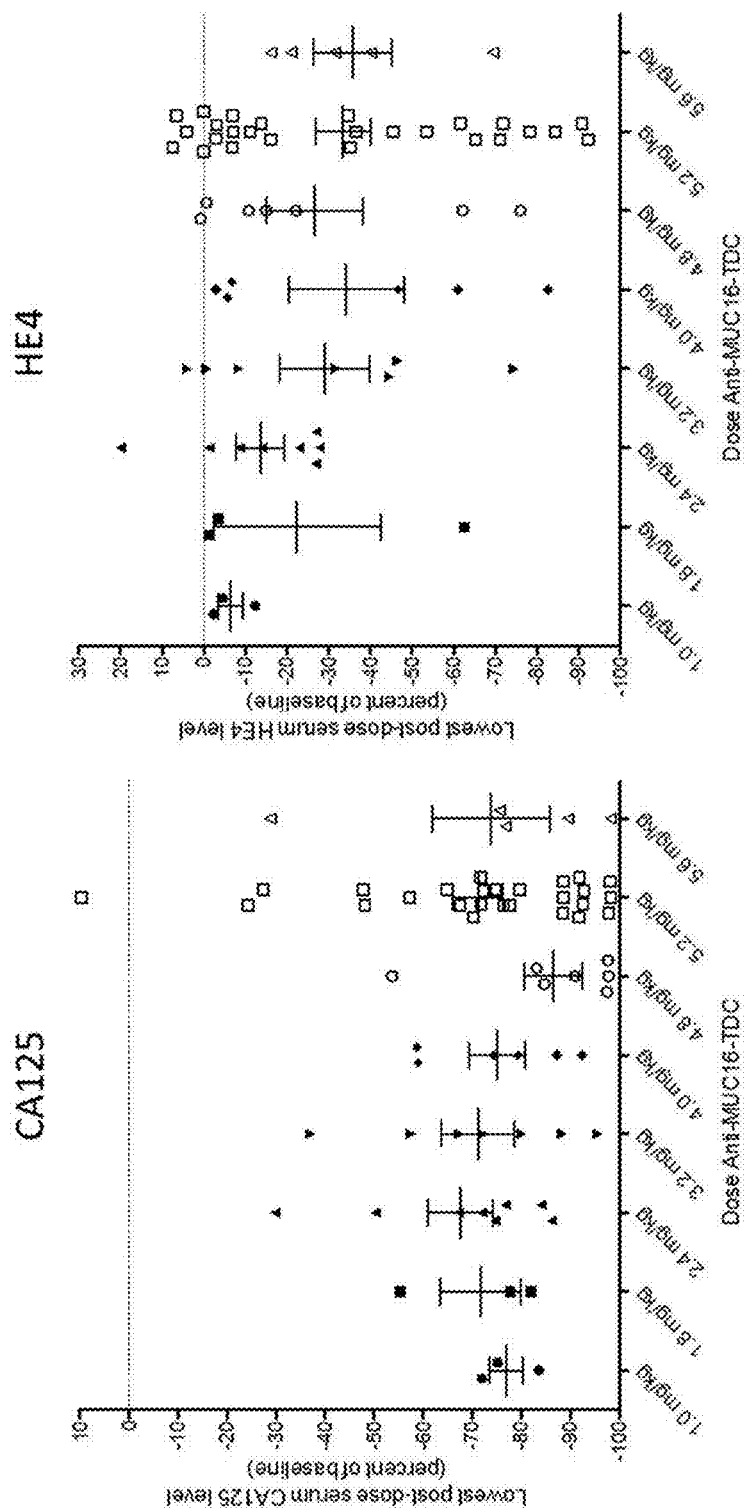

USE OF HUMAN EPIDIDYMIS PROTEIN 4 (HE4) FOR ASSESSING RESPONSIVENESS OF MUC 16-POSITIVE CANCER TREATMENT

CROSS REFERENCE TO RELATED APPLICATIONS

This application is a continuation of International Patent Application No. PCT/US2017/041119, filed Jul. 7, 2017, which claims priority to and the benefit of U.S. provisional application Ser. No. 62/360,027, filed Jul. 8, 2016, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392033200SEQLIST.TXT, date recorded: Nov. 21, 2018, size: 10 KB).

FIELD OF THE INVENTION

The present disclosure relates to compositions and methods for assessing responsiveness of cancers to MUC16 antagonists and efficacy of MUC16 antagonists for the treatment of cancers.

BACKGROUND

MUC16 is a large transmembrane protein that is overexpressed by the majority (80%) of human epithelial ovarian cancers but not in the epithelium of normal ovaries (Bast et al. 1981; O'Brien et al. 2001, Yin and Lloyd 2001; Rosen et al. 2005; Theriault et al. 2011), and on PC cells (50%) (Haglund 1986; Macdonald et al. 1988). While the function of MUC16 remains unclear, MUC16 may facilitate the binding of tumor cells to mesothelial cells lining the peritoneal cavity and may inhibit natural killer cell-mediated anti-tumor cytotoxic responses (Bafna et al. 2010) and it may provide a protective, lubricating barrier against particles and infectious agents at mucosal surfaces. Highly polymorphic, MUC16 is composed of three domains, a Ser-/Thr-rich N-terminal domain, a repeat domain of between eleven and more than 60 partially conserved tandem repeats of on average 156 amino acids each, and a C-terminal non-repeating domain containing a transmembrane sequence and a short cytoplasmic tail. MUC16 is heavily O-glycosylated and N-glycosylated (O'Brien et al (2002) Tumour Biol. 23:154-169; O'Brien et al (2001) Tumour Biol. 22:348-366 (2001); Fendrick et al (1997) Tumour Biol. 18:278-289; Wong et al (2003) J. Biol. Chem. 278:28619-28634; McLemore et al (2005) biol. Res. Nurs. 6:262-267).

mRNA encoding the MUC16 polypeptide expressed from the MUC16 gene is significantly, reproducibly and detectably overexpressed in certain types of human cancerous ovarian, breast and pancreatic tumors as compared to the corresponding normal human ovarian, breast and pancreatic tissues, respectively (WO 2007/001851). A variety of independent and different types of cancerous human ovarian tissue samples quantitatively analyzed for MUC16 expression show the expression level of MUC16 in the cancerous samples is variable, with a significant number of the cancerous samples showing an at least 6-fold (to as high as an about 580-fold) increase in MUC16 expression when compared to the mean level of MUC16 expression for the group of normal ovarian tissue samples analyzed. In particular, detectable and reproducible MUC16 overexpression was observed for ovarian cancer types; endometrioid adenocarcinoma, serous cystadenocarcinoma, including papillary and clear cell adenocarcinoma, as compared to normal ovarian tissue. Due to its overexpression in certain human tumors, the MUC16 polypeptide and the nucleic acid encoding that polypeptide are targets for quantitative and qualitative comparisons among various mammalian tissue samples. The unique expression profiles of MUC16 polypeptide, and the nucleic acid encoding that polypeptide, can be exploited for the diagnosis and therapeutic treatment of certain types of cancerous tumors in mammals.

CA125 (Carcinoma antigen 125 (0772P, CA-0772P, CA-125) is an extracellular shed protein encoded by the MUC16 gene (Yin et al (2002) Intl. J. of Cancer 98(5):737-740), and a serum marker used routinely to monitor patients with ovarian cancer. CA125 is a mullerian duct differentiation antigen that is overexpressed in epithelial ovarian cancer cells and secreted into the blood, although its expression is not entirely confined to ovarian cancer (Bast et al (1981) J. Clin. Invest. 68:1331-1337). Serum CA125 levels are elevated in about 80% of patients with epithelial ovarian cancer (EOC) but in less than 1% of healthy women (Bast et al. (1983) N. Engl. J. Med. 309:883-887). CA125 is a giant mucin-like glycoprotein present on the cell surface of tumor cells associated with beta-galactoside-binding, cell-surface lectins, which are components of the extracellular matrix implicated in the regulation of cell adhesion, apoptosis, cell proliferation and tumor progression (Seelenmeyer et al (2003) Journal of Cell Science 116(7): 1305-1318). High serum concentration of CA125 is typical of serous ovarian adenocarcinoma, whereas it is not elevated in mucinous ovarian cancer. CA125 is not recommended for ovarian cancer screening because normal level does not exclude tumor. However, CA125 detection is a standard tool in monitoring clinical course and disease status in patients who have histologically confirmed malignancies. Numerous studies have confirmed the usefulness of CA125 levels in monitoring the progress of patients with EOC (Bast et al (1998) Int. J. Biol. Markers 13:179-187; Verheijen et al (1999) Sem. Cancer Biol. 9:117-124; Menon et al (2000) Curr. Opin. Obstet. Gynecol. 12:39-42; Meyer et al (2000) Br. J. Cancer 82:1535-1538), and as a cancer serum marker. A rise in CA125 levels typically precedes clinical detection by about 3 months. During chemotherapy, changes in serum CA125 levels correlate with the course of the disease. CA125 is used as a surrogate marker for clinical response in trials of new drugs. On the other hand, CA125 is not useful in the initial diagnosis of EOC because of its elevation in a number of benign conditions (Bast et al (1998) Int. J. Biol. Markers 13:179-187; Meden et al (1998) Int. J. Biol. Markers 13:231-237). The CA125-specific antibody MAb-B43.13 (oregovomab, OvaRex MAb-B43.13) was in clinical trials for patients with ovarian carcinoma as an immunotherapeutic agent Mobus et al (2003) American Journal of Obstetrics and Gynecology 189(1):28-36; Ehlen et al (2005) International journal of gynecological cancer 15(6):1023-34.

Certain anti-MUC16 antibodies, including 3A5 and 11D10, have been disclosed in WO 2007/001851; and U.S. Pat. No. 7,989,595, the contents of which are incorporated by reference in their entirety. The 3A5 monoclonal antibody binds multiple sites of the MUC16 polypeptide with 433 pM affinity by OVCAR-3 Scatchard analysis. The 3A5 and 11D10 anti-MUC16 antibodies have been conjugated to auristatin drug moieties MMAE and MMAF. The conjugates inhibit in vitro tumor cell proliferation (WO 2007/001851). An 11D10 anti-MUC16 antibody was conjugated to the maytansinoid DM1 drug moiety (US 2005/0276812). Certain anti-MUC16 antibody variants have been cysteine engineered by the introduction of a cysteine amino acid unit and conjugated to DM1 (U.S. Pat. No. 7,521,541, the contents of which are incorporated by reference).

It is presently unclear why some cancer patients respond successfully to certain cancer treatments while others fail to respond. Identifying biomarkers that predict how an individual will respond to therapy will lead to more effective diagnostic and prognostic methods and individualized treatment regimens. Cancer biomarkers include those found in cells, tissues, mucosal secretions, and blood. Biomarkers detectable in biological fluids such as serum are highly desirable and preferred over those in other sample types, as serum samples are readily obtained using non-invasive methods and can be sampled longitudinally. As such, there remains a need for the identification of circulating biomarkers useful in the diagnosis, prognosis, and/or monitoring of cancer, such as ovarian cancer.

Traditionally, antibody therapy provides a uniquely effective mechanism for selecting patient populations that are good candidates for the antibody therapy, for tracking the efficacy of the antibody therapy in a patient, and for tracking disease progression. For example, antibodies against cell surface tumor antigens can be used for cancer therapies and can also be conjugated to a detectable marker to detect the tumor and track tumor growth, regression, metastasis, and target specific delivery. Accordingly, the discovery of a therapeutic antibody will often lead to a diagnostic that uses the same antibody or a similar antibody that detects the same target protein. Thus, if one of skill in the art wanted to develop a companion diagnostic for an antibody therapy, they would likely select a diagnostic test that utilized an antibody that binds to the same target as the antibody therapy.

While CA125 is a well-established circulating ovarian cancer disease biomarker, detecting circulating CA125 in patients treated with, for example, anti-MUC16 antibody treatment therapies, is problematic. One problem is that the antibody in such anti-MUC16 antibody treatment therapies can bind to CA125, thus inhibiting the ability to use CA125 as a biomarker. For example, an anti-MUC16 antibody-bound CA125 complex may be effectively cleared from the body, thereby limiting the levels of serum CA125 available to detect for diagnostic and therapeutic monitoring applications. Furthermore, CA125 is not a good candidate for a MUC16-positive cancer biomarker because, as protein fragment that is cleaved from the MUC16 protein, an anti-MUC16 antibody therapeutic that binds CA125 will compete for binding with the anti-CA125 diagnostic antibody-thereby reporting less CA125 circulating protein than actually exists. In other words, because an anti-MUC16 therapeutic antibody may compete for binding with an anti-CA125 diagnostic antibody, false negative results may occur with the diagnostic.

However, a diagnostic antibody that binds to a different target (e.g., a circulating tumor marker) than the clinical antibody is advantageous because a skilled artisan does not need to be concerned with cross-competition between differently targeted diagnostic and clinical antibodies. Because MUC16 is cleaved (i.e., CA125 is cleaved from the membrane bound portion of MUC16 and is released into circulation), CA125 antibodies (the commonly used antibodies to diagnose/monitor ovarian cancer) are not good candidates for tracking treatment efficacy, tumor progression/regression/stability. Thus, there is a need for novel methods to predict and monitor efficacy of anti-MUC16 antibody therapy when the anti-MUC16 antibody binds to the CA125 portion of the protein.

BRIEF SUMMARY OF THE INVENTION

The present disclosure describes methods of measuring or detecting the level of expression of human epididymis protein 4 (HE4) in a subject or patient having cancer for use in methods to treat or delay progression of cancer in a subject or patient with an anti-cancer therapy (e.g., a MUC16 antagonist), methods to modulate/adjust/determine/select the dosing of a subject or patient having cancer who will be/has been/is being treated with an anti-cancer therapy (e.g., a MUC16 antagonist), methods to select a subject or patient having cancer for treatment with an anti-cancer therapy (e.g., a MUC16 antagonist), methods to communicate the likelihood of response of a subject or patient to an anti-cancer therapy (e.g., a MUC16 antagonist), methods to assess the responsiveness of a subject or patient to an anti-cancer therapy (e.g., a MUC16 antagonist), methods to assess progression-free survival of a subject or patient having cancer, methods to assess tumor burden in a subject or patient having cancer, methods to predict cancer progression in a subject or patient having cancer, methods to diagnose a subject or patient having cancer, methods to diagnose a subject of patient having cancer that is responsive to treatment with an anti-cancer therapy (e.g., a MUC16 antagonist), methods to diagnose and treat a subject or patient having cancer, and methods to diagnose cancer progression in a subject or patient having cancer. The present disclosure is based, at least in part, on the discovery that serum levels of the protein HE4 can be used as a surrogate marker to monitor treatment response to cancer therapies (e.g., a MUC16 antagonist) for treating MUC16-positive cancers in subjects in need thereof. Advantageously, measuring serum levels of HE4 protein in subjects in need thereof is less invasive, less time consuming, and easier to perform than, for example, an invasive tissue biopsy.

Accordingly, certain aspects of the present disclosure relate to a method for treating or delaying progression of a MUC16-positive cancer, in a subject in need thereof, the method comprising measuring the expression level of human epididymis protein 4 (HE4) in a sample obtained from the subject at a first time point, wherein the first time point is prior to administering to the subject a MUC16 antagonist; administering to the subject a therapeutically effective amount of the MUC16 antagonist; and measuring the level of expression of HE4 in a sample obtained from the subject at a second time point, wherein the second time point is after administration of the MUC16 antagonist, and wherein the subject is administered one or more additional therapeutically effective amounts of the MUC16 antagonist if the level of expression of HE4 at the second time point is at least 25% lower than the level of expression of HE4 at the first time point. In some embodiments, the subject is administered one or more additional therapeutically effective amounts of the MUC16 antagonist if the level of expression of HE4 at the second time point is at least 40% lower than the level of expression of HE4 at the first time point. In some embodiments, the subject has never received the MUC16 antagonist. In some embodiments, the subject is undergoing treatment with a MUC16 antagonist.

Other aspects of the present disclosure relate to a method for treating or delaying progression of a MUC16-positive cancer in a subject in need thereof, the method comprising measuring the expression level of human epididymis protein 4 (HE4) in a sample obtained from the subject at a first time point, wherein the first time point is prior to administering to the subject a MUC16 antagonist; administering to the subject a therapeutically effective amount of the MUC16 antagonist; measuring the level of expression of HE4 in a sample obtained from the subject at a second time point, wherein the second time point is after administration of the MUC16 antagonist; and administering to the subject one or more additional therapeutically effective amounts of the MUC16 antagonist when the level of expression of HE4 at the second time point is at least 25% lower than the level of expression of HE4 at the first time point. In some embodiments, the subject is administered one or more additional therapeutically effective amounts of the MUC16 antagonist when the level of expression of HE4 at the second time point is at least 40% lower than the level of expression of HE4 at the first time point. In some embodiments, the subject has never received the MUC16 antagonist. In some embodiments, the subject is undergoing treatment with a MUC16 antagonist.

Other aspects of the present disclosure relate to a method of modulating anti-cancer therapy in a subject having a MUC16-positive cancer, the method comprising measuring the expression level of human epididymis protein 4 (HE4) in a sample obtained from the subject at a first time point, wherein the first time point is prior to administering to the subject a MUC16 antagonist; administering to the subject a therapeutically effective amount of the MUC16 antagonist; and measuring the level of expression of HE4 in a sample obtained from the subject at a second time point, wherein the second time point is after administration of the MUC16 antagonist; and modulating the amount of the MUC16 antagonist administered to the subject based on changes in the level of expression of HE4 between the first time point and the second time point. In some embodiments, modulating the amount of MUC16 antagonist administered to the subject comprises maintaining the same level or increasing the level of MUC16 antagonist administered to the subject. In some embodiments, increasing the level of MUC16 antagonist administered to the subject comprises increasing the dose or frequency of the MUC16 antagonist administered to the subject. In some embodiments, modulating the amount of MUC16 antagonist administered to the subject comprises decreasing the level of MUC16 antagonist administered to the subject. In some embodiments, decreasing the level of MUC16 antagonist administered to the subject comprises decreasing the dose or frequency of the MUC16 antagonist.

Other aspects of the present disclosure relate to a method selecting a subject having a MUC16-positive cancer for treatment with a MUC16 antagonist, the method comprising measuring the expression level of human epididymis protein 4 (HE4) in a sample obtained from the subject at a first time point, wherein the first time point is prior to administering to the subject the MUC16 antagonist; measuring the level of expression of HE4 in a sample obtained from the subject at a second time point, wherein the second time point is after administration of the MUC16 antagonist; and selecting the subject for treatment with one or more additional therapeutically effective amounts of the MUC16 antagonist if the level of expression of HE4 at the second time point is at least 25% lower than the level of expression of HE4 at the first time point. In some embodiments, the subject is selected for treatment with one or more additional therapeutically effective amounts of the MUC16 antagonist if the level of expression of HE4 at the second time point is at least 40% lower than the level of expression of HE4 at the first time point. In some embodiments, selecting the subject for treatment comprises selecting the subject for inclusion in a clinical trial.

Other aspects of the present disclosure relate to a method of communicating the likelihood of response of a subject having a MUC16-positive cancer to a MUC16 antagonist, the method comprising measuring the expression level of human epididymis protein 4 (HE4) in a sample obtained from the subject at a first time point, wherein the first time point is prior to administering to the subject the MUC16 antagonist; measuring the level of expression of HE4 in a sample obtained from the subject at a second time point, wherein the second time point is after administration of the MUC16 antagonist; and communicating to a treatment provider that the level of expression of HE4 at the second time point is at least 25% lower than the level of expression of HE4 at the first time point, wherein the treatment provider administers one or more additional therapeutically effective amounts of the MUC16 antagonist to the subject or selects the subject for treatment with one or more additional therapeutically effective amounts of the MUC16 antagonist based on the communication. In some embodiments, the method comprises communicating to a treatment provider that the level of expression of HE4 at the second time point is at least 40% lower than the level of expression of HE4 at the first time point.

Other aspects of the present disclosure relate to a method for treating or delaying progression of a MUC16-positive cancer in a subject in need thereof, the method comprising administering to the subject one or more therapeutically effective amounts of a MUC16 antagonist, wherein a sample obtained from the subject after administration of an initial therapeutically effective amount of a MUC16 antagonist was determined to have an epididymis protein 4 (HE4) expression level that is at least 25% lower than the level of expression of HE4 in a sample obtained from the subject prior to administration of the initial therapeutically effective amount of MUC16 antagonist, wherein the initial therapeutically effective amount of the MUC16 antagonist was administered prior to administration of the one or more therapeutically effective amounts of the MUC16 antagonist. In some embodiments, the method comprises administering to the subject one or more therapeutically effective amounts of a MUC16 antagonist, wherein a sample obtained from the subject after administration of an initial therapeutically effective amount of a MUC16 antagonist was determined to have an epididymis protein 4 (HE4) expression level that is at least 40% lower than the level of expression of HE4 in a sample obtained from the subject prior to administration of the initial therapeutically effective amount of MUC16 antagonist, wherein the initial therapeutically effective amount of the MUC16 antagonist was administered prior to administration of the one or more therapeutically effective amounts of the MUC16 antagonist.

Other aspects of the present disclosure relate to a method for treating or delaying progression of a MUC16-positive cancer in a subject in need thereof, the method comprising administering to the subject one or more therapeutically effective amounts of a MUC16 antagonist, wherein the subject was selected for treatment based on a determination that a sample obtained from the subject after administration of an initial therapeutically effective amount of a MUC16 antagonist has an epididymis protein 4 (HE4) expression level that is at least 25% lower than the level of expression of HE4 in a sample obtained from the subject prior to administration of the initial therapeutically effective amount of MUC16 antagonist, wherein the initial therapeutically effective amount of the MUC16 antagonist was administered prior to administration of the one or more therapeutically effective amounts of the MUC16 antagonist. In some embodiments, the subject was selected for treatment based on a determination that a sample obtained from the subject after administration of an initial therapeutically effective amount of a MUC16 antagonist has an epididymis protein 4 (HE4) expression level that is at least 40% lower than the level of expression of HE4 in a sample obtained from the subject prior to administration of the initial therapeutically effective amount of MUC16 antagonist.

Other aspects of the present disclosure relate to a method for treating or delaying progression of a MUC16-positive cancer in a subject in need thereof, the method comprising administering to the subject one or more therapeutically effective amounts of a MUC16 antagonist, wherein treatment is based upon the subject having a sample that expresses epididymis protein 4 (HE4) at a level that is at least 25% lower after administration of an initial therapeutically effective amount of a MUC16 antagonist than the level of expression of HE4 in a sample obtained from the subject prior to administration of the initial therapeutically effective amount of MUC16 antagonist, wherein the initial therapeutically effective amount of the MUC16 antagonist was administered prior to administration of the one or more therapeutically effective amounts of the MUC16 antagonist. In some embodiments, treatment is based upon the subject having a sample that expresses epididymis protein 4 (HE4) at a level that is at least 40% lower after administration of an initial therapeutically effective amount of a MUC16 antagonist than the level of expression of HE4 in a sample obtained from the subject prior to administration of the initial therapeutically effective amount of MUC16 antagonist.

Other aspects of the present disclosure relate to a method for treating or delaying progression of a MUC16-positive cancer in a subject in need thereof provided that the subject has been found to have a sample that expresses epididymis protein 4 (HE4) at a level that is at least 25% lower after administration of an initial therapeutically effective amount of a MUC16 antagonist than the level of expression of HE4 in a sample obtained from the subject prior to administration of the initial therapeutically effective amount of MUC16 antagonist, wherein the initial therapeutically effective amount of the MUC16 antagonist was administered prior to administration of the one or more therapeutically effective amounts of the MUC16 antagonist, the method comprising administering to the subject one or more therapeutically effective amounts of a MUC16 antagonist. In some embodiments, the subject has been found to have a sample that expresses epididymis protein 4 (HE4) at a level that is at least 40% lower after administration of an initial therapeutically effective amount of a MUC16 antagonist than the level of expression of HE4 in a sample obtained from the subject prior to administration of the initial therapeutically effective amount of MUC16 antagonist.

Other aspects of the present disclosure relate to a method for assessing responsiveness of a subject having a MUC16-positive cancer to a MUC16 antagonist treatment, the method comprising measuring the expression level of human epididymis protein 4 (HE4) in a sample obtained from the subject at a first time point, wherein the first time point is prior to administering to the subject the MUC16 antagonist; and measuring the level of expression of HE4 in a sample obtained from the subject at a second time point, wherein the second time point is after administration of the MUC16 antagonist, wherein a decrease of at least 25% in the level of expression of HE4 from the first time point to the second time point indicates the subject is responsive to the MUC16 antagonist. In some embodiments, a decrease of at least 40% in the level of expression of HE4 from the first time point to the second time point indicates the subject is responsive to the MUC16 antagonist. In some embodiments, responsiveness of the subject comprises treatment efficacy. In some embodiments, responsiveness of the subject comprises reduced tumor volume. In some embodiments, responsiveness of the subject comprises serologic responsiveness. In some embodiments, responsiveness of the subject comprises a higher RECIST score. In some embodiments, responsiveness of the subject comprises a lower sum of the longest diameter (SLD) response. In some embodiments, the subject has never received the MUC16 antagonist. In some embodiments, the subject is undergoing treatment with a MUC16 antagonist. In some embodiments, the method further comprises administering to the subject one or more additional therapeutically effective amounts of the MUC16 antagonist.

Other aspects of the present disclosure relate to a method for assessing responsiveness of a subject having a MUC16-positive cancer to a MUC16 antagonist treatment, the method comprising measuring the expression level of human epididymis protein 4 (HE4) in a sample obtained from the subject at a first time point, wherein the first time point is prior to administering to the subject the MUC16 antagonist; administering to the subject a therapeutically effective amount of the MUC16 antagonist; and measuring the level of expression of HE4 in a sample obtained from the subject at a second time point, wherein the second time point is after administration of the MUC16 antagonist, wherein a decrease of at least 25% in the level of expression of HE4 from the first time point to the second time point indicates the subject is responsive to the MUC16 antagonist. In some embodiments, a decrease of at least 40% in the level of expression of HE4 from the first time point to the second time point indicates the subject is responsive to the MUC16 antagonist. In some embodiments, responsiveness of the subject comprises treatment efficacy. In some embodiments, responsiveness of the subject comprises reduced tumor volume. In some embodiments, responsiveness of the subject comprises serologic responsiveness. In some embodiments, responsiveness of the subject comprises a higher RECIST score. In some embodiments, responsiveness of the subject comprises a lower sum of the longest diameter (SLD) response. In some embodiments, the subject has never received the MUC16 antagonist. In some embodiments, the subject is undergoing treatment with a MUC16 antagonist. In some embodiments, the method further comprises administering to the subject one or more additional therapeutically effective amounts of the MUC16 antagonist.

In some embodiments that may be combined with any of the preceding embodiments, the methods further comprise maintaining the same level or increasing the level of MUC16 antagonist administered to the subject based on the level of expression of HE4 after administration of the MUC16 antagonist. In some embodiments, increasing the level of MUC16 antagonist administered to the subject comprises increasing the dose or frequency of the MUC16 antagonist administered to the subject. In some embodiments that may be combined with any of the preceding embodiments, the methods further comprise decreasing the level of MUC16 antagonist administered to the subject based on the level of expression of HE4 after administration of the MUC16 antagonist. In some embodiments, decreasing the level of MUC16 antagonist administered to the subject comprises decreasing the dose or frequency of the MUC16 antagonist. In some embodiments that may be combined with any of the preceding embodiments, the methods further comprise administering a second treatment therapy to the subject. In some embodiments, the second treatment therapy is a maintenance therapy, a chemotherapy, an antibody therapy, or bevacizumab antibody therapy.

Other aspects of the present disclosure relate to a method for assessing progression-free survival in a subject having a MUC16-positive cancer, the method comprising measuring the expression level of human epididymis protein 4 (HE4) in a sample obtained from the subject at a first time point, wherein the first time point is prior to administering to the subject a MUC16 antagonist; administering to the subject a therapeutically effective amount of the MUC16 antagonist; and measuring the level of expression of HE4 in a sample obtained from the subject at a second time point, wherein the second time point is after administration of the MUC16 antagonist, wherein a decrease of at least 25% in the level of expression of HE4 from the first time point to the second time point indicates the MUC16 antagonist increases progression-free survival. In some embodiments, a decrease of at least 40% in the level of expression of HE4 from the first time point to the second time point indicates the MUC16 antagonist increases progression-free survival.

Other aspects of the present disclosure relate to a method of predicting cancer progression in a subject having a MUC16-positive cancer, the method comprising measuring the expression level of human epididymis protein 4 (HE4) in a sample obtained from the subject at a first time point, wherein the first time point is prior to administering to the subject a MUC16 antagonist; administering to the subject a therapeutically effective amount of the MUC16 antagonist; and measuring the level of expression of HE4 in a sample obtained from the subject at a second time point, wherein the second time point is after administration of the MUC16 antagonist, wherein a decrease of less than 25% in the level of expression of HE4 from the first time point to the second time point indicates the subject has a cancer that is likely to progress. In some embodiments, a decrease of less than 20% in the level of expression of HE4 from the first time point to the second time point indicates the subject has a cancer that is likely to progress. In some embodiments, a decrease of less than 15% in the level of expression of HE4 from the first time point to the second time point indicates the subject has a cancer that is likely to progress. In some embodiments, a decrease of less than 10% in the level of expression of HE4 from the first time point to the second time point indicates the subject has a cancer that is likely to progress. In some embodiments, a decrease of less than 5% in the level of expression of HE4 from the first time point to the second time point indicates the subject has a cancer that is likely to progress. In some embodiments, the present disclosure relates to a method of predicting cancer progression in a subject having a MUC16-positive cancer, the method comprising measuring the expression level of human epididymis protein 4 (HE4) in a sample obtained from the subject at a first time point, wherein the first time point is prior to administering to the subject a MUC16 antagonist; administering to the subject a therapeutically effective amount of the MUC16 antagonist; and measuring the level of expression of HE4 in a sample obtained from the subject at a second time point, wherein the second time point is after administration of the MUC16 antagonist, wherein no difference in the level of expression of HE4 from the first time point to the second time point indicates the subject has a cancer that is likely to progress. In some embodiments, the present disclosure relates to a method of predicting cancer progression in a subject having a MUC16-positive cancer, the method comprising measuring the expression level of human epididymis protein 4 (HE4) in a sample obtained from the subject at a first time point, wherein the first time point is prior to administering to the subject a MUC16 antagonist; administering to the subject a therapeutically effective amount of the MUC16 antagonist; and measuring the level of expression of HE4 in a sample obtained from the subject at a second time point, wherein the second time point is after administration of the MUC16 antagonist, wherein an increase in the level of expression of HE4 from the first time point to the second time point indicates the subject has a cancer that is likely to progress. In some embodiments, an increase of greater than 1% in the level of expression of HE4 from the first time point to the second time point indicates the subject has a cancer that is likely to progress. In some embodiments, an increase of greater than 5% in the level of expression of HE4 from the first time point to the second time point indicates the subject has a cancer that is likely to progress. In some embodiments, an increase of greater than 10% in the level of expression of HE4 from the first time point to the second time point indicates the subject has a cancer that is likely to progress. In some embodiments, an increase of greater than 25% in the level of expression of HE4 from the first time point to the second time point indicates the subject has a cancer that is likely to progress. In some embodiments, an increase of greater than 50% in the level of expression of HE4 from the first time point to the second time point indicates the subject has a cancer that is likely to progress.

In some embodiments that may be combined with any of the preceding embodiments, the first time point occurs at least 3 days before, at least 1 day before, at least 12 hours before, at least 4 hours before, at least 1 hour before, or less than 1 hour before administering the therapeutically effective amount of the MUC16 antagonist. In some embodiments that may be combined with any of the preceding embodiments, the first time point occurs immediately before administering therapeutically effective amount of the MUC16 antagonist. In some embodiments that may be combined with any of the preceding embodiments the second time point occurs at least 1 hour after, at least 4 hours after, at least 12 hours after, at least 1 day after, at least 3 days after, at least 5 days after, at least 1 week after, at least 2 weeks after, or at least 3 weeks after administering the therapeutically effective amount of the MUC16 antagonist.

Other aspects of the present disclosure relate to a method for assessing tumor burden in a subject having a MUC16-positive cancer, the method comprising (a) measuring the expression level of human epididymis protein 4 (HE4) in a sample obtained from the subject at a first time point; and (b) measuring the level of expression of HE4 in a sample obtained from the subject at a second time point, wherein an increase in the level of expression of HE4 from the first time point to the second time point correlates with an increased tumor burden in the subject. In some embodiments, an increase of greater than 1% in the level of expression of HE4 from the first time point to the second time point correlates with an increased tumor burden in the subject. In some embodiments, an increase of greater than 5% in the level of expression of HE4 from the first time point to the second time point correlates with an increased tumor burden in the subject. In some embodiments, an increase of greater than 10% in the level of expression of HE4 from the first time point to the second time point correlates with an increased tumor burden in the subject. In some embodiments, an increase of greater than 25% in the level of expression of HE4 from the first time point to the second time point correlates with an increased tumor burden in the subject. In some embodiments, an increase of greater than 50% in the level of expression of HE4 from the first time point to the second time point correlates with an increased tumor burden in the subject. In some embodiments, the method further comprises administering to the subject a therapeutically effective amount of a MUC16 antagonist after step (a) and prior to step (b). In some embodiments, increased tumor burden indicates that subject is unresponsive to the MUC16 antagonist. In some embodiments, the correlation between increased HE4 expression and increased tumor burden is directly proportional. In some embodiments, increased tumor burden in the subject comprises an increase in tumor size. In some embodiments, increased tumor burden is predictive of cancer progression in the subject.

In some embodiments that may be combined with any of the preceding embodiments, the sample is a blood sample. In some embodiments, the blood sample is a serum sample. In some embodiments that may be combined with any of the preceding embodiments, the sample is a cell sample. In some embodiments that may be combined with any of the preceding embodiments, the subject is a human. In some embodiments that may be combined with any of the preceding embodiments, the level of expression of HE4 is circulating level of HE4 protein. In some embodiments that may be combined with any of the preceding embodiments, the level of expression of HE4 is protein the level of expression of HE4. In some embodiments, the level of HE4 protein is measured by an immunoassay, Western blotting, peptide microarray, immunohistochemistry, flow cytometry, or mass spectrometry. In some embodiments that may be combined with any of the preceding embodiments, the level of expression of HE4 is RNA transcript level of HE4. In some embodiments, the RNA transcript level of HE4 is measured by RT-PCR. In some embodiments that may be combined with any of the preceding embodiments, the MUC16-positive cancer is selected from the group consisting of ovarian cancer, endometrial cancer, triple-negative breast cancer, pancreatic cancer, and non-small cell lung cancer. In some embodiments that may be combined with any of the preceding embodiments, the MUC16-positive cancer is unresectable pancreatic cancer. In some embodiments that may be combined with any of the preceding embodiments, the MUC16-positive cancer is an ovarian cancer selected from the group consisting of primary peritoneal carcinoma, epithelial ovarian carcinoma, metastatic ovarian cancer, fallopian tube carcinoma, and platinum-resistant ovarian cancer. In some embodiments that may be combined with any of the preceding embodiments, the MUC16 antagonist is selected from the group consisting of an anti-MUC16 antibody, a MUC16 inhibitor, a protein, a peptide, a fusion protein, and an immunoadhesin. In some embodiments that may be combined with any of the preceding embodiments, the MUC16 antagonist is an anti-MUC16 antibody. In some embodiments, the anti-MUC16 antibody comprises a heavy chain variable domain and a light chain variable domain, wherein the heavy chain variable domain, or the light chain variable domain, or both comprise the following HVRs: HVR-H1 comprising the amino acid sequence of SEQ ID NO: 4, HVR-H2 comprising the amino acid sequence of SEQ ID NO: 5, HVR-H3 comprising the amino acid sequence of SEQ ID NO: 6, HVR-L1 comprising the amino acid sequence of SEQ ID NO: 1, HVR-L2 comprising the amino acid sequence of SEQ ID NO: 2, and HVR-L3 comprising the amino acid sequence of SEQ ID NO: 3. In some embodiments, the anti-MUC16 antibody comprises a heavy chain variable region comprising the amino acid sequence of SEQ ID NO: 8, or a light chain variable region comprising the amino acid sequence of SEQ ID NO: 7, or both. In some embodiments, the anti-MUC16 antibody is an antibody fragment selected from a Fab, Fab'-SH, Fv, scFv, or (Fab')$_2$ fragment. In some embodiments, one or more amino acid residues are replaced with one or more free cysteine amino acids having a thiol reactivity in the range of 0.6 to 1.0. In some embodiments, the one or more free cysteine amino acid residues are located in a light chain. In some embodiments, the one or more free cysteine amino acid residues are located in a heavy chain. In some embodiments, the antibody comprises a cysteine at one or more positions selected from 15, 43, 110, 144, 149, 168 and 205 of the light chain according to Kabat numbering convention and 41, 88, 115, 118, 120, 171, 172, 282, 375, and 400 of the heavy chain according to EU numbering convention. In some embodiments a cysteine is at position 205 of the light chain. In some embodiments a cysteine is at position 118 of the heavy chain. In some embodiments, the anti-MUC16 antibody is a bispecific antibody. In some embodiments, the anti-MUC16 antibody is covalently attached to a cytotoxic agent. In some embodiments, the cytotoxic agent is selected from the group consisting of a toxin, a chemotherapeutic agent, a drug moiety, an antibiotic, a radioactive isotope, and a nucleolytic enzyme. In some embodiments, the anti-MUC16 antibody is covalently attached to the cytotoxic agent through a linker. In some embodiments, the linker comprises one or more of 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl) cyclohexane-1 carboxylate (SMCC), N-Succinimidyl (4-iodo-acetyl) aminobenzoate (SIAB), and 6-maleimidocaproyl-valine-citrulline-p-aminobenzyloxycarbonyl (MC-vc-PAB). In some embodiments, the linker is attached to the antibody through a thiol group on the antibody. In some embodiments, the cytotoxic agent is a drug moiety selected from the group consisting of an auristatin, a dolastatin, and a maytansinoid. In some embodiments, the cytotoxic agent is a maytansinoid selected from the group consisting of N(2')-deacetyl-N(2')-(3-mercapto-1-oxopropyl)-maytansine (DM1), N(2')-deacetyl-N2-(4-mercapto-1-oxopentyl)-maytansine (DM3), and N(2')-deacetyl-N2-(4-mercapto-4-methyl-1-oxopentyl)-maytansine (DM4). In some embodiments, the cytotoxic agent is monomethyl auristatin E (MMAE). In some embodiments, the cytotoxic agent is monomethyl auristatin F (MMAF). In some embodiments, the cytotoxic agent is selected from the group consisting of selected from ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Sapaonaria officinalis* inhibitor, glucocorticoid, auromycin, yttrium, bismuth, combrestatin, duocarmycins, cc1065, and a cisplatin.

Other aspects of the present disclosure relate to a method for treating or delaying progression of ovarian cancer, endometrial cancer, triple-negative breast cancer, pancreatic cancer, or non-small cell lung cancer in a subject in need thereof, the method comprising measuring human epididymis protein 4 (HE4) expression level in a sample obtained from the subject at a first time point, wherein the first time point is prior to administering to the subject an anti-cancer therapy; administering to the subject a therapeutically effective amount of the anti-cancer therapy; measuring HE4 expression level in a sample obtained from the subject at a second time point, wherein the second time point is after administration of the anti-cancer therapy, and wherein the subject is administered one or more additional therapeutically effective amounts of the anti-cancer therapy if the HE4 expression level at the second time point is at least 25% lower than the HE4 expression level at the first time point. In some embodiments, the subject is administered one or more additional therapeutically effective amounts of the anti-cancer therapy if the HE4 expression level at the second time point is at least 40% lower than the HE4 expression level at the first time point. In some embodiments, the subject has never received the anti-cancer therapy. In some embodiments, the subject is undergoing treatment with the anti-cancer therapy.

Other aspects of the present disclosure relate to a method for treating or delaying progression of ovarian cancer, endometrial cancer, triple-negative breast cancer, pancreatic cancer, or non-small cell lung cancer in a subject in need thereof, the method comprising measuring human epididymis protein 4 (HE4) expression level in a sample obtained from the subject at a first time point, wherein the first time point is prior to administering to the subject an anti-cancer therapy; administering to the subject a therapeutically effective amount of the anti-cancer therapy; measuring HE4 expression level in a sample obtained from the subject at a second time point, wherein the second time point is after administration of the anti-cancer therapy; and administering to the subject one or more additional therapeutically effective amounts of the anti-cancer therapy when the HE4 expression level at the second time point is at least 25% lower than the HE4 expression level at the first time point. In some embodiments, the subject is administered one or more additional therapeutically effective amounts of the anti-cancer therapy when the HE4 expression level at the second time point is at least 40% lower than the HE4 expression level at the first time point. In some embodiments, the subject has never received the anti-cancer therapy. In some embodiments, the subject is undergoing treatment with the anti-cancer therapy.

Other aspects of the present disclosure relate to a method of modulating anti-cancer therapy in a subject having ovarian cancer, endometrial cancer, triple-negative breast cancer, pancreatic cancer, or non-small cell lung cancer, the method comprising measuring human epididymis protein 4 (HE4) expression level in a sample obtained from the subject at a first time point, wherein the first time point is prior to administering to the subject an anti-cancer therapy; administering to the subject a therapeutically effective amount of the anti-cancer therapy; measuring HE4 expression level in a sample obtained from the subject at a second time point, wherein the second time point is after administration of the anti-cancer therapy; and modulating the amount of the anti-cancer therapy administered to the subject based on changes in the HE4 expression level between the first time point and the second time point. In some embodiments, modulating the amount of anti-cancer therapy administered to the subject comprises maintaining the same level or increasing the level of anti-cancer therapy administered to the subject. In some embodiments, increasing the level of anti-cancer therapy administered to the subject comprises increasing the dose or frequency of the anti-cancer therapy administered to the subject. In some embodiments, modulating the amount of anti-cancer therapy administered to the subject comprises decreasing the level of anti-cancer therapy administered to the subject. In some embodiments, decreasing the level of anti-cancer therapy administered to the subject comprises decreasing the dose or frequency of the anti-cancer therapy.

Other aspects of the present disclosure relate to a method for assessing responsiveness of a subject having ovarian cancer, endometrial cancer, triple-negative breast cancer, pancreatic cancer, or non-small cell lung cancer to an anti-cancer therapy, the method comprising measuring human epididymis protein 4 (HE4) expression level in a sample obtained from the subject at a first time point, wherein the first time point is prior to administering to the subject the anti-cancer therapy; and measuring HE4 expression level in a sample obtained from the subject at a second time point, wherein the second time point is after administration of the anti-cancer therapy, wherein a decrease of at least 25% in the HE4 expression level from the first time point to the second time point indicates the subject is responsive to the anti-cancer therapy. In some embodiments, a decrease of at least 40% in the HE4 expression level from the first time point to the second time point indicates the subject is responsive to the anti-cancer therapy. In some embodiments, the subject has never received the anti-cancer therapy. In some embodiments, the subject is undergoing treatment with the anti-cancer therapy.

Other aspects of the present disclosure relate to a method for assessing responsiveness of a subject having ovarian cancer, endometrial cancer, triple-negative breast cancer, pancreatic cancer, or non-small cell lung cancer to an anti-cancer therapy, the method comprising measuring human epididymis protein 4 (HE4) expression level in a sample obtained from the subject at a first time point, wherein the first time point is prior to administering to the subject the anti-cancer therapy; administering to the subject a therapeutically effective amount of the anti-cancer therapy; and measuring HE4 expression level in a sample obtained from the subject at a second time point, wherein the second time point is after administration of the anti-cancer therapy, wherein a decrease of at least 25% in the HE4 expression level from the first time point to the second time point indicates the subject is responsive to the anti-cancer therapy. In some embodiments, a decrease of at least 40% in the HE4 expression level from the first time point to the second time point indicates the subject is responsive to the anti-cancer therapy. In some embodiments, responsiveness comprises treatment efficacy. In some embodiments, responsiveness comprises reduced tumor volume. In some embodiments, responsiveness comprises serologic responsiveness. In some embodiments, responsiveness comprises a higher RECIST response. In some embodiments, responsiveness of the subject comprises a lower sum of the longest diameter (SLD) response. In some embodiments, the subject has never received the anti-cancer therapy. In some embodiments, the subject is undergoing treatment with the anti-cancer therapy.

In some embodiments that may be combined with any of the preceding embodiments, the methods further comprise maintaining the same level or increasing the level of MUC16 antagonist administered to the subject based on the level of expression of HE4 after administration of the MUC16 antagonist. In some embodiments, increasing the level of MUC16 antagonist administered to the subject comprises increasing the dose or frequency of the MUC16 antagonist administered to the subject. In some embodiments that may be combined with any of the preceding embodiments, the methods further comprise decreasing the level of MUC16 antagonist administered to the subject based on the level of expression of HE4 after administration of the MUC16 antagonist. In some embodiments, decreasing the level of MUC16 antagonist administered to the subject comprises decreasing the dose or frequency of the MUC16 antagonist. In some embodiments that may be combined with any of the preceding embodiments, the methods further comprise administering a second treatment therapy to the subject. In some embodiments, the second treatment therapy is a maintenance therapy, a chemotherapy, an antibody therapy, or bevacizumab antibody therapy.

Other aspects of the present disclosure relate to a method for assessing progression-free survival in a subject having ovarian cancer, endometrial cancer, triple-negative breast cancer, pancreatic cancer, or non-small cell lung cancer, the method comprising measuring human epididymis protein 4 (HE4) expression level in a sample obtained from the subject at a first time point, wherein the first time point is prior to administering to the subject an anti-cancer therapy; administering to the subject a therapeutically effective amount of the anti-cancer therapy; and measuring HE4 expression level in a sample obtained from the subject at a second time point, wherein the second time point is after administration of the anti-cancer therapy, wherein a decrease of at least 25% in the HE4 expression level from the first time point to the second time point indicates the anti-cancer therapy increases progression-free survival. In some embodiments, a decrease of at least 40% in the HE4 expression level from the first time point to the second time point indicates the anti-cancer therapy increases progression-free survival.

Other aspects of the present disclosure relate to a method of predicting cancer progression in a subject having a ovarian cancer, endometrial cancer, triple-negative breast cancer, pancreatic cancer, or non-small cell lung cancer, the method comprising measuring human epididymis protein 4 (HE4) expression level in a sample obtained from the subject at a first time point, wherein the first time point is prior to administering to the subject an anti-cancer therapy; administering to the subject a therapeutically effective amount of the anti-cancer therapy; and measuring HE4 expression level in a sample obtained from the subject at a second time point, wherein the second time point is after administration of the anti-cancer therapy, wherein a decrease of less than 25% in the HE4 expression level from the first time point to the second time point indicates the subject has a cancer that is likely to progress. In some embodiments, a decrease of less than 20% in the HE4 expression level from the first time point to the second time point indicates the subject has a cancer that is likely to progress. In some embodiments, a decrease of less than 15% in the HE4 expression level from the first time point to the second time point indicates the subject has a cancer that is likely to progress. In some embodiments, a decrease of less than 10% in the HE4 expression level from the first time point to the second time point indicates the subject has a cancer that is likely to progress. In some embodiments, a decrease of less than 5% in the HE4 expression level from the first time point to the second time point indicates the subject has a cancer that is likely to progress. In some embodiments, the present disclosure relates to a method of predicting cancer progression in a subject having a ovarian cancer, endometrial cancer, triple-negative breast cancer, pancreatic cancer, or non-small cell lung cancer, the method comprising measuring human epididymis protein 4 (HE4) expression level in a sample obtained from the subject at a first time point, wherein the first time point is prior to administering to the subject an anti-cancer therapy; administering to the subject a therapeutically effective amount of the anti-cancer therapy; and measuring HE4 expression level in a sample obtained from the subject at a second time point, wherein the second time point is after administration of the anti-cancer therapy, wherein no difference in the HE4 expression level from the first time point to the second time point indicates the subject has a cancer that is likely to progress. In some embodiments, the present disclosure relates to a method of predicting cancer progression in a subject having a ovarian cancer, endometrial cancer, triple-negative breast cancer, pancreatic cancer, or non-small cell lung cancer, the method comprising measuring human epididymis protein 4 (HE4) expression level in a sample obtained from the subject at a first time point, wherein the first time point is prior to administering to the subject an anti-cancer therapy; administering to the subject a therapeutically effective amount of the anti-cancer therapy; and measuring HE4 expression level in a sample obtained from the subject at a second time point, wherein the second time point is after administration of the anti-cancer therapy, wherein an increase in the HE4 expression level from the first time point to the second time point indicates the subject has a cancer that is likely to progress. In some embodiments, an increase of greater than 5% in the HE4 expression level from the first time point to the second time point indicates the subject has a cancer that is likely to progress. In some embodiments, an increase of greater than 15% in the HE4 expression level from the first time point to the second time point indicates the subject has a cancer that is likely to progress. In some embodiments, an increase of greater than 25% in the HE4 expression level from the first time point to the second time point indicates the subject has a cancer that is likely to progress. In some embodiments, an increase of greater than 50% in the HE4 expression level from the first time point to the second time point indicates the subject has a cancer that is likely to progress.

In some embodiments that may be combined with any of the preceding embodiments, the cancer is ovarian cancer. In some embodiments, the ovarian cancer is an ovarian cancer selected from the group consisting of primary peritoneal carcinoma, epithelial ovarian carcinoma, metastatic ovarian cancer, fallopian tube carcinoma, and platinum-resistant ovarian cancer. In some embodiments that may be combined with any of the preceding embodiments, the cancer is a MUC16-positive cancer. In some embodiments, the MUC16-positive cancer is unresectable pancreatic cancer. In some embodiments that may be combined with any of the preceding embodiments, the anti-cancer therapy is selected from the group consisting of a chemotherapeutic or growth inhibitory agent, a targeted therapeutic agent, a T cell expressing a chimeric antigen receptor, an antibody or antigen-binding fragment thereof, an immunoconjugate, an angiogenesis inhibitor, an antineoplastic agent, a cancer vaccine, an adjuvant, and combinations thereof. In some embodiments that may be combined with any of the preceding embodiments, the anti-cancer therapy is an immunoconjugate. In some embodiments that may be combined with any of the preceding embodiments, the anti-cancer therapy is a NaPi2b antagonist therapy. In some embodiments, the NaPi2b antagonist is selected from the group consisting of an anti-NaPi2b antibody, a NaPi2b inhibitor, a protein, a peptide, a fusion protein, and an immunoadhesin. In some embodiments, the NaPi2b antagonist is an anti-NaPi2b antibody. In some embodiments that may be combined with any of the preceding embodiments the anticancer therapy is a MUC16 antagonist therapy. In some embodiments that may be combined with any of the preceding embodiments, the MUC16 antagonist is selected from the group consisting of an anti-MUC16 antibody, a MUC16 inhibitor, a protein, a peptide, a fusion protein, and an immunoadhesin. In some embodiments that may be combined with any of the preceding embodiments, the MUC16 antagonist is an anti-MUC16 antibody. In some embodiments, the anti-MUC16 antibody comprises a heavy chain variable domain and a light chain variable domain, wherein the heavy chain variable domain, or the light chain variable domain, or both comprise the following HVRs: HVR-H1 comprising the amino acid sequence of SEQ ID NO: 4, HVR-H2 comprising the amino acid sequence of SEQ ID NO: 5, HVR-H3 comprising the amino acid sequence of SEQ ID NO: 6, HVR-L1 comprising the amino acid sequence of SEQ ID NO: 1, HVR-L2 comprising the amino acid sequence of SEQ ID NO: 2, and HVR-L3 comprising the amino acid sequence of SEQ ID NO: 3. In some embodiments, the anti-MUC16 antibody comprises a heavy chain variable region comprising the amino acid sequence of SEQ ID NO: 8, or a light chain variable region comprising the amino acid sequence of SEQ ID NO: 7, or both. In some embodiments, the anti-MUC16 antibody or the anti-NaPi2b antibody is an antibody fragment selected from a Fab, Fab'-SH, Fv, scFv, or (Fab')$_2$ fragment. In some embodiments, one or more amino acid residues are replaced with one or more free cysteine amino acids having a thiol reactivity in the range of 0.6 to 1.0. In some embodiments, the one or more free cysteine amino acid residues are located in a light chain. In some embodiments, the one or more free cysteine amino acid residues are located in a heavy chain. In some embodiments, the antibody comprises a cysteine at one or more positions selected from 15, 43, 110, 144, 149, 168 and 205 of the light chain according to Kabat numbering convention and 41, 88, 115, 118, 120, 171, 172, 282, 375, and 400 of the heavy chain according to EU numbering convention. In some embodiments a cysteine is at position 205 of the light chain. In some embodiments a cysteine is at position 118 of the heavy chain. In some embodiments, the anti-MUC16 antibody or the anti-NaPi2b antibody is a bispecific antibody. In some embodiments, the anti-MUC16 antibody or the anti-NaPi2b antibody is covalently attached to a cytotoxic agent. In some embodiments, the cytotoxic agent is selected from the group consisting of a toxin, a chemotherapeutic agent, a drug moiety, an antibiotic, a radioactive isotope, and a nucleolytic enzyme. In some embodiments, the anti-MUC16 antibody or the anti-NaPi2b antibody is covalently attached to the cytotoxic agent through a linker. In some embodiments, the linker comprises one or more of 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl) cyclohexane-1 carboxylate (SMCC), N-Succinimidyl (4-iodo-acetyl) aminobenzoate (SIAB), and 6-maleimidocaproyl-valine-citrulline-p-aminobenzyloxycarbonyl (MC-vc-PAB). In some embodiments, the linker is attached to the antibody through a thiol group on the antibody. In some embodiments, the cytotoxic agent is a drug moiety selected from the group consisting of an auristatin, a dolastatin, and a maytansinoid. In some embodiments, the cytotoxic agent is a maytansinoid selected from the group consisting of N(2')-deacetyl-N(2')-(3-mercapto-1-oxopropyl)-maytansine (DM1), N(2')-deacetyl-N2-(4-mercapto-1-oxopentyl)-maytansine (DM3), and N(2')-deacetyl-N2-(4-mercapto-4-methyl-1-oxopentyl)-maytansine (DM4). In some embodiments, the cytotoxic agent is monomethyl auristatin E (MMAE). In some embodiments, the cytotoxic agent is monomethyl auristatin F (MMAF). In some embodiments, the cytotoxic agent is selected from the group consisting of selected from ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Sapaonaria officinalis* inhibitor, glucocorticoid, auromycin, yttrium, bismuth, combrestatin, duocarmycins, cc1065, and a cisplatin. In some embodiments that may be combined with any of the preceding embodiments, the first time point occurs at least 3 days before, at least 1 day before, at least 12 hours before, at least 4 hours before, at least 1 hour before, or less than 1 hour before administering the therapeutically effective amount of the MUC16 antagonist. In some embodiments that may be combined with any of the preceding embodiments, the first time point occurs immediately before administering therapeutically effective amount of the MUC16 antagonist. In some embodiments that may be combined with any of the preceding embodiments the second time point occurs at least 1 hour after, at least 4 hours after, at least 12 hours after, at least 1 day after, at least 3 days after, at least 5 days after, at least 1 week after, at least 2 weeks after, or at least 3 weeks after administering the therapeutically effective amount of the MUC16 antagonist. In some embodiments that may be combined with any of the preceding embodiments, the sample is a blood sample. In some embodiments, the blood sample is a serum sample. In some embodiments that may be combined with any of the preceding embodiments, the sample is a cell sample. In some embodiments that may be combined with any of the preceding embodiments, the subject is a human. In some embodiments that may be combined with any of the preceding embodiments, the level of expression of HE4 is circulating level of HE4 protein. In some embodiments that may be combined with any of the preceding embodiments, the level of expression of HE4 is protein the level of expression of HE4. In some embodiments, the level of HE4 protein is measured by an immunoassay, Western blotting, peptide microarray, immunohistochemistry, flow cytometry, or mass spectrometry. In some embodiments that may be combined with any of the preceding embodiments, the level of expression of HE4 is RNA transcript level of HE4. In some embodiments, the RNA transcript level of HE4 is measured by RT-PCR.

Other aspects of the present disclosure relate to a method of diagnosing a MUC16-positive cancer that is responsive to treatment with a MUC16 antagonist in a patient, said method comprising obtaining a sample from a human patient and detecting the expression level of human epididymis protein 4 (HE4) in the sample; detecting whether the expression level of HE4 in the patient decreases after treatment with the MUC16 antagonist by administering to the patient a therapeutically effective amount of an anti-MUC16 antibody and detecting the expression level of HE4 in sample obtained from the patient after administration of the anti-MUC16 antibody, wherein the anti-MUC16 antibody comprises a heavy chain variable domain and a light chain variable domain, wherein the heavy chain variable domain and the light chain variable domain comprise the following HVRs: (i) HVR-H1 comprising the amino acid sequence of SEQ ID NO: 4, (ii)

HVR-H2 comprising the amino acid sequence of SEQ ID NO: 5, (iii) HVR-H3 comprising the amino acid sequence of SEQ ID NO: 6, (iv) HVR-L1 comprising the amino acid sequence of SEQ ID NO: 1, (v) HVR-L2 comprising the amino acid sequence of SEQ ID NO: 2, and (vi) HVR-L3 comprising the amino acid sequence of SEQ ID NO: 3; and diagnosing the patient with a MUC16-positive cancer that is responsive to treatment with a MUC16 antagonist when the level of expression of HE4 after administration of the anti-MUC16 antibody is at least 25% lower than the level of expression of HE4 before administration of the anti-MUC16 antibody. In some embodiments, a MUC16-positive cancer that is responsive to treatment with a MUC16 antagonist is diagnosed when the level of expression of HE4 after administration of the anti-MUC16 antibody is at least 40% lower than the level of expression of HE4 before administration of the anti-MUC16 antibody. In some embodiments, responsive to treatment with a MUC16 antagonist comprises treatment efficacy. In some embodiments, responsive to treatment with a MUC16 antagonist comprises reduced tumor volume. In some embodiments, responsive to treatment with a MUC16 antagonist comprises serologic responsiveness. In some embodiments, responsive to treatment with a MUC16 antagonist comprises a higher RECIST response. In some embodiments, responsive to treatment with a MUC16 antagonist comprises a lower sum of the longest diameter (SLD) response. In some embodiments, the patient has never received a MUC16 antagonist. In some embodiments, the patient is undergoing treatment with a MUC16 antagonist. In some embodiments, the method further comprises administering to the patient one or more additional therapeutically effective amounts of the anti-MUC16 antibody.

Other aspects of the present disclosure relate to a method of diagnosing MUC16-positive cancer in a patient, said method comprising obtaining a sample from a human patient and detecting the expression level of human epididymis protein 4 (HE4) in the sample; detecting whether the expression level of HE4 in the patient decreases after treatment with an anti-MUC16 antibody by administering to the patient a therapeutically effective amount of the anti-MUC16 antibody and detecting the expression level of HE4 in sample obtained from the patient after administration of the anti-MUC16 antibody, wherein the anti-MUC16 antibody comprises a heavy chain variable domain and a light chain variable domain, wherein the heavy chain variable domain and the light chain variable domain comprise the following HVRs: (i) HVR-H1 comprising the amino acid sequence of SEQ ID NO: 4, (ii) HVR-H2 comprising the amino acid sequence of SEQ ID NO: 5, (iii) HVR-H3 comprising the amino acid sequence of SEQ ID NO: 6, (iv) HVR-L1 comprising the amino acid sequence of SEQ ID NO: 1, (v) HVR-L2 comprising the amino acid sequence of SEQ ID NO: 2, and (vi) HVR-L3 comprising the amino acid sequence of SEQ ID NO: 3; and diagnosing the patient with MUC16-positive cancer when the level of expression of HE4 after administration of the anti-MUC16 antibody is at least 25% lower than the level of expression of HE4 before administration of the anti-MUC16 antibody. In some embodiments, the patient the patient is diagnosed with MUC16-positive cancer when the level of expression of HE4 after administration of the anti-MUC16 antibody is at least 40% lower than the level of expression of HE4 before administration of the anti-MUC16 antibody.

Other aspects of the present disclosure relate to a method for diagnosing and treating a MUC16-positive cancer, in a patient, the method comprising obtaining a sample from a human patient and detecting the expression level of human epididymis protein 4 (HE4) in the sample; detecting whether the expression level of HE4 in the patient decreases after treatment with an anti-MUC16 antibody by administering to the patient a therapeutically effective amount of the anti-MUC16 antibody and detecting the expression level of HE4 in sample obtained from the patient after administration of the anti-MUC16 antibody, wherein the anti-MUC16 antibody comprises a heavy chain variable domain and a light chain variable domain, wherein the heavy chain variable domain and the light chain variable domain comprise the following HVRs: (i) HVR-H1 comprising the amino acid sequence of SEQ ID NO: 4, (ii) HVR-H2 comprising the amino acid sequence of SEQ ID NO: 5, (iii) HVR-H3 comprising the amino acid sequence of SEQ ID NO: 6, (iv) HVR-L1 comprising the amino acid sequence of SEQ ID NO: 1, (v) HVR-L2 comprising the amino acid sequence of SEQ ID NO: 2, and (vi) HVR-L3 comprising the amino acid sequence of SEQ ID NO: 3; and diagnosing the patient with MUC16-positive cancer when the level of expression of HE4 after administration of the anti-MUC16 antibody is at least 25% lower than the level of expression of HE4 before administration of the anti-MUC16 antibody; and administering one or more additional therapeutically effective amounts of the anti-MUC16 antibody to the diagnosed patient. In some embodiments, the patient the patient is diagnosed with MUC16-positive cancer when the level of expression of HE4 after administration of the anti-MUC16 antibody is at least 40% lower than the level of expression of HE4 before administration of the anti-MUC16 antibody.

Other aspects of the present disclosure relate to a method of diagnosing cancer progression in a patient having a MUC16-positive cancer, the method comprising obtaining a sample from a human patient and detecting the expression level of human epididymis protein 4 (HE4) in the sample; detecting whether the expression level of HE4 in the patient decreases after treatment with an anti-MUC16 antibody by administering to the patient a therapeutically effective amount of the anti-MUC16 antibody and detecting the expression level of HE4 in sample obtained from the patient after administration of the anti-MUC16 antibody, wherein the anti-MUC16 antibody comprises a heavy chain variable domain and a light chain variable domain, wherein the heavy chain variable domain and the light chain variable domain comprise the following HVRs: (i) HVR-H1 comprising the amino acid sequence of SEQ ID NO: 4, (ii) HVR-H2 comprising the amino acid sequence of SEQ ID NO: 5, (iii) HVR-H3 comprising the amino acid sequence of SEQ ID NO: 6, (iv) HVR-L1 comprising the amino acid sequence of SEQ ID NO: 1, (v) HVR-L2 comprising the amino acid sequence of SEQ ID NO: 2, and (vi) HVR-L3 comprising the amino acid sequence of SEQ ID NO: 3; and diagnosing the patient with a MUC16-postivie cancer that is likely to progress when the level of expression of HE4 after administration of the anti-MUC16 antibody is less than 25% lower than the level of expression of HE4 before administration of the anti-MUC16 antibody. In some embodiments, the patient is diagnosed with a MUC16-postivie cancer that is likely to progress when the level of expression of HE4 after administration of the anti-MUC16 antibody is less than 20% lower than the level of expression of HE4 before administration of the anti-MUC16 antibody. In some embodiments, the patient is diagnosed with a MUC16-postivie cancer that is likely to progress when the level of expression of HE4 after administration of the anti-MUC16 antibody is less than 15% lower than the level of expression of HE4 before administration of the anti-MUC16 antibody. In some embodiments, the patient is diagnosed with a MUC16-postivie cancer that is likely to progress when the level of expression of HE4 after administration of the anti-MUC16 antibody is less than 10% lower than the level of expression of HE4 before administration of the anti-MUC16 antibody. In some embodiments, the patient is diagnosed with a MUC16-postivie cancer that is likely to progress when the level of expression of HE4 after administration of the anti-MUC16 antibody is less than 5% lower than the level of expression of HE4 before administration of the anti-MUC16 antibody. In some embodiments, the present disclosure relates to a method of diagnosing cancer progression in a patient having a MUC16-positive cancer, the method comprising obtaining a sample from a human patient and detecting the expression level of human epididymis protein 4 (HE4) in the sample; detecting whether the expression level of HE4 in the patient decreases after treatment with an anti-MUC16 antibody by administering to the patient a therapeutically effective amount of the anti-MUC16 antibody and detecting the expression level of HE4 in sample obtained from the patient after administration of the anti-MUC16 antibody, wherein the anti-MUC16 antibody comprises a heavy chain variable domain and a light chain variable domain, wherein the heavy chain variable domain and the light chain variable domain comprise the following HVRs: (i) HVR-H1 comprising the amino acid sequence of SEQ ID NO: 4, (ii) HVR-H2 comprising the amino acid sequence of SEQ ID NO: 5, (iii) HVR-H3 comprising the amino acid sequence of SEQ ID NO: 6, (iv) HVR-L1 comprising the amino acid sequence of SEQ ID NO: 1, (v) HVR-L2 comprising the amino acid sequence of SEQ ID NO: 2, and (vi) HVR-L3 comprising the amino acid sequence of SEQ ID NO: 3; and diagnosing the patient with a MUC16-postivie cancer that is likely to progress when the level of expression of HE4 after administration of the anti-MUC16 antibody is no different than the level of expression of HE4 before administration of the anti-MUC16 antibody. In some embodiments, the present disclosure relates to a method of diagnosing cancer progression in a patient having a MUC16-positive cancer, the method comprising obtaining a sample from a human patient and detecting the expression level of human epididymis protein 4 (HE4) in the sample; detecting whether the expression level of HE4 in the patient decreases after treatment with an anti-MUC16 antibody by administering to the patient a therapeutically effective amount of the anti-MUC16 antibody and detecting the expression level of HE4 in sample obtained from the patient after administration of the anti-MUC16 antibody, wherein the anti-MUC16 antibody comprises a heavy chain variable domain and a light chain variable domain, wherein the heavy chain variable domain and the light chain variable domain comprise the following HVRs: (i) HVR-H1 comprising the amino acid sequence of SEQ ID NO: 4, (ii) HVR-H2 comprising the amino acid sequence of SEQ ID NO: 5, (iii) HVR-H3 comprising the amino acid sequence of SEQ ID NO: 6, (iv) HVR-L1 comprising the amino acid sequence of SEQ ID NO: 1, (v) HVR-L2 comprising the amino acid sequence of SEQ ID NO: 2, and (vi) HVR-L3 comprising the amino acid sequence of SEQ ID NO: 3; and diagnosing the patient with a MUC16-postivie cancer that is likely to progress when the level of expression of HE4 after administration of the anti-MUC16 antibody is higher than the level of expression of HE4 before administration of the anti-MUC16 antibody. In some embodiments, a patient is diagnosed with a MUC16-postivie cancer that is likely to progress when the level of expression of HE4 after administration of the anti-MUC16 antibody is 1% higher than the level of expression of HE4 before administration of the anti-MUC16 antibody. In some embodiments, a patient is diagnosed with a MUC16-postivie cancer that is likely to progress when the level of expression of HE4 after administration of the anti-MUC16 antibody is 5% higher than the level of expression of HE4 before administration of the anti-MUC16 antibody. In some embodiments, a patient is diagnosed with a MUC16-postivie cancer that is likely to progress when the level of expression of HE4 after administration of the anti-MUC16 antibody is 10% higher than the level of expression of HE4 before administration of the anti-MUC16 antibody. In some embodiments, a patient is diagnosed with a MUC16-postivie cancer that is likely to progress when the level of expression of HE4 after administration of the anti-MUC16 antibody is 15% higher than the level of expression of HE4 before administration of the anti-MUC16 antibody. In some embodiments, a patient is diagnosed with a MUC16-postivie cancer that is likely to progress when the level of expression of HE4 after administration of the anti-MUC16 antibody is 25% higher than the level of expression of HE4 before administration of the anti-MUC16 antibody. In some embodiments, a patient is diagnosed with a MUC16-postivie cancer that is likely to progress when the level of expression of HE4 after administration of the anti-MUC16 antibody is 50% higher than the level of expression of HE4 before administration of the anti-MUC16 antibody.

In some embodiments that may be combined with any of the preceding embodiments, the anti-MUC16 antibody comprises a heavy chain variable region comprising the amino acid sequence of SEQ ID NO: 8, or a light chain variable region comprising the amino acid sequence of SEQ ID NO: 7, or both. In some embodiments that may be combined with any of the preceding embodiments, the anti-MUC16 antibody is an antibody fragment selected from a Fab, Fab'-SH, Fv, scFv, or (Fab')$_2$ fragment. In some embodiments that may be combined with any of the preceding embodiments, one or more amino acid residues are replaced with one or more free cysteine amino acids having a thiol reactivity in the range of 0.6 to 1.0. In some embodiments, the one or more free cysteine amino acid residues are located in a light chain. In some embodiments, the one or more free cysteine amino acid residues are located in a heavy chain. In some embodiments, the antibody comprises a cysteine at one or more positions selected from 15, 43, 110, 144, 149, 168 and 205 of the light chain according to Kabat numbering convention and 41, 88, 115, 118, 120, 171, 172, 282, 375, and 400 of the heavy chain according to EU numbering convention. In some embodiments, a cysteine is at position 205 of the light chain. In some embodiments, a cysteine is at position 118 of the heavy chain. In some embodiments, the anti-MUC16 antibody is a bispecific antibody. In some embodiments, the anti-MUC16 antibody is covalently attached to a cytotoxic agent. In some embodiments, the cytotoxic agent is selected from the group consisting of a toxin, a chemotherapeutic agent, a drug moiety, an antibiotic, a radioactive isotope, and a nucleolytic enzyme. In some embodiments, the anti-MUC16 antibody is covalently attached to the cytotoxic agent through a linker. In some embodiments, the linker comprises one or more of 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl) cyclohexane-1 carboxylate (SMCC), N-Succinimidyl (4-iodo-acetyl) aminobenzoate (SIAB), and 6-maleimidocaproyl-valine-citrulline-p-aminobenzyloxycarbonyl (MC-vc-PAB). In some embodiments, the linker is attached to the antibody through a thiol group on the antibody. In some embodiments, the cytotoxic agent is a drug moiety selected from the group consisting of an auristatin, a dolastatin, and a maytansinoid. In some embodiments, the cytotoxic agent is a maytansinoid selected from the group consisting of N(2')-deacetyl-N(2')-(3-mercapto-1-oxopropyl)-maytansine (DM1), N(2')-deacetyl-N2-(4-mercapto-1-oxopentyl)-maytansine (DM3), and N(2')-deacetyl-N2-(4-mercapto-4-methyl-1-oxopentyl)-maytansine (DM4). In some embodiments, the cytotoxic agent is monomethyl auristatin E (MMAE). In some embodiments, the cytotoxic agent is monomethyl auristatin F (MMAF). In some embodiments, the cytotoxic agent is selected from the group consisting of selected from ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstricin, phenomycin, enomycin, curicin, crotin, calicheamicin, *Sapaonaria officinalis* inhibitor, glucocorticoid, auromycin, yttrium, bismuth, combrestatin, duocarmycins, cc1065, and a cisplatin. In some embodiments that may be combined with any of the preceding embodiments, the methods further comprise maintaining the same level or increasing the level of anti-MUC16 antibody administered to the patient based on the level of expression of HE4 after administration of the anti-MUC16 antibody. In some embodiments, increasing the level of anti-MUC16 antibody administered to the patient comprises increasing the dose or frequency of the anti-MUC16 antibody administered to the patient. In some embodiments that may be combined with any of the preceding embodiments, the methods further comprise decreasing the level of anti-MUC16 antibody administered to the patient based on the level of expression of HE4 after administration of the anti-MUC16 antibody. In some embodiments, decreasing the level of anti-MUC16 antibody administered to the patient comprises decreasing the dose or frequency of the anti-MUC16 antibody. In some embodiments that may be combined with any of the preceding embodiments, the methods further comprise administering a second treatment therapy to the subject. In some embodiments, the second treatment therapy is a maintenance therapy, a chemotherapy, an antibody therapy, or bevacizumab antibody therapy. In some embodiments that may be combined with any of the preceding embodiments, the first time point occurs at least 3 days before, at least 1 day before, at least 12 hours before, at least 4 hours before, at least 1 hour before, or less than 1 hour before administering the therapeutically effective amount of the anti-MUC16 antibody. In some embodiments that may be combined with any of the preceding embodiments, the first time point occurs immediately before administering therapeutically effective amount of the anti-MUC16 antibody. In some embodiments that may be combined with any of the preceding embodiments the second time point occurs at least 1 hour after, at least 4 hours after, at least 12 hours after, at least 1 day after, at least 3 days after, at least 5 days after, at least 1 week after, at least 2 weeks after, or at least 3 weeks after administering the therapeutically effective amount of the anti-MUC16 antibody. In some embodiments that may be combined with any of the preceding embodiments, the sample is a blood sample. In some embodiments, the blood sample is a serum sample. In some embodiments that may be combined with any of the preceding embodiments, the sample is a cell sample. In some embodiments that may be combined with any of the preceding embodiments, the subject is a human. In some embodiments that may be combined with any of the preceding embodiments, the level of expression of HE4 is circulating level of HE4 protein. In some embodiments that may be combined with any of the preceding embodiments, the level of expression of HE4 is protein the level of expression of HE4. In some embodiments, the level of HE4 protein is measured by an immunoassay, Western blotting, peptide microarray, immunohistochemistry, flow cytometry, or mass spectrometry. In some embodiments that may be combined with any of the preceding embodiments, the level of expression of HE4 is RNA transcript level of HE4. In some embodiments, the RNA transcript level of HE4 is measured by RT-PCR. In some embodiments that may be combined with any of the preceding embodiments, the MUC16-positive cancer is selected from the group consisting of ovarian cancer, endometrial cancer, triple-negative breast cancer, pancreatic cancer, and non-small cell lung cancer. In some embodiments that may be combined with any of the preceding embodiments, the MUC16-positive cancer is unresectable pancreatic cancer. In some embodiments that may be combined with any of the preceding embodiments, the MUC16-positive cancer is an ovarian cancer selected from the group consisting of primary peritoneal carcinoma, epithelial ovarian carcinoma, metastatic ovarian cancer, fallopian tube carcinoma, and platinum-resistant ovarian cancer.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A, FIG. 2B, and FIG. 2C show waterfall plots demonstrating investigator-assessed best radiologic responses for ovarian cancer patients treated at doses of 2.4 mg/kg q3w (FIG. 2A), ovarian cancer patients treated in q1w cohorts (FIG. 2B), and pancreatic cancer patients treated at doses of 2.4 mg/kg q3w (FIG. 2C).

FIG. 12A shows percent decrease in serum CA125 levels from baseline levels for ovarian cancer patients after treatment with the indicated doses of anti-MUC16-TDC. The reduction in measured serum levels of CA125 in post-dose samples is partially due to drug interference in assay. FIG. 12B shows percent decrease in serum HE4 levels from baseline levels for ovarian cancer patients after treatment with the indicated doses of anti-MUC16-TDC.

DETAILED DESCRIPTION

I. General Techniques

Figure 1A:
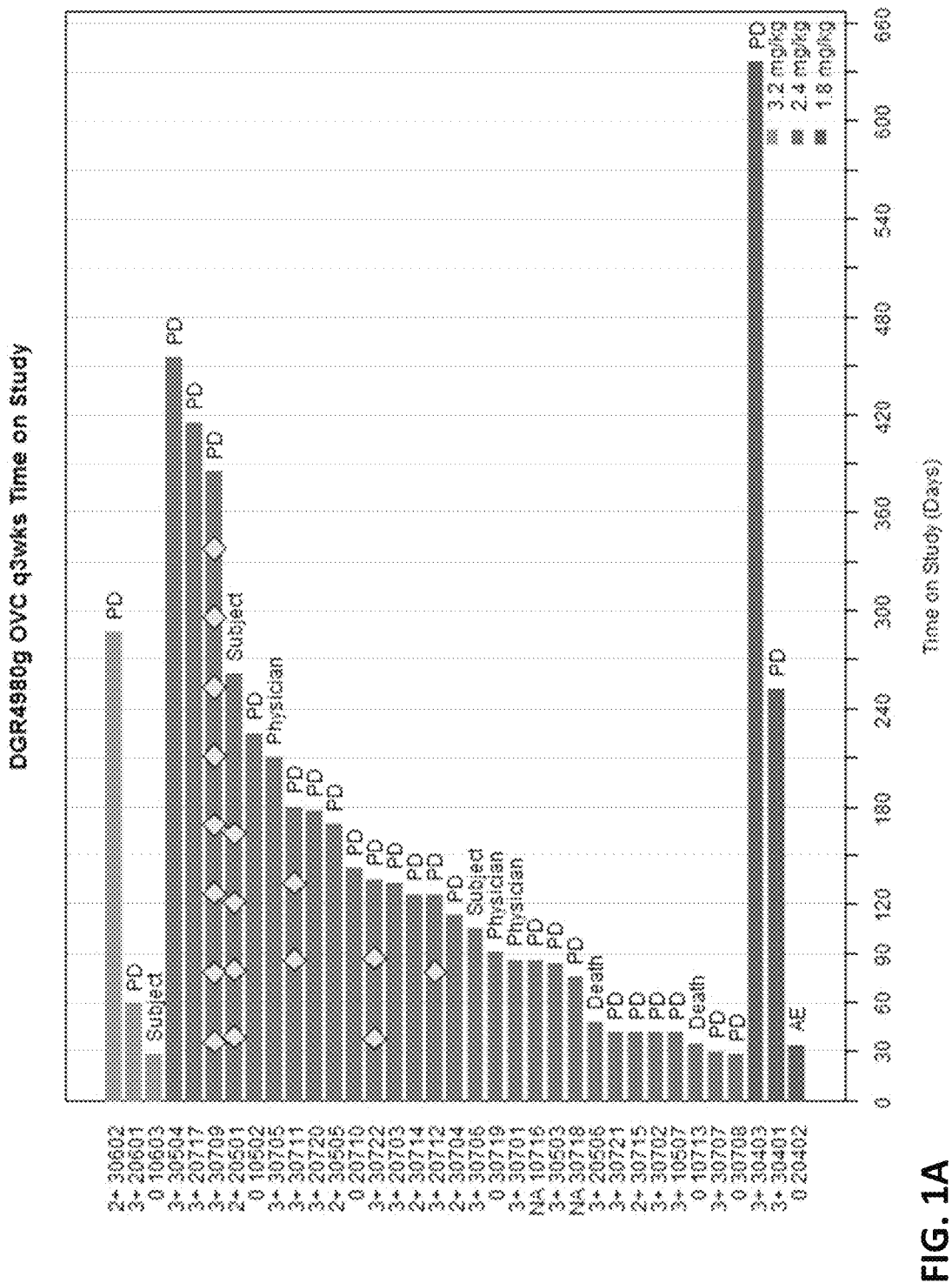
FIG. 1A and FIG. 1B show swimlane plots demonstrating RECIST responses for ovarian (FIG. 1A) and pancreatic (FIG. 1B) cancer patients treated at doses of 2.4 mg/kg q3w.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); Antibodies (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publish-

II. Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used herein and in the appended claims, the singular forms "a," "or," and "the" include plural referents unless the context clearly dictates otherwise.

Reference to "about" a value or parameter herein includes (and describes) variations that are directed to that value or parameter per se. For example, description referring to "about X" includes description of "X".

It is understood that aspects and variations of the invention described herein include "consisting" and/or "consisting essentially of" aspects and variations.

The term "MUC16 antagonist" as used herein may refer to any molecule that decreases, blocks, inhibits, abrogates, or interferes with one or more of the following: a cellular function of MUC16, a binding interaction involving MUC16, and/or the viability of a cell that expresses MUC16. For example, a molecule that may be used as a MUC16 antagonist may include without limitation an anti-MUC16 antibody, a MUC16 inhibitor, a protein, a peptide, a fusion protein, and an immunoadhesin. In specific embodiments, the term MUC16 antagonist refers to a MUC16 antibody or antibody drug conjugate thereof.

The terms "anti-MUC16 antibody" and "an antibody that binds to MUC16" refer to an antibody that is capable of binding MUC16 with sufficient affinity such that the antibody is useful as a diagnostic agent in targeting MUC16. In specific embodiments, the anti-MUC16 antibody comprises the following CDRs:

```
HVR-L1:
                                        (SEQ ID NO: 1)
Lys Ala Ser Asp Leu Ile His Asn Trp Leu Ala

HVR-L2:
                                        (SEQ ID NO: 2)
Tyr Gly Ala Thr Ser Leu Glu Thr

HVR-L3:
                                        (SEQ ID NO: 3)
Gln Gln Tyr Trp Thr Thr Pro Phe Thr

HVR-H1:
                                        (SEQ ID NO: 4)
Gly Tyr Ser Ile Thr Asn Asp Tyr Ala Trp Asn

HVR-H2:
                                        (SEQ ID NO: 5)
Gly Tyr Ile Ser Tyr Ser Gly Tyr Thr Thr Tyr
Asn Pro Ser Leu Lys Ser

HVR-H3:
                                        (SEQ ID NO: 6)
Ala Arg Trp Thr Ser Gly Leu Asp Tyr;
``` or comprise the following VL and VH sequences:

```
VL:
                                        (SEQ ID NO: 7)
Asp Ile Gln Met Thr Gln Ser Pro Ser Ser Leu

Ser Ala Ser Val Gly Asp Arg Val Thr Ile Thr

Cys Lys Ala Ser Asp Leu Ile His Asn Trp Leu

Ala Trp Tyr Gln Gln Lys Pro Gly Lys Ala Pro

Lys Leu Leu Ile Tyr Gly Ala Thr Ser Leu Glu

Thr Gly Val Pro Ser Arg Phe Ser Gly Ser Gly

Ser Gly Thr Asp Phe Thr Leu Thr Ile Ser Ser

Leu Gln Pro Glu Asp Phe Ala Thr Tyr Tyr Cys

Gln Gln Tyr Trp Thr Thr Pro Phe Thr Phe Gly

Gln Gly Thr Lys Val Glu Ile Lys Arg;
and

VH:
                                        (SEQ ID NO: 8)
Glu Val Gln Leu Val Glu Ser Gly Gly Gly Leu

Val Gln Pro Gly Gly Ser Leu Arg Leu Ser Cys

Ala Ala Ser Gly Tyr Ser Ile Thr Asn Asp Tyr

Ala Trp Asn Trp Val Arg Gln Ala Pro Gly Lys

Gly Leu Glu Trp Val Gly Tyr Ile Ser Tyr Ser

Gly Tyr Thr Thr Tyr Asn Pro Ser Leu Lys Ser

Arg Phe Thr Ile Ser Arg Asp Thr Ser Lys Asn

Thr Leu Tyr Leu Gln Met Asn Ser Leu Arg Ala

Glu Asp Thr Ala Val Tyr Tyr Cys Ala Arg Trp

Thr Ser Gly Leu Asp Tyr Trp Gly Gln Gly Thr

Leu Val Thr Val Ser Ser
```

The term "MUC16-ADC" refers to an anti-MUC16 antibody-drug conjugate. In specific embodiments, the MUC16-ADC is an antibody that is conjugated to a chemotherapeutic drug at its endogenous cysteine and/or lysine residues. In specific embodiments, the MUC16-ADC is a THIOMAB™ antibody (a "MUC16-TDC").

The term "3A5" refers to an anti-MUC16 antibody.

The term "cysteine engineered antibody" or "cysteine engineered antibody variant" is an antibody in which one or more residues of an antibody are substituted with cysteine residues. The thiol group(s) of the cysteine engineered antibodies can be conjugated to a drug moiety (e.g., via a linker) to form a THIOMAB™ antibody (i.e., a THIOMAB™ antibody drug conjugate (TDC)). In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. For example, a THIOMAB™ antibody may be an antibody with a single mutation of a non-cysteine native residue to a cysteine in the light chain (e.g., G64C, K149C, R142C, and V205C according to Kabat numbering) or in the heavy chain (e.g., D101C, A118C, V184C or T205C according to Kabat numbering). In specific examples, a THIOMAB™ antibody has a single cysteine mutation in either the heavy or light chain such that each full-length antibody (i.e., an antibody with two heavy chains and two light chains) has two engineered cysteine residues.

The term "MUC16-TDC" refers to a MUC16 antibody with an engineered cysteine in its heavy or light chain. In specific embodiments, the MUC16-TDC is a MUC16 antibody with an engineered cysteine at position A118C on the heavy chain. In specific embodiments, the MUC16-TDC is a MUC16 antibody with an engineered cysteine at position K149C on the light chain. In specific embodiments, the MUC16-TDC is conjugated to an auristatin. In specific embodiments, the auristatin is MMAE.

The term "NaPi2b antagonist" as used herein may refer to any molecule that decreases, blocks, inhibits, abrogates, or interferes with one or more of the following: a cellular function of NaPi2b, a binding interaction involving NaPi2b, and/or the viability of a cell that expresses NaPi2b. For example, a molecule that may be used as a NaPi2b antagonist may include without limitation an anti-NaPi2b antibody, a NaPi2b inhibitor, a protein, a peptide, a fusion protein, and an immunoadhesin. In specific embodiments, the term NaPi2b antagonist refers to a NaPi2b antibody or antibody drug conjugate thereof.

The terms "anti-NaPi2b antibody" and "an antibody that binds to NaPi2b" refer to an antibody that is capable of binding NaPi2b with sufficient affinity such that the antibody is useful as a diagnostic agent in targeting NaPi2b.

The term "NaPi2b-ADC" refers to an anti-NaPi2b antibody-drug conjugate. In specific embodiments, the NaPi2b-ADC is an antibody that is conjugated to a chemotherapeutic drug at its endogenous cysteine and/or lysine residues. In specific embodiments, the NaPi2b-ADC is a THIOMAB™ antibody (a "NaPi2b-TDC").

The term "NaPi2b-TDC" refers to a NaPi2b antibody with an engineered cysteine in its heavy or light chain. In specific embodiments, the NaPi2b-TDC is a NaPi2b antibody with an engineered cysteine at position A118C on the heavy chain. In specific embodiments, the NaPi2b-TDC is a NaPi2b antibody with an engineered cysteine at position K149C on the light chain. In specific embodiments, the NaPi2b-TDC is conjugated to an auristatin. In specific embodiments, the auristatin is MMAE.

The term "MUC16-positive cancer" refers to a cancer or tumor comprising cells that express MUC16 on their surface. In certain embodiments, the MUC16-positive cancer overexpresses MUC16. In some embodiments, expression of MUC16 on the cell surface is determined, for example, using antibodies to MUC16 in a method such as immunohistochemistry, FACS, etc. Alternatively, MUC16 mRNA expression is considered to correlate to MUC16 expression on the cell surface and can be determined by a method selected from in situ hybridization and RT-PCR (including quantitative RT-PCR).

A cancer which "overexpresses" a protein is one which has significantly higher levels of the protein, such as MUC16, compared to a noncancerous cell of the same tissue type. Such overexpression may be caused by gene amplification or by increased transcription or translation. Protein overexpression may be determined in a diagnostic or prognostic assay by evaluating increased levels of the protein present on the surface of a cell (e.g., via an immunohistochemistry assay; IHC). Alternatively, or additionally, one may measure levels of protein-encoding nucleic acid in the cell, e.g., via fluorescent in situ hybridization (FISH; see WO 98/45479), southern blotting, or polymerase chain reaction (PCR) techniques, such as real time quantitative PCR (RT-PCR).

The term "MUC16-positive cell" refers to a cell that expresses MUC16 on its surface.

The terms "cancer" and "cancerous" refer to or describe the physiological condition in mammals that is typically characterized by unregulated cell growth. A "tumor" comprises one or more cancerous cells. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the present disclosure include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is endometrial cancer, triple negative breast cancer, pancreatic cancer, non-small cell lung cancer, or ovarian cancer. In certain embodiments of this invention, the cancer is ovarian, endometrial cancer, pancreatic cancer, triple negative breast cancer, and/or non-small cell lung cancer. In specific embodiments of this invention, the cancer is ovarian and/or endometrial cancer.

The term "tumor" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein. In some embodiments, a tumor may refer to a physical mass containing a plurality of cancer cells, e.g., cells showing the characteristics of any of the cancers described herein. Examples of tumors may include primary tumors of any of the above types of cancer or metastatic tumors at a second site derived from any of the above types of cancer.

The term "tumor" or "cancer", as used interchangeably herein, can include any medical condition characterized by neoplastic or malignant cell growth, proliferation, or metastasis, and includes both solid cancers and non-solid cancers.

The terms "cell proliferative disorder" and "proliferative disorder" refer to disorders that are associated with some degree of abnormal cell proliferation. In one embodiment, the cell proliferative disorder is cancer.

The term "ovarian cancer" or "ovarian tumor" as used herein, refers to cancer or tumor that is originated from ovarian tissue.

The term "stage" in the context of a disease (such as cancer or tumor), refers to the progression status of the disease which is indicative of the severity of the disease.

The term "staging" as used herein refers to identifying the particular stage at which the disease has progressed.

The term "diagnosis" (along with grammatical variations thereof such as "diagnosing" or "diagnostic") refers to the identification or classification of a molecular or pathological state, disease or condition, such as the identification or classification of cancer, or refers to the identification or classification of a cancer patient who may benefit from a particular treatment regimen. For example, "diagnosis" may refer to identification of a particular type of cancer. "Diagnosis" may also refer to the classification of a particular subtype of cancer, e.g., by histopathological criteria, or by molecular features (e.g., a subtype characterized by expression of one or a combination of biomarkers or particular genes or proteins encoded by said gene)).

The term "prognosis" (and grammatical variations thereof such as "prognosing" or "prognostic") refers to the prediction of the likelihood of benefit from a treatment such as a cancer therapy.

The term "prediction" or "predicting" is used herein to refer to the likelihood that a patient will respond either favorably or unfavorably to a particular anti-prostate cancer therapy. In one embodiment, prediction or predicting relates to the extent of those responses.

In one embodiment, the prediction or predicting relates to whether and/or the probability that a patient will survive or improve following treatment, for example treatment with a particular therapeutic agent, and for a certain period of time without disease progression.

The term "benefit" is used in the broadest sense and refers to any desirable effect and specifically includes clinical benefit as defined herein.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "anti-angiogenic agent" refers to a compound which blocks, or interferes with to some degree, the development of blood vessels. An anti-angiogenic agent may, for instance, be a small molecule or antibody that binds to a growth factor or growth factor receptor involved in promoting angiogenesis. In one embodiment, an anti-angiogenic agent is an antibody that binds to vascular endothelial growth factor (VEGF), such as bevacizumab (AVASTIN).

As use herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay. In certain embodiments, the antibody blocks binding of the reference antibody to its antigen in a competition assay by 50%, and conversely, the reference antibody blocks binding of the antibody to its antigen in a competition assay by 50%. In certain embodiments, the antibody blocks binding of the reference antibody to its antigen in a competition assay by 75%, and conversely, the reference antibody blocks binding of the antibody to its antigen in a competition assay by 75%. In certain embodiments, the antibody blocks binding of the reference antibody to its antigen in a competition assay by 90%, and conversely, the reference antibody blocks binding of the antibody to its antigen in a competition assay by 90%. In certain embodiments, the antibody blocks binding of the reference antibody to its antigen in a competition assay by 95% or more, and conversely, the reference antibody blocks binding of the antibody to its antigen in a competition assay by 95% or more. An exemplary competition assay is provided herein.

The term "binding domain" refers to the region of a polypeptide that binds to another molecule. In the case of an FcR, the binding domain can comprise a portion of a polypeptide chain thereof (e.g. the alpha chain thereof) which is responsible for binding an Fc region. One useful binding domain is the extracellular domain of an FcR alpha chain.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

The term "cytostatic agent" refers to a compound or composition which arrests growth of a cell either in vitro or in vivo. Thus, a cytostatic agent may be one which significantly reduces the percentage of cells in S phase. Further examples of cytostatic agents include agents that block cell cycle progression by inducing G0/G1 arrest or M-phase arrest. The humanized anti-Her2 antibody trastuzumab (HERCEPTIN®) is an example of a cytostatic agent that induces G0/G1 arrest. Classical M-phase blockers include the vincas (vincristine and vinblastine), taxanes, and topoisomerase II inhibitors such as doxorubicin, epirubicin, daunorubicin, etoposide, and bleomycin. Certain agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{86}$, $Re^{88}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

In one embodiment the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine (e.g., erlotinib). In one embodiment the cytotoxic agent is a RAF inhibitor. In one embodiment, the RAF inhibitor is a BRAF and/or CRAF inhibitor. In one embodiment the RAF inhibitor is vemurafenib. In one embodiment the cytotoxic agent is a PI3K inhibitor.

A "therapeutically effective amount" means an amount of a compound that is found to (i) treat a particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder. In some embodiments, a "therapeutically effective amount" is a standard amount of a compound selected based upon the results from pre-clinical and/or clinical data of use of the compound in one or more populations or subjects. In the case of cancer, therapeutically effective amount of a compound may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the compound may prevent growth and/or kill existing cancer cells, it may be cytostatic and/or cytotoxic.

The terms "full length antibody," "intact antibody," and "whole antibody" are used herein interchangeably to refer to an antibody having a structure substantially similar to a native antibody structure or having heavy chains that contain an Fc region as defined herein.

An "immunoconjugate" is an antibody conjugated to one or more heterologous molecule(s), including, but not limited to, a cytotoxic agent. In some embodiments, the antibody is an unmodified antibody. In some embodiments, the antibody is a cysteine engineered antibody. In some embodiments, the antibody is a THIOMAB™.

An "individual", "subject", or "patient" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain. A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the present disclosure are used to delay development of a disease or to slow the progression of a disease.

In certain embodiments, treatment refers to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

"Chemotherapeutic agent" includes chemical compounds useful in the treatment of cancer.

The term "cytotoxic activity" refers to a cell-killing, cytostatic or growth inhibitory effect of an antibody-drug conjugate or an intracellular metabolite of an antibody-drug conjugate. Cytotoxic activity may be expressed as the IC50 value, which is the concentration (molar or mass) per unit volume at which half the cells survive.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: $-(CR2)_nO(CR_2)_n-$, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

The term "biomarker" or "marker" as used herein refers generally to a molecule, including a gene, mRNA, protein, carbohydrate structure, or glycolipid, the expression of which in or on a tissue or cell or secreted can be detected by known methods (or methods disclosed herein) and is predictive or can be used to predict (or aid prediction) for a cell, tissue, or patient's responsiveness to treatment regimes. In some embodiments, a biomarker may refer to a gene or protein, e.g., the expression level of the gene or protein detected in one or more cells. In some embodiments, a biomarker may refer to a cell type of interest, e.g., the number of a cell type of interest detected in one or more samples. In specific embodiments, the biomarker is HE4.

By "patient sample" or "sample" is meant a collection of cells or fluids obtained from a cancer patient. The source of the tissue or cell sample may be solid tissue as from a fresh, frozen and/or preserved organ or tissue sample or biopsy or aspirate; blood or any blood constituents; bodily fluids such as cerebrospinal fluid, amniotic fluid, peritoneal fluid, or interstitial fluid; cells from any time in gestation or development of the subject. The tissue sample may contain compounds which are not naturally intermixed with the tissue in nature such as preservatives, anticoagulants, buffers, fixatives, nutrients, antibiotics, or the like. Examples of tumor samples herein include, but are not limited to, tumor biopsy, fine needle aspirate, bronchiolar lavage, pleural fluid, sputum, urine, a surgical specimen, circulating tumor cells, serum, plasma, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples. In specific embodiments, the patient sample is a blood sample.

The phrase "based on expression of" or "based on changes in the level of expression of" when used herein means that information about expression level or presence or absence of expression (e.g., presence or absence or prevalence of (e.g., percentage of cells displaying) of the one or more biomarkers herein (e.g., presence or absence of or amount or prevalence of HE4) is used to inform a treatment decision, information provided on a package insert, or marketing/promotional guidance etc.

The term "detection" includes any means of detecting, including direct and indirect detection. In specific embodiments, detection refers to the detection of the HE4 biomarker.

The "amount" or "level" of a biomarker associated with an increased clinical benefit to an individual is a detectable level in a biological sample. These can be measured by methods known to one skilled in the art and also disclosed herein. The expression level or amount of biomarker assessed can be used to determine the response to the treatment. In specific embodiments, amount biomarker is the amount of HE4 expression.

"Elevated expression," "elevated expression levels," or "elevated levels" refers to an increased expression or increased levels of a biomarker (e.g., HE4) in an individual relative to a control, such as an individual or individuals who are not suffering from the disease or disorder (e.g., cancer), a tumor with a known responsiveness to a treatment (e.g., with a MUC16 antagonist), an internal control (e.g., housekeeping biomarker), or a reference number (e.g., a set threshold amount, such as a threshold based on clinical outcome data).

"Reduced expression," "reduced expression levels," or "reduced levels" refers to a decrease expression or decreased levels of a biomarker (e.g., HE4) in an individual relative to a control, such as an individual or individuals who are not suffering from the disease or disorder (e.g., cancer), a tumor with a known responsiveness to a treatment (e.g., with a MUC16 antagonist), an internal control (e.g., housekeeping biomarker), or a reference number (e.g., a set threshold amount, such as a threshold based on clinical outcome data). In some embodiments, reduced expression is little or no expression.

The phrase "disease sample" and variations thereof refers to any sample obtained from a subject of interest that would be expected or is known to contain the cellular and/or molecular entity that is to be characterized. Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebrospinal fluid, saliva, sputum, tears, perspiration, mucus, tumor lysates, and tissue culture medium, tissue extracts such as homogenized tissue, tumor tissue, cellular extracts, and combinations thereof.

The phrase "tissue sample" or "cell sample" refers to a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

As used herein, a "section" of a tissue sample is meant a single part or piece of a tissue sample, e.g. a thin slice of tissue or cells cut from a tissue sample. It is understood that multiple sections of tissue samples may be taken and subjected to analysis according to the present disclosure, provided that it is understood that the present disclosure comprises a method whereby the same section of tissue sample is analyzed at both morphological and molecular levels, or is analyzed with respect to protein or nucleic acid.

By "correlate(s)" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

"Individual response" or "response" can be assessed using any endpoint indicating a benefit to the individual, including, without limitation, (1) inhibition, to some extent, of disease progression (e.g., cancer progression), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e. reduction, slowing down or complete stopping) of metastasis; (5) relief, to some extent, of one or more symptoms associated with the disease or disorder (e.g., cancer); (6) increase or extend in the length of survival, including overall survival and progression free survival; and/or (9) decreased mortality at a given point of time following treatment.

An "effective response" of a patient or a patient's "responsiveness" to treatment with a medicament and similar wording refers to the clinical or therapeutic benefit imparted to a patient at risk for, or suffering from, a disease or disorder, such as cancer. In one embodiment, such benefit includes any one or more of: extending survival (including overall survival and progression free survival); resulting in an objective response (including a complete response or a partial response); or improving signs or symptoms of cancer.

The phrase "extending survival" is meant increasing overall or progression free survival in a treated patient relative to an untreated patient (i.e. relative to a patient not treated with the medicament), or relative to a patient who does not express a biomarker at the designated level, and/or relative to a patient treated with an approved anti-tumor agent. An objective response refers to a measurable response, including complete response (CR) or partial response (PR).

III. Methods

The present disclosure relates to methods of measuring or detecting the level of expression of human epididymis protein 4 (HE4) in a subject or patient having cancer to assess, for example, responsiveness of the subject or patient to an anti-cancer therapy. Such methods may be used, inter alia, to treat or delay progression of cancer in a subject or patient with an anti-cancer therapy (e.g., a MUC16 antagonist), to modulate/adjust/determine/select the dosing of a subject or patient having cancer who will be/has been/is being treated with an anti-cancer therapy (e.g., a MUC16 antagonist), to select a subject or patient having cancer for treatment with an anti-cancer therapy (e.g., a MUC16 antagonist), to communicate the likelihood of response of a subject or patient to an anti-cancer therapy (e.g., a MUC16 antagonist), to assess the responsiveness of a subject or patient to an anti-cancer therapy (e.g., a MUC16 antagonist), to assess progression-free survival of a subject or patient having cancer, to assess tumor burden in a subject or patient having cancer, to predict cancer progression in a subject or patient having cancer, to diagnose a subject or patient having cancer, to diagnose a subject of patient having cancer that is responsive to treatment, to diagnose and treat a subject or patient having cancer, and to diagnose cancer progression in a subject or patient having cancer. Examples of cancers may include, but are not limited to, ovarian cancer, endometrial cancer, triple-negative breast cancer, pancreatic cancer, and/or non-small cell lung cancer. In some embodiments, the cancer is a MUC16-positive cancer. In certain embodiments, the anti-cancer therapy is a MUC16 antagonist. In some embodiments the MUC16 antagonist is an antibody. In some embodiments the anti-MUC16 antibody is an ADC or TDC.

In some embodiments, the methods of the present disclosure include the step of measuring or detecting the expression level of human epididymis protein 4 (HE4) in a sample obtained from the subject or patient at a first time point, wherein the first time point is prior to administering to the subject or patient an anti-cancer therapy (e.g., a MUC16 antagonist); administering to the subject or patient a therapeutically effective amount of the anti-cancer therapy (e.g., a MUC16 antagonist); and measuring or detecting the level of expression of HE4 in a sample obtained from the subject or patient at a second time point, wherein the second time point is after administration of the anti-cancer therapy (e.g., a MUC16 antagonist), and wherein the subject or patient is administered one or more additional therapeutically effective amounts of the anti-cancer therapy (e.g., a MUC16 antagonist) if the level of expression of HE4 at the second time point is at least 25% lower than the level of expression of HE4 at the first time point.

Without wishing to be bound by theory, it is thought that the combined steps of measuring or detecting the level of expression of HE4 in a subject or patient and of administering a particular treatment (e.g., a therapeutically effective amount of a MUC16 antagonist) to identify changes in the level of expression of HE4 in the subject or patient before and after the administration of the MUC16 antagonist integrate the determination of changes in the level of expression of HE4 before and after administration of the MUC16 antagonist into the identification and treatment process. Moreover, these combined steps are not routine or conventional and ensure that subjects or patients with MUC16-positive cancers will be accurately diagnosed (based on a decrease of least 25% in the level of expression of HE4 after the administration of therapeutically effective amount of the MUC16 antagonist) and properly treated with the treatment regimen most effective for their individual case. As such, the methods of the present disclosure relate to significantly more than merely using changes in the expression level in a subject or patient to provide instructions to generically treat the MUC16-postive cancer, as they provide concrete steps for accurately identifying subjects or patients having a MUC16-positive cancer that would benefit from treatment with a specific treatment (e.g., a MUC16 antagonist).

Accordingly, certain embodiments of the methods described herein relate to measuring or detecting the level of expression of HE4 in a subject or patient having cancer (e.g., a MUC16-positive cancer), treating or delaying progression of cancer (e.g., a MUC16-positive cancer) in a subject or patient in need thereof by administering an anti-cancer therapy (e.g., a MUC16 antagonist); assessing, monitoring, or predicting responsiveness of a subject or patient having cancer (e.g., a MUC16-positive cancer) to an anti-cancer therapy (e.g., a MUC16 antagonist treatment); selecting a subject or patient having cancer (e.g., a MUC16-positive cancer) for anti-cancer therapy (e.g., a MUC16 antagonist) treatment; communicating the likelihood of response of a subject or patient having cancer (e.g., a MUC16-positive cancer) to an anti-cancer therapy (e.g., a MUC16 antagonist) treatment; methods for continuing, discontinuing, or modulating an anti-cancer therapy (e.g., a MUC16 antagonist) in a subject or patient having cancer (e.g., a MUC16-positive cancer); further administering a second treatment therapy to a subject or patient having a cancer (e.g., a MUC16-positive cancer); monitoring pharmacodynamic (PD) activity of an anti-cancer therapy (e.g., a MUC16 antagonist treatment) that is being administered or has been administered to a subject or patient having cancer (e.g., a MUC16-positive cancer); assessing tumor burden in a subject or patient having cancer (e.g., a MUC16-positive cancer); assessing progression-free survival in a subject or patient having cancer (e.g., a MUC16-positive cancer); marketing an anti-cancer therapy (e.g., a MUC16 antagonist, such as an anti-MUC16 antibody, MUC16 ADC, or MUC16 TDC) for use in cancer (e.g., a MUC16-positive cancer) patient subpopulation; diagnosing cancer (e.g., a MUC16-positive cancer or ovarian cancer) in a subject or patient; diagnosing a cancer (e.g., a MUC16-positive cancer or ovarian cancer) that is responsive to treatment in a subject or patient; diagnosing cancer progression (e.g., a MUC16-positive cancer or ovarian cancer) in a subject or patient; diagnosing and treating cancer (e.g., a MUC16-positive cancer or ovarian cancer) in a subject or patient; and use of HE4 expression levels for assessing responsiveness of treatment for ovarian cancer, endometrial cancer, triple-negative breast cancer, pancreatic cancer, and/or non-small cell lung cancer and related applications.

HE4 Expression

In certain embodiments, the methods of the present disclosure relate to measuring or detecting the level of expression of human epididymis protein 4 (HE4) in one or more samples obtained from a subject or patient having cancer to assess, for example, responsiveness of the subject to an anti-cancer therapy (e.g., a MUC16 antagonist). HE4 is also known as WAP four-disulfide core domain 2, dJ461P17.6, EDDM4, Epididymal secretory protein E4, Major epididymis-specific protein E4, MGC57529, WAP5, or WAP four-disulfide core domain protein 2. In some embodiments, the HE4 protein includes the amino acid sequence of a human HE4 protein (e.g., as described by GenBank Accession No. AAH46106.1). In some embodiments, the HE4 protein is a protein transcribed from a human HE4 gene (e.g., a human WFDC2 gene, such as the one described by NCBI Gene ID No. 10406). In some embodiments, HE4 refers to a nucleotide sequence of, or transcribed from, a human HE4 gene (e.g., a human WFDC2 gene, such as the one described by NCBI Gene ID No. 10406). Additional descriptions of HE4 may be found, e.g., in WO2012170513.

HE4 was identified in the epithelium of the distal epididymis using Northern blot analysis and in situ transcript hybridization (Kirchhoff et al, 1991 Biol Reprod, 45:350-357). Subsequent studies using RNA dot blots, reverse transcription polymerase chain reaction (RT-PCR) and Northern blot analysis suggested that HE4 RNA expression is widespread (Clauss et al, 2002 Biochem J, 368:233-242). Previous studies using comparative genomic hybridization and in silico chromosomal clustering reported that human chromosome 20q12-13.2 is consistently amplified in ovarian carcinomas and harbors genes that may play causal roles in the pathogenesis of the disease. This region contains a cluster of 14 genes with homology to whey acidic protein (WAP). Among these genes is HE4 that is overexpressed in, for example, ovarian and endometrial cancers. The expression of HE4 protein is highly restricted in normal human tissues and is largely limited to the epithelium of the reproductive tracts and to the respiratory epithelium of the proximal airways. In malignant neoplasms, gene expression profiling has consistently identified up-regulation of HE4 in carcinoma of the ovary (Wang et al, 1999 Gene, 229: 101-108; Hough C D et al, 2000 Cancer Res, 60:6281-6287; Gilks C B et al, 2005 Gynecol Oncol, 96:684-694).

In malignant tumor tissues, HE4 is considered a biomarker for epithelial ovarian carcinoma (WO/2007/081768; WO/2007/081767; Moore R G et al, 2008 Gynecologic Oncology, 1 10: 196-201; Moore R G et al, 2009 Gynecologic Oncology, 1 12:40-46 and others). Similarly, malignancies of corpus uteri are also positive for HE4. (Drapkin R et al, 2005 Cancer Res, 65:2162-2169). HE4 is also a marker for other MUllerian-derived tumors. In cell line studies, secreted HE4 was also seen in cell lines that express endogenous HE4 RNA (e.g., CaOV-3 and OVCAR5). Intracellular immunofluorescence studies revealed that HE4 is distributed in a region of the cytoplasm, or endoplasmic reticulum and the Golgi apparatus organelles (Drapkin R et al, 2005 Cancer Res, 65:2162-2169).

However, there are no previous reports of HE4 being a biomarker specific for MUC16-positive cancers. Furthermore, there are no previous reports of HE4 being used or contemplated as a surrogate biomarker for monitoring the efficacy an anti-MUC16 antibody therapy, specifically anti-MUC16 ADCs and TDCs. There are also no previous reports or suggestions of using an HE4 diagnostic to select patient populations for efficacy an anti-MUC16 antibody therapy, specifically anti-MUC16 ADCs and TDCs. There are also no previous reports or suggestions of using an HE4 diagnostic to adjust and optimize the dosing of a patient with an anti-MUC16 antibody therapy, specifically anti-MUC16 ADCs and TDCs. There are also no previous reports or suggestions of using an HE4 diagnostic to predict the efficacy of an anti-MUC16 antibody therapy, specifically anti-MUC16 ADCs and TDCs. There are also no previous reports or suggestions of using an HE4 diagnostic to select a patient population who would respond to a combination therapy of an anti-MUC16 antibody and a second or third chemotherapeutic, specifically anti-MUC16 ADCs and TDCs.

Additionally, there are no previous reports indicating that a specific threshold change in the level of expression of HE4 in a patient could be used as a surrogate biomarker for monitoring the efficacy of an anti-cancer therapy (e.g., a MUC16 antagonist) in the patient. Furthermore, there are no previous reports indicating what time point is useful as a baseline to determine the specific threshold change in the level of expression of HE4 in a patient for monitoring efficacy of an anti-cancer therapy (e.g., a MUC16 antagonist). There are also no previous reports or suggestions of using a specific threshold change in the level of expression of HE4 in a patient as a diagnostic to adjust and optimize the dosing of the patient with an anti-cancer therapy (e.g., a MUC16 antagonist). There are also no previous reports or suggestions of using a specific threshold change in the level of expression of HE4 in a patient as a diagnostic to predict the efficacy of an anti-cancer therapy (e.g., a MUC16 antagonist). There are also no previous reports or suggestions of using a specific threshold change in the level of expression of HE4 in a patient as a diagnostic to select a patient who would respond to a combination therapy of an anti-cancer therapy (e.g., a MUC16 antagonist) and a second or third chemotherapeutic. In contrast, the present disclosure is based, at least in part, on the determination that an at least 25% decrease in the level of expression of HE4 in a subject having cancer after the administration of a therapeutically effective amount of an anti-cancer therapy (e.g., a MUC16 antagonist), as compared to the level of expression of HE4 in the subject before administration of the immunoconjugate, indicates that the subject is responsive to the anti-cancer therapy (e.g., a MUC16 antagonist) and would be benefit from continued treatment with the anti-cancer therapy (e.g., a MUC16 antagonist). Advantageously, the at least 25% decrease in the level of expression of HE4 in a subject having cancer after the administration of a therapeutically effective amount of an anti-cancer therapy (e.g., a MUC16 antagonist), as compared to the level of expression of HE4 in the subject before administration of the anti-cancer therapy (e.g., a MUC16 antagonist), is also indicative of the anti-cancer therapy (e.g., a MUC16 antagonist) increasing progression-free survival.

Treating or Delaying Progression of Cancer

In certain embodiments, the methods of the present disclosure relate to methods for treating or delaying progression of cancer (e.g., a MUC16-positive cancer) in a subject or patient in need thereof by administering an anti-cancer therapy (e.g., a MUC16 antagonist). In some embodiments, the methods include measuring or detecting the level of expression of HE4 in a sample obtained from the subject at a first time point, administering to the subject a therapeutically effective amount of a MUC16 antagonist, measuring or detecting the level of expression of HE4 in a sample obtained from the subject at a second time point, and administering one or more therapeutically effective amounts of the MUC16 antagonist if the level of expression of HE4 at the second time point is lower than the level of expression of HE4 at the first time point. In some embodiments, the first time point is prior to administering to the subject a MUC16 antagonist. In some embodiments, the second time point is after administration of the MUC16 antagonist. In some embodiments, the subject has never received the MUC16 antagonist. In some embodiments, the subject is undergoing treatment with a MUC16 antagonist.

In some embodiments, the subject is administered one or more additional therapeutically effective amounts of the MUC16 antagonist if the level of expression of HE4 at the second time point is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% lower than the level of expression of HE4 at the first time point. In some embodiments, the subject is administered one or more additional therapeutically effective amounts of the MUC16 antagonist if the level of expression of HE4 at the second time point is at least at least 10% lower than the level of expression of HE4 at the first time point. In some embodiments, the subject is administered one or more additional therapeutically effective amounts of the MUC16 antagonist if the level of expression of HE4 at the second time point is at least at least 25% lower than the level of expression of HE4 at the first time point. In some embodiments, the subject is administered one or more additional therapeutically effective amounts of the MUC16 antagonist if the level of expression of HE4 at the second time point is at least at least 40% lower than the level of expression of HE4 at the first time point.

Predicting/Monitoring/Assessing Responsiveness

In certain embodiments, the methods of the present disclosure relate to methods for assessing, monitoring, or predicting responsiveness of a subject or patient having cancer (e.g., a MUC16-positive cancer) to an anti-cancer therapy (e.g., a MUC16 antagonist treatment). In some embodiments, the method comprises measuring or detecting the level of expression of HE4 in a sample obtained from a subject at a first time point, and measuring or detecting the level of expression of HE4 in a sample obtained from a subject at a second time point. In some embodiments, the second time point is after administration of the MUC16 antagonist. In some embodiments, the subject has never received the MUC16 antagonist. In some embodiments, the subject is undergoing treatment with a MUC16 antagonist.

In some embodiments, the method comprises measuring or detecting the level of expression of HE4 in a sample obtained from a subject at a first time point, administering to the subject a therapeutically effective amount of the MUC16 antagonist, and measuring or detecting the level of expression of HE4 in a sample obtained from a subject at a second time. In some embodiments, the first time point is prior to administering to the subject a MUC16 antagonist. In some embodiments, the second time point is after administration of the MUC16 antagonist. In some embodiments, the subject has never received the MUC16 antagonist. In some embodiments, the subject is undergoing treatment with a MUC16 antagonist.

In some embodiments, the method comprises classifying the subject or patient as responsive or non-responsive to treatment with the MUC16 antagonist based on the level of expression of HE4 in the sample obtained from the subject at the second time point, as compared to the first time point, where decreased the level of expression of HE4 at the second time point indicates the subject is or may be responsive to treatment with the MUC16 antagonist.

In some embodiments, a decrease of less than 25%, less than 20%, less than 15%, less than 10%, less than 9%, less than 8%, less than 7%, less than 6%, less than 5%, less than 4%, less than 3%, less than 2%, less than 1%, no decrease, or an increase of greater than 1%, greater than 2%, greater than 3%, greater than 4%, greater than 5%, greater than 10%, greater than 5%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or greater than 100% in the level of expression of HE4 from the first time point to the second time point indicates the subject is non-responsive to the MUC16 antagonist. In some embodiments, a decrease of less than 25% in the level of expression of HE4 from the first time point to the second time point indicates the subject is non-responsive to the MUC16 antagonist. In some embodiments, a decrease of less 10% in the level of expression of HE4 from the first time point to the second time point indicates the subject is non-responsive to the MUC16 antagonist. In some embodiments, a decrease of less than 5% in the level of expression of HE4 from the first time point to the second time point indicates the subject is non-responsive to the MUC16 antagonist. In some embodiments, no decrease in the level of expression of HE4 from the first time point to the second time point indicates the subject is non-responsive to the MUC16 antagonist. In some embodiments, an increase in the level of expression of HE4 from the first time point to the second time point indicates the subject is non-responsive to the MUC16 antagonist. In some embodiments, an increase of greater than 5% in the level of expression of HE4 from the first time point to the second time point indicates the subject is non-responsive to the MUC16 antagonist. In some embodiments, an increase of greater than 15% in the level of expression of HE4 from the first time point to the second time point indicates the subject is non-responsive to the MUC16 antagonist. In some embodiments, an increase of greater than 25% in the level of expression of HE4 from the first time point to the second time point indicates the subject is non-responsive to the MUC16 antagonist. In some embodiments, an increase of greater than 50% in the level of expression of HE4 from the first time point to the second time point indicates the subject is non-responsive to the MUC16 antagonist.

In some embodiments, a decrease of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in the level of expression of HE4 from the first time point to the second time point indicates the subject is responsive to the MUC16 antagonist. In some embodiments, a decrease of at least 10% in the level of expression of HE4 from the first time point to the second time point indicates the subject is responsive to the MUC16 antagonist. In some embodiments, a decrease of at least 25% in the level of expression of HE4 from the first time point to the second time point indicates the subject is responsive to the MUC16 antagonist. In some embodiments, a decrease of at least 40% in the level of expression of HE4 from the first time point to the second time point indicates the subject is responsive to the MUC16 antagonist.

In some embodiments, responsiveness refers to treatment efficacy. It will be appreciated by one of skill in the art that many measures of treatment efficacy, and combinations thereof, may be useful. In some embodiments, treatment efficacy may include a tumor response (e.g., a stabilization or reduction in tumor size, growth, or histological stage). In some embodiments, treatment efficacy may include increased survival (e.g., one-year, 5-year, disease-free, or overall), increased quality of life, increased time to progression, or decreased morbidity. Such factors may be assessed, e.g., by using a statistical tool such as logistic regression, Cox's proportional hazards regression, or Kaplan-Meier estimates.

In some embodiments, responsiveness refers to reduced tumor volume. For example, in some embodiments, responsiveness refers to a reduction of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in tumor volume. In some embodiments, responsiveness refers to a reduction in tumor volume that is less than about any of the following percentages: 100, 95, 90, 85, 80, 75, 70, 65, 60, 55, 50, 45, 40, 35, 30, 25, 20, 15, or 10. In some embodiments, responsiveness refers to a reduction in tumor volume that is greater than about any of the following percentages: 5, 10, 15, 20, 25, 30, 35, 40, 45, 50, 55, 60, 65, 70, 75, 80, 85, 90, or 95. That is, responsiveness may refer to a reduction in tumor volume that can be any of a range of percentages having an upper limit of 100, 95, 90, 85, 80, 75, 70, 65, 60, 55, 50, 45, 40, 35, 30, 25, 20, 15, or 10 and an independently selected lower limit of 5, 10, 15, 20, 25, 30, 35, 40, 45, 50, 55, 60, 65, 70, 75, 80, 85, 90, or 95, wherein the lower limit is less than the upper limit. Tumor volume may refer to the volume of a signal tumor, or it may refer to the aggregate volume of multiple tumors. In some embodiments, a reduction in tumor volume is measured in comparison with the tumor volume before treatment, e.g., with a MUC16 antagonist treatment.

In some embodiments, responsiveness refers to serologic responsiveness. In some embodiments, serologic responsiveness may refer to an improvement in or an alteration of one or more serologic markers indicative of a response to treatment. In some embodiments, a serologic marker is a marker present in a serum or blood sample or a cell present therein. Examples of serologic markers include without limitation red blood cells (RBCs), white blood cells (WBCs), a circulating biomarker, albumin, hemoglobin, DNA adducts (e.g., in plasma, RBCs, or WBCs), serum alpha fetoprotein (alpha-FP), human chorionic gonadotropin (e.g., beta-hCG), estradiol, inhibin, carcinoembryonic antigen (CEA), ferritin, human telomerase reverse transcriptase (hTERT), topoisomerase II, urinary gonadotropin fragment, squamous cell carcinoma (SCC) antigen, Mullerian inhibiting substance (MIS), carbohydrate antigen 19-9, cancer antigen 27-29, cyclin E, OVX1, CA-15-3, CA-19-9, insulinlike growth factor-binding protein-3, macrophage colony-stimulating factor (M-CSF), IL-8, VEGF, osteopontin, mesothelin, lysophosphatidic acid, MIB 1-determined tumor growth fraction, L1 (CAM), and the like. Exemplary serologic markers may be found, e.g., in Eagle, K. and Ledermann, J. A. (1997) *Oncologist* 2:324-329 and Gadducci, A. et al. (2004) *Biomed. Pharmacother.* 58:24-38.

In some embodiments, responsiveness to treatment may refer to any one or more of: extending survival (including overall survival and progression free survival); resulting in an objective response (including a complete response or a partial response); or improving signs or symptoms of cancer. In some embodiments, responsiveness refers to a lower sum of the longest diameter (SLD) response. For example, in some embodiments, responsiveness refers to a reduction of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in the SLD of target lesions. In some embodiments, responsiveness refers to a higher RECIST response, e.g., an improvement of one or more factors according to the published set of RECIST for determining the status of a tumor (such as responding, stabilizing, or progressing) in a cancer patient. For a more detailed discussion of these guidelines, see Eisenhauer et al., Eur J Cancer 2009; 45: 228-47; Topalian et al., N Engl J Med 2012; 366:2443-54; Wolchok et al., Clin Can Res 2009; 15:7412-20; and Therasse, P., et al. J. Natl. Cancer Inst. 92:205-16 (2000). A responsive subject may refer to a subject whose cancer(s) show improvement, e.g., according to one or more factors based on RECIST. A non-responsive subject may refer to a subject whose cancer(s) do not show improvement, e.g., according to one or more factors based on RECIST.

Conventional response criteria may not be adequate to characterize the anti-tumor activity of immunotherapeutic agents, which can produce delayed responses that may be preceded by initial apparent radiological progression, including the appearance of new lesions. Therefore, modified response criteria have been developed that account for the possible appearance of new lesions and allow radiological progression to be confirmed at a subsequent assessment. Accordingly, in some embodiments, responsiveness may refer to improvement of one of more factors according to immune-related response criteria (irRC). See, e.g., Wolchok et al., Clin Can Res 2009; 15:7412-20. In some embodiments, new lesions are added into the defined tumor burden and followed, e.g., for radiological progression at a subsequent assessment. In some embodiments, presence of non-target lesions are included in assessment of complete response and not included in assessment of radiological progression. In some embodiments, radiological progression may be determined only on the basis of measurable disease and/or may be confirmed by a consecutive assessment ≥4 weeks from the date first documented.

In some embodiments, a decrease in the level of expression of HE4 of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% correlates with stable disease and/or a partial RECIST response. In certain embodiments, a decrease of at least 10% in the level of expression of HE4 correlates with stable disease and/or a partial RECIST response. In certain embodiments, a decrease of at least 25% in the level of expression of HE4 correlates with stable disease and/or a partial RECIST response. In certain embodiments, a decrease of at least 40% in the level of expression of HE4 correlates with stable disease and/or a partial RECIST response.

Selecting a Subject for Treatment/Communicating Likelihood of Response

In certain embodiments, the methods of the present disclosure relate to methods for selecting a subject or patient having cancer (e.g., a MUC16-positive cancer) for anti-cancer therapy (e.g., a MUC16 antagonist) treatment. In some embodiments, the method comprises measuring or detecting the level of expression of HE4 in a sample obtained from the subject at a first time point prior to administering to the subject a MUC16 antagonist, measuring or detecting the level of expression of HE4 in a sample obtained from the subject at a second time point after administering to the subject a MUC16 antagonist, and selecting the subject for treatment with one or more additional therapeutically effective amounts of the MUC16 antagonist. In some embodiments, selecting the subject for treatment comprises selecting the subject for inclusion in a clinical trial.

In some embodiments, the subject is selected for treatment with one or more additional therapeutically effective amounts of the MUC16 antagonist if the level of expression of HE4 at the second time point is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% lower than the level of expression of HE4 at the first time point. In some embodiments, the subject is selected for treatment with one or more additional therapeutically effective amounts of the MUC16 antagonist if the level of expression of HE4 at the second time point is at least at least 10% lower than the level of expression of HE4 at the first time point. In some embodiments, the subject is selected for treatment with one or more additional therapeutically effective amounts of the MUC16 antagonist if the level of expression of HE4 at the second time point is at least at least 25% lower than the level of expression of HE4 at the first time point. In some embodiments, the subject is selected for treatment with one or more additional therapeutically effective amounts of the MUC16 antagonist if the level of expression of HE4 at the second time point is at least at least 40% lower than the level of expression of HE4 at the first time point.

In certain embodiments, the methods of the present disclosure relate to methods for communicating the likelihood of response of a subject or patient having cancer (e.g., a MUC16-positive cancer) to an anti-cancer therapy (e.g., a MUC16 antagonist) treatment. In some embodiments, the method comprises measuring or detecting the level of expression of HE4 in a sample obtained from the subject at a first time point, prior to administering to the subject a MUC16 antagonist; measuring or detecting the level of expression of HE4 in a sample obtained from the subject at a second time point, after administration of a MUC16 antagonist; and communicating to a treatment provider the level of expression of HE4 at the second time point relative to the first time point. In some embodiments, the treatment provider takes action based upon the communication. In some embodiments, the treatment provider administers one or more additional therapeutically effective amount of MUC16 antagonist to the subject. In some embodiments, the treatment provider selects the subject for treatment with one or more additional therapeutically effective amounts of the MUC16 antagonist based on the communication.

In some embodiments, the treatment provider takes action if the level of expression of HE4 at the second time point is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% lower than the level of expression of HE4 at the first time point. In some embodiments, the treatment provider takes action if the level of expression of HE4 at the second time point is at least at least 10% lower than the level of expression of HE4 at the first time point. In some embodiments, the treatment provider takes action if the level of expression of HE4 at the second time point is at least at least 25% lower than the level of expression of HE4 at the first time point. In some embodiments, the treatment provider takes action if the level of expression of HE4 at the second time point is at least at least 40% lower than the level of expression of HE4 at the first time point.

Continuing/Discontinuing/Modulating Treatment

As disclosed herein, a measurement of the level of expression of HE4 in a sample from a subject after administration of an anti-cancer therapy (e.g., a MUC16 antagonist) and/or undergoing anti-cancer therapy (e.g., a MUC16 antagonist) treatment) may be used to guide subsequent treatment, for example, continuing the anti-cancer therapy (e.g., a MUC16 antagonist treatment), discontinuing the anti-cancer therapy (e.g., a MUC16 antagonist treatment), or modulating the anti-cancer therapy (e.g., a MUC16 antagonist treatment). Accordingly, in certain embodiments, the methods of the present disclosure relate to methods for modulating an anti-cancer therapy (e.g., a MUC16 antagonist) in a subject or patient having cancer (e.g., a MUC16-positive cancer). In some embodiments, the method comprises measuring or detecting the level of expression of HE4 in a sample obtained from the subject at a first time point, administering to the subject a therapeutically effective amount of a MUC16 antagonist, measuring or detecting the level of expression of HE4 in a sample obtained from the subject at a second time point, and modulating the amount of MUC16 antagonist administered to the subject based on the changes in the level of expression of HE4 between the first and second time points. In some embodiments, the first time point is prior to administering to the subject a MUC16 antagonist. In some embodiments, the second time point is after administration of the MUC16 antagonist.

In some embodiments, modulating the amount of MUC16 antagonist administered to the subject comprises maintaining the same level of MUC16 antagonist administered to the subject.

In some embodiments, modulating the amount of MUC16 antagonist administered to the subject comprises increasing the level of MUC16 antagonist administered to the subject. An increase in the level of MUC16 antagonist administered to the subject may refer without limitation to one or more of: increasing the amount, dose, number or frequency of doses, or concentration of the MUC16 antagonist administered to the subject.

In some embodiments, modulating the amount of MUC16 antagonist administered to the subject comprises decreasing the level of MUC16 antagonist administered to the subject. A decrease in the level of MUC16 antagonist administered to the subject may refer without limitation to one or more of: decreasing the amount, dose, number or frequency of doses, or concentration of the MUC16 antagonist administered to the subject.

Further Treatment Therapies

In certain embodiments, the methods of the present disclosure that relate to administration of an anti-cancer therapy (e.g., a MUC16 antagonist) may further include administration of a second treatment therapy to the subject or patient. In some embodiments, the subject or patient has been classified as responsive to the MUC16 antagonist treatment. In certain embodiments, the second treatment therapy (or "combination therapy") comprises an anti-MUC16 antibody (e.g., an ADC or TDC) and a second therapeutic agent. In some embodiments, the second therapeutic agent is an antibody therapy. In certain embodiments, the second treatment therapy is Avastin®.

In some embodiments, the second treatment therapy may include a maintenance therapy. By "maintenance therapy" is meant a therapeutic regimen that is given to reduce the likelihood of disease recurrence or progression after a beneficial outcome of an initial therapeutic intervention. Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy.

In some embodiments, the second treatment therapy may include a chemotherapy. For example, one or more of any of the chemotherapeutic agents described herein may be used in a chemotherapy treatment.

Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, and U.S. Patent Application 60/991,302, the content of these patent applications are expressly incorporated herein by reference. For additional antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., Journal of Immunological Methods 288:149-164 (2004). Other antibodies include those that bind to a functional epitope on human VEGF comprising of residues F17, M18, D19, Y21, Y25, Q89, 1191, K101, E103, and C104 or, alternatively, comprising residues F17, Y21, Q22, Y25, D63, 183 and Q89.

In some embodiments, the maintenance therapy can comprise an anti-VEGF therapy after completion of a chemotherapeutic regimen. For example, the maintenance therapy can be provided for at least 16 cycles after completion of chemotherapy concurrently with 5 cycles of anti-VEGF therapy. In other embodiments, maintenance therapy is provided for at least 12 cycles after completion of the chemotherapy concurrently with 6 cycles of anti-VEGF therapy. A "maintenance" dose refers to one or more doses of a therapeutic agent administered to the patient over or after a treatment period. Usually, the maintenance doses are administered at spaced treatment intervals, such as approximately every week, approximately every 2 weeks, approximately every 3 weeks, or approximately every 4 weeks. Anti-VEGF therapeutic regiments are known in the art; the particular regimen chosen for an individual will depend on the type of cancer to be treated, as defined above, the severity and course of the cancer, whether the antibody is administered for preventive or therapeutic purposes, previous therapy, the patient's clinical history and response to the drug, and the discretion of the attending physician.

Monitoring Pharmacodynamic (PD) Activity

In certain embodiments, the methods of the present disclosure relate to methods for monitoring pharmacodynamic (PD) activity of an anti-cancer therapy (e.g., a MUC16 antagonist treatment) that is being administered or has been administered to a subject having cancer (e.g., a MUC16-positive cancer). In some embodiments, the methods include measuring the level of expression of HE4 in a sample from the subject at a first time point, where the subject has been treated with an MUC16 antagonist; and determining the treatment as demonstrating pharmacodynamic activity based on the expression level of the HE4 in the sample obtained from the subject at a second time point, as compared with the first time point, where a decreased expression level of the HE4 at the second time point as compared with the first time point indicates pharmacodynamic activity to the MUC16 antagonist treatment.

In some embodiments, pharmacodynamic activity to the MUC16 antagonist is indicated if the level of expression of HE4 at the second time point is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% lower than the level of expression of HE4 at the first time point. In some embodiments, pharmacodynamic activity to the MUC16 antagonist is indicated if the level of expression of HE4 at the second time point is at least at least 10% lower than the level of expression of HE4 at the first time point. In some embodiments, pharmacodynamic activity to the MUC16 antagonist is indicated if the level of expression of HE4 at the second time point is at least at least 25% lower than the level of expression of HE4 at the first time point. In some embodiments, pharmacodynamic activity to the MUC16 antagonist is indicated if the level of expression of HE4 at the second time point is at least at least 40% lower than the level of expression of HE4 at the first time point.

As used herein, "pharmacodynamic (PD) activity" may refer to an effect of a treatment (e.g., a MUC16 antagonist treatment) to the subject. An example of a PD activity may include modulation of the expression level of one or more genes or proteins. Without wishing to be bound to theory, it is thought that monitoring PD activity, such as by measuring expression of a gene marker or protein, may be advantageous during a clinical trial examining an MUC16 antagonist. Monitoring PD activity may be used, for example, to monitor response to treatment, toxicity, and the like.

Assessing Tumor Burden

In certain embodiments, the methods of the present disclosure relate to methods for assessing tumor burden in a subject or patient having cancer (e.g., a MUC16-positive cancer). In some embodiments, the method comprises measuring or detecting the level of expression of HE4 in a sample obtained from the subject at a first time point, and measuring or detecting the level of expression of HE4 in a sample obtained from the subject at a second time point. In some embodiments, an increase in the level of expression of HE4 from the first time point to the second time point correlates with an increased tumor burden in the subject. In some embodiments, the correlation between increased HE4 expression and increased tumor burden is directly proportional. In some embodiments, an increase in tumor burden in the subject comprises an increase in tumor size and or tumor volume. In some embodiments, an increase in tumor size and or tumor volume refers to an increase of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in tumor size and/or volume. In some embodiments, an increase in tumor burden is predictive of cancer progression in the subject.

In some embodiments, the subject is administered a therapeutically effective amount of a MUC16 antagonist after the first time point and prior to the second time point. In some embodiments, an increased tumor burden indicates that the subject is unresponsive to the MUC16 antagonist. In some embodiments, the first time point is prior to administering to the subject a MUC16 antagonist. In some embodiments, the second time point is after administration of the MUC16 antagonist.

Predicting Cancer Progression

In certain embodiments, the methods of the present disclosure relate to methods for assessing progression-free survival in a subject or patient having cancer (e.g., a MUC16-positive cancer). In some embodiments, the method comprises measuring or detecting the level of expression of HE4 in a sample obtained from the subject at a first time point, administering to the subject a therapeutically effective amount of a MUC16 antagonist, and measuring or detecting the level of expression of HE4 in a sample obtained from the subject at a second time point. In some embodiments, the first time point is prior to administering to the subject a MUC16 antagonist. In some embodiments, the second time point is after administration of the MUC16 antagonist.

In some embodiments, a decrease of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in the level of expression of HE4 from the first time point to the second time point indicates the MUC16 antagonist increases progression-free survival. In some embodiments, a decrease of at least 10% in the level of expression of HE4 from the first time point to the second time point indicates the MUC16 antagonist increases progression-free survival. In some embodiments, a decrease of at least 25% in the level of expression of HE4 from the first time point to the second time point indicates the MUC16 antagonist increases progression-free survival. In some embodiments, a decrease of at least 40% in the level of expression of HE4 from the first time point to the second time point indicates the MUC16 antagonist increases progression-free survival.

Also provided herein are methods for predicting cancer progression in a subject or patient having a MUC16-positive cancer. In some embodiments, the method comprises measuring or detecting the level of expression of HE4 in a sample obtained from the subject at a first time point, administering to the subject a therapeutically effective amount of a MUC16 antagonist, and measuring or detecting the level of expression of HE4 in a sample obtained from the subject at a second time point. In some embodiments, the first time point is prior to administering to the subject a MUC16 antagonist. In some embodiments, the second time point is after administration of the MUC16 antagonist.

In some embodiments, a decrease of less than 25%, less than 20%, less than 15%, less than 10%, less than 9%, less than 8%, less than 7%, less than 6%, less than 5%, less than 4%, less than 3%, less than 2%, less than 1%, no decrease, or an increase of greater than 1%, greater than 2%, greater than 3%, greater than 4%, greater than 5%, greater than 10%, greater than 5%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or greater than 100% in the level of expression of HE4 from the first time point to the second time point indicates the subject has a cancer that is likely to progress. In some embodiments, a decrease of less than 25% in the level of expression of HE4 from the first time point to the second time point indicates the subject has a cancer that is likely to progress. In some embodiments, a decrease of less 10% in the level of expression of HE4 from the first time point to the second time point indicates the subject has a cancer that is likely to progress. In some embodiments, a decrease of less than 5% in the level of expression of HE4 from the first time point to the second time point indicates the subject has a cancer that is likely to progress. In some embodiments, no decrease in the level of expression of HE4 from the first time point to the second time point indicates the subject has a cancer that is likely to progress. In some embodiments, an increase in the level of expression of HE4 from the first time point to the second time point indicates the subject has a cancer that is likely to progress. In some embodiments, an increase of greater than 5% in the level of expression of HE4 from the first time point to the second time point indicates the subject has a cancer that is likely to progress. In some embodiments, an increase of greater than 15% in the level of expression of HE4 from the first time point to the second time point indicates the subject has a cancer that is likely to progress. In some embodiments, an increase of greater than 25% in the level of expression of HE4 from the first time point to the second time point indicates the subject has a cancer that is likely to progress. In some embodiments, an increase of greater than 50% in the level of expression of HE4 from the first time point to the second time point indicates the subject has a cancer that is likely to progress.

Marketing

In certain embodiments, the methods of the present disclosure relate to methods for marketing an anti-cancer therapy (e.g., a MUC16 antagonist, such as an anti-MUC16 antibody, MUC16 ADC, or MUC16 TDC) or a pharmaceutically acceptable composition thereof for use in cancer (e.g., a MUC16-positive cancer) patient subpopulation. In some embodiments, the methods include informing a target audience about the use of a MUC16 antagonist (e.g., an anti-MUC16 antibody, MUC16 ADC, or MUC16 TDC) for treating the patient subpopulation characterized by the patients of such subpopulation having an elevated the level of expression of HE4 at a second time point as compared with a first time point.

Diagnosis

In certain embodiments, the methods of the present disclosure relate to methods for diagnosing a MUC16-positive cancer in a patient. In some embodiments, the method comprises obtaining a sample from a human patient, detecting the expression level of HE4 in the sample, detecting whether the expression level of HE4 in the patient decreases after treatment with an anti-MUC16 antibody by administering to the patient a therapeutically effective amount of an anti-MUC16 antibody and detecting the expression level of HE4 in the sample obtained from the patient after administration of the anti-MUC16 antibody, and diagnosing the patient with a MUC16-positive cancer when the level of expression of HE4 after administration of the anti-MUC16 antibody is lower than the level of expression of HE4 before administration of the anti-MUC16 antibody.

In some embodiments, a patient is diagnosed with a MUC16-positive cancer when the level of expression of HE4 after administration of the anti-MUC16 antibody is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% lower than the level of expression of HE4 before administration of the anti-MUC16 antibody. In some embodiments, a patient is diagnosed with a MUC16-positive cancer when the level of expression of HE4 after administration of the anti-MUC16 antibody is at least 10% lower than the level of expression of HE4 before administration of the anti-MUC16 antibody. In some embodiments, a patient is diagnosed with a MUC16-positive cancer when the level of expression of HE4 after administration of the anti-MUC16 antibody is at least 25% lower than the level of expression of HE4 before administration of the anti-MUC16 antibody. In some embodiments, a patient is diagnosed with a MUC16-positive cancer when the level of expression of HE4 after administration of the anti-MUC16 antibody is at least 40% lower than the level of expression of HE4 before administration of the anti-MUC16 antibody.

In certain embodiments, the methods of the present disclosure relate to methods for diagnosing a MUC16-positive cancer that is responsive to treatment with a MUC16 antagonist in a patient. In some embodiments, the method comprises obtaining a sample from a human patient, detecting the expression level of HE4 in the sample, detecting whether the expression level of HE4 in the patient decreases after treatment with the MUC16 antagonist by administering to the patient a therapeutically effective amount of an anti-MUC16 antibody and detecting the expression level of HE4 in the sample obtained from the patient after administration of the anti-MUC16 antibody, and diagnosing the patient with a MUC16-positive cancer that is responsive to treatment with a MUC16 antagonist when the level of expression of HE4 after administration of the anti-MUC16 antibody is lower than the level of expression of HE4 before administration of the anti-MUC16 antibody. In some embodiments, the patient has never received a MUC16 antagonist. In some embodiments, the patient is undergoing treatment with a MUC16 antagonist. In some embodiments, the method further comprises administering to the patient one or more additional therapeutically effective amount of the anti-MUC16 antibody.

In some embodiments, a patient is diagnosed with a MUC16-positive cancer that is responsive to treatment with a MUC16 antagonist when the level of expression of HE4 after administration of the anti-MUC16 antibody is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% lower than the level of expression of HE4 before administration of the anti-MUC16 antibody. In some embodiments, a patient is diagnosed with a MUC16-positive cancer that is responsive to treatment with a MUC16 antagonist when the level of expression of HE4 after administration of the anti-MUC16 antibody is at least 10% lower than the level of expression of HE4 before administration of the anti-MUC16 antibody. In some embodiments, a patient is diagnosed with a MUC16-positive cancer that is responsive to treatment with a MUC16 antagonist when the level of expression of HE4 after administration of the anti-MUC16 antibody is at least 25% lower than the level of expression of HE4 before administration of the anti-MUC16 antibody. In some embodiments, a patient is diagnosed with a MUC16-positive cancer that is responsive to treatment with a MUC16 antagonist when the level of expression of HE4 after administration of the anti-MUC16 antibody is at least 40% lower than the level of expression of HE4 before administration of the anti-MUC16 antibody.

In some embodiments, responsiveness refers to treatment efficacy. It will be appreciated by one of skill in the art that many measures of treatment efficacy, and combinations thereof, may be useful. In some embodiments, treatment efficacy may include a tumor response (e.g., a stabilization or reduction in tumor size, growth, or histological stage). In some embodiments, treatment efficacy may include increased survival (e.g., one-year, 5-year, disease-free, or overall), increased quality of life, increased time to progression, or decreased morbidity. Such factors may be assessed, e.g., by using a statistical tool such as logistic regression, Cox's proportional hazards regression, or Kaplan-Meier estimates.

In some embodiments, responsiveness refers to reduced tumor volume. For example, in some embodiments, responsiveness refers to a reduction of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in tumor volume. In some embodiments, responsiveness refers to a reduction in tumor volume that is less than about any of the following percentages: 100, 95, 90, 85, 80, 75, 70, 65, 60, 55, 50, 45, 40, 35, 30, 25, 20, 15, or 10. In some embodiments, responsiveness refers to a reduction in tumor volume that is greater than about any of the following percentages: 5, 10, 15, 20, 25, 30, 35, 40, 45, 50, 55, 60, 65, 70, 75, 80, 85, 90, or 95. That is, responsiveness may refer to a reduction in tumor volume that can be any of a range of percentages having an upper limit of 100, 95, 90, 85, 80, 75, 70, 65, 60, 55, 50, 45, 40, 35, 30, 25, 20, 15, or 10 and an independently selected lower limit of 5, 10, 15, 20, 25, 30, 35, 40, 45, 50, 55, 60, 65, 70, 75, 80, 85, 90, or 95, wherein the lower limit is less than the upper limit. Tumor volume may refer to the volume of a signal tumor, or it may refer to the aggregate volume of multiple tumors. In some embodiments, a reduction in tumor volume is measured in comparison with the tumor volume before treatment, e.g., with an anti-cancer therapy.

In some embodiments, responsiveness refers to serologic responsiveness. In some embodiments, serologic responsiveness may refer to an improvement in or an alteration of one or more serologic markers indicative of a response to treatment. In some embodiments, a serologic marker is a marker present in a serum or blood sample or a cell present therein. Examples of serologic markers include without limitation red blood cells (RBCs), white blood cells (WBCs), a circulating biomarker, albumin, hemoglobin, DNA adducts (e.g., in plasma, RBCs, or WBCs), serum alpha fetoprotein (alpha-FP), human chorionic gonadotropin (e.g., beta-hCG), estradiol, inhibin, carcinoembryonic antigen (CEA), ferritin, human telomerase reverse transcriptase (hTERT), topoisomerase II, urinary gonadotropin fragment, squamous cell carcinoma (SCC) antigen, Mullerian inhibiting substance (MIS), carbohydrate antigen 19-9, cancer antigen 27-29, cyclin E, OVX1, CA-15-3, CA-19-9, insulinlike growth factor-binding protein-3, macrophage colony-stimulating factor (M-CSF), IL-8, VEGF, osteopontin, mesothelin, lysophosphatidic acid, MIB 1-determined tumor growth fraction, L1 (CAM), and the like. Exemplary serologic markers may be found, e.g., in Eagle, K. and Ledermann, J. A. (1997) *Oncologist* 2:324-329 and Gadducci, A. et al. (2004) *Biomed. Pharmacother.* 58:24-38.

In some embodiments, responsiveness to treatment may refer to any one or more of: extending survival (including overall survival and progression free survival); resulting in an objective response (including a complete response or a partial response); or improving signs or symptoms of cancer. In some embodiments, responsiveness refers to a lower sum of the longest diameter (SLD) response. For example, in some embodiments, responsiveness refers to a reduction of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in the SLD of target lesions. In some embodiments, responsiveness refers to a higher RECIST response, e.g., an improvement of one or more factors according to the published set of RECIST for determining the status of a tumor (such as responding, stabilizing, or progressing) in a cancer patient. For a more detailed discussion of these guidelines, see Eisenhauer et al., Eur J Cancer 2009; 45: 228-47; Topalian et al., N Engl J Med 2012; 366:2443-54; Wolchok et al., Clin Can Res 2009; 15:7412-20; and Therasse, P., et al. J. Natl. Cancer Inst. 92:205-16 (2000). A responsive subject may refer to a subject whose cancer(s) show improvement, e.g., according to one or more factors based on RECIST. A non-responsive subject may refer to a subject whose cancer(s) do not show improvement, e.g., according to one or more factors based on RECIST.

Conventional response criteria may not be adequate to characterize the anti-tumor activity of immunotherapeutic agents, which can produce delayed responses that may be preceded by initial apparent radiological progression, including the appearance of new lesions. Therefore, modified response criteria have been developed that account for the possible appearance of new lesions and allow radiological progression to be confirmed at a subsequent assessment. Accordingly, in some embodiments, responsiveness may refer to improvement of one of more factors according to immune-related response criteria (irRC). See, e.g., Wolchok et al., Clin Can Res 2009; 15:7412-20. In some embodiments, new lesions are added into the defined tumor burden and followed, e.g., for radiological progression at a subsequent assessment. In some embodiments, presence of non-target lesions are included in assessment of complete response and not included in assessment of radiological progression. In some embodiments, radiological progression may be determined only on the basis of measurable disease and/or may be confirmed by a consecutive assessment ≥4 weeks from the date first documented.

In certain embodiments, the methods of the present disclosure relate to methods for diagnosing and treating a MUC16-positive cancer in a patient. In some embodiments, the method comprises obtaining a sample from a human patient, detecting the expression level of HE4 in the sample, detecting whether the expression level of HE4 in the patient decreases after treatment with the MUC16 antagonist by administering to the patient a therapeutically effective amount of an anti-MUC16 antibody and detecting the expression level of HE4 in the sample obtained from the patient after administration of the anti-MUC16 antibody, diagnosing the patient with a MUC16-positive cancer that is responsive to treatment with a MUC16 antagonist when the level of expression of HE4 after administration of the anti-MUC16 antibody is lower than the level of expression of HE4 before administration of the anti-MUC16 antibody, and administering one or more additional therapeutically effective amounts of the anti-MUC16 antibody to the diagnosed patient. In some embodiments, the method further comprises administering one or more additional therapeutically effective amounts of the anti-MUC16 antibody to the diagnosed patient.

In some embodiments, a patient is diagnosed with a MUC16-positive cancer when the level of expression of HE4 after administration of the anti-MUC16 antibody is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% lower than the level of expression of HE4 before administration of the anti-MUC16 antibody. In some embodiments, a patient is diagnosed with a MUC16-positive cancer when the level of expression of HE4 after administration of the anti-MUC16 antibody is at least 10% lower than the level of expression of HE4 before administration of the anti-MUC16 antibody. In some embodiments, a patient is diagnosed with a MUC16-positive cancer when the level of expression of HE4 after administration of the anti-MUC16 antibody is at least 25% lower than the level of expression of HE4 before administration of the anti-MUC16 antibody. In some embodiments, a patient is diagnosed with a MUC16-positive cancer when the level of expression of HE4 after administration of the anti-MUC16 antibody is at least 40% lower than the level of expression of HE4 before administration of the anti-MUC16 antibody.

In certain embodiments, the methods of the present disclosure relate to methods for diagnosing cancer progression in a patient having MUC16-positive cancer. In some embodiments, the method comprises obtaining a sample from a human patient, detecting the expression level of HE4 in the sample, detecting whether the expression level of HE4 in the patient decreases after treatment with an anti-MUC16 antibody by administering to the patient a therapeutically effective amount of an anti-MUC16 antibody and detecting the expression level of HE4 in the sample obtained from the patient after administration of the anti-MUC16 antibody, and diagnosing the patient with a MUC16-positive cancer that is likely to progress when the level of expression of HE4 after administration of the antiMUC16 antibody is less than 25% lower than the level of expression of HE4 before administration of the anti-MUC16 antibody. In some embodiments, the method comprises obtaining a sample from a human patient, detecting the expression level of HE4 in the sample, detecting whether the expression level of HE4 in the patient decreases after treatment with an anti-MUC16 antibody by administering to the patient a therapeutically effective amount of an anti-MUC16 antibody and detecting the expression level of HE4 in the sample obtained from the patient after administration of the anti-MUC16 antibody, and diagnosing the patient with a MUC16-positive cancer that is likely to progress when the level of expression of HE4 after administration of the antiMUC16 antibody is the same as the level of expression of HE4 before administration of the anti-MUC16 antibody. In some embodiments, the method comprises obtaining a sample from a human patient, detecting the expression level of HE4 in the sample, detecting whether the expression level of HE4 in the patient decreases after treatment with an anti-MUC16 antibody by administering to the patient a therapeutically effective amount of an anti-MUC16 antibody and detecting the expression level of HE4 in the sample obtained from the patient after administration of the anti-MUC16 antibody, and diagnosing the patient with a MUC16-positive cancer that is likely to progress when the level of expression of HE4 after administration of the antiMUC16 antibody is more than the level of expression of HE4 before administration of the anti-MUC16 antibody.

In some embodiments, a patient is diagnosed with a MUC16-positive cancer that is likely to progress when the level of expression of HE4 after administration of the anti-MUC16 antibody is less than 25%, less than 20%, less than 15%, less than 10%, less than 9%, less than 8%, less than 7%, less than 6%, less than 5%, less than 4%, less than 3%, less than 2%, less than 1% lower than the level of expression of HE4 before administration of the anti-MUC16 antibody. In some embodiments, a patient is diagnosed with a MUC16-positive cancer that is likely to progress when the level of expression of HE4 after administration of the anti-MUC16 antibody is the same as the level of expression of HE4 before administration of the anti-MUC16 antibody. In some embodiments, a patient is diagnosed with a MUC16-positive cancer that is likely to progress when the level of expression of HE4 after administration of the anti-MUC16 antibody is more than 1%, more than 2%, more than 3%, more than 4%, more than 5%, more than 10%, more than 5%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, or more than 100% higher than the level of expression of HE4 before administration of the anti-MUC16 antibody. In some embodiments, a patient is diagnosed with a MUC16-positive cancer that is likely to progress when the level of expression of HE4 after administration of the anti-MUC16 antibody is less than 25% lower than the level of expression of HE4 before administration of the anti-MUC16 antibody. In some embodiments, a patient is diagnosed with a MUC16-positive cancer that is likely to progress when the level of expression of HE4 after administration of the anti-MUC16 antibody is less than 10% lower than the level of expression of HE4 before administration of the anti-MUC16 antibody. In some embodiments, a patient is diagnosed with a MUC16-positive cancer that is likely to progress when the level of expression of HE4 after administration of the anti-MUC16 antibody is less than 5% lower than the level of expression of HE4 before administration of the anti-MUC16 antibody. In some embodiments, a patient is diagnosed with a MUC16-positive cancer that is likely to progress when the level of expression of HE4 after administration of the anti-MUC16 antibody is more than 5% higher than the level of expression of HE4 before administration of the anti-MUC16 antibody. In some embodiments, a patient is diagnosed with a MUC16-positive cancer that is likely to progress when the level of expression of HE4 after administration of the anti-MUC16 antibody is more than 15% higher than the level of expression of HE4 before administration of the anti-MUC16 antibody. In some embodiments, a patient is diagnosed with a MUC16-positive cancer that is likely to progress when the level of expression of HE4 after administration of the anti-MUC16 antibody is more than 25% higher than the level of expression of HE4 before administration of the anti-MUC16 antibody. In some embodiments, a patient is diagnosed with a MUC16-positive cancer that is likely to progress when the level of expression of HE4 after administration of the anti-MUC16 antibody is more than 50% higher than the level of expression of HE4 before administration of the anti-MUC16 antibody.

Further provided herein are methods for detecting a MUC16-positive cancer or ovarian cancer in a subject or patient, comprising measuring or detecting the level of expression of HE4 in a sample obtained from the subject or patient at a first time point and a second time point, where an increased the level of expression of HE4 at the second time point as compared with the first time point is indicative of presence of a MUC16-positive cancer or ovarian cancer in the subject or patient.

Also provided herein are methods for assessing predisposition of a subject or patient to develop a MUC16-positive cancer or ovarian cancer, comprising measuring or detecting the level of expression of HE4 in a sample obtained from the subject at a first time point and a second time point, where an increased the level of expression of HE4 at the second time point as compared with the first time point is indicative of a predisposition for the subject to develop a MUC16-positive cancer or ovarian cancer.

Further provided herein are methods for diagnosing a MUC16-positive cancer or ovarian cancer in a subject or patient by measuring or detecting the level of expression of HE4 in a sample obtained from the subject at a first time point and a second time point; and if the level of expression of HE4 in the sample obtained from the subject at the second time point is higher than the first time point, diagnosing the subject as having a MUC16-positive cancer or ovarian cancer.

The anti-MUC16 antibody and MUC16 antagonists may be any of the anti-MUC16 antibodies or MUC16 antagonists described herein.

The MUC16-positive cancer may be any of the MUC16-positive cancers described herein. In certain embodiments, the MUC16-positive cancer is advanced MUC16-positive cancer, metastatic MUC16-positive cancer, drug-resistant MUC16-positive cancer, refractory MUC16-positive cancer, or unresectable MUC16-positive cancer.

Use of HE4 Expression Levels for Assessing Responsiveness of Treatment for Ovarian Cancer, Endometrial Cancer, Triple-Negative Breast Cancer, Pancreatic Cancer, and/or Non-Small Cell Lung Cancer and Related Applications In certain embodiments, the methods of the present disclosure relate to methods for treating or delaying progression of ovarian cancer, endometrial cancer, triple-negative breast cancer, pancreatic cancer, and/or non-small cell lung cancer in a subject or patient in need thereof. In some embodiments, the methods include measuring or detecting the level of expression of HE4 in a sample obtained from the subject at a first time point, administering to the subject a therapeutically effective amount of an anti-cancer therapy, measuring or detecting the level of expression of HE4 in a sample obtained from the subject at a second time point, and administering one or more therapeutically effective amounts of the anti-cancer therapy if the level of expression of HE4 at the second time point is lower than the level of expression of HE4 at the first time point. In some embodiments, the first time point is prior to administering to the subject the anti-cancer therapy. In some embodiments, the second time point is after administration of the anti-cancer therapy. In some embodiments, the subject has never received the anti-cancer therapy. In some embodiments, the subject is undergoing treatment with the anti-cancer therapy.

In some embodiments, the anti-cancer therapy is a chemotherapeutic or growth inhibitory agent, a targeted therapeutic agent, a T cell expressing a chimeric antigen receptor, an antibody or antigen-binding fragment thereof, an immunoconjugate, an angiogenesis inhibitor, an antineoplastic agent, a cancer vaccine, an adjuvant, or any combination thereof. In some embodiments, the anti-cancer therapy is an immunoconjugate. In some embodiments, the anti-cancer therapy is a MUC16 antagonist. In some embodiments, the anti-cancer therapy is a NaPi2b antagonist.

Any of the methods described herein may include administration of one or more additional therapeutically effective amounts of an anti-cancer therapy.

In some embodiments, the one or more additional therapeutically effective amounts of an anti-cancer therapy may be maintained at the same level as the initial dose of the anti-cancer therapy.

In some embodiments, the one or more additional therapeutically effective amounts of an anti-cancer therapy may be increased relative to the initial dose of the anti-cancer therapy. An increase in the one or more additional therapeutically effective amounts of the anti-cancer therapy administered to the subject may refer without limitation to one or more of: increasing the amount, dose, number or frequency of doses, or concentration of the anti-cancer therapy administered to the subject.

In some embodiments, the one or more additional therapeutically effective amounts of an anti-cancer therapy may be decreased relative to the initial dose of the anti-cancer therapy. A decrease in the one or more additional therapeutically effective amounts of the anti-cancer therapy administered to the subject may refer without limitation to one or more of: decreasing the amount, dose, number or frequency of doses, or concentration of the anti-cancer therapy administered to the subject.

In some embodiments, the subject is administered one or more additional therapeutically effective amounts of the anti-cancer therapy if the level of expression of HE4 at the second time point is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% lower than the level of expression of HE4 at the first time point. In some embodiments, the subject is administered one or more additional therapeutically effective amounts of the anti-cancer therapy if the level of expression of HE4 at the second time point is at least at least 10% lower than the level of expression of HE4 at the first time point. In some embodiments, the subject is administered one or more additional therapeutically effective amounts of the anti-cancer therapy if the level of expression of HE4 at the second time point is at least at least 25% lower than the level of expression of HE4 at the first time point. In some embodiments, the subject is administered one or more additional therapeutically effective amounts of the anti-cancer therapy if the level of expression of HE4 at the second time point is at least at least 40% lower than the level of expression of HE4 at the first time point.

Also provided herein are methods for modulating anti-cancer therapy in a subject or patient having ovarian cancer, endometrial cancer, triple-negative breast cancer, pancreatic cancer, and/or non-small cell lung cancer. In some embodiments, the methods include measuring or detecting the level of expression of HE4 in a sample obtained from the subject at a first time point, administering to the subject a therapeutically effective amount of an anti-cancer therapy, measuring or detecting the level of expression of HE4 in a sample obtained from the subject at a second time point, and modulating the amount of anti-cancer therapy administered to the subject based on changes in the HE4 level between the first and second time points. In some embodiments, the first time point is prior to administering to the subject the anti-cancer therapy. In some embodiments, the second time point is after administration of the anti-cancer therapy.

In some embodiments, modulating the amount of anti-cancer therapy administered to the subject comprises maintaining the same level of anti-cancer therapy administered to the subject. In some embodiments the maintenance dose is the same as the initial treatment dose. In some embodiments the maintenance dose is administered at the same frequency as the initial treatment dose.

In some embodiments, modulating the amount of anti-cancer therapy administered to the subject comprises increasing the level of anti-cancer therapy administered to the subject. An increase in the level of anti-cancer therapy administered to the subject may refer without limitation to one or more of: increasing the amount, dose, number or frequency of doses, or concentration of the anti-cancer therapy administered to the subject.

In some embodiments, modulating the amount of anti-cancer therapy administered to the subject comprises decreasing the level of anti-cancer therapy administered to the subject. A decrease in the level of anti-cancer therapy administered to the subject may refer without limitation to one or more of: decreasing the amount, dose, number or frequency of doses, or concentration of the anti-cancer therapy administered to the subject.

Also provided herein are methods for assessing, monitoring, or predicting responsiveness of a subject or patient having ovarian cancer, endometrial cancer, triple-negative breast cancer, pancreatic cancer, and/or non-small cell lung cancer to an anti-cancer therapy. In some embodiments, the method comprises measuring or detecting the level of expression of HE4 in a sample obtained from a subject at a first time point, and measuring or detecting the level of expression of HE4 in a sample obtained from a subject at a second time point. In some embodiments, the second time point is after administration of the anti-cancer therapy. In some embodiments, the method comprises measuring or detecting the level of expression of HE4 in a sample obtained from a subject at a first time point, administering to the subject a therapeutically effective amount of the anti-cancer therapy, and measuring or detecting the level of expression of HE4 in a sample obtained from a subject at a second time. In some embodiments, the first time point is prior to administering to the subject the anti-cancer therapy. In some embodiments, the second time point is after administration of the anti-cancer therapy. In some embodiments, the subject has never received the anti-cancer therapy. In some embodiments, the subject is undergoing treatment with the anti-cancer therapy.

In some embodiments, the method comprises classifying the subject or patient as responsive or non-responsive to treatment with the anti-cancer therapy antibody based on the level of expression of HE4 in the sample obtained from the subject at the second time point, as compared to the first time point, where decreased the level of expression of HE4 at the second time point indicates the subject is or may be responsive to treatment with the anti-cancer therapy.

In some embodiments, a decrease of less than 25%, less than 20%, less than 15%, less than 10%, less than 9%, less than 8%, less than 7%, less than 6%, less than 5%, less than 4%, less than 3%, less than 2%, less than 1%, no decrease, or an increase of greater than 1%, greater than 2%, greater than 3%, greater than 4%, greater than 5%, greater than 10%, greater than 5%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or greater than 100% in the level of expression of HE4 from the first time point to the second time point indicates the subject is non-responsive to the anti-cancer therapy. In some embodiments, a decrease of less than 25% in the level of expression of HE4 from the first time point to the second time point indicates the subject is non-responsive to the anti-cancer therapy. In some embodiments, a decrease of less 10% in the level of expression of HE4 from the first time point to the second time point indicates the subject is non-responsive to the anti-cancer therapy. In some embodiments, a decrease of less than 5% in the level of expression of HE4 from the first time point to the second time point indicates the subject is non-responsive to the anti-cancer therapy. In some embodiments, no decrease in the level of expression of HE4 from the first time point to the second time point indicates the subject is non-responsive to the anti-cancer therapy. In some embodiments, an increase in the level of expression of HE4 from the first time point to the second time point indicates the subject is non-responsive to the anti-cancer therapy. In some embodiments, an increase of greater than 5% in the level of expression of HE4 from the first time point to the second time point indicates the subject is non-responsive to the anti-cancer therapy. In some embodiments, an increase of greater than 15% in the level of expression of HE4 from the first time point to the second time point indicates the subject is non-responsive to the anti-cancer therapy. In some embodiments, an increase of greater than 25% in the level of expression of HE4 from the first time point to the second time point indicates the subject is non-responsive to the anti-cancer therapy. In some embodiments, an increase of greater than 50% in the level of expression of HE4 from the first time point to the second time point indicates the subject is non-responsive to the anti-cancer therapy.

In some embodiments, a decrease of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in the level of expression of HE4 from the first time point to the second time point indicates the subject is responsive to the anti-cancer therapy. In some embodiments, a decrease of at least 10% in the level of expression of HE4 from the first time point to the second time point indicates the subject is responsive to the anti-cancer therapy. In some embodiments, a decrease of at least 25% in the level of expression of HE4 from the first time point to the second time point indicates the subject is responsive to the anti-cancer therapy. In some embodiments, a decrease of at least 40% in the level of expression of HE4 from the first time point to the second time point indicates the subject is responsive to the anti-cancer therapy.

In some embodiments, responsiveness refers to treatment efficacy. It will be appreciated by one of skill in the art that many measures of treatment efficacy, and combinations thereof, may be useful. In some embodiments, treatment efficacy may include a tumor response (e.g., a stabilization or reduction in tumor size, growth, or histological stage). In some embodiments, treatment efficacy may include increased survival (e.g., one-year, 5-year, disease-free, or overall), increased quality of life, increased time to progression, or decreased morbidity. Such factors may be assessed, e.g., by using a statistical tool such as logistic regression, Cox's proportional hazards regression, or Kaplan-Meier estimates.

In some embodiments, responsiveness refers to reduced tumor volume. For example, in some embodiments, responsiveness refers to a reduction of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in tumor volume. In some embodiments, responsiveness refers to a reduction in tumor volume that is less than about any of the following percentages: 100, 95, 90, 85, 80, 75, 70, 65, 60, 55, 50, 45, 40, 35, 30, 25, 20, 15, or 10. In some embodiments, responsiveness refers to a reduction in tumor volume that is greater than about any of the following percentages: 5, 10, 15, 20, 25, 30, 35, 40, 45, 50, 55, 60, 65, 70, 75, 80, 85, 90, or 95. That is, responsiveness may refer to a reduction in tumor volume that can be any of a range of percentages having an upper limit of 100, 95, 90, 85, 80, 75, 70, 65, 60, 55, 50, 45, 40, 35, 30, 25, 20, 15, or 10 and an independently selected lower limit of 5, 10, 15, 20, 25, 30, 35, 40, 45, 50, 55, 60, 65, 70, 75, 80, 85, 90, or 95, wherein the lower limit is less than the upper limit. Tumor volume may refer to the volume of a signal tumor, or it may refer to the aggregate volume of multiple tumors. In some embodiments, a reduction in tumor volume is measured in comparison with the tumor volume before treatment, e.g., with an anti-cancer therapy.

In some embodiments, responsiveness refers to serologic responsiveness. In some embodiments, serologic responsiveness may refer to an improvement in or an alteration of one or more serologic markers indicative of a response to treatment. In some embodiments, a serologic marker is a marker present in a serum or blood sample or a cell present therein. Examples of serologic markers include without limitation red blood cells (RBCs), white blood cells (WBCs), a circulating biomarker, albumin, hemoglobin, DNA adducts (e.g., in plasma, RBCs, or WBCs), serum alpha fetoprotein (alpha-FP), human chorionic gonadotropin (e.g., beta-hCG), estradiol, inhibin, carcinoembryonic antigen (CEA), ferritin, human telomerase reverse transcriptase (hTERT), topoisomerase II, urinary gonadotropin fragment, squamous cell carcinoma (SCC) antigen, Mullerian inhibiting substance (MIS), carbohydrate antigen 19-9, cancer antigen 27-29, cyclin E, OVX1, CA-15-3, CA-19-9, insulinlike growth factor-binding protein-3, macrophage colony-stimulating factor (M-CSF), IL-8, VEGF, osteopontin, mesothelin, lysophosphatidic acid, MIB 1-determined tumor growth fraction, L1 (CAM), and the like. Exemplary serologic markers may be found, e.g., in Eagle, K. and Ledermann, J. A. (1997) *Oncologist* 2:324-329 and Gaducci, A. et al. (2004) *Biomed. Pharmacother.* 58:24-38.

In some embodiments, responsiveness to treatment may refer to any one or more of: extending survival (including overall survival and progression free survival); resulting in an objective response (including a complete response or a partial response); or improving signs or symptoms of cancer. In some embodiments, responsiveness refers to a lower sum of the longest diameter (SLD) response. For example, in some embodiments, responsiveness refers to a reduction of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in the SLD of target lesions. In some embodiments, responsiveness refers to a higher RECIST response, e.g., an improvement of one or more factors according to the published set of RECIST for determining the status of a tumor (such as responding, stabilizing, or progressing) in a cancer patient. For a more detailed discussion of these guidelines, see Eisenhauer et al., Eur J Cancer 2009; 45: 228-47; Topalian et al., N Engl J Med 2012; 366:2443-54; Wolchok et al., Clin Can Res 2009; 15:7412-20; and Therasse, P., et al. J. Natl. Cancer Inst. 92:205-16 (2000). A responsive subject may refer to a subject whose cancer(s) show improvement, e.g., according to one or more factors based on RECIST. A non-responsive subject may refer to a subject whose cancer(s) do not show improvement, e.g., according to one or more factors based on RECIST.

Conventional response criteria may not be adequate to characterize the anti-tumor activity of immunotherapeutic agents, which can produce delayed responses that may be preceded by initial apparent radiological progression, including the appearance of new lesions. Therefore, modified response criteria have been developed that account for the possible appearance of new lesions and allow radiological progression to be confirmed at a subsequent assessment. Accordingly, in some embodiments, responsiveness may refer to improvement of one of more factors according to immune-related response criteria (irRC). See, e.g., Wolchok et al., Clin Can Res 2009; 15:7412-20. In some embodiments, new lesions are added into the defined tumor burden and followed, e.g., for radiological progression at a subsequent assessment. In some embodiments, presence of non-target lesions are included in assessment of complete response and not included in assessment of radiological progression. In some embodiments, radiological progression may be determined only on the basis of measurable disease and/or may be confirmed by a consecutive assessment ≥4 weeks from the date first documented.

In some embodiments, a decrease in the level of expression of HE4 of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% correlates with stable disease and/or a partial RECIST response. In some embodiments, a decrease of at least 10% in the level of expression of HE4 correlates with stable disease and/or a partial RECIST response. In some embodiments, a decrease of at least 25% in the level of expression of HE4 correlates with stable disease and/or a partial RECIST response. In some embodiments, a decrease of at least 40% in the level of expression of HE4 correlates with stable disease and/or a partial RECIST response.

Also provided herein are methods for assessing progression-free survival in a subject or patient having ovarian cancer, endometrial cancer, triple-negative breast cancer, pancreatic cancer, and/or non-small cell lung cancer. In some embodiments, the method comprises measuring or detecting the level of expression of HE4 in a sample obtained from the subject at a first time point, administering to the subject a therapeutically effective amount of an anti-cancer therapy, and measuring or detecting the level of expression of HE4 in a sample obtained from the subject at a second time point. In some embodiments, the first time point is prior to administering to the subject the anti-cancer therapy. In some embodiments, the second time point is after administration of the M anti-cancer therapy.

In some embodiments, a decrease of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in the level of expression of HE4 from the first time point to the second time point indicates the anti-cancer therapy increases progression-free survival. In some embodiments, a decrease of at least 10% in the level of expression of HE4 from the first time point to the second time point indicates the anti-cancer therapy increases progression-free survival. In some embodiments, a decrease of at least 25% in the level of expression of HE4 from the first time point to the second time point indicates the anti-cancer therapy increases progression-free survival. In some embodiments, a decrease of at least 40% in the level of expression of HE4 from the first time point to the second time point indicates the anti-cancer therapy increases progression-free survival.

Also provided herein are methods for predicting cancer progression in a subject or patient having ovarian cancer, endometrial cancer, triple-negative breast cancer, pancreatic cancer, and/or non-small cell lung cancer. In some embodiments, the method comprises measuring or detecting the level of expression of HE4 in a sample obtained from the subject at a first time point, administering to the subject a therapeutically effective amount of an anti-cancer therapy, and measuring or detecting the level of expression of HE4 in a sample obtained from the subject at a second time point. In some embodiments, the first time point is prior to administering to the subject the anti-cancer therapy. In some embodiments, the second time point is after administration of the anti-cancer therapy.

In some embodiments, a decrease of less than 25%, less than 20%, less than 15%, less than 10%, less than 9%, less than 8%, less than 7%, less than 6%, less than 5%, less than 4%, less than 3%, less than 2%, less than 1%, no decrease, or an increase of greater than 1%, greater than 2%, greater than 3%, greater than 4%, greater than 5%, greater than 10%, greater than 5%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or greater than 100% in the level of expression of HE4 from the first time point to the second time point indicates the subject has a cancer that is likely to progress. In some embodiments, a decrease of less than 25% in the level of expression of HE4 from the first time point to the second time point indicates the subject has a cancer that is likely to progress. In some embodiments, a decrease of less than 10% in the level of expression of HE4 from the first time point to the second time point indicates the subject has a cancer that is likely to progress. In some embodiments, a decrease of less than 5% in the level of expression of HE4 from the first time point to the second time point indicates the subject has a cancer that is likely to progress. In some embodiments, no decrease in the level of expression of HE4 from the first time point to the second time point indicates the subject has a cancer that is likely to progress. In some embodiments, an increase in the level of expression of HE4 from the first time point to the second time point indicates the subject has a cancer that is likely to progress. In some embodiments, an increase of greater than 5% in the level of expression of HE4 from the first time point to the second time point indicates the subject has a cancer that is likely to progress. In some embodiments, an increase of greater than 15% in the level of expression of HE4 from the first time point to the second time point indicates the subject has a cancer that is likely to progress. In some embodiments, an increase of greater than 25% in the level of expression of HE4 from the first time point to the second time point indicates the subject has a cancer that is likely to progress. In some embodiments, an increase of greater than 50% in the level of expression of HE4 from the first time point to the second time point indicates the subject has a cancer that is likely to progress.

Any of the methods described herein may include administration of one or more additional therapeutically effective amounts of an anti-cancer therapy to a subject or patient. In some embodiments, the one or more additional therapeutically effective amounts are administered based upon the level of expression of HE4 in the subject after administration of an initial anti-cancer therapy.

In some embodiments, the one or more additional therapeutically effective amounts anti-cancer therapy administered to the subject or patient comprises maintaining the same level of anti-cancer therapy administered to the subject. In some embodiments the maintenance dose is the same as the initial treatment dose. In some embodiments the maintenance dose is administered at the same frequency as the initial treatment dose.

In some embodiments, the one or more additional therapeutically effective amounts anti-cancer therapy administered to the subject or patient comprises increasing the level of anti-cancer therapy administered to the subject. An increase in the level of anti-cancer therapy administered to the subject may refer without limitation to one or more of: increasing the amount, dose, number or frequency of doses, or concentration of the anti-cancer therapy administered to the subject.

In some embodiments, the one or more additional therapeutically effective amounts anti-cancer therapy administered to the subject or patient comprises decreasing the level of anti-cancer therapy administered to the subject. A decrease in the level of anti-cancer therapy administered to the subject may refer without limitation to one or more of: decreasing the amount, dose, number or frequency of doses, or concentration of the anti-cancer therapy administered to the subject.

Any of the methods described herein that relate to administration of an anti-cancer therapy (e.g., a MUC16 antagonist or NaPi2b antagonist) may further include administration of a second treatment therapy to the subject or patient. In some embodiments, the subject is classified as responsive to the anti-cancer therapy. In certain embodiments, the second treatment therapy (or "combination therapy") comprises an anti-cancer therapy (e.g., a MUC16 antagonist or NaPi2b antagonist) and a second therapeutic agent. In some embodiments, the second therapeutic agent is an antibody therapy. In certain embodiments, the second treatment therapy is Avastin®.

In some embodiments, the second treatment therapy may include a maintenance therapy. By "maintenance therapy" is meant a therapeutic regimen that is given to reduce the likelihood of disease recurrence or progression after a beneficial outcome of an initial therapeutic intervention. Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy.

In some embodiments, the second treatment therapy may include a chemotherapy. For example, one or more of any of the chemotherapeutic agents described herein may be used in a chemotherapy treatment.

Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, and U.S. Patent Application 60/991,302, the content of these patent applications are expressly incorporated herein by reference. For additional antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., Journal of Immunological Methods 288:149-164 (2004). Other antibodies include those that bind to a functional epitope on human VEGF comprising of residues F17, M18, D19, Y21, Y25, Q89, 1191, K101, E103, and C104 or, alternatively, comprising residues F17, Y21, Q22, Y25, D63, 183 and Q89.

In some embodiments, the maintenance therapy can comprise an anti-VEGF therapy after completion of a chemotherapeutic regimen. For example, the maintenance therapy can be provided for at least 16 cycles after completion of chemotherapy concurrently with 5 cycles of anti-VEGF therapy. In other embodiments, maintenance therapy is provided for at least 12 cycles after completion of the chemotherapy concurrently with 6 cycles of anti-VEGF therapy. A "maintenance" dose refers to one or more doses of a therapeutic agent administered to the patient over or after a treatment period. Usually, the maintenance doses are administered at spaced treatment intervals, such as approximately every week, approximately every 2 weeks, approximately every 3 weeks, or approximately every 4 weeks. Anti-VEGF therapeutic regiments are known in the art; the particular regimen chosen for an individual will depend on the type of cancer to be treated, as defined above, the severity and course of the cancer, whether the antibody is administered for preventive or therapeutic purposes, previous therapy, the patient's clinical history and response to the drug, and the discretion of the attending physician.

IV. Specific Elements of the Methods

Certain aspects of the methods described herein relate to measuring or detecting the level of expression of human epididymis protein 4 (HE4) in a subject or patient having cancer (e.g., a MUC16-positive cancer) for use in treating or delaying progression of cancer (e.g., a MUC16-positive cancer) in a subject in need thereof by administering an anti-cancer therapy (e.g., a MUC16 antagonist); assessing, monitoring, or predicting responsiveness of a subject or patient having cancer (e.g., a MUC16-positive cancer) to an anti-cancer therapy (e.g., a MUC16 antagonist treatment); selecting a subject or patient having cancer (e.g., a MUC16-positive cancer) for anti-cancer therapy (e.g., a MUC16 antagonist) treatment; communicating the likelihood of response of a subject or patient having cancer (e.g., a MUC16-positive cancer) to an anti-cancer therapy (e.g., a MUC16 antagonist) treatment; methods for continuing, discontinuing, or modulating an anti-cancer therapy (e.g., a MUC16 antagonist) in a subject or patient having cancer (e.g., a MUC16-positive cancer); further administering a second treatment therapy to a subject or patient having a cancer (e.g., a MUC16-positive cancer); monitoring pharmacodynamic (PD) activity of an anti-cancer therapy (e.g., a MUC16 antagonist treatment) that is being administered or has been administered to a subject or patient having cancer (e.g., a MUC16-positive cancer); assessing tumor burden in a subject or patient having cancer (e.g., a MUC16-positive cancer); assessing progression-free survival in a subject or patient having cancer (e.g., a MUC16-positive cancer); marketing an anti-cancer therapy (e.g., a MUC16 antagonist, such as an anti-MUC16 antibody, MUC16 ADC, or MUC16 TDC) for use in cancer (e.g., a MUC16-positive cancer) patient subpopulation; diagnosing cancer (e.g., a MUC16-positive cancer or ovarian cancer) in a subject or patient; and assessing responsiveness of treatment for ovarian cancer, endometrial cancer, triple-negative breast cancer, pancreatic cancer, and/or non-small cell lung cancer and related applications.

As disclosed herein, specific elements of the methods described herein include, without limitation, MUC16-positive cancers, samples obtained from subjects or patients having cancer (e.g., a MUC16-positive cancer), MUC16 antagonist dosing, time point measurements, HE4 expression level measurements, and anti-cancer therapies (e.g., a MUC16 antagonist).

MUC16-Positive Cancers

In certain embodiments, the methods of the present disclosure may be used, inter alia, to treat or delay progression of a MUC16-positive cancer in a subject or patient in need thereof with a MUC16 antagonist, to modulate/adjust/determine/select the dosing of a subject having a MUC16- positive cancer who will be/has been/is being treated with MUC16 antagonist, to select a subject having MUC16-positive cancer for treatment with a MUC16 antagonist, to communicate the likelihood of response of a subject to a MUC16 antagonist, to assess the responsiveness of a subject to a MUC16 antagonist, to assess progression-free survival of a subject having MUC16-positive cancer, to assess tumor burden in a subject having MUC16-positive cancer, and to predict cancer progression in a subject having MUC16-positive cancer. In some embodiments the MUC16 antagonist is an antibody. In some embodiments the anti-MUC16 antibody is an ADC or TDC.

In certain embodiments, the MUC16-positive cancer is endometrial cancer, triple negative breast cancer, pancreatic cancer, non-small cell lung cancer, or ovarian cancer. In some embodiments, a triple negative breast cancer (TNBC) refers to a breast cancer that does not express the genes for estrogen receptor (ER), progesterone receptor (PR), or Her2/neu. In some embodiments, the MUC16-positive cancer is unresectable pancreatic cancer. In some embodiments, the MUC16-positive cancer is an ovarian cancer selected from primary peritoneal carcinoma, epithelial ovarian carcinoma, metastatic ovarian cancer, fallopian tube carcinoma, or platinum-resistant ovarian cancer. In certain embodiments, the MUC16-positive cancer is endometrial cancer. In certain embodiments, the MUC16-positive cancer is ovarian cancer. In certain embodiments, the MUC16-positive cancer is pancreatic cancer.

Samples

In the methods of the present disclosure, the level of expression of HE4 is measured or detected in a sample obtained from a subject or patient having cancer (e.g., a MUC16-positive cancer). In some embodiments, a sample may be a blood sample, a serum sample, a cell sample, or a tumor sample. In some embodiments, the sample may be obtained from a human subject.

In some embodiments, the sample may be a blood sample, such as a peripheral blood sample. A peripheral blood sample may include red blood cells, white blood cells, PBMCs, serum, one or more circulating markers, and the like. Any technique known in the art for isolating leukocytes from a peripheral blood sample may be used. For example, a blood sample may be drawn, red blood cells may be lysed, and a white blood cell pellet may be isolated and used for the sample. In another example, density gradient separation may be used to separate leukocytes (e.g., PBMCs) from red blood cells. Isolated leukocytes from a peripheral blood sample may be assayed by any technique described herein for measuring marker gene expression level. Any suitable technique may be used to separate blood cells from serum and/or a circulating marker, such as a protein, peptide antigen, carbohydrate, lipid, and so forth.

A tumor sample may include cancer cells, lymphocytes, leukocytes, stroma, blood vessels, connective tissue, basal lamina, and any other cell type in association with the tumor. In some embodiments, the sample is a tumor tissue sample containing tumor-infiltrating leukocytes. As used herein, any leukocyte associated with a tumor may be considered a tumor-infiltrating leukocyte. Examples of tumor-infiltrating leukocytes include without limitation T lymphocytes (such as CD8+T lymphocytes and/or CD4+T lymphocytes), B lymphocytes, or other bone marrow-lineage cells including granulocytes (neutrophils, eosinophils, basophils), monocytes, macrophages, dendritic cells (i.e., interdigitating dendritic cells), histiocytes, and natural killer cells. In some embodiments, a tumor-infiltrating leukocyte may be associated with cancer cells of a tumor. In some embodiments, a tumor-infiltrating leukocyte may be associated with tumor stroma. In some embodiments, the tumor samples are enriched for tumor area by macrodissection.

In some embodiments, the sample may be processed to separate or isolate one or more cell types (e.g., leukocytes). In some embodiments, the sample may be used without separating or isolating cell types. A tumor sample may be obtained from a subject by any method known in the art, including without limitation a biopsy, endoscopy, phlebotomy, or surgical procedure. In some embodiments, a tumor sample may be prepared by methods such as freezing, fixation (e.g., by using formalin or a similar fixative), and/or embedding in paraffin wax. In some embodiments, a tumor sample may be sectioned. In some embodiments, a fresh tumor sample (i.e., one that has not been prepared by the methods described above) may be used. In some embodiments, a sample may be prepared by incubation in a solution to preserve mRNA and/or protein integrity. A tumor sample may be assayed by any technique described herein for measuring marker gene expression level.

In some embodiments, a cell sample (e.g., a blood cell sample, such as an RBC or WBC sample) may be derived from a blood sample. In other embodiments, a cell sample (e.g., a tumor cell sample) may be derived from a tumor sample. In yet other embodiments, a cell sample may be derived from a healthy tissue.

In certain embodiments, the sample is a blood sample. One benefit of using HE4 as a biomarker is that it is a circulating protein which can be detected in blood. Accordingly, a blood sample can be drawn and efficacy and treatment of a MUC16-positive cancer can be monitored and assessed based on the circulating HE4 protein, rather than the commonly used CA125 protein which is not a candidate when the treatment of the MUC16-positive cancer comprises an anti-MUC16 antibody that competes for binding with an anti-CA125 diagnostic antibody.

MUC16 Antagonist Doses

In certain embodiments, the methods of the present disclosure relate to administering one or more therapeutically effective amounts of a MUC16 antagonist to a subject or patient in need thereof.

In certain embodiments, the MUC16 antagonist is an anti-MUC16 antibody that is used in a method of the present disclosure and which can be administered in a therapeutically effective amount of about 0.8 mg/kg-4.0 mg/kg, 0.8 mg/kg-3.2 mg/kg, 0.8 mg/kg-2.4 mg/kg, 0.8 mg/kg-1.8 mg/kg, 0.8 mg/kg-1.4 mg/kg, 0.8 mg/kg-1.1 mg/kg, 1.1 mg/kg-4.0 mg/kg, 1.1 mg/kg-3.2 mg/kg, 1.1 mg/kg-2.4 mg/kg, 1.1 mg/kg-1.8 mg/kg, 1.1 mg/kg-1.4 mg/kg, 1.4 mg/kg-4.0 mg/kg, 1.4 mg/kg-3.2 mg/kg, 1.4 mg/kg-2.4 mg/kg, 1.4 mg/kg-1.8 mg/kg, 1.8 mg/kg-4.0 mg/kg, 1.8 mg/kg-3.2 mg/kg, 1.8 mg/kg-2.4 mg/kg, 2.4 mg/kg-4.0 mg/kg, 2.4 mg/kg-3.2 mg/kg, or 3.2 mg/kg-4.0 mg/kg.

In certain embodiments, the MUC16 antagonist is an anti-MUC16 antibody disclosed herein that is conjugated to a drug using endogenous cysteine and/or lysine residues (i.e., an ADC) that is used in a method of the present disclosure and which can be administered in a therapeutically effective amount of about 0.8 mg/kg-4.0 mg/kg, 0.8 mg/kg-3.2 mg/kg, 0.8 mg/kg-2.4 mg/kg, 0.8 mg/kg-1.8 mg/kg, 0.8 mg/kg-1.4 mg/kg, 0.8 mg/kg-1.1 mg/kg, 1.1 mg/kg-4.0 mg/kg, 1.1 mg/kg-3.2 mg/kg, 1.1 mg/kg-2.4 mg/kg, 1.1 mg/kg-1.8 mg/kg, 1.1 mg/kg-1.4 mg/kg, 1.4 mg/kg-4.0 mg/kg, 1.4 mg/kg-3.2 mg/kg, 1.4 mg/kg-2.4 mg/kg, 1.4 mg/kg-1.8 mg/kg, 1.8 mg/kg-4.0 mg/kg, 1.8 mg/kg-3.2 mg/kg, 1.8 mg/kg-2.4 mg/kg, 2.4 mg/kg-4.0 mg/kg, 2.4 mg/kg-3.2 mg/kg, or 3.2 mg/kg-4.0 mg/kg. In some embodiments, the MUC16-ADC is administered in a therapeutically effective amount of about 0.8 mg/kg. In some embodiments, the MUC16-ADC is administered in a therapeutically effective amount of about 1.1 mg/kg. In some embodiments, the MUC16-ADC is administered in a therapeutically effective amount about 1.4 mg/kg. In some embodiments, the MUC16-ADC is administered in a therapeutically effective amount about 1.8 mg/kg. In some embodiments, the MUC16-ADC is administered in a therapeutically effective amount of about 3.2 mg/kg. In some embodiments, the MUC16-ADC is administered in a therapeutically effective amount of about 4.0 mg/kg. In certain embodiments, the MUC16-ADC is administered in a therapeutically effective amount of about 2.4 mg/kg.

In certain embodiments, the MUC16 antagonist is an anti-MUC16 antibody disclosed herein that is conjugated to a drug using an engineered cysteine residue (i.e., a TDC) that is used in a method of the present disclosure and which can be administered in a therapeutically effective amount of about 1.0 mg/kg-10 mg/kg, 1.0 mg/kg-9.8 mg/kg, 1.0 mg/kg-9.4 mg/kg, 1.0 mg/kg-9.0 mg/kg, 1.0 mg/kg-8.6 mg/kg, 1.0 mg/kg-8.2 mg/kg, 1.0 mg/kg-7.8 mg/kg, 1.0 mg/kg-7.4 mg/kg, 1.0 mg/kg-7.0 mg/kg, 1.0 mg/kg-6.6 mg/kg, 1.0 mg/kg-6.2 mg/kg, 1.0 mg/kg-5.6 mg/kg, 1.0 mg/kg-5.2 mg/kg, 1.0 mg/kg-4.8 mg/kg, 1.0 mg/kg-4.0 mg/kg, 1.0 mg/kg-3.2 mg/kg, 1.0 mg/kg-2.4 mg/kg, 1.0 mg/kg-1.8 mg/kg, 1.8 mg/kg-10 mg/kg, 1.8 mg/kg-9.8 mg/kg, 1.8 mg/kg-9.4 mg/kg, 1.8 mg/kg-9.0 mg/kg, 1.8 mg/kg-8.6 mg/kg, 1.8 mg/kg-8.2 mg/kg, 1.8 mg/kg-7.8 mg/kg, 1.8 mg/kg-7.4 mg/kg, 1.8 mg/kg-7.0 mg/kg, 1.8 mg/kg-6.6 mg/kg, 1.8 mg/kg-6.2 mg/kg, 1.8 mg/kg-5.6 mg/kg, 1.8 mg/kg-5.2 mg/kg, 1.8 mg/kg-4.8 mg/kg, 1.8 mg/kg-4.0 mg/kg, 1.8 mg/kg-3.2 mg/kg, 1.8 mg/kg-2.4 mg/kg, 2.4 mg/kg-10 mg/kg, 2.4 mg/kg-9.8 mg/kg, 2.4 mg/kg-9.4 mg/kg, 2.4 mg/kg-9.0 mg/kg, 2.4 mg/kg-8.6 mg/kg, 2.4 mg/kg-8.2 mg/kg, 2.4 mg/kg-7.8 mg/kg, 2.4 mg/kg-7.4 mg/kg, 2.4 mg/kg-7.0 mg/kg, 2.4 mg/kg-6.6 mg/kg, 2.4 mg/kg-6.2 mg/kg, 2.4 mg/kg-5.6 mg/kg, 2.4 mg/kg-5.2 mg/kg, 2.4 mg/kg-4.8 mg/kg, 2.4 mg/kg-4.0 mg/kg, 2.4 mg/kg-3.2 mg/kg, 3.2 mg/kg-10 mg/kg, 3.2 mg/kg-9.8 mg/kg, 3.2 mg/kg-9.4 mg/kg, 3.2 mg/kg-9.0 mg/kg, 3.2 mg/kg-8.6 mg/kg, 3.2 mg/kg-8.2 mg/kg, 3.2 mg/kg-7.8 mg/kg, 3.2 mg/kg-7.4 mg/kg, 3.2 mg/kg-7.0 mg/kg, 3.2 mg/kg-6.6 mg/kg, 3.2 mg/kg-6.2 mg/kg, 3.2 mg/kg-5.6 mg/kg, 3.2 mg/kg-5.2 mg/kg, 3.2 mg/kg-4.8 mg/kg, 3.2 mg/kg-4.0 mg/kg, 4.0 mg/kg-10 mg/kg, 4.0 mg/kg-9.8 mg/kg, 4.0 mg/kg-9.4 mg/kg, 4.0 mg/kg-9.0 mg/kg, 4.0 mg/kg-8.6 mg/kg, 4.0 mg/kg-8.2 mg/kg, 4.0 mg/kg-7.8 mg/kg, 4.0 mg/kg-7.4 mg/kg, 4.0 mg/kg-7.0 mg/kg, 4.0 mg/kg-6.6 mg/kg, 4.0 mg/kg-6.2 mg/kg, 4.0 mg/kg-5.6 mg/kg, 4.0 mg/kg-5.2 mg/kg, 4.0 mg/kg-4.8 mg/kg, 4.8 mg/kg-10 mg/kg, 4.8 mg/kg-9.8 mg/kg, 4.8 mg/kg-9.4 mg/kg, 4.8 mg/kg-9.0 mg/kg, 4.8 mg/kg-8.6 mg/kg, 4.8 mg/kg-8.2 mg/kg, 4.8 mg/kg-7.8 mg/kg, 4.8 mg/kg-7.4 mg/kg, 4.8 mg/kg-7.0 mg/kg, 4.8 mg/kg-6.6 mg/kg, 4.8 mg/kg-6.2 mg/kg, 4.8 mg/kg-5.6 mg/kg, 4.8 mg/kg-5.2 mg/kg, 5.2 mg/kg-10 mg/kg, 5.2 mg/kg-9.8 mg/kg, 5.2 mg/kg-9.4 mg/kg, 5.2 mg/kg-9.0 mg/kg, 5.2 mg/kg-8.6 mg/kg, 5.2 mg/kg-8.2 mg/kg, 5.2 mg/kg-7.8 mg/kg, 5.2 mg/kg-7.4 mg/kg, 5.2 mg/kg-7.0 mg/kg, 5.2 mg/kg-6.6 mg/kg, 5.2 mg/kg-6.2 mg/kg, 5.2 mg/kg-5.6 mg/kg, 5.6 mg/kg-10 mg/kg, 5.6 mg/kg-9.8 mg/kg, 5.6 mg/kg-9.4 mg/kg, 5.6 mg/kg-9.0 mg/kg, 5.6 mg/kg-8.6 mg/kg, 5.6 mg/kg-8.2 mg/kg, 5.6 mg/kg-7.8 mg/kg, 5.6 mg/kg-7.4 mg/kg, 5.6 mg/kg-7.0 mg/kg, 5.6 mg/kg-6.6 mg/kg, 5.6 mg/kg-6.2 mg/kg, 6.2 mg/kg-10 mg/kg, 6.2 mg/kg-9.8 mg/kg, 6.2 mg/kg-9.4 mg/kg, 6.2 mg/kg-9.0 mg/kg, 6.2 mg/kg-8.6 mg/kg, 6.2 mg/kg-8.2 mg/kg, 6.2 mg/kg-7.8 mg/kg, 6.2 mg/kg-7.4 mg/kg, 6.2 mg/kg-7.0 mg/kg, 6.2 mg/kg-6.6 mg/kg, 6.6 mg/kg-10 mg/kg, 6.6 mg/kg-9.8 mg/kg, 6.6 mg/kg-9.4 mg/kg, 6.6 mg/kg-9.0 mg/kg, 6.6 mg/kg-8.6 mg/kg, 6.6 mg/kg-8.2 mg/kg, 6.6 mg/kg-7.8 mg/kg, 6.6 mg/kg-7.4 mg/kg, 6.6 mg/kg-7.0 mg/kg, 7.0 mg/kg-10 mg/kg, 7.0 mg/kg-9.8 mg/kg, 7.0 mg/kg-9.4 mg/kg, 7.0 mg/kg-9.0 mg/kg, 7.0 mg/kg-8.6 mg/kg, 7.0 mg/kg-8.2 mg/kg, 7.0 mg/kg-7.8 mg/kg, 7.0 mg/kg-7.4 mg/kg, 7.4 mg/kg-10 mg/kg, 7.4 mg/kg-9.8 mg/kg, 7.4 mg/kg-9.4 mg/kg, 7.4 mg/kg-9.0 mg/kg, 7.4 mg/kg-8.6 mg/kg, 7.4 mg/kg-8.2 mg/kg, 7.4 mg/kg-7.8 mg/kg, 7.8 mg/kg-10 mg/kg, 7.8 mg/kg-9.8 mg/kg, 7.8 mg/kg-9.4 mg/kg, 7.8 mg/kg-9.0 mg/kg, 7.8 mg/kg-8.6 mg/kg, 7.8 mg/kg-8.2 mg/kg, 8.2 mg/kg-10 mg/kg, 8.2 mg/kg-9.8 mg/kg, 8.2 mg/kg-9.4 mg/kg, 8.2 mg/kg-9.0 mg/kg, 8.2 mg/kg-8.6 mg/kg, 8.6 mg/kg-10 mg/kg, 8.6 mg/kg-9.8 mg/kg, 8.6 mg/kg-9.4 mg/kg, 8.6 mg/kg-9.0 mg/kg, 9.0 mg/kg-10 mg/kg, 9.0 mg/kg-9.8 mg/kg, 9.0 mg/kg-9.4 mg/kg, 9.4 mg/kg-10 mg/kg, 9.4 mg/kg-9.8 mg/kg, or 9.6 mg/kg-10 mg/kg, In some embodiments, the MUC16-TDC is administered in a therapeutically effective amount of about 1.0 mg/kg. In some embodiments, the MUC16-TDC is administered in a therapeutically effective amount of about 1.8 mg/kg. In some embodiments, the MUC16-TDC is administered in a therapeutically effective amount of about 2.4 mg/kg. In some embodiments, the MUC16-TDC is administered in a therapeutically effective amount of about 3.2 mg/kg. In some embodiments, the MUC16-TDC is administered in a therapeutically effective amount of about 4.8 mg/kg. In some embodiments, the MUC16-TDC is administered in a therapeutically effective amount of about 5.2 mg/kg. In some embodiments, the MUC16-TDC is administered in a therapeutically effective amount of about 5.6 mg/kg. In some embodiments, the MUC16-TDC is administered in a therapeutically effective amount of about 6.2 mg/kg. In some embodiments, the MUC16-TDC is administered in a therapeutically effective amount of about 6.6 mg/kg. In some embodiments, the MUC16-TDC is administered in a therapeutically effective amount of about 7.0 mg/kg. In some embodiments, the MUC16-TDC is administered in a therapeutically effective amount of about 7.4 mg/kg. In some embodiments, the MUC16-TDC is administered in a therapeutically effective amount of about 7.8 mg/kg. In some embodiments, the MUC16-TDC is administered in a therapeutically effective amount of about 8.2 mg/kg. In some embodiments, the MUC16-TDC is administered in a therapeutically effective amount of about 8.6 mg/kg. In some embodiments, the MUC16-TDC is administered in a therapeutically effective amount of about 9.0 mg/kg. In some embodiments, the MUC16-TDC is administered in a therapeutically effective amount of about 9.4 mg/kg. In some embodiments, the MUC16-TDC is administered in a therapeutically effective amount of about 9.8 mg/kg. In some embodiments, the MUC16-TDC is administered in a therapeutically effective amount of about 10 mg/kg.

Any of the methods described herein may include administration of one or more additional therapeutically effective amounts of a MUC16 antagonist.

In some embodiments, the one or more additional therapeutically effective amounts of a MUC16 antagonist may be maintained at the same level as the initial dose of MUC16 antagonist.

In some embodiments, the one or more additional therapeutically effective amounts of a MUC16 antagonist may be increased relative to the initial dose of MUC16 antagonist.

An increase in the one or more additional therapeutically effective amounts of MUC16 antagonist administered to the subject may refer without limitation to one or more of: increasing the amount, dose, number or frequency of doses, or concentration of the MUC16 antagonist administered to the subject.

In some embodiments, the one or more additional therapeutically effective amounts of a MUC16 antagonist may be decreased relative to the initial dose of MUC16 antagonist. A decrease in the one or more additional therapeutically effective amounts of MUC16 antagonist administered to the subject may refer without limitation to one or more of: decreasing the amount, dose, number or frequency of doses, or concentration of the MUC16 antagonist administered to the subject.

The above dosages are exemplary of the average case, but there can be individual instances in which higher or lower dosages are merited, and such are within the scope of this disclosure. In practice, the physician determines the actual dosing regimen that is most suitable for an individual subject, which can vary with the age, weight, and response of the particular subject. Such doses may be administered daily or intermittently, e.g., every week or every three weeks (e.g., such that the patient receives from about two to about twenty, or e.g., about six doses of the MUC16 antagonist). An initial higher loading dose, followed by one or more lower doses may be administered. However, other dosage regimens may be useful. The progress of the dosage regime is easily monitored by conventional techniques and assays.

Dosage amounts and intervals can be adjusted individually to provide plasma levels of the MUC16 antagonist that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a MUC16 antagonist can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days' rest, and another five daily doses (5/2/5); or, any dose regimen determined to be appropriate for the circumstance.

In some embodiments, the MUC16 antagonist may be an immunoconjugate, such as an ADC or cysteine engineered antibody-drug conjugate (such as a TDC). For the prevention or treatment of disease, the appropriate dosage of an immunoconjugate will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments.

For repeated administrations over several days or longer, depending on the condition, the treatment is sustained until a desired suppression of disease symptoms occurs. An exemplary dosing regimen comprises administering a high initial loading dose of followed by a weekly or bi-monthly maintenance dose that is less than or equal to the initial dose of an MUC16 antagonist. Other dosage regimens may be useful. The progress of this therapy is easily monitored by conventional techniques and assays including ultrasound imaging.

A therapeutically effective amount of a MUC16 antagonist may be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished, e.g., by using a needle and syringe or by using a high pressure technique. Various dosing schedules including but not limited to single or multiple administrations over various time-points, bolus administration, and pulse infusion are contemplated herein. In certain embodiments, the MUC16 antagonist is an anti-MUC16 antibody (e.g., an ADC or TDC) which is administered intravenously.

Pharmaceutical compositions containing MUC16 antagonists can be manufactured, for example, by conventional mixing, dissolving, granulating, dragee-making, emulsifying, encapsulating, entrapping, or lyophilizing processes. Exemplary pharmaceutical compositions comprising anti-MUC16 antibodies are provided in U.S. Pat. Nos. 7,989,595 and 7,723,485, both of which are herein incorporated by reference in their entireties.

MUC16 antagonists can be readily combined with pharmaceutically acceptable carriers well-known in the art. Exemplary pharmaceutically acceptable carriers are provided in U.S. Pat. Nos. 7,989,595 and 7,723,485, both of which are herein incorporated by reference in their entireties.

NaPi2b Antagonist Doses

In certain embodiments, the methods of the present disclosure relate to administering one or more therapeutically effective amounts of a NaPi2b antagonist to a subject or patient in need thereof.

In certain embodiments, the NaPi2b antagonist is an anti-NaPi2b antibody that is used in a method of the present disclosure and which can be administered in a therapeutically effective amount of about 0.8 mg/kg-4.0 mg/kg, 0.8 mg/kg-3.2 mg/kg, 0.8 mg/kg-2.4 mg/kg, 0.8 mg/kg-1.8 mg/kg, 0.8 mg/kg-1.4 mg/kg, 0.8 mg/kg-1.1 mg/kg, 1.1 mg/kg-4.0 mg/kg, 1.1 mg/kg-3.2 mg/kg, 1.1 mg/kg-2.4 mg/kg, 1.1 mg/kg-1.8 mg/kg, 1.1 mg/kg-1.4 mg/kg, 1.4 mg/kg-4.0 mg/kg, 1.4 mg/kg-3.2 mg/kg, 1.4 mg/kg-2.4 mg/kg, 1.4 mg/kg-1.8 mg/kg, 1.8 mg/kg-4.0 mg/kg, 1.8 mg/kg-3.2 mg/kg, 1.8 mg/kg-2.4 mg/kg, 2.4 mg/kg-4.0 mg/kg, 2.4 mg/kg-3.2 mg/kg, or 3.2 mg/kg-4.0 mg/kg.

In certain embodiments, the NaPi2b antagonist is an anti-NaPi2b antibody disclosed herein that is conjugated to a drug using endogenous cysteine and/or lysine residues (i.e., an ADC) that is used in a method of the present disclosure and which can be administered in a therapeutically effective amount of about 0.8 mg/kg-4.0 mg/kg, 0.8 mg/kg-3.2 mg/kg, 0.8 mg/kg-2.4 mg/kg, 0.8 mg/kg-1.8 mg/kg, 0.8 mg/kg-1.4 mg/kg, 0.8 mg/kg-1.1 mg/kg, 1.1 mg/kg-4.0 mg/kg, 1.1 mg/kg-3.2 mg/kg, 1.1 mg/kg-2.4 mg/kg, 1.1 mg/kg-1.8 mg/kg, 1.1 mg/kg-1.4 mg/kg, 1.4 mg/kg-4.0 mg/kg, 1.4 mg/kg-3.2 mg/kg, 1.4 mg/kg-2.4 mg/kg, 1.4 mg/kg-1.8 mg/kg, 1.8 mg/kg-4.0 mg/kg, 1.8 mg/kg-3.2 mg/kg, 1.8 mg/kg-2.4 mg/kg, 2.4 mg/kg-4.0 mg/kg, 2.4 mg/kg-3.2 mg/kg, or 3.2 mg/kg-4.0 mg/kg. In some embodiments, the NaPi2b-ADC is administered in a therapeutically effective amount of about 0.8 mg/kg. In some embodiments, the NaPi2b-ADC is administered in a therapeutically effective amount of about 1.1 mg/kg. In some embodiments, the NaPi2b-ADC is administered in a therapeutically effective amount about 1.4 mg/kg. In some embodiments, the NaPi2b-ADC is administered in a therapeutically effective amount about 1.8 mg/kg. In some embodiments, the NaPi2b-ADC is administered in a therapeutically effective amount of about 3.2 mg/kg. In some embodiments, the NaPi2b-ADC is administered in a therapeutically effective amount of about 4.0 mg/kg. In certain embodiments, the NaPi2b-ADC is administered in a therapeutically effective amount of about 2.4 mg/kg.

In certain embodiments, the NaPi2b antagonist is an anti-NaPi2b antibody disclosed herein that is conjugated to a drug using an engineered cysteine residue (i.e., a TDC) that is used in a method of the present disclosure and which can be administered in a therapeutically effective amount of about 1.0 mg/kg-10 mg/kg, 1.0 mg/kg-9.8 mg/kg, 1.0 mg/kg-9.4 mg/kg, 1.0 mg/kg-9.0 mg/kg, 1.0 mg/kg-8.6 mg/kg, 1.0 mg/kg-8.2 mg/kg, 1.0 mg/kg-7.8 mg/kg, 1.0 mg/kg-7.4 mg/kg, 1.0 mg/kg-7.0 mg/kg, 1.0 mg/kg-6.6 mg/kg, 1.0 mg/kg-6.2 mg/kg, 1.0 mg/kg-5.6 mg/kg, 1.0 mg/kg-5.2 mg/kg, 1.0 mg/kg-4.8 mg/kg, 1.0 mg/kg-4.0 mg/kg, 1.0 mg/kg-3.2 mg/kg, 1.0 mg/kg-2.4 mg/kg, 1.0 mg/kg-1.8 mg/kg, 1.8 mg/kg-10 mg/kg, 1.8 mg/kg-9.8 mg/kg, 1.8 mg/kg-9.4 mg/kg, 1.8 mg/kg-9.0 mg/kg, 1.8 mg/kg-8.6 mg/kg, 1.8 mg/kg-8.2 mg/kg, 1.8 mg/kg-7.8 mg/kg, 1.8 mg/kg-7.4 mg/kg, 1.8 mg/kg-7.0 mg/kg, 1.8 mg/kg-6.6 mg/kg, 1.8 mg/kg-6.2 mg/kg, 1.8 mg/kg-5.6 mg/kg, 1.8 mg/kg-5.2 mg/kg, 1.8 mg/kg-4.8 mg/kg, 1.8 mg/kg-4.0 mg/kg, 1.8 mg/kg-3.2 mg/kg, 1.8 mg/kg-2.4 mg/kg, 2.4 mg/kg-10 mg/kg, 2.4 mg/kg-9.8 mg/kg, 2.4 mg/kg-9.4 mg/kg, 2.4 mg/kg-9.0 mg/kg, 2.4 mg/kg-8.6 mg/kg, 2.4 mg/kg-8.2 mg/kg, 2.4 mg/kg-7.8 mg/kg, 2.4 mg/kg-7.4 mg/kg, 2.4 mg/kg-7.0 mg/kg, 2.4 mg/kg-6.6 mg/kg, 2.4 mg/kg-6.2 mg/kg, 2.4 mg/kg-5.6 mg/kg, 2.4 mg/kg-5.2 mg/kg, 2.4 mg/kg-4.8 mg/kg, 2.4 mg/kg-4.0 mg/kg, 2.4 mg/kg-3.2 mg/kg, 3.2 mg/kg-10 mg/kg, 3.2 mg/kg-9.8 mg/kg, 3.2 mg/kg-9.4 mg/kg, 3.2 mg/kg-9.0 mg/kg, 3.2 mg/kg-8.6 mg/kg, 3.2 mg/kg-8.2 mg/kg, 3.2 mg/kg-7.8 mg/kg, 3.2 mg/kg-7.4 mg/kg, 3.2 mg/kg-7.0 mg/kg, 3.2 mg/kg-6.6 mg/kg, 3.2 mg/kg-6.2 mg/kg, 3.2 mg/kg-5.6 mg/kg, 3.2 mg/kg-5.2 mg/kg, 3.2 mg/kg-4.8 mg/kg, 3.2 mg/kg-4.0 mg/kg, 4.0 mg/kg-10 mg/kg, 4.0 mg/kg-9.8 mg/kg, 4.0 mg/kg-9.4 mg/kg, 4.0 mg/kg-9.0 mg/kg, 4.0 mg/kg-8.6 mg/kg, 4.0 mg/kg-8.2 mg/kg, 4.0 mg/kg-7.8 mg/kg, 4.0 mg/kg-7.4 mg/kg, 4.0 mg/kg-7.0 mg/kg, 4.0 mg/kg-6.6 mg/kg, 4.0 mg/kg-6.2 mg/kg, 4.0 mg/kg-5.6 mg/kg, 4.0 mg/kg-5.2 mg/kg, 4.0 mg/kg-4.8 mg/kg, 4.8 mg/kg-10 mg/kg, 4.8 mg/kg-9.8 mg/kg, 4.8 mg/kg-9.4 mg/kg, 4.8 mg/kg-9.0 mg/kg, 4.8 mg/kg-8.6 mg/kg, 4.8 mg/kg-8.2 mg/kg, 4.8 mg/kg-7.8 mg/kg, 4.8 mg/kg-7.4 mg/kg, 4.8 mg/kg-7.0 mg/kg, 4.8 mg/kg-6.6 mg/kg, 4.8 mg/kg-6.2 mg/kg, 4.8 mg/kg-5.6 mg/kg, 4.8 mg/kg-5.2 mg/kg, 5.2 mg/kg-10 mg/kg, 5.2 mg/kg-9.8 mg/kg, 5.2 mg/kg-9.4 mg/kg, 5.2 mg/kg-9.0 mg/kg, 5.2 mg/kg-8.6 mg/kg, 5.2 mg/kg-8.2 mg/kg, 5.2 mg/kg-7.8 mg/kg, 5.2 mg/kg-7.4 mg/kg, 5.2 mg/kg-7.0 mg/kg, 5.2 mg/kg-6.6 mg/kg, 5.2 mg/kg-6.2 mg/kg, 5.2 mg/kg-5.6 mg/kg, 5.6 mg/kg-10 mg/kg, 5.6 mg/kg-9.8 mg/kg, 5.6 mg/kg-9.4 mg/kg, 5.6 mg/kg-9.0 mg/kg, 5.6 mg/kg-8.6 mg/kg, 5.6 mg/kg-8.2 mg/kg, 5.6 mg/kg-7.8 mg/kg, 5.6 mg/kg-7.4 mg/kg, 5.6 mg/kg-7.0 mg/kg, 5.6 mg/kg-6.6 mg/kg, 5.6 mg/kg-6.2 mg/kg, 6.2 mg/kg-10 mg/kg, 6.2 mg/kg-9.8 mg/kg, 6.2 mg/kg-9.4 mg/kg, 6.2 mg/kg-9.0 mg/kg, 6.2 mg/kg-8.6 mg/kg, 6.2 mg/kg-8.2 mg/kg, 6.2 mg/kg-7.8 mg/kg, 6.2 mg/kg-7.4 mg/kg, 6.2 mg/kg-7.0 mg/kg, 6.2 mg/kg-6.6 mg/kg, 6.6 mg/kg-10 mg/kg, 6.6 mg/kg-9.8 mg/kg, 6.6 mg/kg-9.4 mg/kg, 6.6 mg/kg-9.0 mg/kg, 6.6 mg/kg-8.6 mg/kg, 6.6 mg/kg-8.2 mg/kg, 6.6 mg/kg-7.8 mg/kg, 6.6 mg/kg-7.4 mg/kg, 6.6 mg/kg-7.0 mg/kg, 7.0 mg/kg-10 mg/kg, 7.0 mg/kg-9.8 mg/kg, 7.0 mg/kg-9.4 mg/kg, 7.0 mg/kg-9.0 mg/kg, 7.0 mg/kg-8.6 mg/kg, 7.0 mg/kg-8.2 mg/kg, 7.0 mg/kg-7.8 mg/kg, 7.0 mg/kg-7.4 mg/kg, 7.4 mg/kg-10 mg/kg, 7.4 mg/kg-9.8 mg/kg, 7.4 mg/kg-9.4 mg/kg, 7.4 mg/kg-9.0 mg/kg, 7.4 mg/kg-8.6 mg/kg, 7.4 mg/kg-8.2 mg/kg, 7.4 mg/kg-7.8 mg/kg, 7.8 mg/kg-10 mg/kg, 7.8 mg/kg-9.8 mg/kg, 7.8 mg/kg-9.4 mg/kg, 7.8 mg/kg-9.0 mg/kg, 7.8 mg/kg-8.6 mg/kg, 7.8 mg/kg-8.2 mg/kg, 8.2 mg/kg-10 mg/kg, 8.2 mg/kg-9.8 mg/kg, 8.2 mg/kg-9.4 mg/kg, 8.2 mg/kg-9.0 mg/kg, 8.2 mg/kg-8.6 mg/kg, 8.6 mg/kg-10 mg/kg, 8.6 mg/kg-9.8 mg/kg, 8.6 mg/kg-9.4 mg/kg, 8.6 mg/kg-9.0 mg/kg, 9.0 mg/kg-10 mg/kg, 9.0 mg/kg-9.8 mg/kg, 9.0 mg/kg-9.4 mg/kg, 9.4 mg/kg-10 mg/kg, 9.4 mg/kg-9.8 mg/kg, or 9.6 mg/kg-10 mg/kg, In some embodiments, the NaPi2b-TDC is administered in a therapeutically effective amount of about 1.0 mg/kg. In some embodiments, the NaPi2b-TDC is administered in a therapeutically effective amount of about 1.8 mg/kg. In some embodiments, the NaPi2b-TDC is administered in a therapeutically effective amount of about 2.4 mg/kg. In some embodiments, the NaPi2b-TDC is administered in a therapeutically effective amount of about 3.2 mg/kg. In some embodiments, the NaPi2b-TDC is administered in a therapeutically effective amount of about 4.8 mg/kg. In some embodiments, the NaPi2b-TDC is administered in a therapeutically effective amount of about 5.2 mg/kg. In some embodiments, the NaPi2b-TDC is administered in a therapeutically effective amount of about 5.6 mg/kg. In some embodiments, the NaPi2b-TDC is administered in a therapeutically effective amount of about 6.2 mg/kg. In some embodiments, the NaPi2b-TDC is administered in a therapeutically effective amount of about 6.6 mg/kg. In some embodiments, the NaPi2b-TDC is administered in a therapeutically effective amount of about 7.0 mg/kg. In some embodiments, the NaPi2b-TDC is administered in a therapeutically effective amount of about 7.4 mg/kg. In some embodiments, the NaPi2b-TDC is administered in a therapeutically effective amount of about 7.8 mg/kg. In some embodiments, the NaPi2b-TDC is administered in a therapeutically effective amount of about 8.2 mg/kg. In some embodiments, the NaPi2b-TDC is administered in a therapeutically effective amount of about 8.6 mg/kg. In some embodiments, the NaPi2b-TDC is administered in a therapeutically effective amount of about 9.0 mg/kg. In some embodiments, the NaPi2b-TDC is administered in a therapeutically effective amount of about 9.4 mg/kg. In some embodiments, the NaPi2b-TDC is administered in a therapeutically effective amount of about 9.8 mg/kg. In some embodiments, the NaPi2b-TDC is administered in a therapeutically effective amount of about 10 mg/kg.

Any of the methods described herein may include administration of one or more additional therapeutically effective amounts of a NaPi2b antagonist.

In some embodiments, the one or more additional therapeutically effective amounts of a NaPi2b antagonist may be maintained at the same level as the initial dose of NaPi2b antagonist.

In some embodiments, the one or more additional therapeutically effective amounts of a NaPi2b antagonist may be increased relative to the initial dose of NaPi2b antagonist. An increase in the one or more additional therapeutically effective amounts of NaPi2b antagonist administered to the subject may refer without limitation to one or more of:

increasing the amount, dose, number or frequency of doses, or concentration of the NaPi2b antagonist administered to the subject.

In some embodiments, the one or more additional therapeutically effective amounts of a NaPi2b antagonist may be decreased relative to the initial dose of NaPi2b antagonist. A decrease in the one or more additional therapeutically effective amounts of NaPi2b antagonist administered to the subject may refer without limitation to one or more of: decreasing the amount, dose, number or frequency of doses, or concentration of the NaPi2b antagonist administered to the subject.

The above dosages are exemplary of the average case, but there can be individual instances in which higher or lower dosages are merited, and such are within the scope of this disclosure. In practice, the physician determines the actual dosing regimen that is most suitable for an individual subject, which can vary with the age, weight, and response of the particular subject. Such doses may be administered daily or intermittently, e.g., every week or every three weeks (e.g., such that the patient receives from about two to about twenty, or e.g., about six doses of the NaPi2b antagonist). An initial higher loading dose, followed by one or more lower doses may be administered. However, other dosage regimens may be useful. The progress of the dosage regime is easily monitored by conventional techniques and assays.

Dosage amounts and intervals can be adjusted individually to provide plasma levels of the NaPi2b antagonist that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a NaPi2b antagonist can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days' rest, and another five daily doses (5/2/5); or, any dose regimen determined to be appropriate for the circumstance.

In some embodiments, the NaPi2b antagonist may be an immunoconjugate, such as an ADC or cysteine engineered antibody-drug conjugate (such as a TDC). For the prevention or treatment of disease, the appropriate dosage of an immunoconjugate will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments.

For repeated administrations over several days or longer, depending on the condition, the treatment is sustained until a desired suppression of disease symptoms occurs. An exemplary dosing regimen comprises administering a high initial loading dose of followed by a weekly or bi-monthly maintenance dose that is less than or equal to the initial dose of a NaPi2b antagonist. Other dosage regimens may be useful. The progress of this therapy is easily monitored by conventional techniques and assays including ultrasound imaging.

A therapeutically effective amount of a NaPi2b antagonist may be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished, e.g., by using a needle and syringe or by using a high pressure technique. Various dosing schedules including but not limited to single or multiple administrations over various time-points, bolus administration, and pulse infusion are contemplated herein. In certain embodiments, the NaPi2b antagonist is an anti-NaPi2b antibody (e.g., an ADC or TDC) which is administered intravenously.

Pharmaceutical compositions containing NaPi2b antagonists can be manufactured, for example, by conventional mixing, dissolving, granulating, dragee-making, emulsifying, encapsulating, entrapping, or lyophilizing processes.

NaPi2b antagonists can be readily combined with pharmaceutically acceptable carriers well-known in the art. Exemplary pharmaceutically acceptable carriers are provided in U.S. Pat. Nos. 7,989,595 and 7,723,485, both of which are herein incorporated by reference in their entireties.

Time Point Measurements

In the methods of the present disclosure, the level of expression of HE4 is compared between a first time point (e.g., a baseline) and a second time point in a subject having cancer (e.g., a MUC16-positive cancer). In some embodiments, the subject has a MUC16-positive cancer.

In some embodiments, the first time point is used to detect the level of expression of HE4 in the subject prior to MUC16 antagonist treatment. For example, the level of expression of HE4 in a subject may be measured prior to MUC16 antagonist treatment, and one or more samples taken subsequent to treatment with a MUC16 antagonist may be used, inter alia, to monitor the efficacy of the treatment, determine whether to continue or discontinue the treatment, modulate the treatment, monitor responsiveness to the treatment, predict responsiveness to a maintenance treatment, predict cancer progression, and so forth.

In some embodiments, the first time point is used to measure or detect the level of expression of HE4 in the subject or patient immediately before, or about 10 seconds before, about 30 seconds before, about 1 minute before, about 5 minutes before, about 10 minutes before, about 15 minutes before, about 30 minutes before, about 45 minutes before, about 1 hour before, about 1.5 hours before, about 2 hours before, about 2.5 hours before, about 3 hours before, about 3.5 hours before, about 4 hours before, about 4.5 hours before, about 5 hours before, about 5.5 hours before, about 6 hours before, about 7 hours before, about 8 hours before, about 9 hours before, about 10 hours before, about 11 hours before, about 12 hours before, about 18 hours before, about 1 day before, about 2 days before, about 3 days before, about 4 days before, about 5 days before, about 6 days before, about 1 week before, about 2 weeks before, about 3 weeks before, or about 4 weeks before MUC16 antagonist treatment. In some embodiments, the first time point is used to measure or detect the level of expression of HE4 in the subject or patient about 1 hour before MUC16 antagonist treatment. In some embodiments, the first time point is used to measure or detect the level of expression of HE4 in the subject or patient about 4 hours before MUC16 antagonist treatment. In some embodiments, the first time point is used to measure or detect the level of expression of HE4 in the subject or patient about 1 day before MUC16 antagonist treatment. In some embodiments, the first time point is used to measure or detect the level of expression of HE4 in the subject or patient about 3 days before MUC16 antagonist treatment. In specific embodiments, the MUC16 antagonist used in the treatment is an anti-MUC16 antibody which may be a naked antibody, an ADC, or a TDC.

In some embodiments, the first time point is used to measure or detect the level of expression of HE4 in the subject or patient prior to MUC16 antagonist treatment, and can be compared with the level of expression of HE4 at a second time point. In some embodiments, the second time point is used to measure or detect the level of expression of HE4 in the subject or patient after treatment with a MUC16 antagonist (e.g., a first time point can be taken before the initial dose of a therapeutically effective amount of a MUC16 antagonist and compared to a sample taken at a second time point, after the first, second, third, fourth, or later dose of the MUC16 antagonist). In some embodiments, the second time point is used to detect the level of expression of HE4 in the subject about 1 hour after, about 2 hours after, about 3 hours after, about 4 hours after, about 5 hours after, about 6 hours after, about 7 hours after, about 8 hours after, about 9 hours after, about 10 hours after, about 11 hours after, about 12 hours after, about 18 hours after, about 1 day after, about 1.5 days after, about 2 days after, about 2.5 days after, about 3 days after, about 3.5 days after, about 4 days after, about 4.5 days after, about 5 days after, about 5.5 days after, about 6 days after, about 6.5 days after, about 1 week after, about 1.5 weeks after, about 2 weeks after, about 2.5 weeks after, about 3 weeks after, about 3.5 weeks after, about 4 weeks after, about 1 month after, about 1.5 months after, about 2 months after, about 2.5 months after, about 3 months after, about 3.5 months after, about 4 months after, about 4.5 months after, about 5 months after, about 5.5 months after, about 6 months after, about 6.5 months after, about 7 months after, about 7.5 months after, about 8 months after, about 8.5 months after, about 9 months after, about 9.5 months after, about 10 months after, about 10.5 months after, about 11 months after, about 11.5 months after, or about 12 months after MUC16 antagonist treatment. In some embodiments, the second time point is used to detect the level of expression of HE4 in the subject or patient about 1 hour after MUC16 antagonist treatment. In some embodiments, the second time point is used to detect the level of expression of HE4 in the subject or patient about 4 hours after MUC16 antagonist treatment. In some embodiments, the second time point is used to detect the level of expression of HE4 in the subject or patient about 8 hours after MUC16 antagonist treatment. In some embodiments, the second time point is used to detect the level of expression of HE4 in the subject or patient about 12 hours after MUC16 antagonist treatment. In some embodiments, the second time point is used to detect the level of expression of HE4 in the subject or patient about 18 hours after MUC16 antagonist treatment. In some embodiments, the second time point is used to detect the level of expression of HE4 in the subject or patient about 1 day after MUC16 antagonist treatment. In some embodiments, the second time point is used to detect the level of expression of HE4 in the subject or patient about 1.5 days after MUC16 antagonist treatment. In some embodiments, the second time point is used to detect the level of expression of HE4 in the subject or patient about 2 days after MUC16 antagonist treatment. In some embodiments, the second time point is used to detect the level of expression of HE4 in the subject or patient about 2.5 days after MUC16 antagonist treatment. In some embodiments, the second time point is used to detect the level of expression of HE4 in the subject or patient about 3 days after MUC16 antagonist treatment. In some embodiments, the second time point is used to detect the level of expression of HE4 in the subject or patient about 3.5 days after MUC16 antagonist treatment. In some embodiments, the second time point is used to detect the level of expression of HE4 in the subject or patient about 4 days after MUC16 antagonist treatment. In some embodiments, the second time point is used to detect the level of expression of HE4 in the subject or patient about 4.5 day after MUC16 antagonist treatment. In some embodiments, the second time point is used to detect the level of expression of HE4 in the subject or patient about 5 days after MUC16 antagonist treatment. In specific embodiments the MUC16 antagonist used in the treatment is an anti-MUC16 antibody which may be a naked antibody, an ADC, or a TDC.

In some embodiments, the second time point is used to measure or detect the level of expression of HE4 in the subject or patient after any later or subsequent treatment with a MUC16 antagonist (e.g., a first time point can be taken after a first dose of a MUC16 antagonist and compared to a sample taken after a second or third dose of the MUC16 antagonist). In some embodiments, the second time point is used to measure or detect the level of expression of HE4 in the subject or patient about 1 hour after, about 2 hours after, about 3 hours after, about 4 hours after, about 5 hours after, about 6 hours after, about 7 hours after, about 8 hours after, about 9 hours after, about 10 hours after, about 11 hours after, about 12 hours after, about 18 hours after, about 1 day after, about 1.5 days after, about 2 days after, about 2.5 days after, about 3 days after, about 3.5 days after, about 4 days after, about 4.5 days after, about 5 days after, about 5.5 days after, about 6 days after, about 6.5 days after, about 1 week after, about 1.5 weeks after, about 2 weeks after, about 2.5 weeks after, about 3 weeks after, about 3.5 weeks after, about 4 weeks after, about 1 month after, about 1.5 months after, about 2 months after, about 2.5 months after, about 3 months after, about 3.5 months after, about 4 months after, about 4.5 months after, about 5 months after, about 5.5 months after, about 6 months after, about 6.5 months after, about 7 months after, about 7.5 months after, about 8 months after, about 8.5 months after, about 9 months after, about 9.5 months after, about 10 months after, about 10.5 months after, about 11 months after, about 11.5 months after, or about 12 months after any later or subsequent MUC16 antagonist treatment. In some embodiments, the second time point is used to measure or detect the level of expression of HE4 in the subject or patient about 1 hour after any later or subsequent MUC16 antagonist treatment. In some embodiments, the second time point is used to measure or detect the level of expression of HE4 in the subject or patient about 4 hours after any later or subsequent MUC16 antagonist treatment. In some embodiments, the second time point is used to measure or detect the level of expression of HE4 in the subject or patient about 8 hours after any later or subsequent MUC16 antagonist treatment. In some embodiments, the second time point is used to measure or detect the level of expression of HE4 in the subject or patient about 12 hours after any later or subsequent MUC16 antagonist treatment. In some embodiments, the second time point is used to measure or detect the level of expression of HE4 in the subject or patient about 18 hours after any later or subsequent MUC16 antagonist treatment. In some embodiments, the second time point is used to measure or detect the level of expression of HE4 in the subject or patient about 1 day after any later or subsequent MUC16 antagonist treatment. In some embodiments, the second time point is used to measure or detect the level of expression of HE4 in the subject or patient about 1.5 days after any later or subsequent MUC16 antagonist treatment. In some embodiments, the second time point is used to measure or detect the level of expression of HE4 in the subject or patient about 2 days after any later or subsequent MUC16 antagonist treatment. In some embodiments, the second time point is used to measure or detect the level of expression of HE4 in the subject or patient about 2.5 days after any later or subsequent MUC16 antagonist treatment. In some embodiments, the second time point is used to measure or detect the level of expression of HE4 in the subject or patient about 3 days after any later or subsequent MUC16 antagonist treatment. In some embodiments, the second time point is used to measure or detect the level of expression of HE4 in the subject or patient about 3.5 days after any later or subsequent MUC16 antagonist treatment. In some embodiments, the second time point is used to measure or detect the level of expression of HE4 in the subject or patient about 4 days after any later or subsequent MUC16 antagonist treatment. In some embodiments, the second time point is used to measure or detect the level of expression of HE4 in the subject or patient about 4.5 days after any later or subsequent MUC16 antagonist treatment. In some embodiments, the second time point is used to measure or detect the level of expression of HE4 in the subject or patient about 5 days after any later or subsequent MUC16 antagonist treatment. In specific embodiments the MUC16 antagonist used in the treatment is an anti-MUC16 antibody which may be a naked antibody, an ADC, or a TDC.

In certain embodiments, changes in the level of expression of HE4 between the first time point and the second time point are used to assess the progression of disease in response to the MUC16 antagonist therapy. In certain embodiments, changes in the level of expression of HE4 between the first time point and the second time point are used to assess disease stability in response to the MUC16 antagonist therapy. In certain embodiments, changes in the level of expression of HE4 between the first time point and the second time point are used to determine the continued dose of the MUC16 antagonist therapy. In certain embodiments, changes in the level of expression of HE4 between the first time point and the second time point are used to determine the course of therapy with the MUC16 antagonist (e.g., continued dosing, discontinued dosing, dosing in combination with a second or third chemotherapeutic agents, increased dosing, decreased dosing, maintenance dosing, etc.). In specific embodiments, the MUC16 antagonist used in the treatment is an anti-MUC16 antibody which may be a naked antibody, an ADC, or a TDC.

Additional embodiments of a baseline are as follows: in certain embodiments, a baseline refers to samples taken from a subject before treatment with an anti-cancer therapy; in some embodiments, the anti-cancer therapy is a MUC16 antagonist; in specific embodiments, the MUC16 antagonist used in the treatment is an anti-MUC16 antibody which may be a naked antibody, an ADC, or a TDC; in specific embodiments, the baseline is a sample taken prior to any treatment with a MUC16 antagonist and can be used in comparison with a sample taken after a treatment with a MUC16 antagonist (e.g., a baseline can be taken before the first dose of an anti-MUC16 antibody and compared to a sample taken after the first, second, third, fourth, or later dose of the anti-MUC16 antibody); and in specific embodiments, the baseline is a sample taken prior to any given treatment with a MUC16 antagonist and can be used in comparison with a sample taken after any later treatment with a MUC16 antagonist (e.g., a baseline can be taken after a first dose of an anti-MUC16 antibody and compared to a sample taken after a second or third dose of the anti-MUC16 antibody).

In other embodiments, a baseline may refer to samples taken from a subject before treatment with an anti-cancer therapy (e.g., a NaPi2b antagonist). In some embodiments, the anti-cancer therapy is a NaPi2b antagonist; in specific embodiments the NaPi2b antagonist used in the treatment is an anti-NaPi2b antibody which may be a naked antibody, an ADC, or a TDC; in specific embodiments, the baseline is a sample taken prior to any treatment with a NaPi2b antagonist and can be used in comparison with a sample taken after a treatment with a NaPi2b antagonist (e.g., a baseline can be taken before the first dose of an anti-NaPi2b antibody and compared to a sample taken after the first, second, third, fourth, or later dose of the anti-NaPi2b antibody); in specific embodiments, the baseline is a sample taken prior to any given treatment with a NaPi2b antagonist and can be used in comparison with a sample taken after any later treatment with a NaPi2b antagonist (e.g., a baseline can be taken after a first dose of an anti-NaPi2b antibody and compared to a sample taken after a second or third dose of the anti-NaPi2b antibody); in certain embodiments, the baseline is used to assess the efficacy of the anti-NaPi2b antibody therapy; in certain embodiments, the baseline is used to assess the progression disease in response to the anti-NaPi2b antibody therapy; in certain embodiments, the baseline is used to assess disease stability in response to the anti-NaPi2b antibody therapy; in certain embodiments, the baseline is used to determine the continued dose of the anti-NaPi2b antibody therapy; in certain embodiments, the baseline is used to determine the course of therapy with the anti-NaPi2b antibody (e.g., continued dosing, discontinued dosing, dosing in combination with a second or third chemotherapeutic agents, increased dosing, decreased dosing, maintenance dosing, etc.).

HE4 Expression Level Measurements

In the methods of the present disclosure, the level of expression of HE4 in a sample from a subject or patient having cancer (e.g., a MUC16-positive cancer) is measured or detected. In some embodiments, the level of expression of HE4 refers to circulating level of HE4 protein. In some embodiments, the circulating level of HE4 includes the level of HE4 in a serum or blood sample.

Any suitable method for measuring or detecting gene expression known in the art may be used to measure the level of expression of HE4. In some embodiments, the expression level may refer to RNA transcript level (e.g., mRNA expression level). mRNA expression level may be measured by many methods. Such methods may quantify the copies of a specific mRNA present in a sample by measuring the amount of hybridization to an mRNA-specific probe. Other methods may amplify mRNA, or cDNA generated from mRNA, and quantify the amount of amplicon generated to extrapolate how much mRNA was present in a sample. Yet other methods may involve next-generation sequencing of part or all of mRNA transcripts, or cDNA generated from mRNA, then quantifying the number of sequences detected that correspond to particular gene(s). In some embodiments, mRNA expression level is measured by quantitative PCR (e.g., RT-PCR), semi-quantitative PCR, nucleotide microarray, RNA-seq, in situ hybridization, and/or Northern blotting.

In certain embodiments, the expression level may refer to protein expression level. Protein expression level, including circulating levels of HE4 protein, may be measured by many methods. Such methods may quantify proteins present in a sample by using a probe that specifically binds to a particular protein, such as an antibody, then detecting the amount of specific binding in a sample. Other methods may fragment proteins into short peptides, then detect these peptides and quantify how many peptides correspond to particular protein(s). In some embodiments, protein expression level is measured by immunoassay (for example ELISA-based assays and proximity extension assays), Western blotting, peptide microarray, immunohistochemistry, flow cytometry, and/or mass spectrometry.

In some embodiments, an HE4 protein includes the amino acid sequence of (SEQ ID NO: 18)
MPACRLGPLAAALLLSLLLFGFTLVSGTGAEKTGVCPELQADQNCTQE

CVSDSECADNLKCCSAGCATFCSLPNDKEGSCPQVNINFPQLGLCRDQ

CQVDSQCPGQMKCCRNGCGKVSCVTPNF.

In some embodiments, the expression level of an mRNA or protein may be normalized to the expression level of a reference gene. Normalizing the expression level of a particular gene to a reference is thought to enhance reproducibility across samples by factoring differences in sample size and/or mRNA/protein extraction. In these examples, expression level relative to the reference is measured. In some embodiments, multiple reference genes may be used, either singly or in aggregate (e.g., by averaging). In other embodiments, expression level of an mRNA or protein may refer to absolute expression level.

In some embodiments, a reference gene may be a housekeeping gene. A housekeeping gene is thought to be constitutively expressed in a cell in normal and/or pathological states, such as a gene encoding a protein required for basic cellular function and/or maintenance. Housekeeping genes are typically used as a reference to ensure they will be expressed at a detectable and/or reproducible level across multiple samples. Exemplary housekeeping genes and further description of the use of such genes as a reference may be found, for example, in de Kok, J. B., et al. (2005) Lab Invest. 85(1):154-9.

Anti-Cancer Therapies

In certain embodiments, the methods of the present disclosure relate to administering anti-cancer therapeutics and/or anti-cancer therapies. Examples of anti-cancer therapeutics and/or anti-cancer therapies may include, but are not limited to, chemotherapeutics or growth inhibitory agents, targeted therapeutic agents, T cells expressing a chimeric antigen receptor, antibodies or antigen-binding fragments thereof, immunoconjugates, angiogenesis inhibitors, antineoplastic agents, cancer vaccines, adjuvants, or any combinations thereof. In some embodiments, the anti-cancer therapy is an immunoconjugate. In some embodiments, the anti-cancer therapy is a MUC16 antagonist. In some embodiments, the MUC16 antagonist is an anti-MUC16 antibody. In some embodiments, the MUC16 antagonist is an immunoconjugate. In some embodiments, the MUC16 antagonist is a MUC16-ADC. In some embodiments, the MUC16-ADC is a MUC16-TDC. In some embodiments, the anti-cancer therapy is a NaPi2b antagonist. In some embodiments, the NaPi2b antagonist is an anti-NaPi2b antibody. In some embodiments, the NaPi2b antagonist is an immunoconjugate. In some embodiments, the NaPi2b antagonist is a NaPi2b-ADC. In some embodiments, the NaPi2b-ADC is a NaPi2b-TDC.

MUC16 Antagonists

In certain embodiments of the methods of the present disclosure, the anti-cancer therapy is a MUC16 antagonist treatment. Any MUC16 antagonist known in the art may be used in any of the methods described herein (for example, antagonists disclosed in U.S. Pat. No. 8,623,828, WO2014160368, U.S. Pat. No. 7,202,346, US20130302270, U.S. Pat. Nos. 7,723,485, and 5,428,130). In some embodiments, the MUC16 antagonist is selected from an anti-MUC16 antibody, a MUC16 inhibitor, a protein (e.g., that binds or inhibits MUC16), a peptide (e.g., that binds or inhibits MUC16), a fusion protein (e.g., that binds or inhibits MUC16), and an immunoadhesin (e.g., that binds or inhibits MUC16). As described herein, in a specific embodiment, the MUC16 antagonist is an anti-MUC16 antibody. Furthermore, the anti-MUC16 antibodies are ADCs or TDCs in specific embodiments.

In certain embodiments, an MUC16 antagonist is an anti-MUC16 antibody, e.g., an isolated antibody that binds to human MUC16. Antibodies suitable for use in the methods of the present disclosure include antibodies that bind to human MUC16. In certain embodiments, the anti-MUC16 antibodies are ADCs or TDCs.

In some embodiments, the anti-MUC16 antibody includes any antibody disclosed in U.S. Pat. Nos. 7,989,595 or 7,723,485. In some embodiments, the anti-MUC16 antibody includes at least one, two, three, four, five, or six HVRs selected from:
(a) HVR-H1 comprising the amino acid sequence of SEQ ID NO: 4 (Gly Tyr Ser Ile Thr Asn Asp Tyr Ala Trp Asn);
(b) HVR-H2 comprising the amino acid sequence of SEQ ID NO: 10 (Gly Tyr Ile Asn Tyr Ser Gly Tyr Thr Thr Tyr Asn Pro Ser Leu);
(c) HVR-H3 comprising the amino acid sequence of SEQ ID NO: 11 (Ala Arg Trp Asp Gly Gly Leu Thr Tyr);
(d) HVR-L1 comprising the amino acid sequence of SEQ ID NO: 1 (Lys Ala Ser Asp Leu Ile His Asn Trp Leu Ala);
(e) HVR-L2 comprising the amino acid sequence of SEQ ID NO: 9 (Ser Gly Ala Thr Ser Leu Glu Thr); and/or
(f) HVR-L3 comprising the amino acid sequence of SEQ ID NO: 3 (Gln Gln Tyr Trp Thr Thr Pro Phe Thr).

In a certain embodiment, the anti-MUC16 antibody comprises the following HVRs:
(a) HVR-H1 comprising the amino acid sequence of SEQ ID NO: 4 (Gly Tyr Ser Ile Thr Asn Asp Tyr Ala Trp Asn);
(b) HVR-H2 comprising the amino acid sequence of SEQ ID NO: 10 (Gly Tyr Ile Asn Tyr Ser Gly Tyr Thr Thr Tyr Asn Pro Ser Leu);
(c) HVR-H3 comprising the amino acid sequence of SEQ ID NO: 11 (Ala Arg Trp Asp Gly Gly Leu Thr Tyr);
(d) HVR-L1 comprising the amino acid sequence of SEQ ID NO: 1 (Lys Ala Ser Asp Leu Ile His Asn Trp Leu Ala);
(e) HVR-L2 comprising the amino acid sequence of SEQ ID NO: 9 (Ser Gly Ala Thr Ser Leu Glu Thr); and
(f) HVR-L3 comprising the amino acid sequence of SEQ ID NO: 3 (Gln Gln Tyr Trp Thr Thr Pro Phe Thr).

In some embodiments, the anti-MUC16 antibody includes at least one, two, three, four, five, or six HVRs selected from
(a) HVR-H1 comprising the amino acid sequence of SEQ ID NO: 4 (Gly Tyr Ser Ile Thr Asn Asp Tyr Ala Trp Asn);
(b) HVR-H2 comprising the amino acid sequence of SEQ ID NO: 5 (Gly Tyr Ile Ser Tyr Ser Gly Tyr Thr Thr Tyr Asn Pro Ser Leu Lys Ser);
(c) HVR-H3 comprising the amino acid sequence of SEQ ID NO: 6 (Ala Arg Trp Thr Ser Gly Leu Asp Tyr);
(d) HVR-L1 comprising the amino acid sequence of SEQ ID NO: 1 (Lys Ala Ser Asp Leu Ile His Asn Trp Leu Ala);

(e) HVR-L2 comprising the amino acid sequence of SEQ ID NO: 2 (Tyr Gly Ala Thr Ser Leu Glu Thr); and/or
(f) HVR-L3 comprising the amino acid sequence of SEQ ID NO: 3 (Gln Gln Tyr Trp Thr Thr Pro Phe Thr).

In some embodiments, the anti-MUC16 antibody the following HVRs:
(a) HVR-H1 comprising the amino acid sequence of SEQ ID NO: 4 (Gly Tyr Ser Ile Thr Asn Asp Tyr Ala Trp Asn);
(b) HVR-H2 comprising the amino acid sequence of SEQ ID NO: 5 (Gly Tyr Ile Ser Tyr Ser Gly Tyr Thr Thr Tyr Asn Pro Ser Leu Lys Ser);
(c) HVR-H3 comprising the amino acid sequence of SEQ ID NO: 6 (Ala Arg Trp Thr Ser Gly Leu Asp Tyr);
(d) HVR-L1 comprising the amino acid sequence of SEQ ID NO: 1 (Lys Ala Ser Asp Leu Ile His Asn Trp Leu Ala);
(e) HVR-L2 comprising the amino acid sequence of SEQ ID NO: 2 (Tyr Gly Ala Thr Ser Leu Glu Thr); and
(f) HVR-L3 comprising the amino acid sequence of SEQ ID NO: 3 (Gln Gln Tyr Trp Thr Thr Pro Phe Thr).

In some embodiments, the anti-MUC16 antibody includes at least one, two, three, four, five, or six HVRs selected from
(a) HVR-H1 comprising the amino acid sequence of SEQ ID NO: 4 (Gly Tyr Ser Ile Thr Asn Asp Tyr Ala Trp Asn);
(b) HVR-H2 comprising the amino acid sequence of SEQ ID NO: 5 (Gly Tyr Ile Ser Tyr Ser Gly Tyr Thr Thr Tyr Asn Pro Ser Leu Lys Ser);
(c) HVR-H3 comprising the amino acid sequence of SEQ ID NO: 14 (Ala Arg Trp Ala Ser Gly Leu Asp Tyr);
(d) HVR-L1 comprising the amino acid sequence of SEQ ID NO: 1 (Lys Ala Ser Asp Leu Ile His Asn Trp Leu Ala);
(e) HVR-L2 comprising the amino acid sequence of SEQ ID NO: 2 (Tyr Gly Ala Thr Ser Leu Glu Thr); and/or
(f) HVR-L3 comprising the amino acid sequence of SEQ ID NO: 3 (Gln Gln Tyr Trp Thr Thr Pro Phe Thr).

In some embodiments, the anti-MUC16 antibody the following HVRs:
(a) HVR-H1 comprising the amino acid sequence of SEQ ID NO: 4 (Gly Tyr Ser Ile Thr Asn Asp Tyr Ala Trp Asn);
(b) HVR-H2 comprising the amino acid sequence of SEQ ID NO: 5 (Gly Tyr Ile Ser Tyr Ser Gly Tyr Thr Thr Tyr Asn Pro Ser Leu Lys Ser);
(c) HVR-H3 comprising the amino acid sequence of SEQ ID NO: 14 (Ala Arg Trp Ala Ser Gly Leu Asp Tyr);
(d) HVR-L1 comprising the amino acid sequence of SEQ ID NO: 1 (Lys Ala Ser Asp Leu Ile His Asn Trp Leu Ala);
(e) HVR-L2 comprising the amino acid sequence of SEQ ID NO: 2 (Tyr Gly Ala Thr Ser Leu Glu Thr); and
(f) HVR-L3 comprising the amino acid sequence of SEQ ID NO: 3 (Gln Gln Tyr Trp Thr Thr Pro Phe Thr).

In some embodiments, the anti-MUC16 antibody includes at least one, two, three, four, five, or six HVRs selected from
(a) HVR-H1 comprising the amino acid sequence of SEQ ID NO: 4 (Gly Tyr Ser Ile Thr Asn Asp Tyr Ala Trp Asn);
(b) HVR-H2 comprising the amino acid sequence of SEQ ID NO: 16 (Gly Tyr Ile Asn Tyr Ala Gly Tyr Thr Thr Tyr Asn Pro Ser Leu Lys Ser);
(c) HVR-H3 comprising the amino acid sequence of SEQ ID NO: 14 (Ala Arg Trp Ala Ser Gly Leu Asp Tyr);
(d) HVR-L1 comprising the amino acid sequence of SEQ ID NO: 1 (Lys Ala Ser Asp Leu Ile His Asn Trp Leu Ala);
(e) HVR-L2 comprising the amino acid sequence of SEQ ID NO: 2 (Tyr Gly Ala Thr Ser Leu Glu Thr); and/or
(f) HVR-L3 comprising the amino acid sequence of SEQ ID NO: 3 (Gln Gln Tyr Trp Thr Thr Pro Phe Thr).

In some embodiments, the anti-MUC16 antibody the following HVRs:
(a) HVR-H1 comprising the amino acid sequence of SEQ ID NO: 4 (Gly Tyr Ser Ile Thr Asn Asp Tyr Ala Trp Asn);
(b) HVR-H2 comprising the amino acid sequence of SEQ ID NO: 16 (Gly Tyr Ile Asn Tyr Ala Gly Tyr Thr Thr Tyr Asn Pro Ser Leu Lys Ser);
(c) HVR-H3 comprising the amino acid sequence of SEQ ID NO: 14 (Ala Arg Trp Ala Ser Gly Leu Asp Tyr);
(d) HVR-L1 comprising the amino acid sequence of SEQ ID NO: 1 (Lys Ala Ser Asp Leu Ile His Asn Trp Leu Ala);
(e) HVR-L2 comprising the amino acid sequence of SEQ ID NO: 2 (Tyr Gly Ala Thr Ser Leu Glu Thr); and
(f) HVR-L3 comprising the amino acid sequence of SEQ ID NO: 3 (Gln Gln Tyr Trp Thr Thr Pro Phe Thr).

In some embodiments, the anti-MUC16 antibody includes a heavy chain variable region (VH) comprising the amino acid sequence of SEQ ID NO: 13:

```
Asp Val Gln Leu Gln Glu Ser Gly Pro Gly Leu
Val Asn Pro Ser Gln Ser Leu Ser Leu Thr Cys
Thr Val Thr Gly Tyr Ser Ile Thr Asn Asp Tyr
Ala Trp Asn Trp Ile Arg Gln Phe Pro Gly Asn
Lys Leu Glu Trp Met Gly Tyr Ile Asn Tyr Ser
Gly Tyr Thr Thr Tyr Asn Pro Ser Leu Lys Ser
Arg Ile Ser Ile Thr Arg Asp Thr Ser Lys Asn
Gln Phe Phe Leu His Leu Asn Ser Val Thr Thr
Glu Asp Thr Ala Thr Tyr Tyr Cys Ala Arg Trp
Asp Gly Gly Leu Thr Tyr Trp Gly Gln Gly Thr
Leu Val Thr Val Ser Ala
```

In some embodiments, the anti-MUC16 antibody includes a light chain variable region (VL) comprising the amino acid sequence of SEQ ID NO: 12:

```
Asp Ile Gln Met Thr Gln Ser Ser Ser Phe Leu
Ser Val Ser Leu Gly Gly Arg Val Thr Ile Thr
Cys Lys Ala Ser Asp Leu Ile His Asn Trp Leu
Ala Trp Tyr Gln Gln Lys Pro Gly Asn Ala Pro
Arg Leu Leu Ile Ser Gly Ala Thr Ser Leu Glu
Thr Gly Val Pro Ser Arg Phe Ser Gly Ser Gly
Ser Gly Asn Asp Tyr Thr Leu Ser Ile Ala Ser
Leu Gln Thr Glu Asp Ala Ala Thr Tyr Tyr Cys
Gln Gln Tyr Trp Thr Thr Pro Phe Thr Phe Gly
Ser Gly Thr Lys Leu Glu Ile Lys
```

In some embodiments, the anti-MUC16 antibody includes a heavy chain variable region (VH) comprising the amino acid sequence of SEQ ID NO: 13 and a light chain variable region (VL) comprising the amino acid sequence of SEQ ID NO: 12. In some embodiments, the sequences include post-translational modifications of the above sequences.

In some embodiments, the anti-MUC16 antibody includes a heavy chain variable region (VH) comprising the amino acid sequence of SEQ ID NO: 8:

```
Glu Val Gln Leu Val Glu Ser Gly Gly Gly Leu

Val Gln Pro Gly Gly Ser Leu Arg Leu Ser Cys

Ala Ala Ser Gly Tyr Ser Ile Thr Asn Asp Tyr

Ala Trp Asn Trp Val Arg Gln Ala Pro Gly Lys

Gly Leu Glu Trp Val Gly Tyr Ile Ser Tyr Ser

Gly Tyr Thr Thr Tyr Asn Pro Ser Leu Lys Ser

Arg Phe Thr Ile Ser Arg Asp Thr Ser Lys Asn

Thr Leu Tyr Leu Gln Met Asn Ser Leu Arg Ala

Glu Asp Thr Ala Val Tyr Tyr Cys Ala Arg Trp

Thr Ser Gly Leu Asp Tyr Trp Gly Gln Gly Thr

Leu Val Thr Val Ser Ser
```

In some embodiments, the anti-MUC16 antibody includes a light chain variable region (VL) comprising the amino acid sequence of SEQ ID NO: 7:

```
Asp Ile Gln Met Thr Gln Ser Pro Ser Ser Leu

Ser Ala Ser Val Gly Asp Arg Val Thr Ile Thr

Cys Lys Ala Ser Asp Leu Ile His Asn Trp Leu

Ala Trp Tyr Gln Gln Lys Pro Gly Lys Ala Pro

Lys Leu Leu Ile Tyr Gly Ala Thr Ser Leu Glu

Thr Gly Val Pro Ser Arg Phe Ser Gly Ser Gly

Ser Gly Thr Asp Phe Thr Leu Thr Ile Ser Ser

Leu Gln Pro Glu Asp Phe Ala Thr Tyr Tyr Cys

Gln Gln Tyr Trp Thr Thr Pro Phe Thr Phe Gly

Gln Gly Thr Lys Val Glu Ile Lys Arg
```

In some embodiments, the anti-MUC16 antibody includes a heavy chain variable region (VH) comprising the amino acid sequence of SEQ ID NO: 8 and a light chain variable region (VL) comprising the amino acid sequence of SEQ ID NO: 7. In some embodiments, the sequences include post-translational modifications of the above sequences.

In some embodiments, the anti-MUC16 antibody includes a heavy chain variable region (VH) comprising the amino acid sequence of SEQ ID NO: 15:

```
Glu Val Gln Leu Val Glu Ser Gly Gly Gly Leu

Val Gln Pro Gly Gly Ser Leu Arg Leu Ser Cys

Ala Ala Ser Gly Tyr Ser Ile Thr Asn Asp Tyr

Ala Trp Asn Trp Val Arg Gln Ala Pro Gly Lys

Gly Leu Glu Trp Val Gly Tyr Ile Ser Tyr Ser

Gly Tyr Thr Thr Tyr Asn Pro Ser Leu Lys Ser

Arg Phe Thr Ile Ser Arg Asp Thr Ser Lys Asn

Thr Leu Tyr Leu Gln Met Asn Ser Leu Arg Ala

Glu Asp Thr Ala Val Tyr Tyr Cys Ala Arg Trp

Ala Ser Gly Leu Asp Tyr Trp Gly Gln Gly Thr

Leu Val Thr Val Ser Ser
```

In some embodiments, the anti-MUC16 antibody includes a light chain variable region (VL) comprising the amino acid sequence of SEQ ID NO: 7:

```
Asp Ile Gln Met Thr Gln Ser Pro Ser Ser Leu

Ser Ala Ser Val Gly Asp Arg Val Thr Ile Thr

Cys Lys Ala Ser Asp Leu Ile His Asn Trp Leu

Ala Trp Tyr Gln Gln Lys Pro Gly Lys Ala Pro

Lys Leu Leu Ile Tyr Gly Ala Thr Ser Leu Glu

Thr Gly Val Pro Ser Arg Phe Ser Gly Ser Gly

Ser Gly Thr Asp Phe Thr Leu Thr Ile Ser Ser

Leu Gln Pro Glu Asp Phe Ala Thr Tyr Tyr Cys

Gln Gln Tyr Trp Thr Thr Pro Phe Thr Phe Gly

Gln Gly Thr Lys Val Glu Ile Lys Arg
```

In some embodiments, the anti-MUC16 antibody includes a heavy chain variable region (VH) comprising the amino acid sequence of SEQ ID NO: 15 and a light chain variable region (VL) comprising the amino acid sequence of SEQ ID NO: 7. In some embodiments, the sequences include post-translational modifications of the above sequences.

In some embodiments, the anti-MUC16 antibody includes a heavy chain variable region (VH) comprising the amino acid sequence of SEQ ID NO: 17:

```
Glu Val Gln Leu Val Glu Ser Gly Gly Gly Leu

Val Gln Pro Gly Gly Ser Leu Arg Leu Ser Cys

Ala Ala Ser Gly Tyr Ser Ile Thr Asn Asp Tyr

Ala Trp Asn Trp Val Arg Gln Ala Pro Gly Lys

Gly Leu Glu Trp Val Gly Tyr Ile Asn Tyr Ala

Gly Tyr Thr Thr Tyr Asn Pro Ser Leu Lys Ser

Arg Phe Thr Ile Ser Arg Asp Thr Ser Lys Asn

Thr Leu Tyr Leu Gln Met Asn Ser Leu Arg Ala

Glu Asp Thr Ala Val Tyr Tyr Cys Ala Arg Trp

Ala Ser Gly Leu Asp Tyr Trp Gly Gln Gly Thr

Leu Val Thr Val Ser Ser
```

In some embodiments, the anti-MUC16 antibody includes a light chain variable region (VL) comprising the amino acid sequence of SEQ ID NO: 7:

```
Asp Ile Gln Met Thr Gln Ser Pro Ser Ser Leu

Ser Ala Ser Val Gly Asp Arg Val Thr Ile Thr

Cys Lys Ala Ser Asp Leu Ile His Asn Trp Leu
```

-continued

```
Ala Trp Tyr Gln Gln Lys Pro Gly Lys Ala Pro

Lys Leu Leu Ile Tyr Gly Ala Thr Ser Leu Glu

Thr Gly Val Pro Ser Arg Phe Ser Gly Ser Gly

Ser Gly Thr Asp Phe Thr Leu Thr Ile Ser Ser

Leu Gln Pro Glu Asp Phe Ala Thr Tyr Tyr Cys

Gln Gln Tyr Trp Thr Thr Pro Phe Thr Phe Gly

Gln Gly Thr Lys Val Glu Ile Lys Arg
```

In some embodiments, the anti-MUC16 antibody includes a heavy chain variable region (VH) comprising the amino acid sequence of SEQ ID NO: 17 and a light chain variable region (VL) comprising the amino acid sequence of SEQ ID NO: 7. In some embodiments, the sequences include post-translational modifications of the above sequences.

In some embodiments, the anti-MUC16 antibody includes a heavy chain variable region (VH) sequence having at least 90%, 91%, 92%, 93%, 94%, 95%, 96%, 97%, 98%, 99%, or 100% sequence identity to the amino acid sequence of SEQ ID NO: 8, 13, 15, or 17. In some embodiments, the anti-MUC16 antibody includes a light chain variable region (VL) sequence having at least 90%, 91%, 92%, 93%, 94%, 95%, 96%, 97%, 98%, 99%, or 100% sequence identity to the amino acid sequence of SEQ ID NO: 7 or 12. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MUC16 antibody comprising that sequence retains the ability to bind to MUC16. In certain embodiments, a total of 1 to 10 amino acids have been substituted, inserted and/or deleted in SEQ ID NO: 8, 13, 15, or 17. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MUC16 antibody comprising that sequence retains the ability to bind to MUC16. In certain embodiments, a total of 1 to 10 amino acids have been substituted, inserted and/or deleted in SEQ ID NO: 7 or 12. In certain embodiments, substitutions, insertions, or deletions occur in regions outside the HVRs (i.e., in the FRs).

In a certain embodiment, the anti-MUC16 antibody comprises the following HVRs:

```
HVR-L1:
                                         (SEQ ID NO: 1)
Lys Ala Ser Asp Leu Ile His Asn Trp Leu Ala

HVR-L2:
                                         (SEQ ID NO: 2)
Tyr Gly Ala Thr Ser Leu Glu Thr

HVR-L3:
                                         (SEQ ID NO: 3)
Gln Gln Tyr Trp Thr Thr Pro Phe Thr

HVR-H1:
                                         (SEQ ID NO: 4)
Gly Tyr Ser Ile Thr Asn Asp Tyr Ala Trp Asn

HVR-H2:
                                         (SEQ ID NO: 5)
Gly Tyr Ile Ser Tyr Ser Gly Tyr Thr Thr Tyr

Asn Pro Ser Leu Lys Ser

HVR-H3:
                                         (SEQ ID NO: 6)
Ala Arg Trp Thr Ser Gly Leu Asp Tyr
```

In a certain embodiment, the anti-MUC16 antibody comprises the following VL and VH:

```
VL:
                                         (SEQ ID NO: 7)
Asp Ile Gln Met Thr Gln Ser Pro Ser Ser Leu

Ser Ala Ser Val Gly Asp Arg Val Thr Ile Thr

Cys Lys Ala Ser Asp Leu Ile His Asn Trp Leu

Ala Trp Tyr Gln Gln Lys Pro Gly Lys Ala Pro

Lys Leu Leu Ile Tyr Gly Ala Thr Ser Leu Glu

Thr Gly Val Pro Ser Arg Phe Ser Gly Ser Gly

Ser Gly Thr Asp Phe Thr Leu Thr Ile Ser Ser

Leu Gln Pro Glu Asp Phe Ala Thr Tyr Tyr Cys

Gln Gln Tyr Trp Thr Thr Pro Phe Thr Phe Gly

Gln Gly Thr Lys Val Glu Ile Lys Arg

VH:
                                         (SEQ ID NO: 8)
Glu Val Gln Leu Val Glu Ser Gly Gly Gly Leu

Val Gln Pro Gly Gly Ser Leu Arg Leu Ser Cys

Ala Ala Ser Gly Tyr Ser Ile Thr Asn Asp Tyr

Ala Trp Asn Trp Val Arg Gln Ala Pro Gly Lys

Gly Leu Glu Trp Val Gly Tyr Ile Ser Tyr Ser

Gly Tyr Thr Thr Tyr Asn Pro Ser Leu Lys Ser

Arg Phe Thr Ile Ser Arg Asp Thr Ser Lys Asn

Thr Leu Tyr Leu Gln Met Asn Ser Leu Arg Ala

Glu Asp Thr Ala Val Tyr Tyr Cys Ala Arg Trp

Thr Ser Gly Leu Asp Tyr Trp Gly Gln Gly Thr

Leu Val Thr Val Ser Ser
```

In one embodiment, an anti-MUC16 antibody is an antibody fragment, e.g., a Fv, Fab, Fab', Fab'-SH, Fv, scFv, diabody, or F(ab')$_2$ fragment. In another embodiment, the antibody is a full length antibody, e.g., an intact IgG1 antibody or other antibody class or isotype as known in the art. In some embodiments, the antibody is a full length intact IgG4 antibody. In some embodiments, the antibody is a bispecific antibody.

In a further aspect of the present disclosure, an anti-MUC16 antibody according to any of the above embodiments is a monoclonal antibody, including a chimeric, humanized or human antibody. In one embodiment, an anti-MUC16 antibody comprises HVRs as in any of the above embodiments and further comprises an acceptor human framework, e.g. a human immunoglobulin framework or a human consensus framework.

In a further aspect, an anti-MUC16 antibody according to any of the above embodiments may incorporate any of the features, singly or in combination, as described below.

NaPi2b Antagonists

In certain embodiments of the methods of the present disclosure, the anti-cancer therapy is a NaPi2b antagonist treatment. Any NaPi2b antagonist known in the art may be used in any of the methods described herein. In some embodiments, the NaPi2b antagonist is selected from an anti-NaPi2b antibody, a NaPi2b inhibitor, a protein (e.g., that binds or inhibits NaPi2b), a peptide (e.g., that binds or inhibits NaPi2b), a fusion protein (e.g., that binds or inhibits NaPi2b), and an immunoadhesin (e.g., that binds or inhibits NaPi2b). As described herein, in a specific embodiment, the NaPi2b antagonist is an anti-NaPi2b antibody. Furthermore, the anti-NaPi2b antibodies are ADCs or TDCs in specific embodiments.

In certain embodiments, a NaPi2b antagonist is an anti-NaPi2b antibody, e.g., an isolated antibody that binds to human NaPi2b. Antibodies suitable for use in the methods of the present disclosure include antibodies that bind to human NaPi2b. In certain embodiments, the anti-NaPi2b antibodies are ADCs or TDCs.

In one embodiment, an anti-NaPi2b antibody is an antibody fragment, e.g., a Fv, Fab, Fab', Fab'-SH, Fv, scFv, diabody, or F(ab')$_2$ fragment. In another embodiment, the antibody is a full length antibody, e.g., an intact IgG1 antibody or other antibody class or isotype as known in the art. In some embodiments, the antibody is a full length intact IgG4 antibody. In some embodiments, the antibody is a bispecific antibody.

In a further aspect of the present disclosure, an anti-NaPi2b antibody according to any of the above embodiments is a monoclonal antibody, including a chimeric, humanized or human antibody. In one embodiment, an anti-NaPi2b antibody comprises HVRs as in any of the above embodiments and further comprises an acceptor human framework, e.g. a human immunoglobulin framework or a human consensus framework.

In a further aspect, an anti-NaPi2b antibody according to any of the above embodiments may incorporate any of the features, singly or in combination, as described below.

Antibody-Drug Conjugates

In certain embodiments of the methods of the present disclosure, the anti-cancer therapy is an immunoconjugate (e.g., antibody-drug conjugate or cysteine-engineered antibody-drug conjugate) treatment. In some embodiments, the immunoconjugate comprises an antibody (e.g., an anti-MUC16 antibody or an anti-NaPi2b antibody) conjugated to a cytotoxic agent such as a chemotherapeutic agent, a drug moiety (e.g., a maytansinoid, an auristatin, a dolastatin, etc.), an antibiotic, a growth inhibitory agent, a toxin (e.g., an enzymatically active toxin of bacterial, fungal, plant, or animal origin, or fragments thereof), a nucleolytic enzyme, or a radioactive isotope (i.e., a radioconjugate). In another aspect, the present disclosure further provides methods of using the immunoconjugates. In some embodiments, an immunoconjugate of the present disclosure comprises any of the above anti-MUC16 antibodies covalently attached to a cytotoxic agent. Exemplary anti-MUC16 antibody-drug conjugates (ADCs) and THIOMAB™ antibodies and descriptions thereof may be found, e.g., in U.S. Pat. No. 7,989,595. In another aspect, an immunoconjugate comprises any of the above anti-NaPi2b antibodies covalently attached to a cytotoxic agent.

In some embodiments, the immunoconjugate comprises an antibody covalently attached to a cytotoxic agent through a linker. In some embodiments, the linker is attached to the antibody through a thiol group on the antibody. Examples of linkers may include, but are not limited to, 6-maleimido-caproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl) cyclohexane-1 carboxylate (SMCC), N-Succinimidyl (4-iodo-acetyl) aminobenzoate (SIAB), 6-maleimido-caproyl-valine-citrulline-p-aminobenzyloxycarbonyl (MC-vc-PAB), and any combinations thereof.

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may affect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Cytotoxic/chemotherapeutic agents useful in the generation of immunoconjugates are described herein. Examples of cytotoxic agents may include, but are not limited to, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Sapaonaria officinalis* inhibitor, glucocorticoid, auromycin, yttrium, bismuth, combrestatin, duocarmycins, cc1065, and a cisplatin. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, 131In $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987) Science, 238:1098. Carbon-14-labeled 1-isothiocyanatobenzyl-3-methyldiethylene triaminepentaacetic acid (MX-DTPA) is an exemplary chelating agent for conjugation of radionucleotide to the antibody (WO94/11026).

Conjugates of an antibody and one or more small molecule toxins, such as a calicheamicin, maytansinoids, dolastatins, auristatins, a trichothecene, and CC1065, and the derivatives of these toxins that have toxin activity, are also contemplated herein. In some embodiments, an antibody described herein is conjugated to a maytansinoid. Examples of maytansinoids may include, but are not limited to, N(2')-deacetyl-N(2')-(3-mercapto-1-oxopropyl)-maytansine (DM1), N(2')-deacetyl-N2-(4-mercapto-1-oxopentyl)-maytansine (DM3), and N(2')-deacetyl-N2-(4-mercapto-4-methyl-1-oxopentyl)-maytansine (DM4). In some embodiments, an antibody described herein is conjugated to an auristatin. Examples or auristatins may include, but are not limited to, monomethyl auristatin E (MMAE) and monomethyl auristatin F (MMAF).

In certain embodiments, the immunoconjugate is an anti-MUC16 antibody that is conjugated to MMAE at endogenous cysteines and/or lysines (i.e., an anti-MUC16-MMAE ADC).

In certain embodiments, the immunoconjugate is an anti-MUC16 antibody that is conjugated to MMAF at endogenous cysteines and/or lysines (i.e., an anti-MUC16-MMAF ADC).

In certain embodiments, the immunoconjugate is an anti-MUC16 antibody that is conjugated to MMAE at engineered cysteines (i.e., an anti-MUC16-MMAE TDC).

In certain embodiments, the immunoconjugate is an anti-MUC16 antibody that is conjugated to MMAF at engineered cysteines (i.e., an anti-MUC16-MMAF TDC).

In certain embodiments, the immunoconjugates comprising an anti-MUC16 antibody are disclosed in U.S. Pat. Nos. 7,989,595 and 7,723,485, both of which are incorporated herein in their entireties by reference.

In other certain embodiments, the immunoconjugate is an anti-NaPi2b antibody that is conjugated to MMAE at endogenous cysteines and/or lysines (i.e., an anti-NaPi2b-MMAE ADC).

In other certain embodiments, the immunoconjugate is an anti-NaPi2b antibody that is conjugated to MMAF at endogenous cysteines and/or lysines (i.e., an anti-NaPi2b-MMAF ADC).

In other certain embodiments, the immunoconjugate is an anti-NaPi2b antibody that is conjugated to MMAE at engineered cysteines (i.e., an anti-NaPi2b-MMAE TDC).

In other certain embodiments, the immunoconjugate is an anti-NaPi2b antibody that is conjugated to MMAF at engineered cysteines (i.e., an anti-NaPi2b-MMAF TDC).

Thio Antibody-Drug Conjugates and Cysteine Engineered Antibodies

In certain embodiments of the methods of the present disclosure, the anti-cancer therapy is a cysteine engineered antibody where one or more amino acids of any form of wild-type or parent antibody is replaced with a cysteine amino acid. The engineered cysteine amino acid is a free cysteine acid and not part of an intrachain or interchain disulfide unit. In some embodiments, any form of anti-MUC16 antibody or anti-NaPi2b antibody may be so engineered, i.e., mutated. For example, a parent Fab antibody fragment may be engineered to form a cysteine engineered Fab, referred to herein as "ThioFab." Similarly, parent monoclonal antibodies may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. The cysteine engineered anti-MUC16 or anti-NaPi2b antibodies of the present disclosure include monoclonal antibodies, humanized or chimeric monoclonal antibodies, antigen-binding fragments of antibodies, fusion polypeptides and analogs that preferentially bind cell-associated MUC16 or NaPi2b polypeptides, respectively. Further description and exemplary cysteine engineered antibodies may be found, e.g., in WO2008/141044.

Cysteine engineered antibodies retain the antigen binding capability of their wild type, parent antibodies counterparts. Thus, cysteine engineered anti-MUC16 antibodies are capable of binding to MUC16 antigens including receptor proteins 0772P (CA 125, MUC16, Genbank accession no. AF361486), as described in Yin et al J. (2001) Biol. Chem.

276 (29):27371-27375); WO2004045553 (Claim 14); WO200292836 (Claim 6; FIG. 12); WO200283866 (Claim 15; Page 116-121); US2003124140 (Example 16); Cross-references: GL34501467; AAK74120.3; AF361486_1. A cysteine engineered anti-MUC16 or anti-NaPi2b antibody comprises one or more free cysteine amino acids with reduced sulfhydryl (thiol) groups wherein the cysteine engineered anti-MUC16 or anti-NaPi2b antibody binds to a MUC16 or NaPi2b polypeptide, respectively.

In one aspect, the antibodies of the present disclosure include cysteine engineered antibodies where one or more amino acids of a parent antibody are replaced with one or more free cysteine amino acid as disclosed in WO2006/034488 and WO2011/156328, both of which are incorporated herein by reference in their entireties. In some embodiments, the one or more free cysteine amino acids has a thiol reactivity in the range of 0.6 to 1.0. In some embodiments, the one or more free cysteine amino acid residues are located in the light chain. In some embodiments, the one or more free cysteine amino acid residues are located in the heavy chain. In some embodiments, a cysteine engineered antibody comprises a cysteine at one or more positions selected from 15, 43, 110, 144, 149, 168 and 205 of the light chain according to Kabat numbering convention and 41, 88, 115, 118, 120, 171, 172, 282, 375, and 400 of the heavy chain according to EU numbering convention. In some embodiments, a cysteine is at position 205 of the light chain. In some embodiments, a cysteine is at position 118 of the heavy chain.

V. Articles of Manufacture or Kits

Certain aspects of the present disclosure relate to articles of manufacture or kits that find use, inter alia, in the methods of the present disclosure.

In some embodiments, the article of manufacture or kit contains, packaged together, a pharmaceutical composition comprising a MUC16 antagonist (in certain embodiments an anti-MUC16 antibody) and a pharmaceutically acceptable carrier, and a label denoting that the MUC16 antagonist or pharmaceutical composition is indicated for treating patients with a MUC16-positive cancer having an elevated the level of expression of HE4 as compared with a baseline.

In some embodiments, the article of manufacture or kit contains, packaged together, a pharmaceutical composition comprising a MUC16 antagonist (in certain embodiments an anti-MUC16 antibody) and a pharmaceutically acceptable carrier, and a label denoting that the MUC16 antagonist or pharmaceutical composition is indicated for treating patients with a MUC16-positive cancer having an elevated the level of expression of HE4 as compared with a baseline.

The article of manufacture or kit typically includes a container and a label or package insert on or associated with the container. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition may be an antibody of the present disclosure, e.g., an anti-MUC16 antibody. The label or package insert indicates that the composition is used for treating the condition of choice, e.g., treating patients with a MUC16-positive cancer having an elevated level of HE4, e.g., as compared with a baseline.

The article of manufacture or kit of the present disclosure will typically comprise the container described above and one or more other containers comprising materials desirable from a commercial and user standpoint, including buffers, diluents, filters, needles, syringes, and package inserts with instructions for use. In some embodiments, the second (or third) container may comprise a pharmaceutically-acceptable buffer, such as bacteriostatic water for injection (BWFI), phosphate-buffered saline, Ringer's solution and dextrose solution.

EXAMPLES

The invention will be more fully understood by reference to the following examples. They should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Study of Safety and Pharmacokinetics of an Anti-MUC16 Antibody-Drug Conjugate in Patients with Platinum-Resistant Ovarian Cancer or Unresectable Pancreatic Cancer Ovarian cancer (OC) is the seventh most common cause of cancer death in women worldwide, with approximately 140,000 deaths annually (Jemal et al. 2010). Because of the insidious onset and progression typical of this disease, more than 70% of patients are diagnosed with advanced OC (Jemal et al. 2010). The much less common diagnoses of primary peritoneal carcinoma and fallopian tube carcinoma are usually grouped with epithelial ovarian carcinomas, since the histologic features, treatment, response to chemotherapy, and prognosis are very similar (Bloss et al. 1993; Schneider et al. 2000). While front-line treatment with surgery and platinum-based chemotherapy is effective in producing complete responses (CR; i.e., absence of any detectable disease), the majority of patients will relapse, after which cure is unlikely and treatment options are mostly palliative (Martin and Schilder 2009).

For patients with long intervals between last platinum-based therapy and disease progression, retreatment with platinum-based therapy is an effective option (Pujade-Lauraine et al. 2002). Eventually, with repeated treatment, disease progression following platinum-based therapy occurs at shorter intervals and becomes platinum resistant. Currently, there is no optimal treatment strategy for platinum-resistant patients whose disease recurs within 6 months of completing initial platinum-based chemotherapy. Despite a wide range of available treatments, prolonged survival has not been shown in this setting, and overall response rate is generally less than 20%.

Pancreatic cancer (PC) is the eighth most common cause of cancer death worldwide, with approximately 266,000 deaths annually (Jemal et al. 2010). Resection represents the only curative treatment option; however, fewer than 15% of patients undergo resection because of the advanced stage of disease at presentation (Shaib et al. 2007), and the majority of these patients will relapse and die from recurrent disease despite aggressive adjuvant treatment (Neoptolemos et al. 2004).

MUC16 is a large transmembrane protein that is overexpressed by the majority (80%) of human epithelial OCs but not in the epithelium of normal ovaries (Bast et al. 1981; O'Brien et al. 2001, Yin and Lloyd 2001; Rosen et al. 2005; Theriault et al. 2011), and is expressed on PC cells (50%) (Haglund 1986; Macdonald et al. 1988). CA125, the extracellular portion of MUC16 cleaved and released into circulation, is a well-established OC disease biomarker. While the function of MUC16 remains unclear, MUC16 may facilitate the binding of tumor cells to mesothelial cells lining the peritoneal cavity and may inhibit natural killer cell-mediated anti-tumor cytotoxic responses (Bafna et al. 2010).

DMUC5754A is an antibody-drug conjugate (ADC) that contains the humanized IgG1 anti-MUC16 monoclonal antibody and a potent anti-mitotic agent, monomethyl auristatin E (MMAE), linked through a protease labile linker, maleimidocaproyl-valine-citrulline-p-aminobenzyloxycarbonyl). DMUC5754A binds to recombinant human MUC16 extracellular domain with high affinity, and shows potent and selective single agent anti-tumor activity in MUC16 expressing mouse ovarian and pancreatic cancer xenograft models. The studies discussed herein investigated DMUC5754A in patients with platinum-resistant OC or patients with unresectable PC, who have a poor prognosis and remain a high unmet medical need.

Methods
Study Design

This multicenter, open-label, dose-escalation study was designed to identify the recommended Phase II dose (RP2D) of DMUC5754A in patients with platinum-resistant OC or unresectable pancreatic cancer. In the single-agent dose escalation stage utilizing a 3+3 enrollment scheme, patients were given intravenous DMUC5754A (Genentech Inc.) 0.3-3.2 mg/kg every 3 weeks (q3w) to evaluate the safety, tolerability, and pharmacokinetics of DMUC5754A. Following determination of the maximum tolerated dose (MTD), dose-expansion cohorts were enrolled at the RP2D of 2.4 mg/kg to further characterize the safety and preliminary clinical efficacy of DMUC5754A.

Dosing on a weekly (q1w) schedule was also evaluated at the RP2D, employing a 3+3 design to determine the MTD of weekly dosing, followed by a cohort expansion to further characterize the safety and activity of q1w dosing.

Patients

OC patients had advanced, epithelial ovarian, primary peritoneal, or fallopian tube cancer that progressed or relapsed within 6 months after the most recent treatment with a platinum-containing chemotherapy regimen and for which no standard therapy exists. Patients had MUC16 expression documented by serum CA125 ≥2× the upper limit of normal or archival tumor tissue biopsy demonstrating MUC16 expression. Progression or relapse from prior platinum-based chemotherapy was documented by RECIST v1.1 or Gynecologic Cancer Intergroup (GCIG) CA125 progression criteria (Vergote et al., 2000). Patients were allowed ≤2 prior chemotherapy regimens.

PC patients had histologic documentation of incurable, locally advanced, or metastatic disease for which no standard therapy exists, consisting of unresectable pancreatic ductal adenocarcinoma (i.e., patients with locally advanced or metastatic disease who are not considered eligible for surgical resection with curative intent), including recurrence of previously-resected disease considered unresectable with curative intent. Patients had MUC16 expression documented by archival or fresh tumor tissue. No more than 1 chemotherapy regimen (approved or experimental) had been administered in the metastatic setting.

Both OC and PC patients had to have measurable disease with at least one lesion that could be accurately measured in at least one dimension (longest dimension ≥2.0 cm recorded using conventional techniques or ≥1.0 cm on spiral CT scan). Patients were excluded if they had current Grade >1 toxicity (except alopecia and anorexia) from prior therapy or Grade >1 neuropathy from any cause. In addition, patients were not allowed to enroll if they had been treated previously with MUC16-targeted therapy.

The protocol was approved by Institutional Review Boards prior to patient recruitment and conducted in accordance with International Conference on Harmonization E6 Guidelines for Good Clinical Practice.

Safety Assessment

Safety was evaluated according to NCI CTCAE v4.0. For dose-escalation purposes, a dose-limiting toxicity (DLT) was defined as any of the following toxicities considered by the investigator to be related to DMUC5754A that occurred during the DLT-assessment window (Days 1-21 of Cycle 1): Grade ≥3 non-hematologic toxicity that required medical intervention and was not attributable to disease progression or another clearly identifiable cause (excluding Grade 3 diarrhea that responded to standard-of-care therapy; Grade 3 nausea or vomiting, in the absence of premedication, that responded to standard of care therapy; Grade 3 infusion reactions that did not limit re-treatment with study drug); Grade ≥4 neutropenia lasting >5 days or associated with fever; Grade ≥4 anemia; Grade ≥4 thrombocytopenia. The maximum tolerated dose (MTD) was defined as the dose at which ≤1 of 6 patients at an assigned dose with protocol-defined DLT. Patients who experienced a DLT or adverse event (AE) meeting DLT criteria after the DLT assessment window were allowed to delay dosing for up to 2 weeks or undergo a dose reduction.

Pharmacokinetics and Pharmacodynamics

Pharmacokinetics (PK) of DMUC5754A was characterized following q3w or q1w dosing schedules in both OC and PC patients. Serum or plasma samples at multiple pre-specified time points were quantified for three analytes (unconjugated MMAE, DMUC5754A total antibody, and DMUC5754A conjugate (measured as antibody-conjugated MMAE, acMMAE)). Total antibody (antibody with MMAE-to-antibody ratio equal or greater than zero, including conjugated, partially deconjugated and fully deconjugated antibody) were analyzed using validated enzyme-linked immunosorbent assay methods with the minimum quantifiable concentration of 60 ng/mL. Plasma acMMAE and unconjugated MMAE were determined by using validated LC/MS/MS assays. The lower limit of quantitation (LLOQ) for the acMMAE assay and unconjugated MMAE were 0.359 ng/mL and 0.0359 ng/mL in human plasma, respectively. PK data after Cycle 1, Day 1 dose of DMUC5754A were analyzed with non-compartmental analysis using Phoenix WinNonlin 6.2 (Certara, L. P.), and further evaluated based on dose regimen and cancer type.

Serum anti-therapeutic antibody (ATA) samples were collected from all treated patients and were analyzed using a validated bridging antibody ELISA. Positive antibody responses were further characterized by competitive binding to determine if the response was primarily directed against the antibody or the linker-drug portion of the ADC.

Clinical Activity

Objective response rate was estimated only for patients with disease that was measurable by RECIST guidelines. Objective response is defined as a complete or partial response, as determined by investigator assessment and confirmed by repeat assessments ≥4 weeks after initial documentation. Duration of objective response was defined as the time from the initial complete or partial response to the time of disease progression or death.

MUC16 Immunohistochemistry (IHC)

For determination of MUC16 protein expression in formalin-fixed, paraffin-embedded archival tissues, a fully automated IHC assay was developed using the anti-MUC16 (3A5.3) mouse monoclonal primary antibody and Ventana ultraView DAB IHC Detection.

MUC16 membranous staining level was scored according the following algorithm, where at least 10% of tumor cells had to be stained in order to qualify as positive in each category; IHC=3+ the predominant staining intensity is 3+ denoting predominantly strong staining; IHC=2+: predominantly moderate staining; IHC=1+, predominantly weak staining; IHC=0, very weak or no staining in >90% of tumor cells.

Assessments of Serum CA125, HE4, and CA19-9

Circulating biomarkers, including CA125 and human epididymis protein 4 (HE4) for ovarian cancer, and CA125 and CA19-9 for pancreatic cancer, were measured in serum samples collected before each cycle of treatment. CA125, HE4 and CA19-9 levels were analyzed using the CA 125 II™, HE4, and CA19-9XR Chemiluminescent Microparticle Immunoassay respectively on the ARCHITECT i system (Abbott).

Statistical Analysis

Design considerations were not made with regard to explicit power and type I error, but to obtain preliminary safety, PK, and PD information. For safety analysis, all patients who received DMUC5754A were included. For activity analyses, all patients with measurable disease at baseline were included.

Results

Baseline Demographics and Treatment 77 patients were enrolled in the q3w and q1w dosing cohorts at 4 study sites. Patient baseline and disease characteristics are shown in Table 1. The median number of cycles of DMUC5754A received was 4.0 (range 1-30) for patients on q3w schedule, and 8.0 (range 2-25) for patients on q1w schedule. DMUC5754A at the RP2D of 2.4 mg/kg q3w was administered to 39 patients; the median number of doses received was 4.0 (range 1-21).

TABLE 1

Patient baseline characteristics.

|  | Ovarian Cancer q3w Cohorts (N = 44) | Ovarian Cancer q1w Cohorts (N = 22) | Pancreatic Cancer (N = 11) |
|---|---|---|---|
| Age in years |  |  |  |
| Median (range) | 63 (44-79) | 61 (27-73) | 60 (39-71) |
| ECOG status, n (%) |  |  |  |
| 0 | 33 (75) | 14 (64) | 6 (55) |
| 1 | 11 (25) | 8 (36) | 5 (46) |
| All prior regimens |  |  |  |
| Median (range) | 4 (1-16) | 5 (2-10) | 1 (1-3) |
| Mean | 4.4 | 5.2 | 1.6 |
| Prior platinum regimens |  |  |  |
| Median (range) | 2 (1-6) | 2 (1-4) | n/a |
| Mean | 2.3 | 2.2 |  |
| Regimens in OC |  |  |  |
| Median (range) | 1 (0-6) | 2 (0-4) | n/a |
| Mean | 1.5 | 1.8 |  |
| Prior treatment with gemcitabine/abraxane, n (%) | n/a | n/a | 5 (46) |
| Prior treatment with FOLFIRINOX, n (%) | n/a | n/a | 4 (36) |

ECOG = Eastern Cooperative Oncology Group;
OC = ovarian cancer.

Safety

In OC patients, 2 protocol-defined DLTs of 1 Grade 4 hypocalcaemia and 1 Grade 3 uric acid increase occurred in 2 of 3 DLT-evaluable patients at the maximally administered dose of 3.2 mg/kg q3w, which was determined to have exceeded MTD. The RP2D was declared at 2.4 mg/kg for q3w schedule and expansion cohorts enrolled both OC and PC patients at that level. In addition, weekly dose escalation cohorts at 0.8-1.6 mg/kg enrolled OC patients; the RP2D was declared at 1.4 mg/kg for q1w schedule and an expansion cohort enrolled 1 PC patient at that level.

In q3w patients, the most common related AEs over all dose levels (Table 2A) were fatigue (57.4%), nausea (37.0%), decreased appetite (29.6%), peripheral sensory neuropathy and vomiting (27.8% each), diarrhea (24.1%), alopecia and pyrexia (20.4% each). In q1w patients, the most common related AEs over all dose levels (Table 2B) were nausea (47.8%), vomiting (39.1%), anemia (34.8%), fatigue (30.4%), neutropenia (26.1%), alopecia, decreased appetite, diarrhea, and hypomagnesaemia (21.7% each).

Most AEs were Grade 1 and 2 in severity. In q3w patients, Grade ≥3 related AEs occurring in ≥5% of q3w patients included neutropenia (4 at 2.4 mg/kg; 9.3% total) and fatigue (4 at 2.4 mg/kg; 7.4% total). Grade ≥3 related AEs occurring in ≥5% of q1w patients included neutropenia (1 at

TABLE 2A

Related adverse events reported in ≥10% patients in q3w cohorts.

| MedDRA Preferred Term | 0.3 mg/kg (n = 3) | 0.6 mg/kg (n = 3) | 1.2 mg/kg (n = 3) | 1.8 mg/kg (n = 3) | 2.4 mg/kg (n = 39) | 3.2 mg/kg (n = 3) | All Patients (n = 54) |
|---|---|---|---|---|---|---|---|
| Any adverse events | 3 (100.0%) | 1 (33.3%) | 3 (100.0%) | 2 (66.7%) | 39 (100.0%) | 3 (100.0%) | 51 (94.4%) |
| Fatigue | 0 | 1 (33.3%) | 1 (33.3%) | 1 (33.3%) | 26 (66.7%) | 2 (66.7%) | 31 (57.4%) |
| Peripheral neuropathy | 1 (33.3%) | 0 | 0 | 2 (66.7%) | 17 (43.6%) | 1 (33.3%) | 21 (38.9%) |
| Nausea | 1 (33.3%) | 0 | 0 | 1 (33.3%) | 15 (38.5%) | 3 (100.0%) | 20 (37.0%) |
| Decreased appetite | 1 (33.3%) | 0 | 2 (66.7%) | 1 (33.3%) | 11 (28.2%) | 1 (33.3%) | 16 (29.6%) |
| Vomiting | 0 | 1 (33.3%) | 1 (33.3%) | 0 | 10 (25.6%) | 3 (100.0%) | 15 (27.8%) |
| Diarrhea | 0 | 1 (33.3%) | 1 (33.3%) | 2 (66.7%) | 8 (20.5%) | 1 (33.3%) | 13 (24.1%) |
| Alopecia | 0 | 0 | 0 | 1 (33.3%) | 9 (23.1%) | 1 (33.3%) | 11 (20.4%) |
| Pyrexia | 0 | 0 | 0 | 2 (66.7%) | 7 (17.9%) | 2 (66.7%) | 11 (20.4%) |
| Hypomagnesaemia | 1 (33.3%) | 0 | 0 | 2 (66.7%) | 6 (15.4%) | 0 | 9 (16.7%) |
| Neutropenia | 0 | 0 | 0 | 0 | 8 (20.5%) | 1 (33.3%) | 9 (16.7%) |
| Arthralgia | 0 | 0 | 0 | 2 (66.7%) | 5 (12.8%) | 1 (33.3%) | 8 (14.8%) |
| Dysgeusia | 0 | 0 | 0 | 0 | 7 (17.9%) | 1 (33.3%) | 8 (14.8%) |
| Asthenia | 0 | 0 | 0 | 0 | 5 (12.8%) | 1 (33.3%) | 6 (11.1%) |
| Hypokalemia | 0 | 0 | 0 | 0 | 4 (10.3%) | 2 (66.7%) | 6 (11.1%) |
| Hypophosphatemia | 0 | 0 | 0 | 1 (33.3%) | 2 (5.1%) | 3 (100.0%) | 6 (11.1%) |
| Any adverse events | 3 (100.0%) | 1 (33.3%) | 3 (100.0%) | 2 (66.7%) | 39 (100.0%) | 3 (100.0%) | 51 (94.4%) |
| Fatigue | 0 | 1 (33.3%) | 1 (33.3%) | 1 (33.3%) | 26 (66.7%) | 2 (66.7%) | 31 (57.4%) |
| Peripheral neuropathy | 1 (33.3%) | 0 | 0 | 2 (66.7%) | 17 (43.6%) | 1 (33.3%) | 21 (38.9%) |
| Nausea | 1 (33.3%) | 0 | 0 | 1 (33.3%) | 15 (38.5%) | 3 (100.0%) | 20 (37.0%) |
| Decreased appetite | 1 (33.3%) | 0 | 2 (66.7%) | 1 (33.3%) | 11 (28.2%) | 1 (33.3%) | 16 (29.6%) |
| Vomiting | 0 | 1 (33.3%) | 1 (33.3%) | 0 | 10 (25.6%) | 3 (100.0%) | 15 (27.8%) |
| Diarrhea | 0 | 1 (33.3%) | 1 (33.3%) | 2 (66.7%) | 8 (20.5%) | 1 (33.3%) | 13 (24.1%) |
| Alopecia | 0 | 0 | 0 | 1 (33.3%) | 9 (23.1%) | 1 (33.3%) | 11 (20.4%) |
| Pyrexia | 0 | 0 | 0 | 2 (66.7%) | 7 (17.9%) | 2 (66.7%) | 11 (20.4%) |
| Hypomagnesaemia | 1 (33.3%) | 0 | 0 | 2 (66.7%) | 6 (15.4%) | 0 | 9 (16.7%) |
| Neutropenia | 0 | 0 | 0 | 0 | 8 (20.5%) | 1 (33.3%) | 9 (16.7%) |
| Arthralgia | 0 | 0 | 0 | 2 (66.7%) | 5 (12.8%) | 1 (33.3%) | 8 (14.8%) |
| Dysgeusia | 0 | 0 | 0 | 0 | 7 (17.9%) | 1 (33.3%) | 8 (14.8%) |
| Asthenia | 0 | 0 | 0 | 0 | 5 (12.8%) | 1 (33.3%) | 6 (11.1%) |
| Hypokalemia | 0 | 0 | 0 | 0 | 4 (10.3%) | 2 (66.7%) | 6 (11.1%) |
| Hypophosphatemia | 0 | 0 | 0 | 1 (33.3%) | 2 (5.1%) | 3 (100.0%) | 6 (11.1%) |

TABLE 2B

Related adverse events reported in ≥10% patients in q1w cohorts.

| MedDRA Preferred Term | 0.8 mg/kg (n = 3) | 1.1 mg/kg (n = 7) | 1.4 mg/kg (n = 7) | 1.6 mg/kg (n = 6) | All Patients (n = 23) |
|---|---|---|---|---|---|
| Any adverse events | 2 (66.7%) | 7 (100.0%) | 5 (71.4%) | 6 (100.0%) | 20 (87.0%) |
| Nausea | 0 | 4 (57.1%) | 4 (57.1%) | 3 (50.0%) | 11 (47.8%) |
| Vomiting | 0 | 2 (28.6%) | 5 (71.4%) | 2 (33.3%) | 9 (39.1%) |
| Anemia | 1 (33.3%) | 3 (42.9%) | 2 (28.6%) | 2 (33.3%) | 8 (34.8%) |
| Fatigue | 0 | 2 (28.6%) | 2 (28.6%) | 3 (50.0%) | 7 (30.4%) |
| Neutropenia | 1 (33.3%) | 1 (14.3%) | 1 (14.3%) | 3 (50.0%) | 6 (26.1%) |
| Alopecia | 0 | 1 (14.3%) | 2 (28.6%) | 2 (33.3%) | 5 (21.7%) |
| Decreased appetite | 0 | 1 (14.3%) | 3 (42.9%) | 1 (16.7%) | 5 (21.7%) |
| Diarrhea | 0 | 3 (42.9%) | 0 | 2 (33.3%) | 5 (21.7%) |
| Hypomagnesaemia | 1 (33.3%) | 2 (28.6%) | 0 | 2 (33.3%) | 5 (21.7%) |
| Aspartate aminotransferase increased | 0 | 2 (28.6%) | 1 (14.3%) | 1 (16.7%) | 4 (17.4%) |
| Peripheral neuropathy | 0 | 1 (14.3%) | 2 (28.6%) | 1 (16.7%) | 4 (17.4%) |
| Arthralgia | 0 | 2 (28.6%) | 1 (14.3%) | 0 | 3 (13.0%) |
| Constipation | 1 (33.3%) | 0 | 2 (28.6%) | 0 | 3 (13.0%) |
| Headache | 0 | 2 (28.6%) | 0 | 1 (16.7%) | 3 (13.0%) |
| Hyponatremia | 0 | 1 (14.3%) | 1 (14.3%) | 1 (16.7%) | 3 (13.0%) |

1.4 mg/kg; 17.4% total), diarrhea (0 at 1.4 mg/kg; 8.7% total), and hyponatraemia (0 at 1.4 mg/kg; 8.7% total).

Drug-related serious AEs (SAE) in q3w patients included small intestine obstruction (2 patients), hypocalcemia (1 patient), and neutropenia (1 patient). Drug-related SAEs in q1w patients included dehydration, diarrhea, nausea, and posterior reversible encephalopathy syndrome (1 patient each). There were 3/54 patients (5.6%) in q3w cohorts and 3/23 patients (13.0%) in q1w cohorts who had AEs leading to treatment discontinuation.

Peripheral neuropathy (PN) is a well-documented toxicity of microtubule inhibitors. Consistent with this, drug-related PN was observed in patients treated with DMUC5754A (Tables 2A&B). Drug-related peripheral neuropathy and associated AEs were reported in 21 patients (38.9%) in q3w cohorts and 4 patients (17.4%) in q1w cohorts. Twenty-five (46%) patients in q3w cohorts and 11 (48%) patients in q1w cohorts had PN prior to study entry. Median time to first PN event on study was 99 days in q3w cohorts, and 190 days in q1w cohorts (Table 3).

TABLE 3

Median time to onset of peripheral neuropathy for A) q3w week and (B) q1w week patients.

|  | On study PN = Yes | On study PN = No | Total | Median time to onset of first PN on study (days) |
|---|---|---|---|---|
| Table 3A. q3w week dosing. | | | | |
| Prior neuropathy = Yes | 5 (9%) | 20 (37%) | 25 (46%) | 148 |
| Prior neuropathy = No | 18 (33%) | 11 (20%) | 29 (54%) | 71 |
| Total | 23 (43%) | 31 (57%) | 54 (100%) | 99 |
| Table 3B. q1w week dosing. | | | | |
| Prior neuropathy = Yes | 2 (9%) | 9 (39%) | 11 (48%) | 190 |
| Prior neuropathy = No | 2 (9%) | 10 (43%) | 12 (52%) | N/A |
| Total | 4 (17%) | 19 (83%) | 23 (100%) | 190 |

PN = peripheral neuropathy.

DMUC5754A Pharmacokinetics

In both the q3w and q1w cohorts, the increase of exposure of acMMAE or total antibody, as measured by $C_{max}$ or $AUC_{inf}$ in Cycle 1, was not dose proportional, and acMMAE or total antibody exhibited nonlinear PK in the studied dose range (0.3-3.2 mg/kg) (Table 4). There was a correlation of acMMAE exposure with total antibody exposure.

TABLE 4

DMUC5754A Cycle 1 pharmacokinetic data summary.

| | | | Total Antibody | | acMMAE | | Unconjugated MMAE | |
|---|---|---|---|---|---|---|---|---|
| Dose (mg/kg) | Cancer Type | N | $C_{max}$ (µg/mL) | $AUC_{inf}$ (day · µg/mL) | $C_{max}$ (ng/mL) | $AUC_{inf}$ (day · ng/mL) | $C_{max}$ (ng/mL) | $AUC_{inf}$ (day · ng/mL) |
| q3w (1st cycle) | | | | | | | | |
| 0.3 | OC | 3 | 6.65 (0.86) | 13.1 (—) [a] | 93.3 (30.2) | 135 (52.6) | 0.675 (0.162) | 4.33 (1.37) |
| 0.6 | OC | 3 | 16.6 (4.97) | 29.5 (6.01) | 226 (42.8) | 310 (83.4) | 2.03 (1.02) | 10.3 (3.88) |
| 1.2 | OC | 3 | 22.5 (3.04) | 81.8 (49.1) | 337 (46.3) | 715 (276) | 2.84 (0.602) | 19.2 (3.28) |
| 1.8 | OC | 3 | 35.5 (1.19) | 106.0 (18.3) | 618 (65.6) | 1050 (146) | 4.7 (1.9) | 33.1 (16) |
| 2.4 | OC | 29 | 42.2 (8.68) | 178.0 (65.9) | 860 (216) | 1850 (538) | 6.77 (3.93) | 55.5 (39.9) [b] |
| 2.4 | PC | 10 | 38.9 (6.09) | 167.0 (43.9) | 737 (115) | 1680 (368) | 7.7 (5.79) | 63.6 (57.9) |
| 3.2 | OC | 3 | 71.4 (14.5) | 324.0 (138.0) | 1220 (55.7) | 3380 (1190) | 20 (15) | 111 (—) [c] |
| q1w (1st Dose) | | | | | | | | |
| 0.8 | OC | 3 | 13 (4.43) | 33.2 (12.2) | 227 (64.6) | 386 (104) | 1.24 (—) [f] | — |
| 1.1 | OC | 7 | 17.7 (4.64) | 56.1 (15.0) | 301 (138) | 612 (195) [d] | 3.23 (0.923) | — |
| 1.4 | OC | 6 | 23.9 (7.32) | 73.0 (15.6) | 449 (98) | 813 (161) [e] | 3.73 (1.56) | — |
| 1.4 | PC | 1 | 17.3 (—) | 55.7 (—) | 204 (—) | 542 (—) | 7.59 (—) | — |
| 1.6 | OC | 4 | 29.7 (4.24) | 82.3 (10.5) | 539 (84.5) | 957 (136) | 5.75 (2.77) | — |

AUCinf = area under the concentration-time profile extrapolating to time of infinity; Cmax = peak concentration; t½ = terminal half-life; Vss = volume of distribution at steady state; acMMAE = monomethyl auristatin E; PC = unresectable pancreatic cancer; OC = platinum-resistant ovarian cancer; — = not available.
[a] n = 2.
[b] n = 28.
[c] n = 1.
[d] n = 6.
[e] n = 5.
[f] n = 2.

Systemic unconjugated MMAE exposure was low and approximately 100-fold less than acMMAE exposure (Table 4). At the MTD dose of 2.4 mg/kg q3w, acMMAE PK followed a multi-exponential decline with terminal $t_{1/2}$ values of 5.01±1.45 days, CL values of 25.4±8.39 mL/day/kg, and Vss values of 82.1±21.1 mL/kg in OC patients, and in addition, acMMAE PK were comparable in OC and PC patients as suggested by the similar exposure and PK parameter values in both OC and PC patients (Table 5). DMUC5754A administration was associated with an immunogenicity rate of 14.1% in patients with minimal impact on the exposure in this study.

TABLE 5

DMUC5754A Cycle 1 antibody-conjugated MMAE pharmacokinetic parameter summary (Mean [SD]) at the MTD (2.4 mg/kg, q3w).

| Dose (mg/kg) | Cancer Type | $C_{max}$ (ng/mL) | $AUC_{inf}$ (day · ng/mL) | $t_{1/2}$ (day) | CL (mL/day/kg) | $V_{ss}$ (mL/kg) |
|---|---|---|---|---|---|---|
| 2.4 (n = 29) | OC | 860 [216] | 1850 [538] | 5.01 [1.45] | 25.4 [8.39] | 82.1 [21.1] |
| 2.4 (n = 10) | PC | 737 [115] | 1680 [368] | 5.42 [1.91] | 26.4 [5.45] | 94.6 [32.4] |

AUCinf = area under the plasma concentration-time profile extrapolating to time of infinity; CL = clearance; Cmax = peak plasma concentration; t½ = terminal half-life; Vss = volume of distribution at steady state; MMAE = monomethyl auristatin E; PC = unresectable pancreatic cancer; OC = platinum-resistant ovarian cancer.

Clinical Activity

Figure 1B:
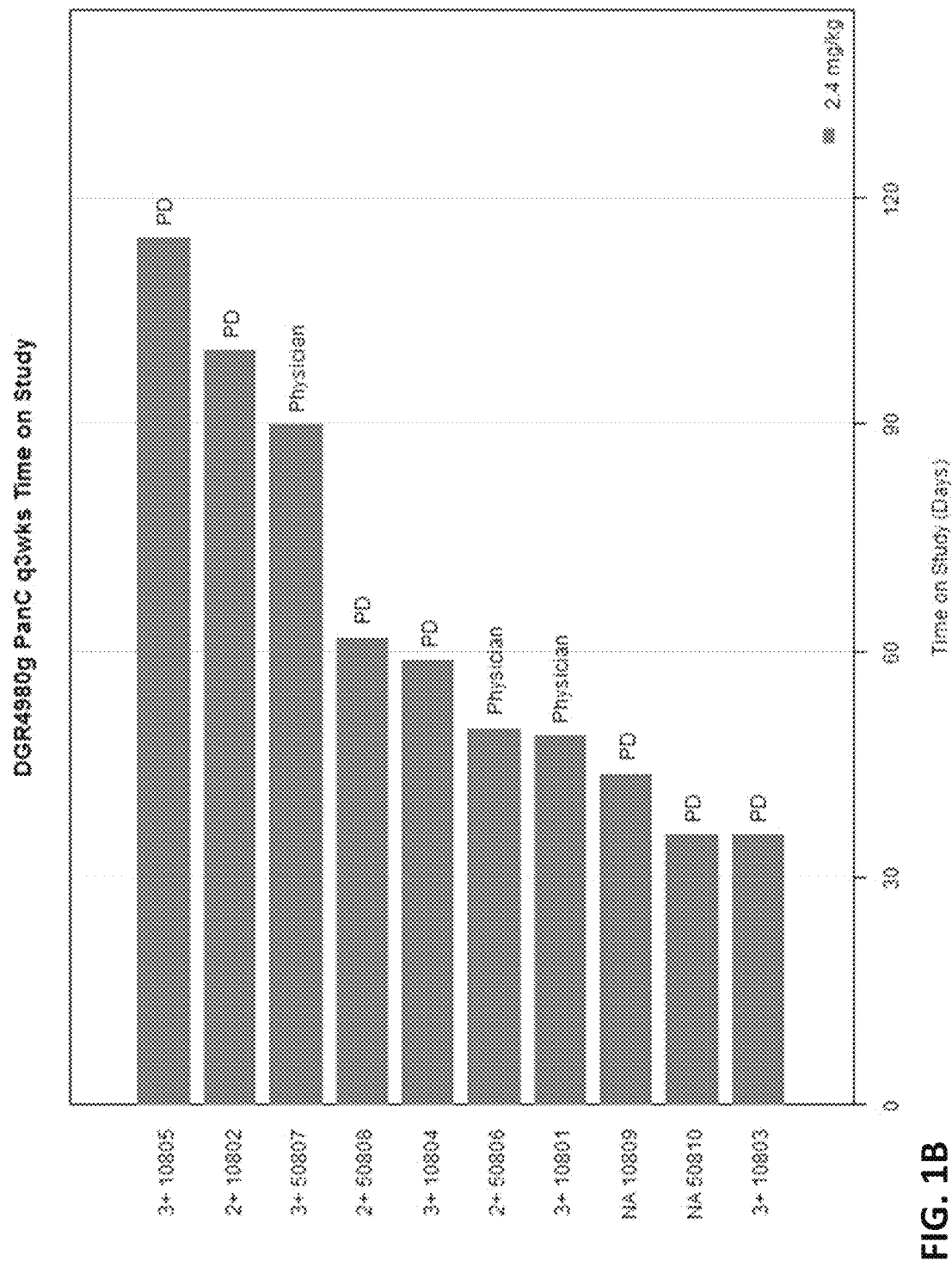

In OC patients, all confirmed responses (1 CR and 3 PRs) in q3w cohorts occurred in patients treated at 2.4 mg/kg; in q w cohorts, 3 confirmed responses were reported at 0.8, 1.1, and 1.4 mg/kg levels (Table 6, FIGS. 1A and 1B).

TABLE 6

Investigator-assessed best responses in ovarian cancer.

| Best Response | 2.4 mg/kg q3w (N = 29) | 0.8 mg/kg q1w (N = 3) | 1.1 mg/kg q1w (N = 7) | 1.4 mg/kg q1w (N = 6) |
|---|---|---|---|---|
| Objective response | | | | |
| Partial response | 3 | 1 | 1 | 1 |
| Complete response | 1 | 0 | 0 | 0 |
| Duration of response (months) | | | | |
| Range | 3.0-11.3 | 3.0-3.0 | 6.8-6.8 | 4.6-4.6 |
| Median | 4.9 | 3.0 | 6.8 | 4.6 |
| Stable disease | 17 | 2 | 3 | 2 |
| Progressive disease | 6 | 0 | 3 | 2 |
| Unable to evaluate | 2 | 0 | 0 | 1 |

<sup>a</sup>Defined as patients who received ≥1 dose of study treatment and had ≥ on-treatment tumor assessment. Disease measured by RECIST v1.1.

Figure 2B:
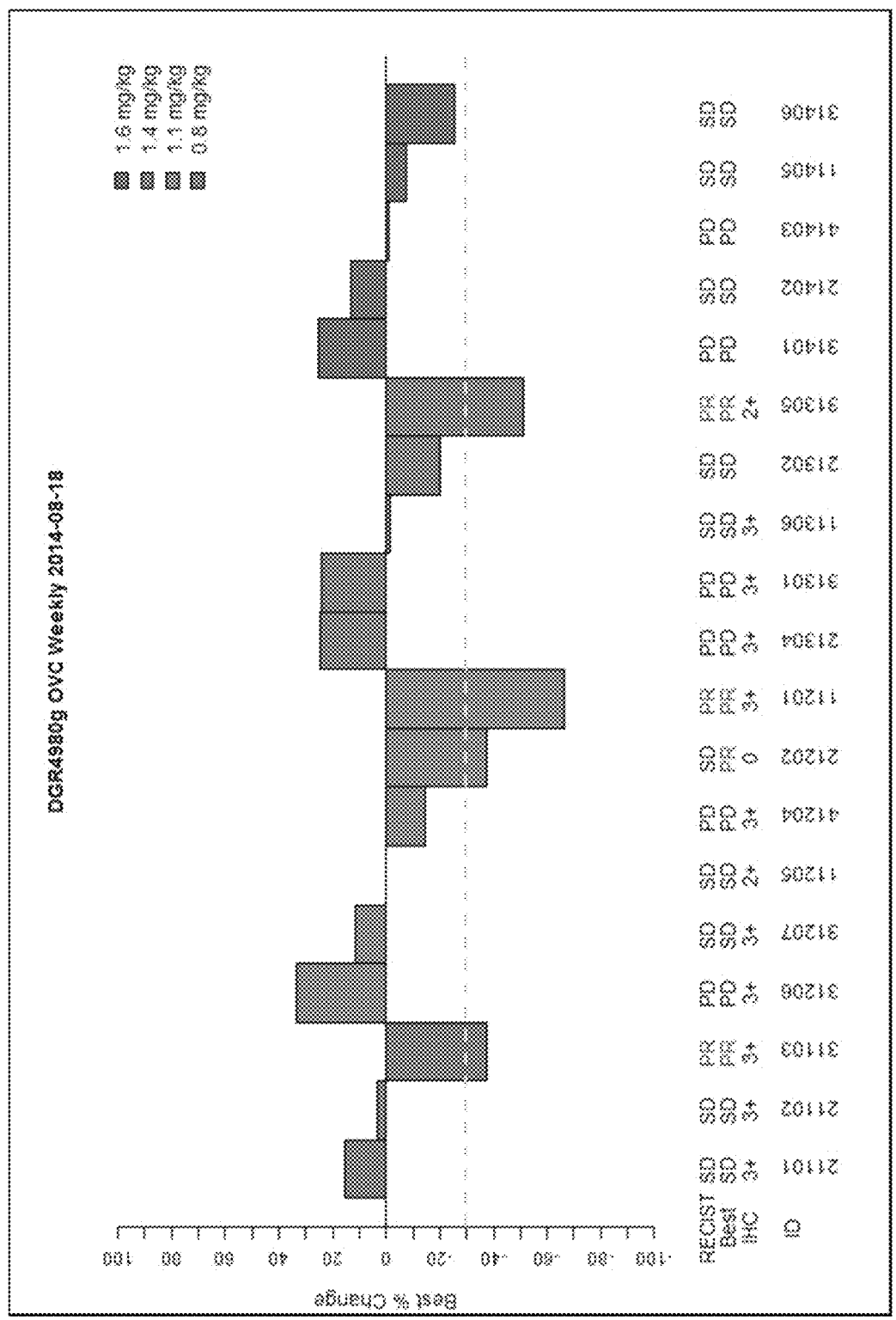
Figure 2C:
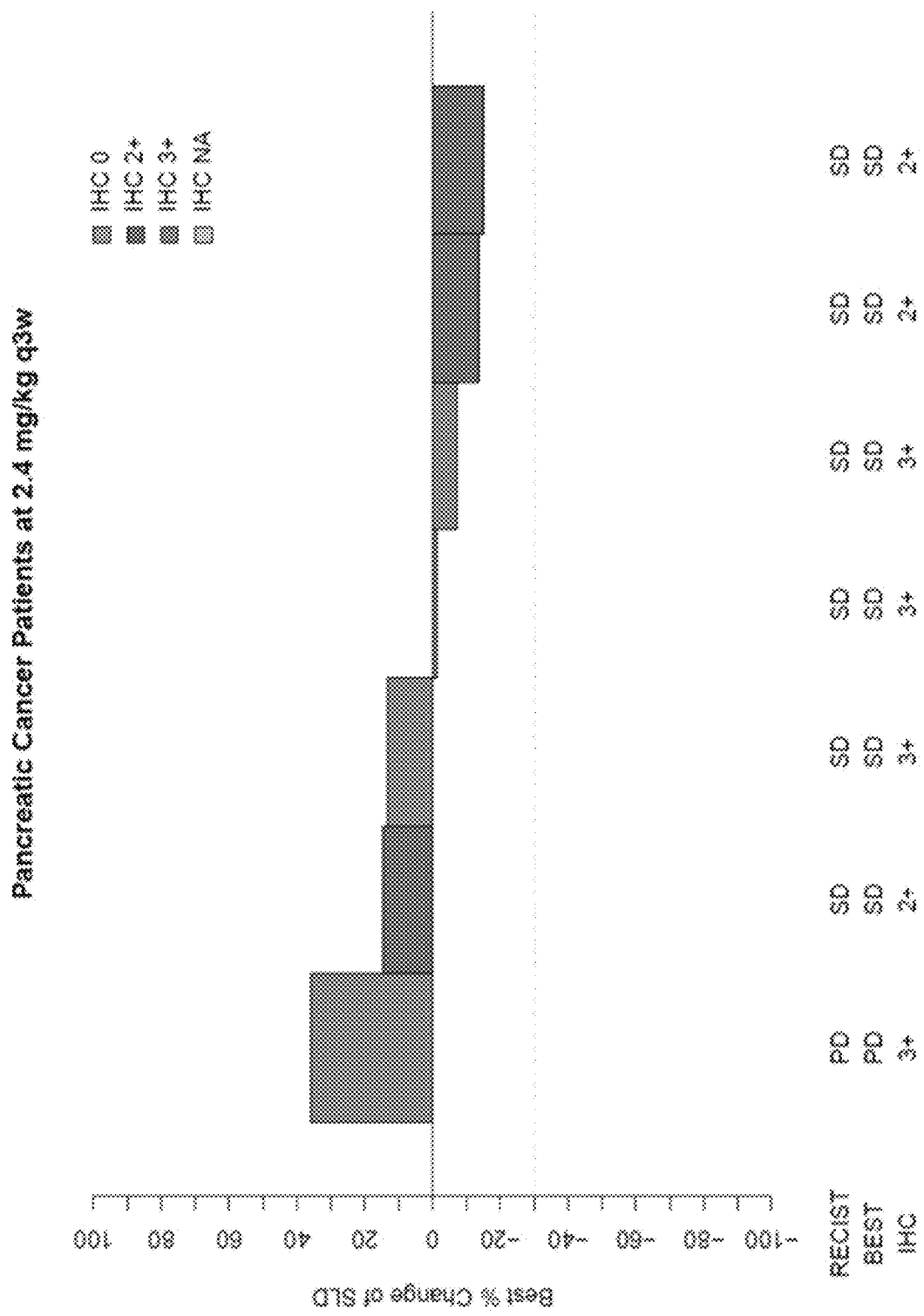

All responders were assessed to have MUC16 IHC scores of 2+ or 3+. In addition, 1 patient at 2.4 mg/kg q3w and 1 patient at 1.1 mg/kg q1w had unconfirmed partial responses. A patient at 3.2 mg/kg q3w had a >30% decrease in SLD of target lesions but PD as overall status due to new lesions. Two patients at 2.4 mg/kg q3w, and 1 each at 3.2 mg/kg q3w, 1.2 mg/kg q3w, 1.4 mg/kg q1w and 1.6 mg/kg q1w had minor responses (FIG. 2A-2C).

Figure 3A:
FIG. 3A shows representative consecutive CT scans of a 60 year old woman who had progressed through 7 prior therapies before enrolling in the study at 2.4 mg/kg. The yellow boxes indicate left abdominal lymph node (LN) lesions at initial assessment (left) and after 8 treatment doses (right).
Figure 3B:
FIG. 3B shows representative consecutive MRI scans of a 58 year old woman who had progressed through 7 prior therapies before enrolling in the study at 2.4 mg/kg. The yellow boxes indicate bladder lesions at initial assessment (left) and after 2 treatment doses (right).
Figure 4:
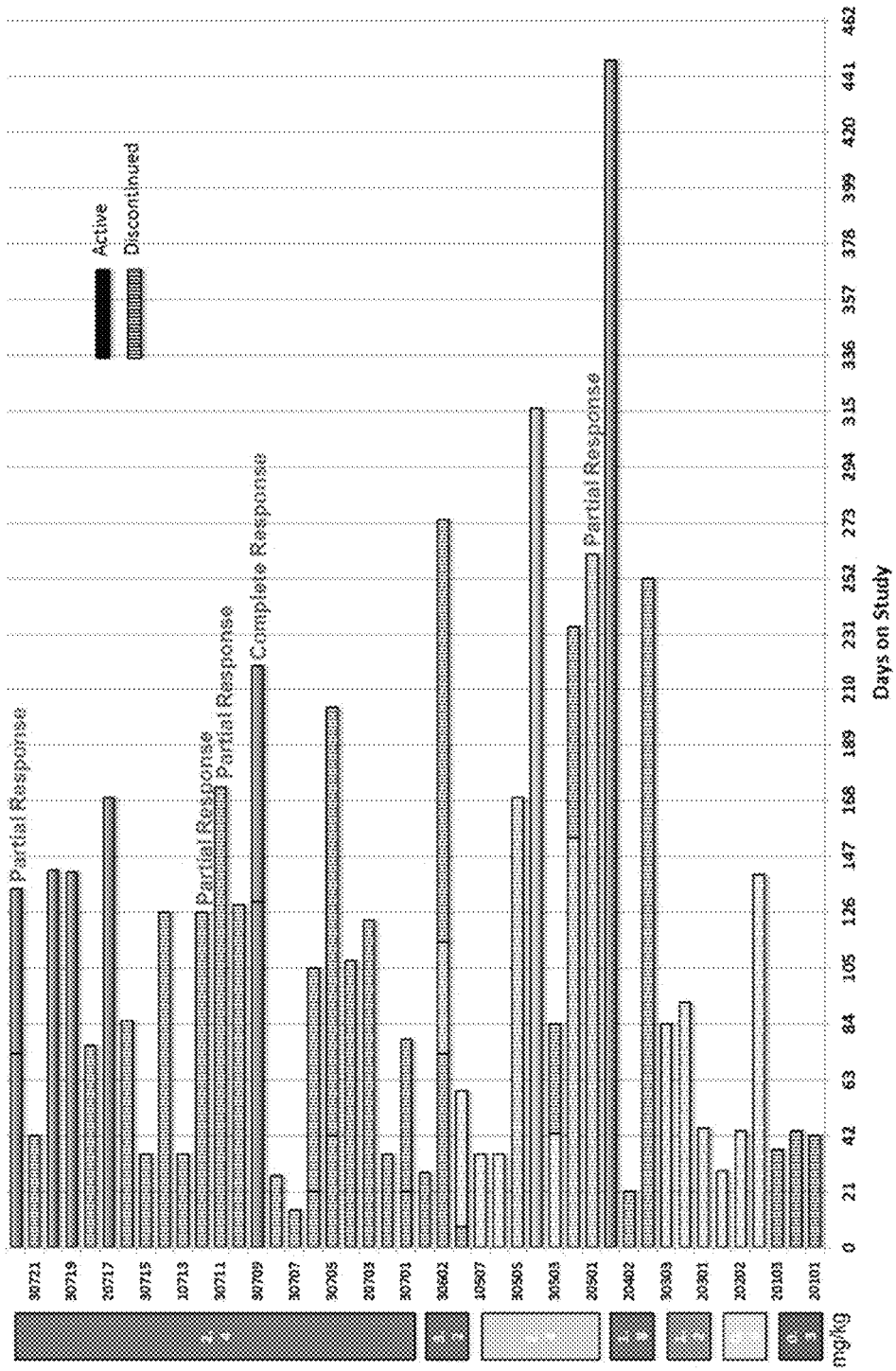
FIG. 4 shows the length of time each patient was on the study, as well as partial and complete RECIST responses. The average length of time on the study was 103 days.

Sixteen of the 29 patients at 2.4 mg/kg q3w dosing were on the study ≥105 days. No patients with PC had radiographic responses and 1 patient had a decline in CA19-9 of >50%. A 60 year old woman who had progressed through 7 prior therapies before enrolling in the study at 2.4 mg/kg had a starting CA125 of 242 U/mL and a MUC16 score of IHC 2+. After two doses, a CT showed a partial response with a 37% reduction in 3 target lesions. Consecutive CT scans showed a continued tumor response to a nadir of 88% reduction after 8 doses, with the total SLD measurement for a left abdominal LN mass decreasing from 48 mm to 6 mm (FIG. 3A). No treatment related adverse events were reported for this patient. She continued to be able to work throughout her treatment and completed 12 cycles before developing a new abdominal lesion. In a second case, a 58 year old woman who had progressed through 7 prior therapies before enrolling in study at 2.4 mg/kg IV q3w had a starting CA125 of 382 U/mL and a MUC16 score of IHC 3+. After two doses, an MRI (no contrast due to allergy) showed a complete response (100% reduction), with the total SLD measurement for a bladder mass decreasing from 25 mm to 0 mm (FIG. 3B). The length of time each patient was on the study, as well as partial and complete responses, is indicated in FIG. 4. The average length of time on the study was 103 days.

Biomarker Analysis

The requirement for a minimal threshold of MUC16 expression for anti-tumor activity from treatment was evaluated. To establish initial signal of clinical activity, MUC16 high patients were prospectively selected in the PC expansion study (tissue IHC 2+ or 3+). MUC16-high patients were also enriched in the OC expansion study (serum CA125 level is ≥2× upper limit of normal level or tissue IHC 2+ or 3+). In the dose escalation study, MUC16 expression was evaluated retrospectively.

Figure 5:
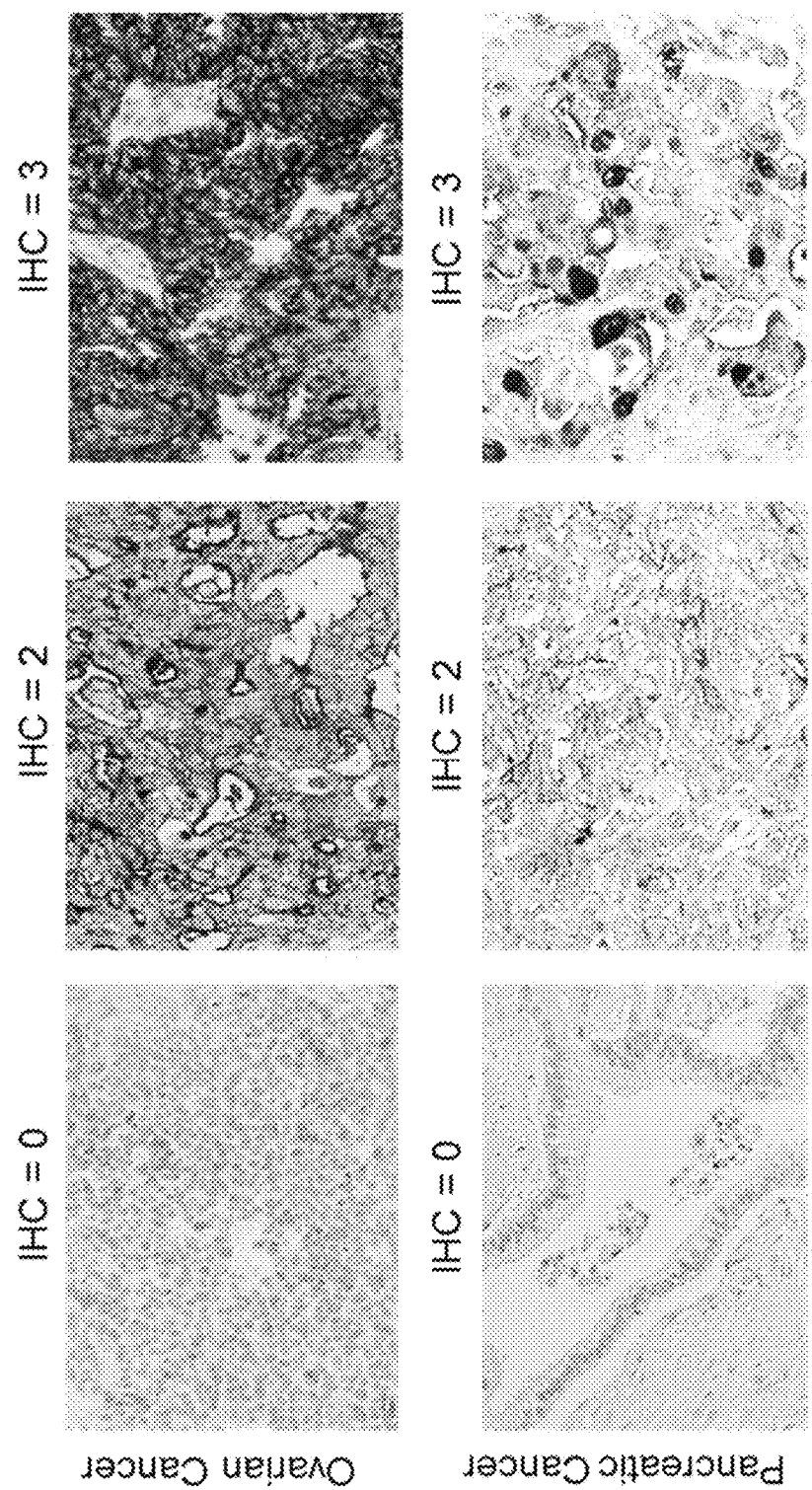
FIG. 5 shows representative images of MUC16 immunohistochemical staining in both ovarian cancer and pancreatic cancer tumor specimens.

Tumor MUC16 expression was evaluated in 42 OC patients, showing 20% IHC 0, 16% IHC 2+, and 64% IHC 3+. Of the 10 pre-selected MUC16 high PC patients treated at 2.4 mg/kg q3wk, 40% were IHC 2+ and 60% were IHC 3+. Representative images of IHC staining in both PC and OC tumor specimens are shown in FIG. 5.

Since anti-MUC16-ADC binds circulating CA125, making it less informative for tracking responses, human epididymis protein 4 (HE4) and CA19-9 were explored as potential surrogate markers for serologic responses in OC and PC, respectively. Longitudinal serum HE4 and CA-125 levels were measured using OLINK PEA 96-plex assays and plotted against both baseline tumor size as measured by CT scan and RECIST responses in patients treated with MUC16 ADC.

Figure 6A:
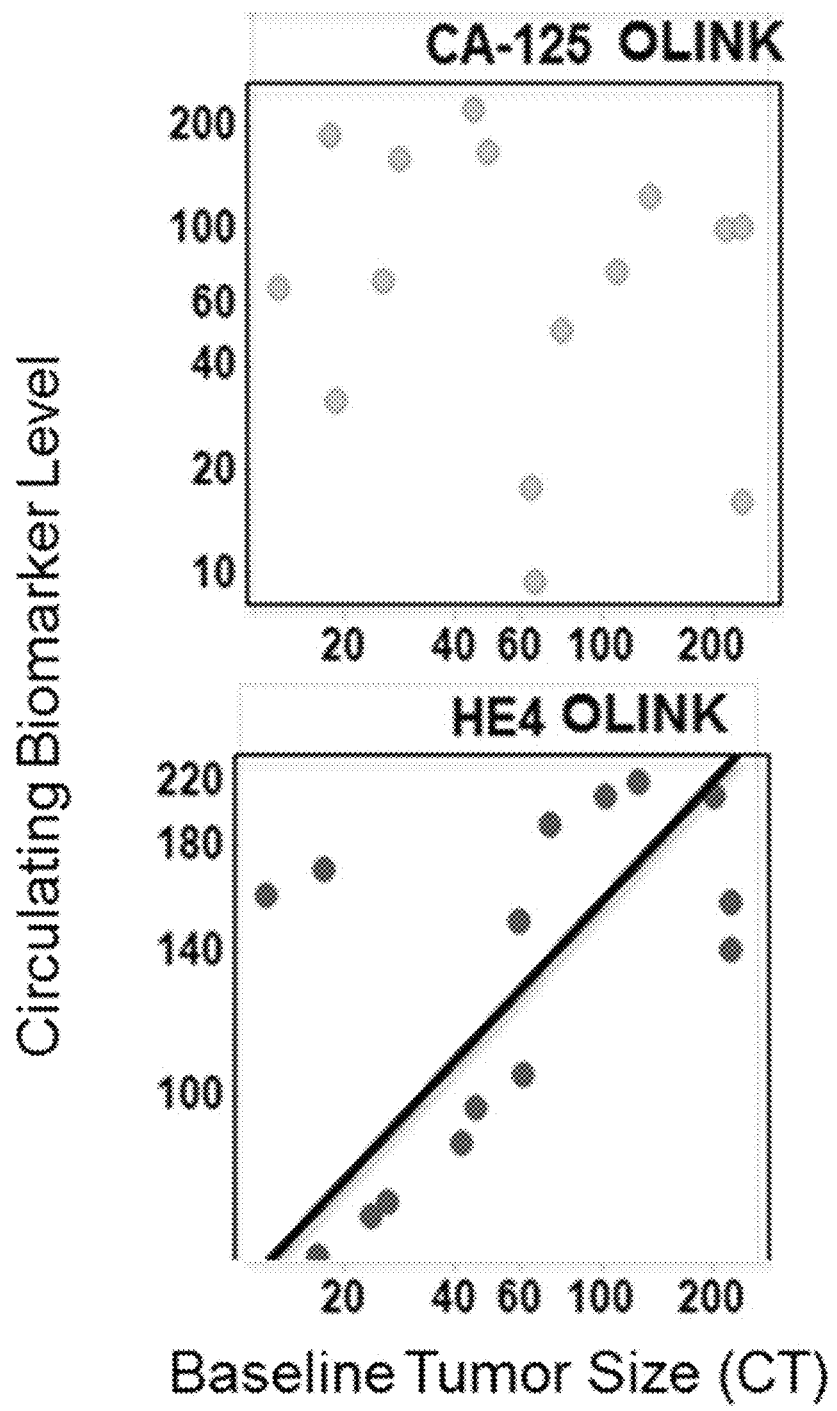
FIG. 6A shows the correlation between tumor size and baseline circulating HE4 and CA125 levels as determined by OLINK assay.
Figure 6B:
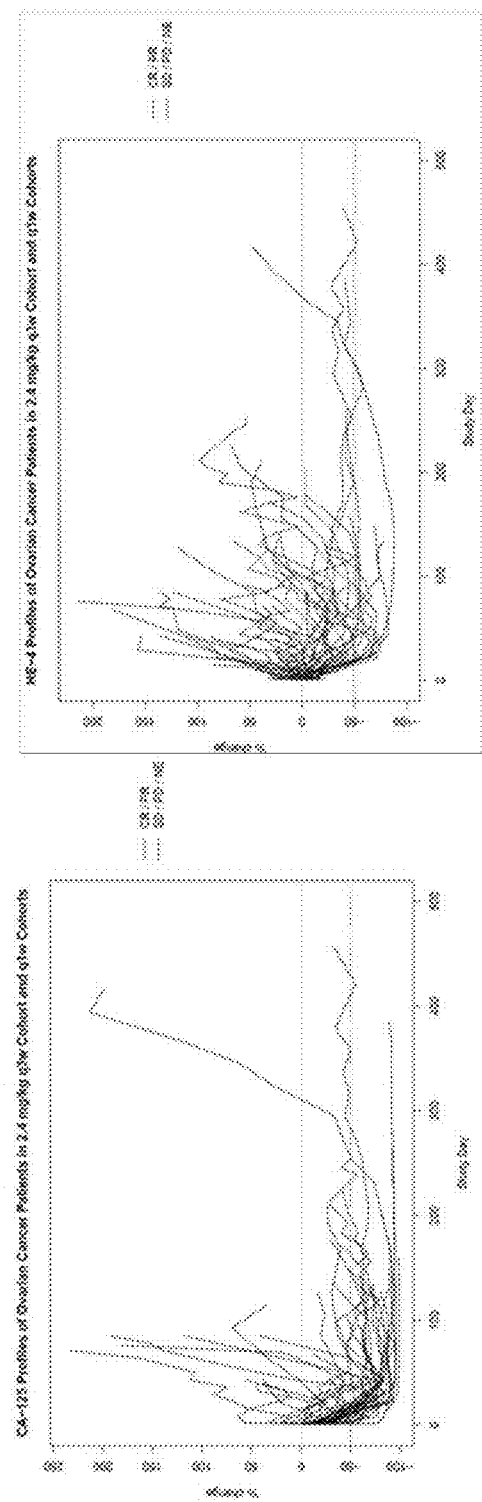
FIG. 6B and FIG. 6C show the change in CA-125 and HE4 levels in ovarian cancer patients in the 2.4 mg/kg q3w and q1w cohorts (FIG. 6B) and the change in CA125 and CA19-9 levels in pancreatic cancer patients in the 2.4 mg/kg q3w cohorts (FIG. 6C).

Baseline HE4 levels better correlated with baseline tumor size than CA-125 (FIG. 6A). For OC, longitudinal serum HE4 levels correlated more specifically with RECIST clinical responses to MUC16 ADC than CA-125 (FIG. 6B-6E). A reduction of at least 40% in HE4 correlated with the partial radiographic responses seen in ovarian cancer patients. (FIG. 6B-6E).

Figure 6C:
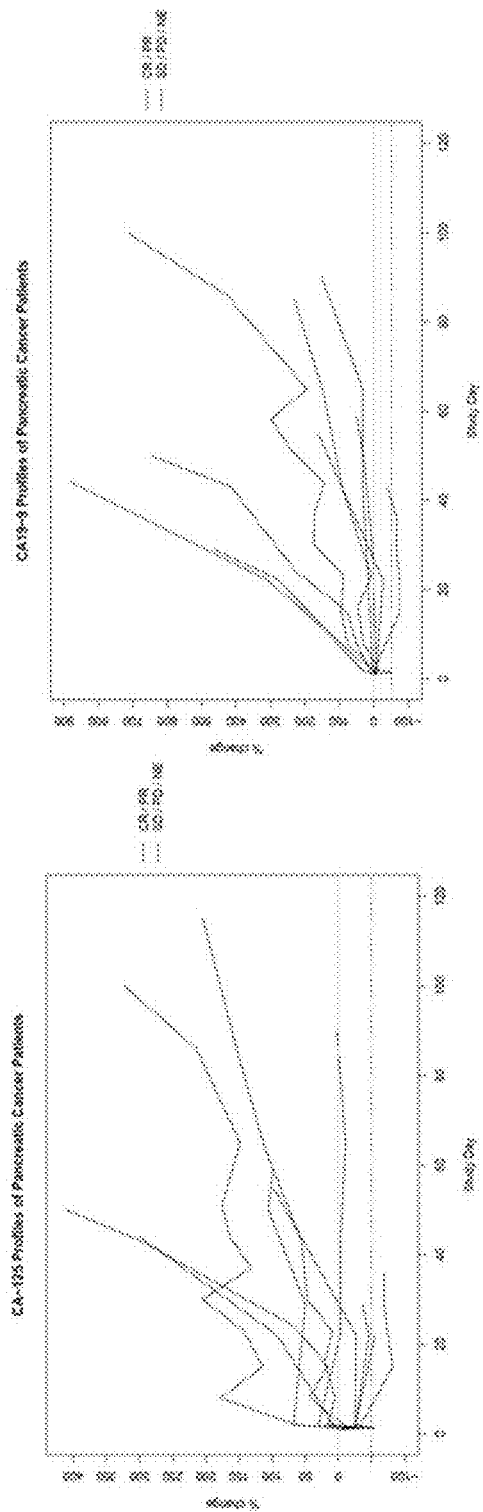
Figure 6D:
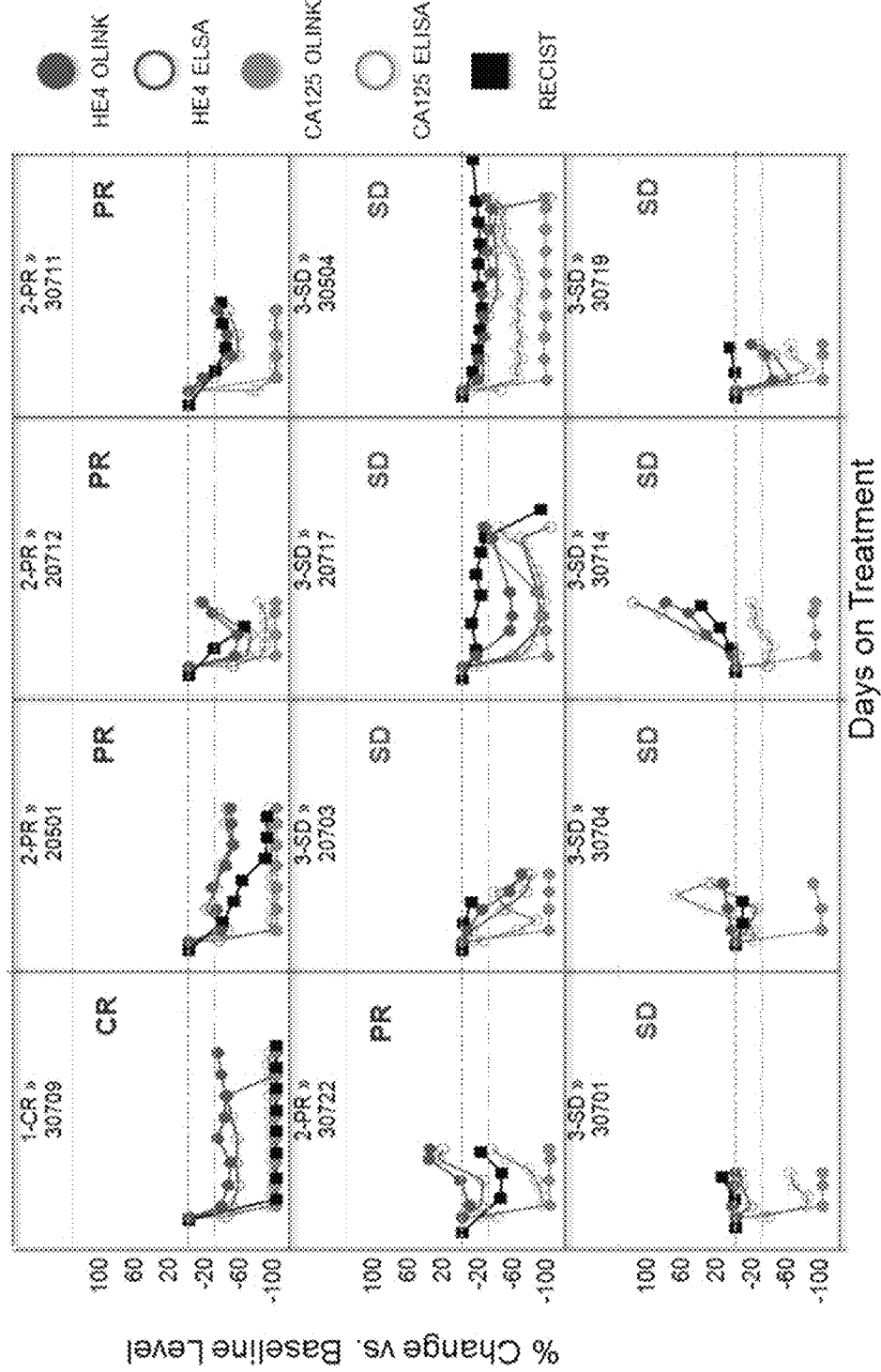
FIG. 6D and FIG. 6E show the correlation between longitudinal serum HE4 and CA125 levels and patient RECIST responses to MUC16 ADC.
Figure 6E:
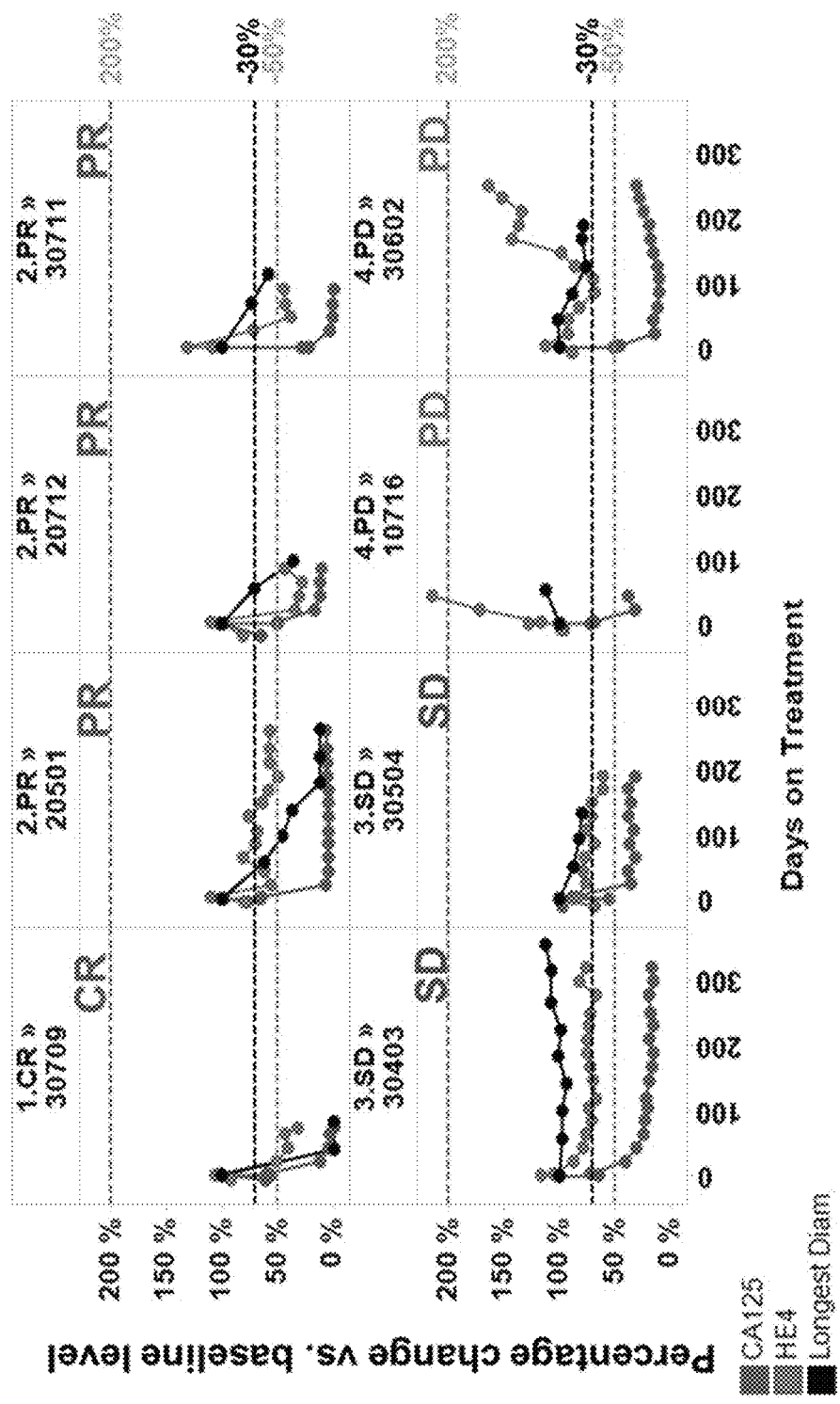

While treatment in PC showed no radiologic responses in 10 patients treated, 1 patient had a confirmed >50% decline in CA19-9 levels, indicating biological effect of the treatment (FIG. 6C).

Figure 7:
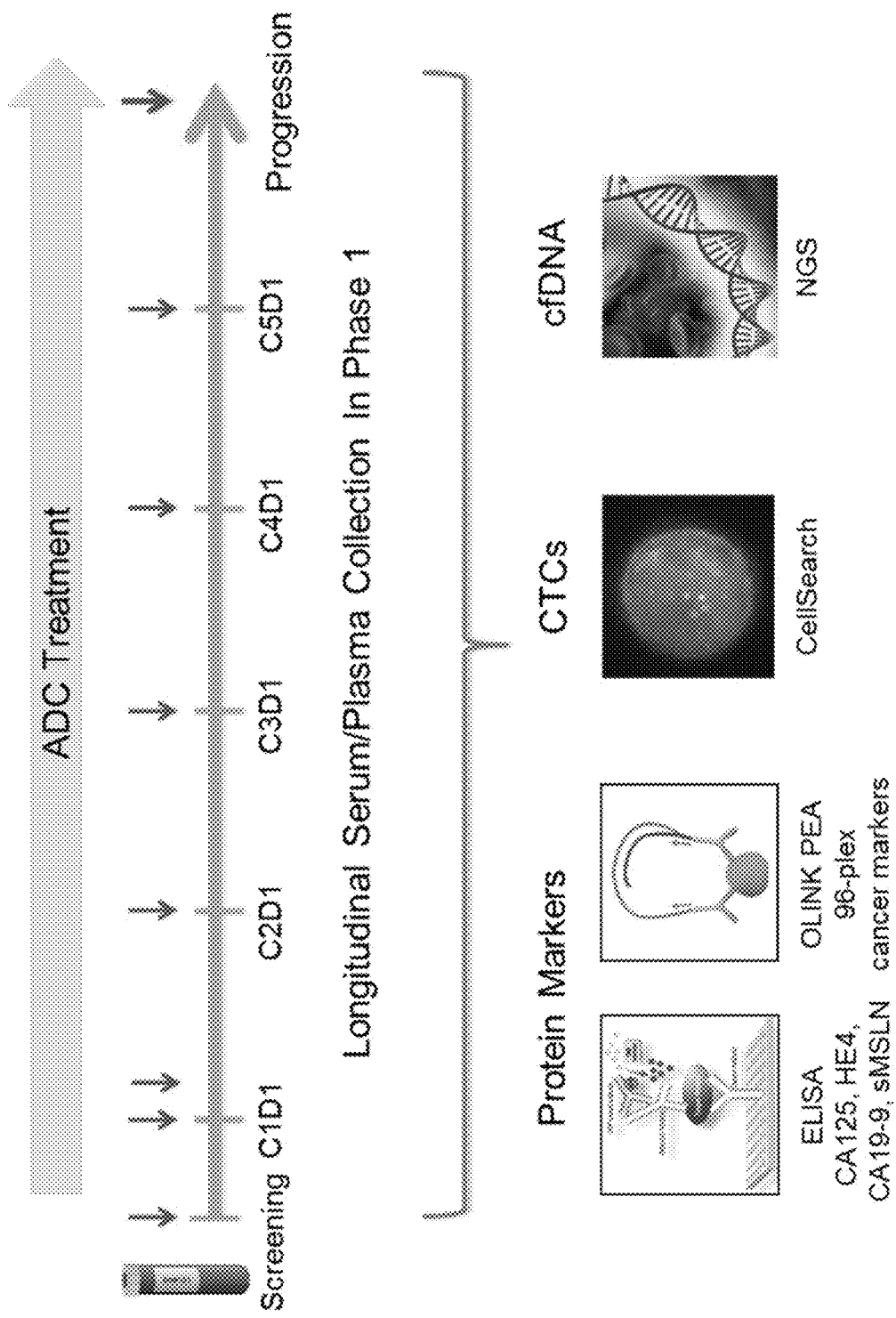
FIG. 7 shows a schematic demonstrating the use of circulating biomarkers as surrogates for clinical activity of MUC16 ADCs.

To further evaluate the utility of serum HE4 as a surrogate biomarker for responses to MUC16 ADC treatment, protein biomarkers, including CA125 and HE4, are measured in serum and plasma samples using ELISA assays. Circulating tumor cells (CTCs) are evaluated using CellSearch, and cell free DNA (cfDNA) is evaluated using Next-Generation Sequencing (NGS) (FIG. 7).

DISCUSSION

ADCs have often been referred to as targeted chemotherapies because they combine the specificity provided by a monoclonal antibody targeting the tumor-specific antigen and the potency of a cytotoxic agent into one drug. Because of this targeted nature, it is critical to use diagnostics to identify patient populations with high expression of the targeted tumor antigen and therefore most likely to benefit from the treatment. To evaluate the correlation between surface expression of MUC16 and responses, an IHC assay for MUC16 was developed and validated prior to and implemented during the study. Archival tissue was required for patients to be enrolled on the study. The tissue was stained with the IHC assay either retrospectively or prospectively (depending on the stage of the trial). Of the 42 evaluable ovarian cancer patients, 80% had high MUC16 expression (IHC 2+/3+) which is consistent with previous assessment of the overall prevalence of MUC16 in epithelial ovarian cancer. Objective responses were only observed in MUC16 high patients indicating that MUC16 target expression is associated with clinical benefit from DMUC5754A treatment. In addition to the assessment of using tissue MUC16 expression by IHC as a potential predictive biomarker for DMUC5754A, the ability of several circulating disease-specific biomarkers to serve as surrogate markers for monitoring treatment response to DMUC5754A was evaluated. The results demonstrated that CA125, a well-established circulating biomarker for ovarian cancer, was not suitable for monitoring treatment response due to the interference between serum CA125 and MUC16 ADC. Conversely, the results demonstrated that circulating HE4 serves as a surrogate PD biomarker for monitoring treatment response of MUC16 ADC and other anti-MUC16 therapies in ovarian cancer. A reduction of at least 40% in this marker correlated with the partial radiographic responses seen in ovarian cancer patients.

Example 2: Study of Safety and Pharmacokinetics of an Anti-MUC16 THIOMAB™ Antibody Drug Conjugate in Patients with Platinum-Resistant Ovarian Cancer or Unresectable Pancreatic Cancer A multi-center human study was performed of an anti-MUC16 THIOMAB™ antibody drug conjugate (TDC) in platinum-resistant ovarian cancer and pancreatic cancer patients. Safety and pharmacokinetic properties were evaluated. Circulating levels of HE4 were measured in serum and correlated to treatment responses.

Methods
Study Design
This Phase I, multicenter, open-label, dose-escalation study was designed to identify the recommended Phase II dose (RP2D) of the anti-MUC16 TDC in patients with platinum-resistant OC or unresectable pancreatic cancer. In the single-agent dose escalation stage utilizing a 3+3 enrollment scheme, patients were given intravenous the anti-MUC16 TDC doses to evaluate the safety, tolerability, and pharmacokinetics of DMUC5754A. Following determination of the maximum tolerated dose (MTD), dose-expansion cohorts will be enrolled at the RP2D to further characterize the safety and preliminary clinical efficacy of the anti-MUC16 TDC.

Dosing on a weekly (q1w) schedule is also evaluated at the RP2D, employing a 3+3 design to determine the MTD of weekly dosing, followed by a cohort expansion to further characterize the safety and activity of q1w dosing.
Patients
OC patients have advanced, epithelial ovarian, primary peritoneal, or fallopian tube cancer that progressed or relapsed within 6 months after the most recent treatment with a platinum-containing chemotherapy regimen and for which no standard therapy exists. Patients have MUC16 expression documented by serum CA125≥2× the upper limit of normal or archival tumor tissue biopsy demonstrating MUC16 expression by central review. Progression or relapse from prior platinum-based chemotherapy is documented by RECIST v1.1 or Gynecologic Cancer Intergroup (GCIG) CA125 progression criteria (Vergote et al., 2000). Patients are allowed ≤2 prior chemotherapy regimens.

PC patients have histologic documentation of incurable, locally advanced, or metastatic disease for which no standard therapy exists, consisting of unresectable pancreatic ductal adenocarcinoma (i.e., patients with locally advanced or metastatic disease who are not considered eligible for surgical resection with curative intent), including recurrence of previously-resected disease considered unresectable with curative intent. Patients have MUC16 expression documented by archival or fresh tumor tissue. No more than 1 chemotherapy regimen (approved or experimental) has been administered in the metastatic setting.

Both OC and PC patients need to have measurable disease with at least one lesion that can be accurately measured in at least one dimension (longest dimension ≥2.0 cm recorded using conventional techniques or ≥1.0 cm on spiral CT scan). Patients are excluded if they have current Grade >1 toxicity (except alopecia and anorexia) from prior therapy or Grade >1 neuropathy from any cause. In addition, patients are not allowed to enroll if they have been treated previously with MUC16-targeted therapy.

Endometrial Cancer (EC) patients may also be recruited for the anti-MUC16 TDC clinical trial.
Safety Assessment
Safety is evaluated according to NCI CTCAE v4.0. For dose-escalation purposes, a dose-limiting toxicity (DLT) is defined as any of the following toxicities considered by the investigator to be related to the anti-MUC16 TDC that occur during the DLT-assessment window (Days 1-21 of Cycle 1): Grade ≥3 non-hematologic toxicity that requires medical intervention and is not attributable to disease progression or another clearly identifiable cause (excluding Grade 3 diarrhea that responds to standard-of-care therapy; Grade 3 nausea or vomiting, in the absence of premedication, that responds to standard of care therapy; Grade 3 infusion reactions that do not limit re-treatment with study drug); Grade ≥4 neutropenia lasting >5 days or associated with fever; Grade ≥4 anemia; Grade ≥4 thrombocytopenia. The maximum tolerated dose (MTD) is defined as the dose at which ≤1 of 6 patients at an assigned dose with protocol-defined DLT. Patients who experience a DLT or adverse event (AE) meeting DLT criteria after the DLT assessment window are allowed to delay dosing for up to 2 weeks or undergo a dose reduction.
Pharmacokinetics and Pharmacodynamics
Pharmacokinetics (PK) of the anti-MUC16 TDC is characterized following q3w or q1w dosing schedules in both OC and PC patients. Serum or plasma samples at multiple pre-specified time points are quantified for three analytes (unconjugated MMAE, the anti-MUC16 TDC total antibody, and the anti-MUC16 TDC conjugate (measured as antibody-conjugated MMAE, acMMAE)). Total antibody (antibody with MMAE-to-antibody ratio equal or greater than zero, including conjugated, partially deconjugated and fully deconjugated antibody) are analyzed using validated enzyme-linked immunosorbent assay methods with the minimum quantifiable concentration of 60 ng/mL. Plasma acMMAE and unconjugated MMAE are determined by using validated LC/MS/MS assays. The lower limit of quantitation (LLOQ) for the acMMAE assay and unconjugated MMAE are 0.359 ng/mL and 0.0359 ng/mL in human plasma, respectively. PK data after Cycle 1, Day 1 dose of the anti-MUC16 TDC are analyzed with non-compartmental analysis using Phoenix WinNonlin 6.2 (Certara, L. P.), and further evaluated based on dose regimen and cancer type.

Serum anti-therapeutic antibody (ATA) samples are collected from all treated patients and are analyzed using a validated bridging antibody ELISA. Positive antibody responses are further characterized by competitive binding to determine if the response is primarily directed against the antibody or the linker-drug portion of the ADC.

Clinical Activity

Objective response rate is estimated only for patients with disease that is measurable by RECIST guidelines. Objective response is defined as a complete or partial response, as determined by investigator assessment and confirmed by repeat assessments ≥4 weeks after initial documentation. Duration of objective response is defined as the time from the initial complete or partial response to the time of disease progression or death.

MUC16 Immunohistochemistry (IHC)

For determination of MUC16 protein expression in formalin-fixed, paraffin-embedded archival tissues, a fully automated IHC assay was developed using the anti-MUC16 (3A5.3) mouse monoclonal primary antibody and Ventana ultraView DAB IHC Detection. MUC16 membranous staining level was scored according the following algorithm, where at least 10% of tumor cells have to be stained in order to qualify as positive in each category; IHC=3+ the predominant staining intensity is 3+ denoting predominantly strong staining; IHC=2+: predominantly moderate staining; IHC=1+, predominantly weak staining; IHC=0, very weak or no staining in >90% of tumor cells.

Assessments of Serum CA125, HE4 and CA19-9

Circulating biomarkers, including CA125 and (human epididymis protein 4 (HE4) for ovarian cancer, and CA125 and CA19-9 for pancreatic cancer, were measured in serum samples collected before each cycle of treatment. CA125, HE4 and CA19-9 levels were analyzed using the CA 125 II™, HE4, and CA19-9$_{XR}$ Chemiluminescent Microparticle Immunoassay respectively on the ARCHITECT i system (Abbott). Circulating biomarkers, including HE4 can also be measured for endometrial cancer.

Statistical Analysis

Design considerations are not made with regard to explicit power and type I error, but to obtain preliminary safety, PK, and PD information. For safety analysis, all patients who receive the anti-MUC16 TDC are included. For activity analyses, all patients with measurable disease at baseline are included.

Example 3: Evaluation of Associations Between SLD and Serum HE4 Levels after Exposure to Anti-MUC16-TDC or Anti-NaPi2b-ADC A study was performed using an anti-MUC16 THIO-MAB™ antibody drug conjugate (TDC) in ovarian cancer patients and pancreatic cancer patients. An additional study was performed using an anti-*naPi2b*-ADC antibody drug conjugate in ovarian cancer patients. Circulating levels of HE4 were measured in serum and correlated to treatment responses to the anti-MUC16-TDC, while circulating levels HE4 and SLD were correlated for patients administered anti-MUC16-TDC or anti-NaPi2b.

Methods

Study Design for Anti-MUC16-TDC Study

This Phase I, multicenter, open-label, dose escalation study was designed to identify the recommended Phase II dose (RP2D) of DMUC4064A (anti-MUC16-TDC) in platinum-resistant ovarian cancer patients and unresectable pancreatic cancer patients. The study employed a traditional 3+3 dose escalation design to determine the maximum tolerated dose (MTD), and the patients were administered intravenous (IV) DMUC4064A (Genentech Inc.) 1.0-5.6 mg/kg every three weeks (q3w) to evaluate the safety, tolerability, and pharmacokinetics of DMUC4064A.

Patients of Anti-MUC16-TDC Study

Ovarian cancer patients had advanced epithelial ovarian, primary peritoneal, or fallopian tube cancer that progressed or relapsed within 6 months after the most recent treatment with a platinum-containing chemotherapy regimen. Patients had MUC16 expression documented by serum CA125 ≥2× the upper limit of normal or archival tumor tissue biopsy demonstrating MUC16 expression. Progression or relapse from prior platinum-based chemotherapy was documented by RECIST v1.1. Patients were allowed ≤2 prior chemotherapy regimens.

Pancreatic cancer patients had histologic documentation of incurable, locally advanced, or metastatic disease, consisting of unresectable pancreatic ductal adenocarcinoma (i.e., patients with locally advanced or metastatic disease who are not considered eligible for surgical resection with curative intent), including recurrence of previously-resected disease. Patients had MUC16 expression documented by archival or fresh tumor tissue. No more than two prior chemotherapy regimens had been administered for the treatment of pancreatic cancer in the adjuvant or advanced/metastatic setting.

Both ovarian cancer and pancreatic cancer patients had to have signed an informed consent form, were 18 years or older, had a life expectance of at least 12 weeks, had an Eastern Cooperative Oncology Group (ECOG) Performance Status of 0 or 1, had measurable disease with at least one bi-dimensionally measurable non-lymph node lesion ≥1 cm long access diameter on CT or MRI scan, or at least one bi-dimensionally measurable lymph node measuring ≥1.5 cm on short access diameter on CT or MRI scan. Patients requiring anti-diabetic medications must have been on a stable dose and regimen for ≥ four weeks. Patients must have had an absolute neutrophil count ≥1500/μL, hemoglobin ≥9 d/dL, a platelet count of ≥100,000/μL, a total bilirubin ≤1.5×ULN, aspartate aminostransferase (AST) and alanine aminotransferase (ALT)≤2.5×ULN, serum creatinine ≤1.5 mg/dL. Absolute neutrophil count must have been assessed at least 14 days from the last growth factor support; hemoglobin and platelet count must have been assessed at least 14 days from the time of prior transfusion. Patients must have had an international normalized ratio (INR)≤1.5 and activated partial thromboplastin time (aPTT)≤1.5×ULN.

Patients were excluded if they had current Grade >1 toxicity (except alopecia and anorexia) from prior therapy or Grade >1 neuropathy from any cause. In addition, patients were not allowed to enroll if they had been treated previously with MUC16-targeted therapy. Patients were not allowed to enroll if they had anti-tumor therapy within four weeks prior to day one, prior treatment with an MMAE-containing ADC, HbA1c≥7.5%, palliative radiation to bone metastases with two weeks prior to day one, prior radiation to lung fields, a major surgical procedure within four weeks prior to day one, known active bacterial, viral, fungal, mycobacterial, parasitic or other infection within four weeks prior to cycle one on day one, evidence of significant uncontrolled concomitant diseases, clinically significant pulmonary symptoms and signs, a clinically significant history of liver disease, other malignancy within the last five years, untreated or active CNS metastases, a history of severe allergic or anaphylactic reactions to monoclonal antibody therapy, were pregnant or breastfeeding, had the inability to comply with the study and follow up procedures, or had any other diseases, metabolic dysfunction, physical examination finding, or clinical laboratory finding giving reasonable suspicion of a disease or condition that contraindicates the use of an investigational drug.

Study Design for Anti-NaPi2b-ADC Study

This was a Phase II, randomized, multicenter, open-label study to evaluate the safety and activity of DNIB0600A (anti-NaPi2b-ADC) in platinum-resistant ovarian cancer patients. The patients were administered intravenous (IV) DNIB0600A (Genentech Inc.) 2.4 mg/kg every three weeks (q3w) to evaluate the safety, tolerability, and pharmacokinetics of DNIB0600A, and to assess the overall response rates and duration of response in patients with NaPi2b-high tumors, as well as in the overall patient population.

Patients of Anti-NaPi2b-ADC Study

Ovarian cancer patients had to have signed an informed consent form, were 18 years of age or older, had a life expectance of at least 12 weeks, had an ECOG Performance Status of 0 or 1, and had histological documentation of epithelial ovarian cancer, primary peritoneal cancer, or fallopian tube cancer. The patients must have been available and willing to provide an adequate archival tumor sample. The patients must have had advanced epithelial ovarian cancer, primary peritoneal, or fallopian tube cancer that had progressed or relapsed during or within six months after the most recent treatment with a platinum-containing chemotherapy regimen. Progression or relapse from prior platinum-based chemotherapy must have been documented radiographically by RECIST v1.1 criteria. Patients must have had measurable disease with at least on lesion that could be accurately measured in at least one dimension per RECIST v1.1 criteria. No more than one prior cytotoxic chemotherapy regimen for the treatment of platinum-resistant ovarian cancer and no more than two total regimens were allowed. Patients must have had an absolute neutrophil count ≥1500/µL, hemoglobin ≥9 d/dL, a platelet count of ≥100,000/µL, a total bilirubin ≤1.5×ULN, aspartate aminostransferase (AST) and alanine aminotransferase (ALT)≤2.5× ULN, serum creatinine ≤2.5 mg/dL. Patients must have had an international normalized ratio (INR)≤1.5 and activated partial thromboplastin time (aPTT)≤1.5×ULN. Patients must have been willing and able to perform a PRO survey.

Patients were excluded if they had primary platinum-refractory disease defined as disease progression during or within two months of a first-line, platinum-containing chemotherapy regimen. Patients were excluded if they had received anti-tumor therapy with four weeks prior to day one, or received palliative radiation within two weeks prior to day one. Patients were excluded if they had prior anthracycline therapy, prior treatment with NaPi2b or SCL34A2 targeted therapies, or a major surgical procedure within four weeks prior to day one. Patients were excluded if they had current Grade >1 toxicity (except alopecia and anorexia) from prior therapy or Grade >1 neuropathy from any cause. Patients were excluded if they had left ventricle ejection fraction defined by multi-gated acquisition or echocardiogram below the institutional lower limit of normal. Patients were excluded if they had evidence of significant, uncontrolled, concomitant disease that could affect compliance with the protocol or interpretation of results. Patients were excluded if they had known active bacterial, viral, fungal, mycobacterial, parasitic or other infection within four weeks prior to cycle one on day one, or had a clinically significant history of liver disease or tested positive for hepatitis B or C, or a known history of HIV seropositive status. Patients were excluded if they had other malignancy within the last 5 years, except for adequately treated carcinoma in situ of the cervix, squamous carcinoma of the skin, adequately controlled limited basal cell skin cancer, or synchronous primary endometrial cancer or prior primary endometrial cancer if all of the following criteria are met: Stage ≤IB, superficial myometrial invasion without vascular or lymphatic invasion, and no poorly differentiated subtypes (i.e., papillary serous, clear cell, or other Federation of Gynecology and Obstetrics [FIGO] Grade 3 lesions). Patients were also excluded if they had untreated or active CNS metastases, a history of severe allergic or anaphylactic reactions to monoclonal antibody therapy, were pregnant or breastfeeding, had a known history of NaPi2b deficiency, or had any other diseases, metabolic dysfunction, physical examination finding, or clinical laboratory finding giving reasonable suspicion of a disease or condition that contraindicates the use of an investigational drug.

Clinical Activity

Treatment (using anti-MUC16-TDC) response rate was estimated for patients with disease that was measurable by RECIST guidelines. Patients were identified as having a partial response (PR), stable disease (SD), or progressive disease (PD) as measured by RECIST v1.1. Objective response is defined as a complete or partial response, as determined by investigator assessment and confirmed by repeat assessments ≥4 weeks after initial documentation. Duration of objective response was defined as the time from the initial complete or partial response to the time of disease progression or death.

MUC16 Immunohistochemistry (IHC)

For determination of MUC16 protein expression in formalin-fixed, paraffin-embedded archival tissues, a fully automated IHC assay was developed using the anti-MUC16 (3A5.3) mouse monoclonal primary antibody and Ventana ultraView DAB IHC Detection.

MUC16 membranous staining level was scored according the following algorithm, where at least 10% of tumor cells had to be stained in order to qualify as positive in each category; IHC=3+ the predominant staining intensity is 3+ denoting predominantly strong staining; IHC=2+: predominantly moderate staining; IHC=1+, predominantly weak staining; IHC=0, very weak or no staining in >90% of tumor cells. HE4 immunohistochemical semi-quantitation was performed using an H-score. Each patient was assigned an H-score ranging from 0 to 300 based upon the intensity level of HE4 staining.

Assessment of Serum HE4

Circulating human epididymis protein 4 (HE4) was measured in serum samples collected before each cycle of treatment. HE4 levels were analyzed using the HE4 Chemiluminescent Microparticle Immunoassay on the ARCHITECT i system (Abbott).

Results

Figure 8:
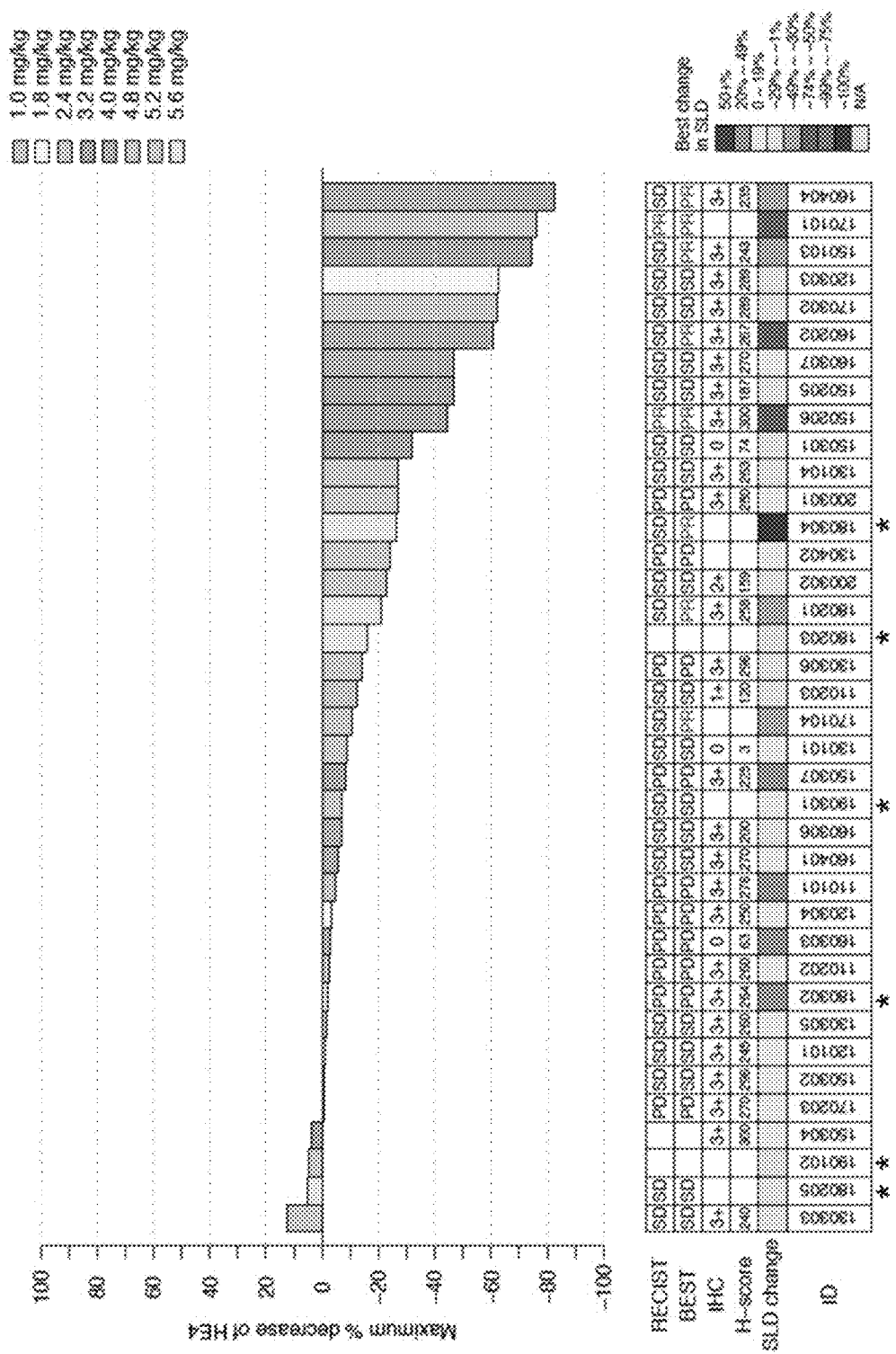
FIG. 8 shows a waterfall plot demonstrating the maximum percent decrease in serum HE4 levels for ovarian cancer patients treated with the indicated doses of anti-MUC16-TDC. In the figure, "*" refers to HE4 data limited to the C2D1 time-point, or earlier. All doses are combined into one waterfall plot. RECIST refers to RECIST confirmed responses while BEST refers to the investigator assessed single best response. The percent change of the sum of the longest diameters (SLD) of the target lesions of the tumors are color coded according to the best change. The immunohistochemistry (IHC) staining score for MUC16 is shown below the waterfall. The H-score (a weighted average of all IHC scores of the tumor ranging from 0-300) is below the IHC score.
Figure 9:
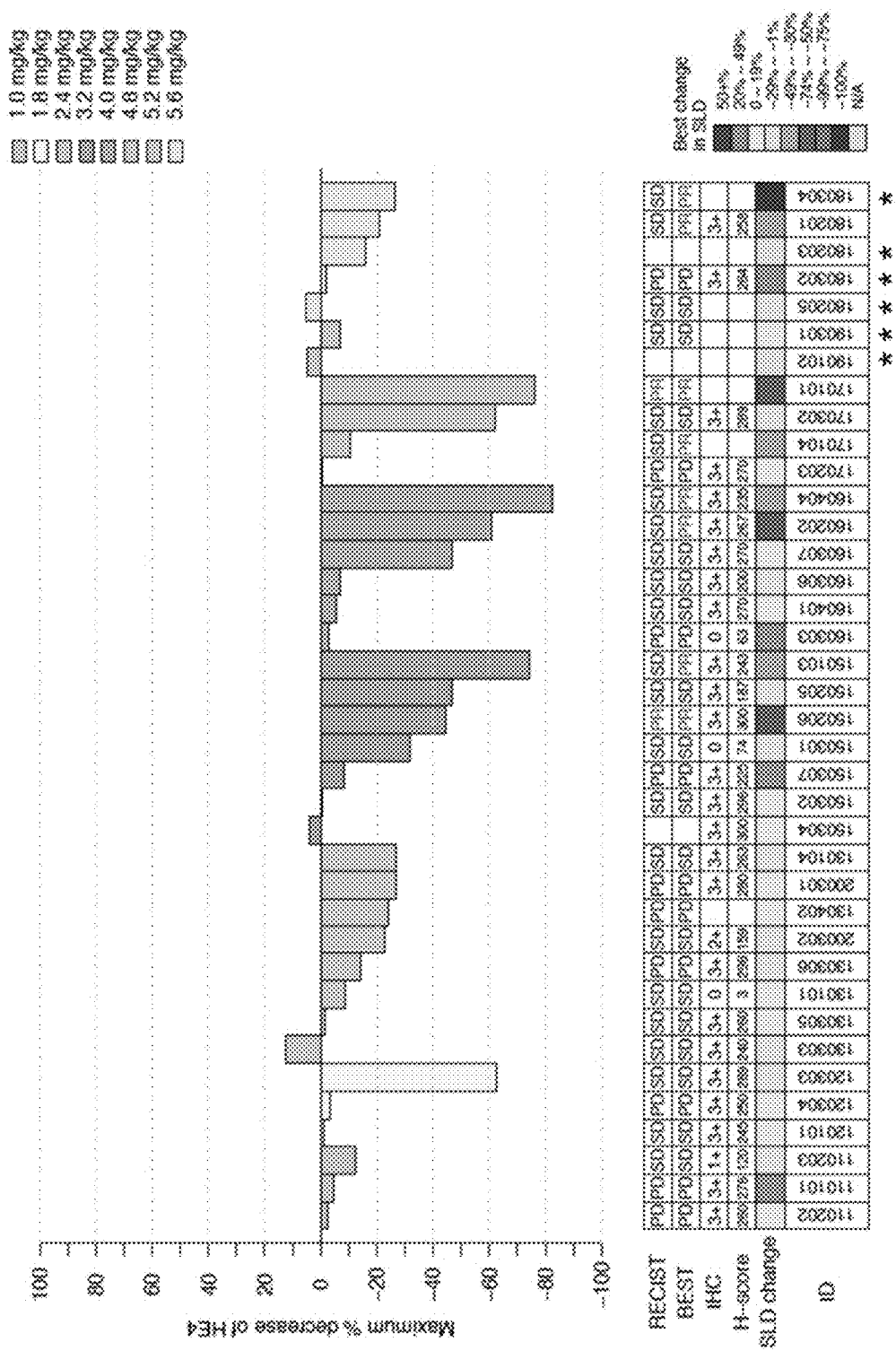
FIG. 9 shows a waterfall plot demonstrating the maximum percent decrease in serum HE4 levels for ovarian cancer patients treated with the indicated doses of anti-MUC16-TDC, grouped by dosage. In the figure "*" refers to HE4 data limited to the C2D1 time-point, or earlier. Escalation doses are separated into individual waterfall plots. RECIST refers to RECIST confirmed responses while BEST refers to the investigator assessed single best response. The percent change of the sum of the longest diameters (SLD) of the target lesions of the tumors are color coded according to the best change. The immunohistochemistry (IHC) staining score for MUC16 is shown below the waterfall. The H-score (a weighted average of all IHC scores of the tumor ranging from 0-300) is below the IHC score.

To evaluate the utility of serum HE4 as a surrogate biomarker for responsiveness to anti-MUC16-TDC treatment, serum HE4 levels were measured in platinum-resistant ovarian cancer patients prior to each administration of anti-MUC16-TDC therapy (dosages ranging between 1.0 and 5.6 mg/kg). The maximum percentage change in serum HE4 levels was calculated and plotted for each patient, and compared to the patient's RECIST responses and SLD changes after administration of anti-MUC16-TDC therapy (FIGS. 8 and 9). At the end point of the clinical trial, 23 patients maintained stable disease, while two patients had a partial response to treatment. An additional six patients showed a partial response to treatment at some point during the course of the study. Progressive disease was observed in ten patients at the conclusion of the study. Surprisingly, patients that showed an approximately 25% or greater maximum decrease in HE4 serum levels after administration of anti-MUC16-TDC had either a partial response to treatment or stable disease, suggesting that this level of reduction in serum HE4 may act as a surrogate biomarker for responsiveness to anti-MUC16-TDC treatment.

Figure 10:
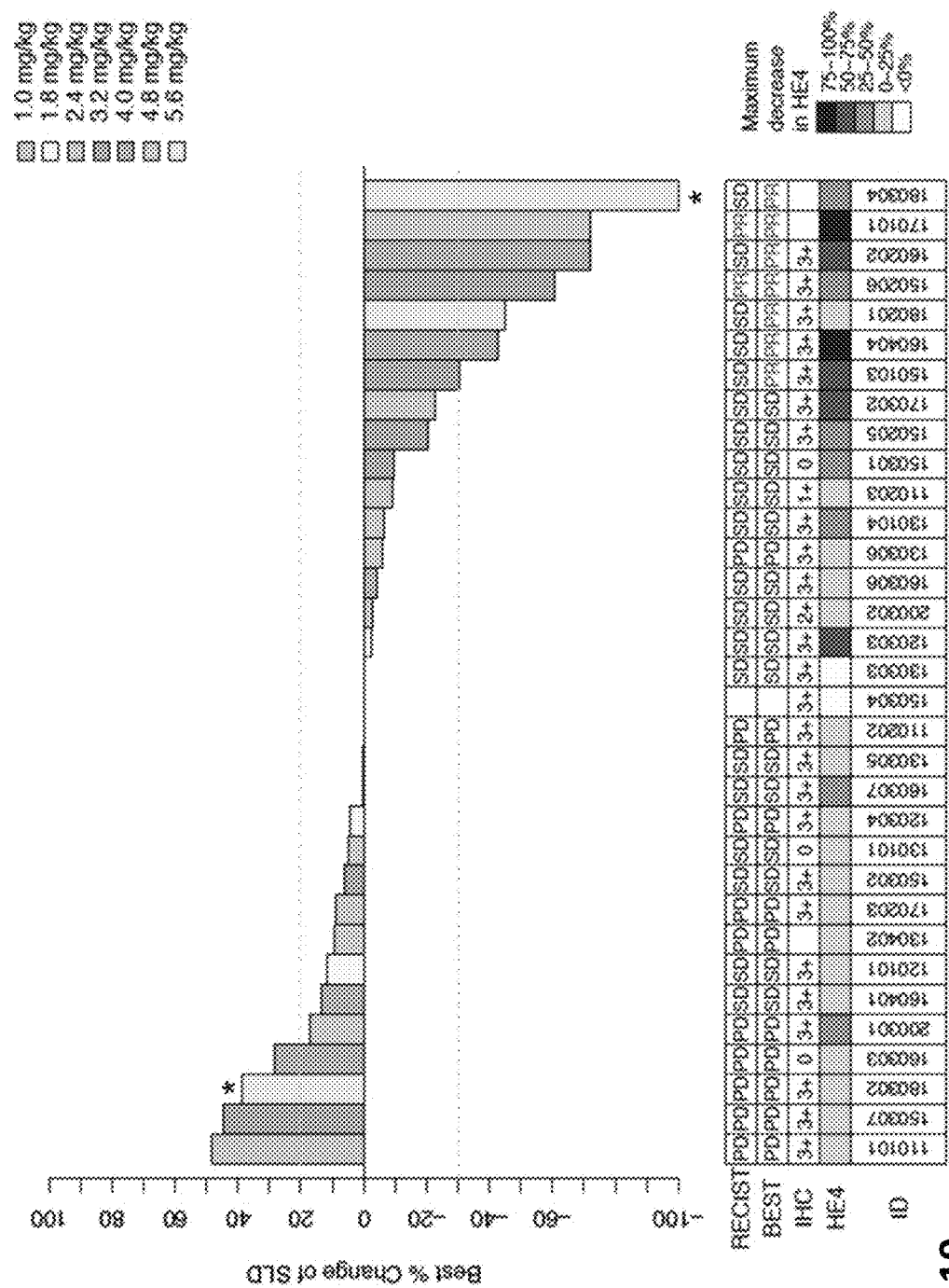
FIG. 10 shows a waterfall plot demonstrating investigator-assessed best radiologic responses for ovarian cancer patients treated with the indicated doses of anti-MUC16-TDC. In the figure, "*" refers to data in which only C2D1 post-dose data was available. All doses are combined into one waterfall plot. RECIST refers to RECIST confirmed responses while BEST refers to the investigator assessed single best response. The percent change of the sum of the longest diameters (SLD) of the target lesions of the tumors are color coded according to the best change. The immunohistochemistry (IHC) staining score for MUC16 is shown below the waterfall.

Additionally, the best percentage change of SLD was plotted for each patient and compared to the patient's RECIST responses and maximum decrease in serum HE4 levels (FIG. 10). In agreement with the results described above, a large decrease in serum HE4 levels was associated with an improved clinical response to anti-MUC16-TDC treatment.

Figure 11A:
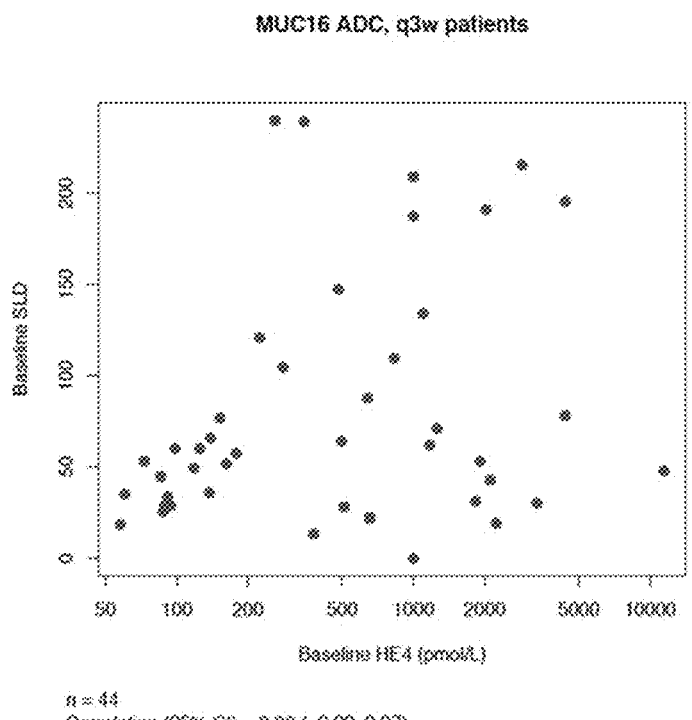
FIG. 11A, FIG. 11B, and FIG. 11C show the correlation between baseline sum of the longest diameter (SLD) measurements and baseline circulating HE4 levels for ovarian cancer patients enrolled in one of three clinical studies: a clinical study of anti-MUC16-ADC (FIG. 11A), a clinical study of anti-MUC16-TDC (FIG. 11B), and a clinical study of anti-NaPi2b (FIG. 11C).
Figure 11B:
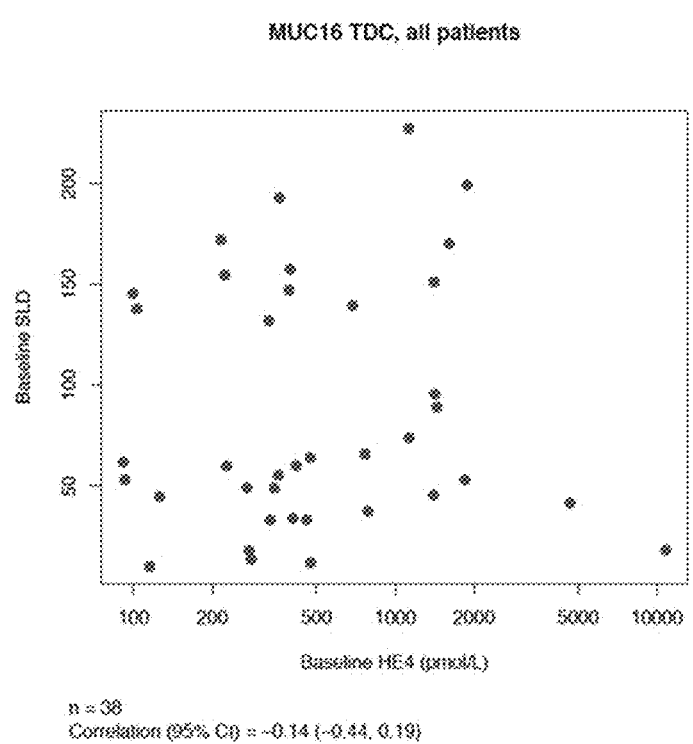
Figure 11C:
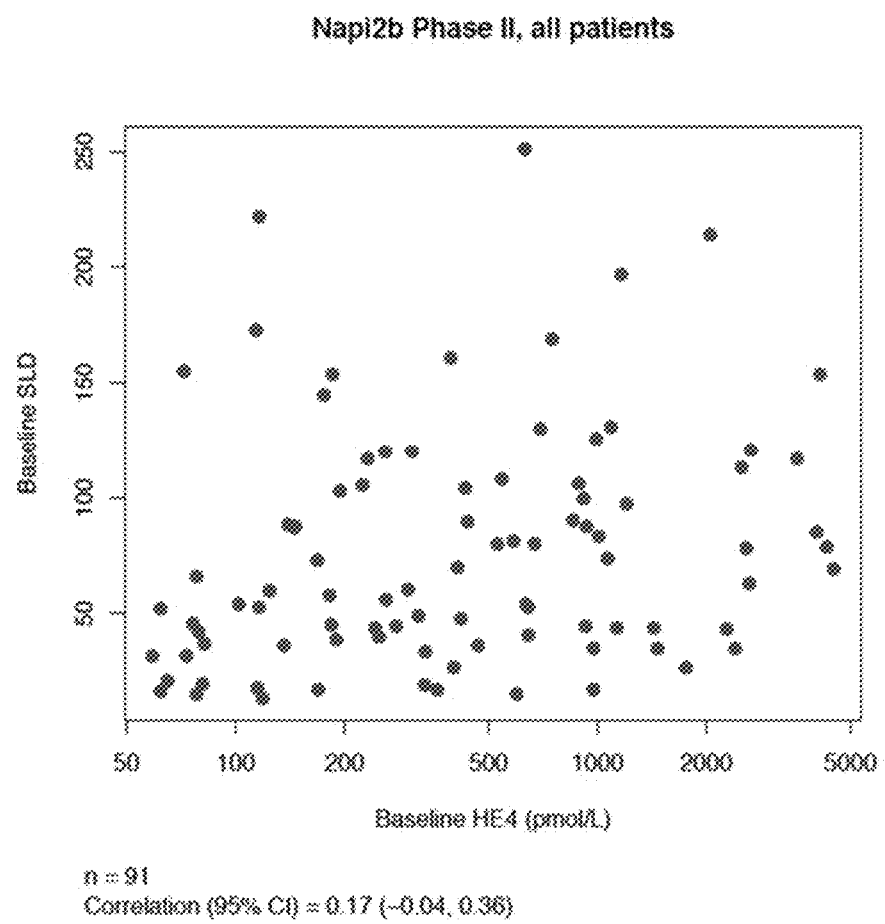

To characterize whether an association exists between baseline HE4 levels and SLD measurements, baseline SLD measurements and serum HE4 levels were plotted for ovarian cancer patients enrolled in three clinical studies: ovarian cancer patients receiving anti-MUC16-ADC (FIG. 11A), ovarian cancer patients receiving anti-MUC16-TDC (FIG. 11B), and ovarian cancer patients receiving anti-NaPi2b-ADC (FIG. 11C). Only a low correlation between baseline SLD measurements and serum HE4 levels was observed for ovarian cancer patients enrolled in these studies, in contrast to the strong correlation observed between baseline tumor size and serum HE4 levels (FIG. 6A). The low correlation between baseline SLD and serum HE4 levels may be explained in part because SLD is a measure of particular patient's tumor(s) for the purposes of determining clinical response, and thus may not reflect total tumor burden in the patient. Interestingly, while only a low correlation between baseline SLD measurements and serum HE4 levels was observed in ovarian cancer patients, decreases in HE4 levels (particularly decreases of 25% or more) after administration of anti-MUC16-TDC strongly correlated with improved clinical responses (FIG. 8-10).

Taken together this data suggests that the maximum decrease in serum HE4 is associated with higher doses of anti-MUC16-TDC, and improved clinical responses to anti-MUC16-TDC are associated with large decreases in circulating HE4 levels (FIG. 8-10). While only a low association between baseline SLD and serum HE4 levels was observed (FIG. 11A-C), the data indicates that a reduction of at least 25% in circulating HE4 levels correlated with disease stabilization or partial radiographic responses seen in ovarian cancer patients, suggesting that this level of reduction in serum HE4 may act as a surrogate biomarker for responsiveness to anti-MUC16-TDC treatment.

Example 4: Evaluation of Associations Between Serum HE4 Levels and Dose or Length of Exposure to Anti-MUC16-TDC A study was performed using an anti-MUC16 THIO-MAB™ antibody drug conjugate (TDC) in ovarian cancer patients and pancreatic cancer patients. Circulating levels of HE4 and CA125 were measured in serum of patients before and during treatment and then changes in circulating CA125 and HE4 levels were correlated to anti-MUC16-TDC dose level and time on treatment.

Methods

Study Design for Anti-MUC16-TDC Study

This Phase I, multicenter, open-label, dose escalation study was designed to identify the recommended Phase II dose (RP2D) of DMUC4064A (anti-MUC16-TDC) in platinum-resistant epithelial ovarian cancer, primary peritoneal cancer or fallopian tube cancer patients, and locally advanced or metastatic pancreatic cancer patients. The study employed a traditional 3+3 dose escalation design to determine the maximum tolerated dose (MTD), and the patients were administered intravenous (IV) DMUC4064A (Genentech Inc.) 1.0-5.6 mg/kg every three weeks (q3w) to evaluate the safety, tolerability, and pharmacokinetics of DMUC4064A until disease progression. Patients were on study for a period of time that ranged from 25 days to 400 days.

Patients of Anti-MUC16-TDC Study

Ovarian cancer patients had advanced epithelial ovarian, primary peritoneal, or fallopian tube cancer that progressed or relapsed within 6 months after the most recent treatment with a platinum-containing chemotherapy regimen. Patients had MUC16 expression documented by serum CA125 ≥2× the upper limit of normal or archival tumor tissue biopsy demonstrating MUC16 expression. Progression or relapse from prior platinum-based chemotherapy was documented by RECIST v1.1. Patients were allowed ≤2 prior chemotherapy regimens.

Pancreatic cancer patients had histologic documentation of incurable, locally advanced, or metastatic disease, consisting of unresectable pancreatic ductal adenocarcinoma (i.e., patients with locally advanced or metastatic disease who are not considered eligible for surgical resection with curative intent), including recurrence of previously-resected disease. Patients had MUC16 expression documented by archival or fresh tumor tissue. No more than two prior chemotherapy regimens had been administered for the treatment of pancreatic cancer in the adjuvant or advanced/metastatic setting.

Both ovarian cancer and pancreatic cancer patients had to have signed an informed consent form, were 18 years or older, had a life expectancy of at least 12 weeks, had an Eastern Cooperative Oncology Group (ECOG) Performance Status of 0 or 1, had measurable disease with at least one bi-dimensionally measurable non-lymph node lesion ≥1 cm long access diameter on CT or MRI scan, or at least one bi-dimensionally measurable lymph node measuring ≥1.5 cm on short access diameter on CT or MRI scan. Patients requiring anti-diabetic medications must have been on a stable dose and regimen for ≥four weeks. Patients must have had an absolute neutrophil count ≥1500/µL, hemoglobin ≥9 d/dL, a platelet count of ≥100,000/µL, a total bilirubin ≤1.5×ULN, aspartate aminostransferase (AST) and alanine aminotransferase (ALT)≤2.5×ULN, serum creatinine ≤1.5 mg/dL. Absolute neutrophil count must have been assessed at least 14 days from the last growth factor support; hemoglobin and platelet count must have been assessed at least 14 days from the time of prior transfusion. Patients must have had an international normalized ratio (INR)≤1.5 and activated partial thromboplastin time (aPTT)≤1.5×ULN.

Patients were excluded if they had current Grade >1 toxicity (except alopecia and anorexia) from prior therapy or Grade >1 neuropathy from any cause. In addition, patients were not allowed to enroll if they had been treated previously with MUC16-targeted therapy. Patients were not allowed to enroll if they had anti-tumor therapy within four weeks prior to day one, prior treatment with an MMAE-containing ADC, HbA1c ≥7.5%, palliative radiation to bone metastases with two weeks prior to day one, prior radiation to lung fields, a major surgical procedure within four weeks prior to day one, known active bacterial, viral, fungal, mycobacterial, parasitic or other infection within four weeks prior to cycle one on day one, evidence of significant uncontrolled concomitant diseases, clinically significant pulmonary symptoms and signs, a clinically significant history of liver disease, other malignancy within the last five years, untreated or active CNS metastases, a history of severe allergic or anaphylactic reactions to monoclonal antibody therapy, were pregnant or breastfeeding, had the inability to comply with the study and follow up procedures, or had any other diseases, metabolic dysfunction, physical examination finding, or clinical laboratory finding giving reasonable suspicion of a disease or condition that contraindicates the use of an investigational drug.

Assessment of Serum CA125 and HE4

Circulating human epididymis protein 4 (HE4) was measured in serum samples collected at the end of treatment period. HE4 levels were analyzed using the HE4 Chemiluminescent Microparticle Immunoassay on the ARCHITECT i system (Abbott).

Circulating Carcinoma antigen 125 (CA125) was measured in serum samples collected at the end of treatment period. CA125 levels were analyzed using the CA125 II™ Chemiluminescent Microparticle Immunoassay on the ARCHITECT i system (Abbott).

Results

Serum HE4 levels were measured in platinum-resistant ovarian cancer patients after administration of anti-MUC16-TDC therapy (dosages ranging between 1.0 and 5.6 mg/kg), and compared with serum levels of CA125. The lowest post-dose levels as a percentage of baseline in serum CA125 and HE4 levels were calculated and plotted for each patient (FIG. 12). As shown in FIGS. 12A and 12B, maximal decreases in serum levels of both CA125 and HE4 after treatment did not appear to be dependent on the dose of anti-MUC16-TDC.

Figures 13A, 13B:
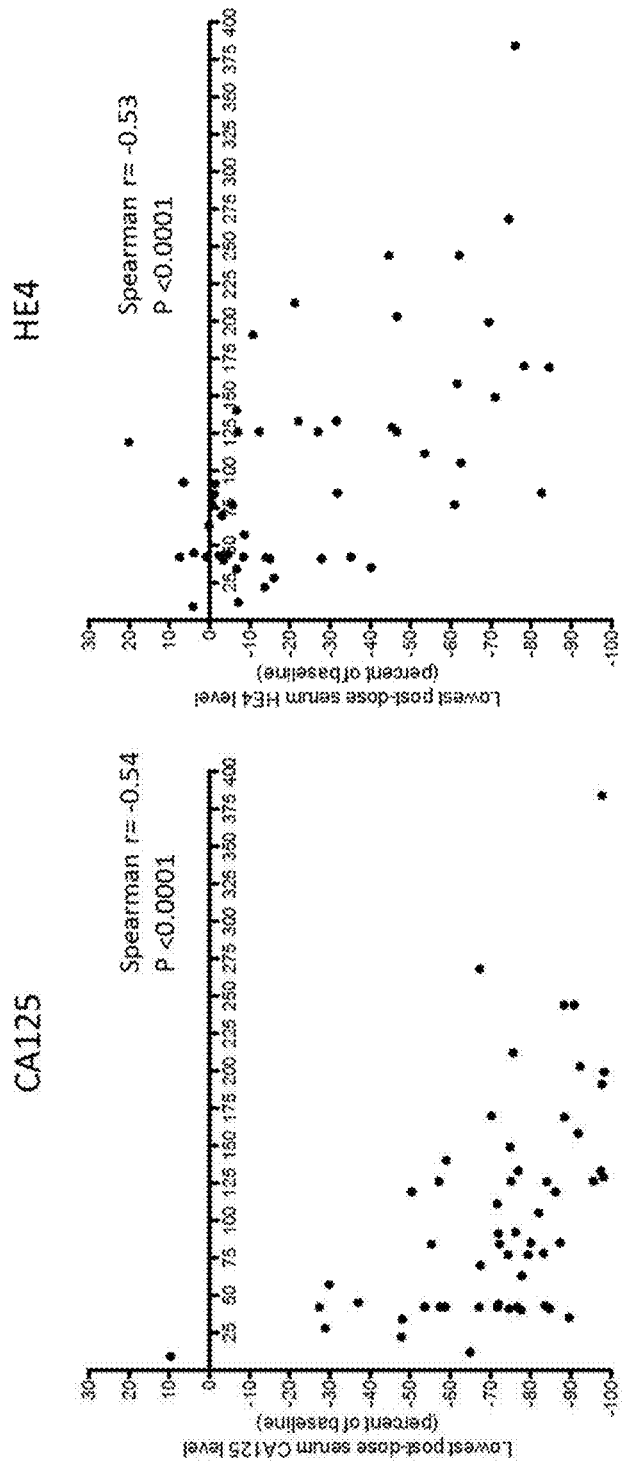
FIG. 13A shows percent decrease in serum CA125 levels from baseline levels for ovarian cancer patients after treatment with anti-MUC16-TDC and indicated length of time on treatment. The reduction in measured serum levels of CA125 in post-dose samples is partially due to drug interference in assay. Statistical analysis indicated a Spearman's rank correlation coefficient of 0.54 and a p-value of: p<0.0001.
FIG. 13B shows percent decrease in serum HE4 levels from baseline levels for ovarian cancer patients after treatment with anti-MUC16-TDC and indicated length of time on treatment. Statistical analysis indicated a Spearman's rank correlation coefficient of 0.53 and a p-value of: p<0.0001.

Additionally, comparison of post-treatment serum levels of CA125 and HE4 in patients to length of time on anti-MUC16-TDC treatment indicated that there was a correlation between length of time on treatment and reduction in serum levels of CA125 and HE4 (FIGS. 13A and 13B). Spearman's rank correlation coefficient for CA125 was calculated to be 0.54 and a p-value was calculated to be p<0.0001 for CA125 (FIG. 13A). Spearman's rank correlation coefficient for HE4 was calculated to be 0.53 and a p-value was calculated to be p<0.0001 for HE4 (FIG. 13B).

Figure 14A:
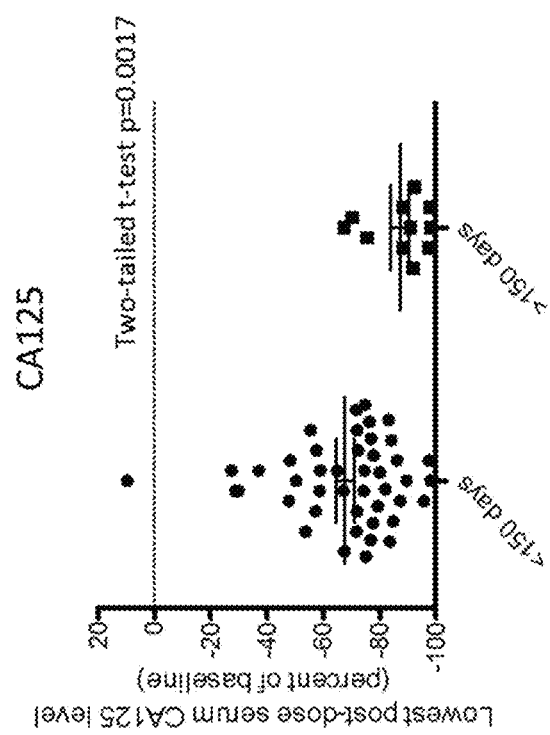
FIG. 14A shows percent decrease in serum CA125 levels from baseline levels for ovarian cancer patients who remained on treatment with anti-MUC16-TDC for less than 5 months (150 days) or for more than 5 months (150 days). Two-tailed t-test analysis gave a p-value of: p=0.0017.
Figure 14B:
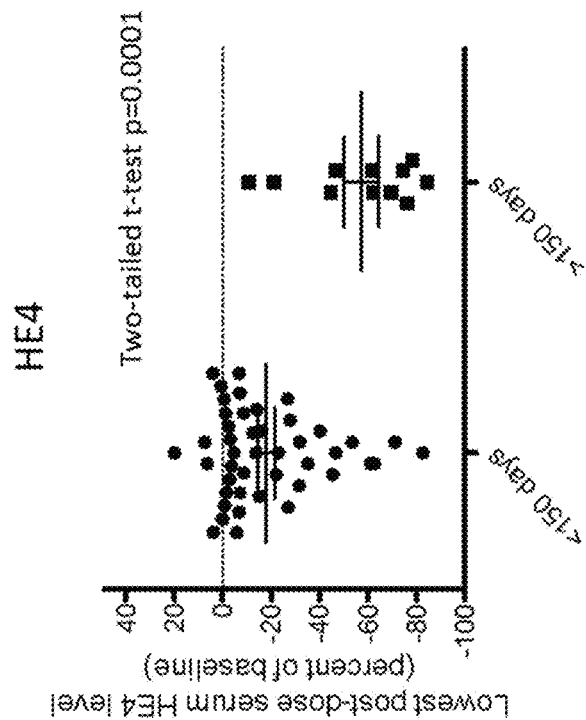
FIG. 14B shows percent decrease in serum HE4 levels from baseline levels for ovarian cancer patients who remained on treatment with anti-MUC16-TDC for less than 5 months (150 days) or for more than 5 months (150 days). Two-tailed t-test analysis gave a p-value of: p=0.0001.

Moreover, reduction in serum levels of both CA125 and HE4 in patients who were on treatment with anti-MUC16-TDC for greater than five months (over 150 days) was significantly lower than the reduction in serum levels of CA125 and HE4 in patients who were on treatment with anti-MUC16-TDC for less than five months (FIGS. 14A and 14B). Statistical significance was determined using a two-tailed t-test. The "p-value" for reduced serum levels of CA125 in patients who were on treatment with anti-MUC16-TDC for greater than five months was p=0.0017 (FIG. 14A), while the "p-value" for reduced serum levels of HE4 in patients who were on treatment with anti-MUC16-TDC for greater than five months was p=0.0001 (FIG. 14B).

Taken together these data suggest that reduction in serum levels of HE4 is positively correlated with length of time on anti-MUC16-TDC therapy. While the reduction in serum levels of HE4 is consistent with reduction in serum levels of CA125, unlike CA125, the measurement of HE4 levels in post-dose serum samples is not affected by the presence of MUC16 targeted agents.

REFERENCES

1. Jemal A, Siegel R, Xu J, et al. Cancer Statistics, 2010. CA Cancer J Clin 2010; 60:277-300.
2. Bloss J D, Liao S Y, Buller R E, et al. Extraovarian peritoneal serous papillary carcinoma: a case-control retrospective comparison to papillary adenocarcinoma of the ovary. Gynecol Oncol 1993; 50:347-51.
3. Schneider C, Wright E, Perucchini D, et al. Primary carcinoma of the fallopian tube: a report of 19 cases with literature review. Eur J Gynecol Oncol 2000; 21:578-82.
4. Martin L P, Schilder R J. Management of recurrent ovarian carcinoma: current status and future directions. Semin Oncol 2009; 36:112-25.
5. Pujade-Lauraine D, Paraiso D, Cure H, et al. Predicting the effectiveness of chemotherapy (Cx) in patients with recurrent ovarian cancer (ROC): a GINECO study. Proc Am Soc Clin Oncol 2002:21 (abstract 829).
6. Shaib Y, Davila J, Naumann C, et al. The impact of curative intent surgery on the survival of pancreatic cancer patients: a U.S. population-based study. Am J Gastroenterol 2007; 102:1377-82.
7. Neoptolemos J P, Stocken D D, Friess H, et al. A randomized trial of chemoradiotherapy and chemotherapy after resection of pancreatic cancer. N Engl J Med 2004; 350:1200-10.
8. Bast R C Jr, Feeney M E, Lazarus H, et al. Reactivity of a monoclonal antibody with human ovarian carcinoma. J Clin Invest 1981; 68:1331-7.
9. O'Brien T J, Beard J B, Underwood L J, et al. The CA 125 gene: an extracellular superstructure dominated by repeat sequences. Tumour Biol 2001; 22:348-66
10. Yin B W T, Lloyd K O. Molecular cloning of the CA125 ovarian cancer antigen: identification as a new mucin, MUC16. J Biol Chem 2001:276:27371-5.
11. Rosen D G, Wang L, Atkinson J N, et al. Potential markers that complement expression of CA125 in epithelial ovarian cancer. Gynecol Oncol 2005; 99:267-77.
12. Theriault C, Pinard M, Comamala M, et al. MUC16 (CA125) regulates epithelial ovarian cancer cell growth, tumorigenesis and metastasis. Gynecol Oncol. 2011 121 (3):434-43.
13. Haglund C. Tumor marker antigen CA125 in pancreatic cancer: a comparison with CA19-9 and CEA. Br. J. Cancer 1986; 54:897-901.
14. Macdonald F, Downing R. and W. H. Allum. Expression of CA125 in pancreatic carcinoma and chronic pancreatitis. Br J Cancer 1988; 58:505-6.
15. Bafna S, Kaur, S, Batra S K. Membrane-bound mucins: the mechanistic basis for alterations in the growth and survival of cancer cells. Oncogene 2010; 29:2893-904
16. Vergote I, Rustin G J S, Eisenhauer E A, et al. Re: new guidelines to evaluate the response to treatment in solid tumors [ovarian cancer]. JNCI 2000:92:1534-5.
17. Bai R L, Petit G R, Hamel E. Binding of dolastatin 10 to tubulin at a distinct site for peptide antimitotic agents near the exchangeable nucleotide and vinca alkaloid sites. J Biol Chem 1990; 265:17141-9.

18. Bloss J D, Liao S Y, Buller R E, et al. Extraovarian peritoneal serous papillary carcinoma: a case-control retrospective comparison to papillary adenocarcinoma of the ovary. Gynecol Oncol 1993; 50:347-51.
19. Burris H A III, Moore M J, Andersen J, et al. Improvements in survival and clinical benefit with gemcitabine as first-line therapy for patients with advanced pancreas cancer: a randomized trial. J Clin Oncol 1997; 15:2403-13.
20. Chen Y, Clark S, Wong T, et al. Armed antibodies targeting the mucin repeats of the ovarian cancer antigen, MUC16, are highly efficacious in animal tumor models. Cancer Res 2007; 67:4924-32.
21. DeGeorge J J, Ahn C-H, Andrews P A, et al. Regulatory considerations for preclinical development of anticancer drugs. Cancer Chemother Pharmacol 1998; 48:173-85.
22. Doronina S O, Toki B E, Torgov M Y, et al. Development of potent monoclonal antibody auristatin conjugates for cancer therapy. Nat Biotechnol 2003; 21:778-84.
23. Fanale M, Barlett N L, Forero-Torres A, et al. The antibody-drug conjugate brentuximab vedotin (SGN-35) induced multiple objective responses in patients with relapsed or refractory CD30-positive lymphomas in a Phase 1 weekly dosing study. Blood 2009; 114: abstract 2731.
24. Francisco J A, Cerveny C G, Meyer D L, et al. cAC10-vcMMAE, an anti CD30 monomethyl auristatin E conjugate with potent and selective antitumor activity. Blood 2003; 102:1458-65.
25. Haisma H J, Battaile A, Stradtman E W, et al. Antibody-antigen complex formation following injection of OC125 monoclonal antibody in patients with ovarian cancer. Int J Cancer 1987; 40:758-62.
26. Hamid O, Sznol M, Pavlick A C, et al. Frequent dosing and GPNMB expression with DCX-011 (CRO11-vcMMAE), an antibody-drug conjugate (ADC), in patients with advanced melanoma. J Clin Oncol 2010:28: abstract 8525.
27. McQuarrie S A, Riauka T, Baum R P, et al. The effects of circulating antigen on the pharmacokinetics and radio-immunoscintigraphic properties of 99mTc labelled monoclonal antibodies in cancer patients. J Pharm Pharmaceut Sci 1998; 1:115-25.
28. Monk B J, Herzog, T J, Kay S B, et al. Trabectedin plus pegylated liposomal doxorubicin in recurrent ovarian cancer. J Clin Oncol 2010; 29:3107-14.
29. Moore M J, Goldstein D, Hamm J, et al. Erlotinib plus gemcitabine compared with gemcitabine alone in patients with advanced pancreatic cancer: A Phase III trial of the National Cancer Institute of Canada Clinical Trials Group. J Clin Oncol 2007; 25(15):1960-66.
30. Pastuskovas C, Mallet W, Clark S, et al. Effect of immune complex formation on the distribution of a novel antibody to the ovarian tumor antigen CA125. Drug Metab Dispos 2010; 38:2309-19.
31. Tolcher A W, Ochoa L, Hammond L A, et al. Catuzumab mertasine, a maytansinoid immunoconjugate directed to the CanAg antigen: a Phase I, pharmacokinetic, and biologic correlative study. J Clin Oncol 2003; 21:211-22.
32. Yin B W T, Dinistrian A, Lloyd K O, et al. Ovarian cancer antigen CA125 is encoded by the MUC16 mucin gene. Int J Cancer 2002:98:737-40.

What is claimed is:

1. A method for treating or delaying progression of a MUC16-positive cancer in a subject in need thereof, the method comprising:
   (a) measuring the expression level of human epididymis protein 4 (HE4) in a sample obtained from the subject at a first time point, wherein the first time point is prior to administering to the subject a MUC16 antagonist;
   (b) administering to the subject a therapeutically effective amount of the MUC16 antagonist; and
   (c) measuring the expression level of HE4 in a sample obtained from the subject at a second time point, wherein the second time point is after administration of the MUC16 antagonist, and
   wherein the subject is administered one or more additional therapeutically effective amounts of the MUC16 antagonist if the expression level of HE4 at the second time point is at least 25% lower than the expression level of HE4 at the first time point.

2. The method of claim 1, further comprising step (d): administering to the subject the one or more additional therapeutically effective amounts of the MUC16 antagonist when the expression level of HE4 at the second time point is at least 25% lower than the expression level of HE4 at the first time point.

3. The method of claim 1, wherein the subject has never received the MUC16 antagonist.

4. The method of claim 1, wherein the subject is undergoing treatment with the MUC16 antagonist.

5. A method for treating or delaying progression of a MUC16-positive cancer in a subject in need thereof, the method comprising administering to the subject one or more therapeutically effective amounts of a MUC16 antagonist, wherein an initial therapeutically effective amount of the MUC16 antagonist was administered prior to administration of the one or more therapeutically effective amounts of the MUC16 antagonist, and:
   wherein a sample obtained from the subject after administration of the initial therapeutically effective amount of the MUC16 antagonist was determined to have an epididymis protein 4 (HE4) expression level that is at least 25% lower than the expression level of HE4 in a sample obtained from the subject prior to administration of the initial therapeutically effective amount of the MUC16 antagonist; or
   wherein the subject was selected for treatment based on a determination that a sample obtained from the subject after administration of the initial therapeutically effective amount of the MUC16 antagonist has an epididymis protein 4 (HE4) expression level that is at least 25% lower than the expression level of HE4 in a sample obtained from the subject prior to administration of the initial therapeutically effective amount of the MUC16 antagonist; or
   wherein treatment is based upon the subject having a sample that expresses epididymis protein 4 (HE4) at a level that is at least 25% lower after administration of the initial therapeutically effective amount of the MUC16 antagonist than the expression level of HE4 in a sample obtained from the subject prior to administration of the initial therapeutically effective amount of the MUC16 antagonist; or
   provided that the subject has been found to have a sample that expresses epididymis protein 4 (HE4) at a level that is at least 25% lower after administration of the initial therapeutically effective amount of the MUC16 antagonist than the expression level of HE4 in a sample obtained from the subject prior to administration of the initial therapeutically effective amount of the MUC16 antagonist.

6. The method of claim 1, further comprising administering a second treatment therapy to the subject.

7. The method of claim 1, wherein:
   the first time point occurs at least 3 days before, at least 1 day before, at least 12 hours before, at least 4 hours before, at least 1 hour before, less than 1 hour before, or immediately before administering the therapeutically effective amount of the MUC16 antagonist; and/or
   the second time point occurs at least 1 hour after, at least 4 hours after, at least 12 hours after, at least 1 day after, at least 3 days after, at least 5 days after, at least 1 week after, at least 2 weeks after, or at least 3 weeks after administering the therapeutically effective amount of the MUC16 antagonist.

8. The method of claim 1, wherein the sample is a blood sample, a serum sample, or a cell sample.

9. The method of claim 1, wherein the expression level of HE4 is circulating level of HE4 protein, protein expression level of HE4, or RNA transcript level of HE4.

10. The method of claim 1, wherein the subject is administered one or more additional therapeutically effective amounts of the MUC16 antagonist if the expression level of HE4 at the second time point is at least 40% lower than the expression level of HE4 at the first time point.

11. The method of claim 1, wherein the MUC16-positive cancer is selected from the group consisting of ovarian cancer, endometrial cancer, triple-negative breast cancer, pancreatic cancer, and non-small cell lung cancer.

12. The method of claim 1, wherein the MUC16-positive cancer is unresectable pancreatic cancer.

13. The method of claim 1, wherein the MUC16-positive cancer is an ovarian cancer selected from the group consisting of primary peritoneal carcinoma, epithelial ovarian carcinoma, metastatic ovarian cancer, fallopian tube carcinoma, and platinum-resistant ovarian cancer.

14. The method of claim 1, wherein the MUC16 antagonist is selected from the group consisting of an anti-MUC16 antibody, a MUC16 inhibitor, a protein, a peptide, a fusion protein, and an immunoadhesin.

15. The method of claim 1, wherein the MUC16 antagonist is an anti-MUC16 antibody.

16. The method of claim 15, wherein the anti-MUC16 antibody comprises a heavy chain variable domain and a light chain variable domain, wherein the heavy chain variable domain, or the light chain variable domain, or both comprise the following HVRs:
   (a) HVR-H1 comprising the amino acid sequence of SEQ ID NO: 4;
   (b) HVR-H2 comprising the amino acid sequence of SEQ ID NO: 5;
   (c) HVR-H3 comprising the amino acid sequence of SEQ ID NO: 6;
   (d) HVR-L1 comprising the amino acid sequence of SEQ ID NO: 1;
   (e) HVR-L2 comprising the amino acid sequence of SEQ ID NO: 2; and
   (f) HVR-L3 comprising the amino acid sequence of SEQ ID NO: 3.

17. The method of claim 15, wherein the anti-MUC16 antibody comprises a heavy chain variable region comprising the amino acid sequence of SEQ ID NO: 8, or a light chain variable region comprising the amino acid sequence of SEQ ID NO: 7, or both.

18. The method of claim 15, wherein the anti-MUC16 antibody is an antibody fragment selected from a Fab, Fab'-SH, Fv, scFv, or F(ab')$_2$.

19. The method of claim 15, wherein one or more amino acid residues are replaced with one or more free cysteine amino acids having a thiol reactivity in the range of 0.6 to 1.0.

20. The method of claim 19, wherein the antibody comprises a cysteine at one or more positions selected from 15, 43, 110, 144, 149, 168 and 205 of the light chain according to Kabat numbering convention and 41, 88, 115, 118, 120, 171, 172, 282, 375, and 400 of the heavy chain according to EU numbering convention.

21. The method of claim 15, wherein the anti-MUC16 antibody is covalently attached to a cytotoxic agent.

22. The method of claim 21, wherein the anti-MUC16 antibody is covalently attached to the cytotoxic agent through a linker and the linker comprises one or more of 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl) cyclohexane-1 carboxylate (SMCC), N-Succinimidyl (4-iodo-acetyl) aminobenzoate (SIAB), and 6-maleimidocaproyl-valine-citrulline-p-aminobenzyloxycarbonyl (MC-vc-PAB).

23. The method of claim 22, wherein the linker is attached to the antibody through a thiol group on the antibody.

24. The method of claim 21, wherein the cytotoxic agent is monomethyl auristatin E (MMAE) or monomethyl auristatin F (MMAF).

25. The method of claim 1, wherein the MUC16-positive cancer is a platinum-resistant ovarian cancer.

26. The method of claim 5, wherein the MUC16-positive cancer is a platinum-resistant ovarian cancer.

27. The method of claim 1, wherein the subject is administered one or more additional therapeutically effective amounts of the MUC16 antagonist if the expression level of HE4 at the second time point is at least 25% to up to 45% lower than the expression level of HE4 at the first time point.

28. The method of claim 5, wherein:
   a sample obtained from the subject after administration of the initial therapeutically effective amount of a MUC16 antagonist was determined to have an epididymis protein 4 (HE4) expression level that is at least 25% to up to 45% lower than the expression level of HE4 in a sample obtained from the subject prior to administration of the initial therapeutically effective amount of the MUC16 antagonist; or
   the subject was selected for treatment based on a determination that a sample obtained from the subject after administration of the initial therapeutically effective amount of the MUC16 antagonist has an epididymis protein 4 (HE4) expression level that is at least 25% to up to 45% lower than the expression level of HE4 in a sample obtained from the subject prior to administration of the initial therapeutically effective amount of the MUC16 antagonist; or
   treatment is based upon the subject having a sample that expresses epididymis protein 4 (HE4) at a level that is at least 25% to up to 45% lower after administration of the initial therapeutically effective amount of the MUC16 antagonist than the expression level of HE4 in a sample obtained from the subject prior to administration of the initial therapeutically effective amount of the MUC16 antagonist; or
   provided that the subject has been found to have a sample that expresses epididymis protein 4 (HE4) at a level that is at least 25% to up to 45% lower after administration of the initial therapeutically effective amount of the MUC16 antagonist than the expression level of HE4 in a sample obtained from the subject prior to administration of the initial therapeutically effective amount of the MUC16 antagonist.

\* \* \* \* \*

SEQUENCE LISTING

```
<160> NUMBER OF SEQ ID NOS: 18

<210> SEQ ID NO 1
<211> LENGTH: 11
<212> TYPE: PRT
<213> ORGANISM: Artificial Sequence
<220> FEATURE:
<223> OTHER INFORMATION: Synthetic construct

<400> SEQUENCE: 1

Lys Ala Ser Asp Leu Ile His Asn Trp Leu Ala
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic construct

<400> SEQUENCE: 2

Tyr Gly Ala Thr Ser Leu Glu Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic construct

<400> SEQUENCE: 3

Gln Gln Tyr Trp Thr Thr Pro Phe Thr
```

```
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic construct

<400> SEQUENCE: 4

Gly Tyr Ser Ile Thr Asn Asp Tyr Ala Trp Asn
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Synthetic construct

<400> SEQUENCE: 5

Gly Tyr Ile Ser Tyr Ser Gly Tyr Thr Thr Tyr Asn Pro Ser Leu Lys
1               5                   10                  15

Ser

<210> SEQ ID NO 6
<211> LENGTH: 9
<212> TYPE: PRT
<213> ORGANISM: Artificial Sequence
<220> FEATURE:
<223> OTHER INFORMATION: Synthetic construct

<400> SEQUENCE: 6

Ala Arg Trp Thr Ser Gly Leu Asp Tyr
1               5

<210> SEQ ID NO 7
<211> LENGTH: 108
<212> TYPE: PRT
<213> ORGANISM: Artificial Sequence
<220> FEATURE:
<223> OTHER INFORMATION: Synthetic construct

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys Arg
            100                 105

<210> SEQ ID NO 8
<211> LENGTH: 116
<212> TYPE: PRT
<213> ORGANISM: Artificial Sequence
```

```
<220> FEATURE:
<223> OTHER INFORMATION: Synthetic construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Ser Tyr Ser Gly Tyr Thr Thr Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Thr Ser Gly Leu Asp Tyr Trp Gly Gln Gly Thr Leu Val
            100                 105                 110

Thr Val Ser Ser
        115

<210> SEQ ID NO 9
<211> LENGTH: 8
<212> TYPE: PRT
<213> ORGANISM: Artificial Sequence
<220> FEATURE:
<223> OTHER INFORMATION: Synthetic construct

<400> SEQUENCE: 9

Ser Gly Ala Thr Ser Leu Glu Thr
1               5

<210> SEQ ID NO 10
<211> LENGTH: 15
<212> TYPE: PRT
<213> ORGANISM: Artificial Sequence
<220> FEATURE:
<223> OTHER INFORMATION: Synthetic construct

<400> SEQUENCE: 10

Gly Tyr Ile Asn Tyr Ser Gly Tyr Thr Thr Tyr Asn Pro Ser Leu
1               5                   10                  15

<210> SEQ ID NO 11
<211> LENGTH: 9
<212> TYPE: PRT
<213> ORGANISM: Artificial Sequence
<220> FEATURE:
<223> OTHER INFORMATION: Synthetic construct

<400> SEQUENCE: 11

Ala Arg Trp Asp Gly Gly Leu Thr Tyr
1               5

<210> SEQ ID NO 12
<211> LENGTH: 107
<212> TYPE: PRT
<213> ORGANISM: Artificial Sequence
<220> FEATURE:
<223> OTHER INFORMATION: Synthetic construct

<400> SEQUENCE: 12

Asp Ile Gln Met Thr Gln Ser Ser Ser Phe Leu Ser Val Ser Leu Gly
```

```
                1               5                  10                  15
Gly Arg Val Thr Ile Thr Cys Lys Ala Ser Asp Leu Ile His Asn Trp
            20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
            50                  55                  60

Ser Gly Ser Gly Asn Asp Tyr Thr Leu Ser Ile Ala Ser Leu Gln Thr
65                  70                  75                  80

Glu Asp Ala Ala Thr Tyr Tyr Cys Gln Gln Tyr Trp Thr Thr Pro Phe
                85                  90                  95

Thr Phe Gly Ser Gly Thr Lys Leu Glu Ile Lys
                100                 105

<210> SEQ ID NO 13
<211> LENGTH: 116
<212> TYPE: PRT
<213> ORGANISM: Artificial Sequence
<220> FEATURE:
<223> OTHER INFORMATION: Synthetic construct

<400> SEQUENCE: 13

Asp Val Gln Leu Gln Glu Ser Gly Pro Gly Leu Val Asn Pro Ser Gln
1               5                   10                  15

Ser Leu Ser Leu Thr Cys Thr Val Thr Gly Tyr Ser Ile Thr Asn Asp
            20                  25                  30

Tyr Ala Trp Asn Trp Ile Arg Gln Phe Pro Gly Asn Lys Leu Glu Trp
            35                  40                  45

Met Gly Tyr Ile Asn Tyr Ser Gly Tyr Thr Thr Tyr Asn Pro Ser Leu
            50                  55                  60

Lys Ser Arg Ile Ser Ile Thr Arg Asp Thr Ser Lys Asn Gln Phe Phe
65                  70                  75                  80

Leu His Leu Asn Ser Val Thr Thr Glu Asp Thr Ala Thr Tyr Tyr Cys
                85                  90                  95

Ala Arg Trp Asp Gly Gly Leu Thr Tyr Trp Gly Gln Gly Thr Leu Val
                100                 105                 110

Thr Val Ser Ala
            115

<210> SEQ ID NO 14
<211> LENGTH: 9
<212> TYPE: PRT
<213> ORGANISM: Artificial Sequence
<220> FEATURE:
<223> OTHER INFORMATION: Synthetic construct

<400> SEQUENCE: 14

Ala Arg Trp Ala Ser Gly Leu Asp Tyr
1               5

<210> SEQ ID NO 15
<211> LENGTH: 116
<212> TYPE: PRT
<213> ORGANISM: Artificial Sequence
<220> FEATURE:
<223> OTHER INFORMATION: Synthetic construct

<400> SEQUENCE: 15

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Ser Tyr Ser Gly Tyr Thr Thr Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ala Ser Gly Leu Asp Tyr Trp Gly Gln Gly Thr Leu Val
            100                 105                 110

Thr Val Ser Ser
        115

<210> SEQ ID NO 16
<211> LENGTH: 17
<212> TYPE: PRT
<213> ORGANISM: Artificial Sequence
<220> FEATURE:
<223> OTHER INFORMATION: Synthetic construct

<400> SEQUENCE: 16

Gly Tyr Ile Asn Tyr Ala Gly Tyr Thr Thr Tyr Asn Pro Ser Leu Lys
1               5                   10                  15

Ser

<210> SEQ ID NO 17
<211> LENGTH: 116
<212> TYPE: PRT
<213> ORGANISM: Artificial Sequence
<220> FEATURE:
<223> OTHER INFORMATION: Synthetic construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Asn Tyr Ala Gly Tyr Thr Thr Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ala Ser Gly Leu Asp Tyr Trp Gly Gln Gly Thr Leu Val
            100                 105                 110

Thr Val Ser Ser
        115

<210> SEQ ID NO 18
<211> LENGTH: 124
<212> TYPE: PRT
<213> ORGANISM: Homo sapiens

<400> SEQUENCE: 18

-continued

```
Met Pro Ala Cys Arg Leu Gly Pro Leu Ala Ala Ala Leu Leu Leu Ser
1               5                   10                  15

Leu Leu Leu Phe Gly Phe Thr Leu Val Ser Gly Thr Gly Ala Glu Lys
            20              25              30

Thr Gly Val Cys Pro Glu Leu Gln Ala Asp Gln Asn Cys Thr Gln Glu
        35              40                  45

Cys Val Ser Asp Ser Glu Cys Ala Asp Asn Leu Lys Cys Cys Ser Ala
    50              55              60

Gly Cys Ala Thr Phe Cys Ser Leu Pro Asn Asp Lys Glu Gly Ser Cys
65              70              75                      80

Pro Gln Val Asn Ile Asn Phe Pro Gln Leu Gly Leu Cys Arg Asp Gln
            85              90                      95

Cys Gln Val Asp Ser Gln Cys Pro Gly Gln Met Lys Cys Cys Arg Asn
            100             105             110

Gly Cys Gly Lys Val Ser Cys Val Thr Pro Asn Phe
            115             120
```